US008633355B2

(12) United States Patent
Spangenberg et al.

(10) Patent No.: US 8,633,355 B2
(45) Date of Patent: Jan. 21, 2014

(54) MODIFICATION OF PLANT FLAVONOID METABOLISM

(75) Inventors: German Spangenberg, Bundoora (AU); Aidyn Mouradov, Mill Park (AU)

(73) Assignee: Agriculture Victoria Services Pty Ltd, Attwood (AU)

( * ) Notice: Subject to any disclaimer, the term of this patent is extended or adjusted under 35 U.S.C. 154(b) by 383 days.

(21) Appl. No.: 12/666,859

(22) PCT Filed: Jun. 25, 2008

(86) PCT No.: PCT/AU2008/000926
§ 371 (c)(1),
(2), (4) Date: Dec. 28, 2009

(87) PCT Pub. No.: WO2009/003216
PCT Pub. Date: Jan. 8, 2009

(65) Prior Publication Data
US 2010/0186114 A1  Jul. 22, 2010

(30) Foreign Application Priority Data

Jun. 29, 2007 (AU) ................ 2007903525

(51) Int. Cl.
*A01H 5/00* (2006.01)
*C07K 14/415* (2006.01)
*C12N 15/11* (2006.01)
*C12N 15/29* (2006.01)
*C12N 15/82* (2006.01)

(52) U.S. Cl.
USPC ........... 800/282; 800/279; 800/284; 800/301; 530/370; 536/23.6; 435/91.1; 435/468; 435/419; 435/320.1

(58) Field of Classification Search
None
See application file for complete search history.

(56) References Cited

U.S. PATENT DOCUMENTS

| | | | |
|---|---|---|---|
| 5,990,386 | A | 11/1999 | An |
| 7,396,979 | B2 | 7/2008 | Alexandrov et al. |
| 2004/0031072 | A1 | 2/2004 | La Rosa et al. |
| 2004/0034888 | A1 | 2/2004 | Liu et al. |
| 2005/0108791 | A1 | 5/2005 | Edgerton |
| 2006/0075522 | A1 | 4/2006 | Cleveland et al. |
| 2006/0107345 | A1 | 5/2006 | Alexandrov et al. |
| 2006/0150283 | A1 | 7/2006 | Alexandrov et al. |
| 2007/0039067 | A1 | 2/2007 | Feldmann et al. |
| 2007/0061916 | A1 | 3/2007 | Kovalic et al. |
| 2007/0192889 | A1* | 8/2007 | La Rosa et al. ............ 800/278 |
| 2007/0214517 | A1 | 9/2007 | Alexandrov et al. |
| 2008/0148432 | A1 | 6/2008 | Abad |

FOREIGN PATENT DOCUMENTS

WO  2007009181 A1  1/2007

OTHER PUBLICATIONS

Endt et al (Phytochemistry 61 (2002) p. 107-114).*
Friedberg (Brief. Bioinformatics (2006) 7: 225-242).*
de Majnik et al (Aust. J. Plant Physiol.,2000, 27, p. 659-667).*
Sequence alignment comparing the nucleic acid sequence of instant SEQ ID No. 64 to the back-translation of sequence SEQ ID No. 31925 of LaRosa et al (U.S. Patent Publication 2007/0192889 A1, filed on May 14, 2003.*
Manthey, K. et al. "Detection of transcript sequences from mycorrhizal roots of the model mycorrhiza *Medicago truncatula* genotype A17-Glomus intraradices using the approach of an EST genome project" GENBANK Accession No. AJ501444, Published: 2002.
Manthey, K. et al. "Detection of transcript sequences from mycorrhizal roots of the model mycorrhiza *Medicago truncatula* genotype A17-Glomus intraradices using the approach of an EST genome project" GENBANK Accession No. AJ501534, Published: 2002.
Watson, B.S. et al. "Expressed sequence Tags from the Samuel Robets Noble Foundation *Medicago truncatula* nodulated root library" GENBANK Accession No. AW684753, Published: 2000.
Vandenbosch, K. et al. "ESTs from uninoculated seedling roots of *Medicago truncatula*" GENBANK Accession No. BE205242, Published: 1999.
Torres-Jerez, I. et al. "Expressed sequence tags from the Samuel Roberts Noble Foundation—Center for *Medicago* Genomics Research" GENBANK Accession No. BF647711, Published: 2000.
Torres-Jerez, I. et al. "Expressed sequence tags from the Samuel Roberts Noble Foundation—Center for *Medicago truncatula* leaf library " GENBANK Accession No. BG453241, Published: 2000.
Harrison, M. J. "ESTs from roots of *Medicago truncatula* after colonization with *Glomus versiforme*" GENBANK Accession No. BG584386, Published: 2001.
Bowman, C.L. et al. "ESTs from roots of *Medicago truncatula* 72 h after *Rhizobium* inoculation" GENBANK Accession No. BG644817, Published: 2001.
Vandenbosch, K. et al. "The *Medicago truncatula* 6K unigene set: cDNA clones selected and re-arrayed from various libraries" GENBANK Accession No. CF068180, Published: 2002.
Achnine, L et al. "*Medicago truncatula* Methyl Jasmonate-Elicited Root Cell Suspension Culture Expressed Sequence Tags from the Samuel Roberts Noble Foundation—Center for *Medicago* Genomics Research" GENBANK Accession No. CX528687, Published: 2005.
Liu, J et al. "ESTs from roots of *Medicago truncatula* after colonization with *Glomus versiforme* from the Samuel Roberts Noble Foundation—Center for *Medicago* Genomics Research" GENBANK Accession No. CX549581, Published: 2005.
Ban, Yusuke et al. "Isolation and Functional Analysis of a MYB Transcription Factor Gene that is a Key Regulator for the Development of Red Coloration in Apple Skin", Plant Cell Physiol, 2007, pp. 958-970, vol. 48, No. 7.

(Continued)

*Primary Examiner* — Brent T Page
*Assistant Examiner* — Lee A Visone
(74) *Attorney, Agent, or Firm* — Larson & Anderson, LLC

(57) ABSTRACT

The present invention relates to nucleic acids encoding flavonoid biosynthetic enzymes, flavonoid-regulating transcription factors and a flavonoid-specific membrane transporter in plants, and the use thereof for the modification of flavonoid biosynthesis in plants. The present invention also relates to constructs and vectors including such nucleic acids, and related polypeptides. More particularly, the protein involved in flavonoid biosynthesis is selected from the group consisting of: MADS box factor, WRKY box factor, MYC factor, TT1, HLH factor, MYB factor, FMT, UG3E, GST, OMT, RT, CYTb5, laccase, and ABC transporter proteins, and functionally active fragments and variants thereof.

13 Claims, 75 Drawing Sheets

(56) References Cited

OTHER PUBLICATIONS

De Majnik, John et al. "Anthocyanin regulatory gene expression in transgenic white clover can result in an altered pattern of pigmentation", Aust. J. Plant Physiol, Jan. 1, 2000, pp. 659-667, vol. 27, No. 27.

EMBL Accession # AC149079; *Medicago truncatula* chromosome 8 clone mth2-7518, complete sequence, May 13, 2004, website: http://srs.ebi.ac.uk/srsbin/cgi-bin/wgetz?-e+[EMBL:AC149079]=newid.
TF ID Mtr000513; *Medicago truncatula*, Plant Transcription Factor Database, Jun. 20, 2011, website: http://planttfdb.cbi.edu.cn/tf.php?sp-Mtr&did-Mtr000513.

* cited by examiner

FIGURE 1

```
               *        20         *        40         *        60
TrFMTa : ATCTCTCAACAGTTCCTTAACCCCATTTTCATATCATTCTTAAGTAACAGATCTCATCTT :   60

*        80         *       100         *       120
TrFMTa : TCGATCCATCATCTAAATTTTCTTCCTTTCTTAATTTGCTTAATATTATTTTTACGATCC :  120

*       140         *       160         *       180
TrFMTa : AAGGTTCTAGATGGCAAAACCAAGTGCTGCTGATAATAGGACTAGAAGTTCTGTGCAGAT :  180

*       200         *       220         *       240
TrFMTa : CTTTATAGTAGTTGGTTTGTGCTGTTTCTTCTATATATTGGGAGCGTGGCAAAGAAGTGG :  240

*       260         *       280         *       300
TrFMTa : ATTTGGAAAAGGAGATAGCATAGCATTAGAGATTACCAAGAATAATGCTGAATGTGATGT :  300

*       320         *       340         *       360
TrFMTa : AGTTCCAAATTTAAGTTTTGATTCACACCATGCTGGAGAAGTTAGTCAAATCGATGAATC :  360

*       380         *       400         *       420
TrFMTa : TGATTCAAAGGCTAAGGTGTTTAAACCGTGTGATGCTCGTTATACGGATTACACTCCGTG :  420

*       440         *       460         *       480
TrFMTa : TCAAGATCAACGTCGTGCTATGACATTTCCTAGAGAAAACATGAACTATAGAGAGAGACA :  480

*       500         *       520         *       540
TrFMTa : TTGCCCTCCAGAGGAAGAGAAGTTACACTGTATGATCCCTGCACCAAAAGGTTATGTAAC :  540

*       560         *       580         *       600
TrFMTa : ACCTTTTCCATGGCCTAAGAGTAGGGATTATGTTCCTTATGCTAATGCACCCTACAAGAG :  600

*       620         *       640         *       660
TrFMTa : TCTCACAGTTGAGAAGGCCATTCAGAATTGGATCCAATATGAGGGAAATGTGTTAAGATT :  660

*       680         *       700         *       720
TrFMTa : CCCTGGTGGTGGAACTCAATTTCCTCAAGGTGCTGATAAATATATTGATCAACTTGCATC :  720

*       740         *       760         *       780
TrFMTa : TGTGGTTCCTATAGATGATGGGACGGTTAGGACGGCGCTTGACACCGGTTGTGGGGTTGC :  780
```

FIGURE 1, cont'd

```
                *         800         *         820         *         840
TrFMTa : AAGTTGGGGTGCATATCTCTGGAGCAGAAATGTTGTTGCCATGTCGTTTGCACCAAGGGA :  840

*         860         *         880         *         900
TrFMTa : CTCTCATGAAGCACAAGTGCAATTTGCTCTTGAAAGGGGTGTACCTGCTGTTATTGGTGT :  900

*         920         *         940         *         960
TrFMTa : TCTTGGAACAATAAAGTTGCCATATCCATCTAGAGCCTTCGACATGGCTCATTGCTCTCG :  960

*         980         *        1000         *        1020
TrFMTa : CTGTTTGATTCCGTGGGGAGCAAATGCTGGAATATATATGATGGAAGTTGATAGAGTTCT : 1020

*        1040         *        1060         *        1080
TrFMTa : AAGGCCTGGTGGTTATTGGGTGCTTTCTGGTCCTCCAATCAATTGGAAGGTCAACTACAA : 1080

*        1100         *        1120         *        1140
TrFMTa : ACCATGGCAAAGACCAAAGGAGGAACTCGAGGAAGAACAAAGAAATATTGAAGAGGTTGC : 1140

*        1160         *        1180         *        1200
TrFMTa : TAAGAAACTTTCCTGGGAGAAGAAGTCTGAGAAGGCTGAAATTGCCATTTGGCAAAAGAC : 1200

*        1220         *        1240         *        1260
TrFMTa : TACCGACTCTGAATCTTGTCGTAGCAGACAAGATGACTCCAGTGTAGAATTTTGTGAAGC : 1260

*        1280         *        1300         *        1320
TrFMTa : ATCAGATCCTGATGATGTCTGGTATAAGAAAATGGAGGCCTGTGTTACTCCAACACCTAA : 1320

*        1340         *        1360         *        1380
TrFMTa : AGTTTTGGGTGGTGATCTTAAACCATTTCCAAACAGGCTATATGCGATCCCTCCTAGAGT : 1380

*        1400         *        1420         *        1440
TrFMTa : TTCTAGTGGTTCTATTCCTGGAGTTTCTTCTGAGACATACCAGAATGATAACAAAGAGTG : 1440

*        1460         *        1480         *        1500
TrFMTa : GAAAAAGCATGTCAGTGCTTACAAGAAAATTAATTCACTCTTGGATTCCGGTAGATATCG : 1500

*        1520         *        1540         *        1560
TrFMTa : CAACATTATGGATATGAATGCTGGTTTGGGTAGTTTCGCTGCAGCTATTCATTCGTCGAA : 1560

*        1580         *        1600         *        1620
TrFMTa : ATCATGGGTCATGAATGTTGTGCCAACTATAGCTGAGAAAAGTACTCTCGGTGCGATATA : 1620

*        1640         *        1660         *        1680
TrFMTa : TGAGCGAGGACTGATTGGCATCTATCATGATTGGTGTGAAGCCTTTTCCACATATCCAAG : 1680
```

FIGURE 1, cont'd

```
                *         1700         *         1720         *         1740
TrFMTa : AACATACGATCTCATTCATGCTAATGGCCTCTTTAGTCTGTACAAGGATAAATGCAATAC : 1740

*         1760         *         1780         *         1800
TrFMTa : AGAAGACATTCTTCTCGAAATGGACCGGATTTTGCGACCAGAAGGTGCTGTCATAATCCG : 1800

*         1820         *         1840         *         1860
TrFMTa : CGACGAAGTCGATGTATTAATTCAGGTAAAGAAATTAATCGGAGGAATGAGATGGAATAT : 1860

*         1880         *         1900         *         1920
TrFMTa : GAAATTAGTTGATCATGAAGATGGTCCTCTTGTTCCTGAGAAAGTACTAATTGCTGTCAA : 1920

*         1940         *         1960         *         1980
TrFMTa : ACAGTATTGGGTTACTGATGGAAATTCCACATCAACACAATAATCACTGAAAAACAAGTT : 1980

*         2000         *         2020         *         2040
TrFMTa : GAATTTACATCCCTACCCTTATCTATATACAACAATAGTCAAAGAGTTCATATGGTTTTG : 2040

*
TrFMTa : TGTCATCATCACAACTA : 2057
```

FIGURE 2

```
             *        20         *        40         *        60
TrFMTa :  MAKPSAADNRTRSSVQIFIVVGLCCFFYILGAWQRSGFGKGDSIALEITKNNAECDVVPN :  60

*        80         *       100         *       120
TrFMTa :  LSFDSHHAGEVSQIDESDSKAKVFKPCDARYTDYTPCQDQRRAMTFPRENMNYRERHCPP : 120

*       140         *       160         *       180
TrFMTa :  EEEKLHCMIPAPKGYVTPFPWPKSRDYVPYANAPYKSLTVEKAIQNWIQYEGNVLRFPGG : 180

*       200         *       220         *       240
TrFMTa :  GTQFPQGADKYIDQLASVVPIDDGTVRTALDTGCGVASWGAYLWSRNVVAMSFAPRDSHE : 240

*       260         *       280         *       300
TrFMTa :  AQVQFALERGVPAVIGVLGTIKLPYPSRAFDMAHCSRCLIPWGANAGIYMMEVDRVLRPG : 300

*       320         *       340         *       360
TrFMTa :  GYWVLSGPPINWKVNYKPWQRPKEELEEEQRNIEEVAKKLSWEKKSEKAEIAIWQKTTDS : 360

*       380         *       400         *       420
TrFMTa :  ESCRSRQDDSSVEFCEASDPDDVWYKKMEACVTPTPKVLGGDLKPFPNRLYAIPPRVSSG : 420

*       440         *       460         *       480
TrFMTa :  SIPGVSSETYQNDNKEWKKHVSAYKKINSLLDSGRYRNIMDMNAGLGSFAAAIHSSKSWV : 480

*       500         *       520         *       540
TrFMTa :  MNVVPTIAEKSTLGAIYERGLIGIYHDWCEAFSTYPRTYDLIHANGLFSLYKDKCNTEDI : 540

*       560         *       580         *       600
TrFMTa :  LLEMDRILRPEGAVIIRDEVDVLIQVKKLIGGMRWNMKLVDHEDGPLVPEKVLIAVKQYW : 600

*
TrFMTa :  VTDGNSTSTQ : 610
```

FIGURE 3

```
                    *         20         *         40         *         60
TrFMTa1 : ATCTCTCAACAGTTCCTTAACCCCATTTTCATATCATTCTTAAGTAACAGATCTCATCTT :  60
TrFMTa2 : ------------------------------------------------------------ :   -
TrFMTa3 : ------------------------------------------------------------ :   -
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          ATCTCTCAACAGTTCCTTAACCCCATTTTCATATCATTCTTAAGTAACAGATCTCATCTT

*         80         *        100         *        120
TrFMTa1 : TCGATCCATCATCTAAATTTTCTTCCTTTCTTAATTTGCTTAATATTATTTTTACGATCC : 120
TrFMTa2 : ------------------------------------------------------------ :   -
TrFMTa3 : ------------------------------------------------------------ :   -
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          TCGATCCATCATCTAAATTTTCTTCCTTTCTTAATTTGCTTAATATTATTTTTACGATCC

*        140         *        160         *        180
TrFMTa1 : AAGGTTCTAGATGGCAAAACCAAGTGCTGCTGATAATAGGACTAGAAGTTCTGTGCAGAT : 180
TrFMTa2 : ------------------------------------------------------------ :   -
TrFMTa3 : ------------------------------------------------------------ :   -
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          AAGGTTCTAGATGGCAAAACCAAGTGCTGCTGATAATAGGACTAGAAGTTCTGTGCAGAT

*        200         *        220         *        240
TrFMTa1 : CTTTATAGTAGTTGGTTTGTGCTGTTTCTTCTATATATTGGGAGCGTGGCAAAGAAGTGG : 240
TrFMTa2 : ------------------------------------------------------------ :   -
TrFMTa3 : ------------------------------------------------------------ :   -
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          CTTTATAGTAGTTGGTTTGTGCTGTTTCTTCTATATATTGGGAGCGTGGCAAAGAAGTGG

*        260         *        280         *        300
TrFMTa1 : ATTTGGAAAAGGAGATAGCATAGCATTAGAGATTACCAAGAATAATGCTGAATGTGATGT : 300
TrFMTa2 : ------------------------------------------------------------ :   -
TrFMTa3 : ------------------------------------------------------------ :   -
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          ATTTGGAAAAGGAGATAGCATAGCATTAGAGATTACCAAGAATAATGCTGAATGTGATGT
```

FIGURE 3, cont'd

```
                  *        320         *        340         *        360
TrFMTa1  : AGTTCCAAATTTAAGTTTTGATTCACACCATGCTGGAGAAGTTAGTCAAATCGATGAATC : 360
TrFMTa2  : ------------------------------------------------------------ :   -
TrFMTa3  : ------------------------------------------------------------ :   -
TrFMTa4  : ------------------------------------------------------------ :   -
TrFMTa5  : ------------------------------------------------------------ :   -
TrFMTa6  : ------------------------------------------------------------ :   -
TrFMTa7  : ------------------------------------------------------------ :   -
TrFMTa8  : ------------------------------------------------------------ :   -
           AGTTCCAAATTTAAGTTTTGATTCACACCATGCTGGAGAAGTTAGTCAAATCGATGAATC

*        380         *        400         *        420
TrFMTa1  : TGATTCAAAGGCTAAGGTGTTTAAACCGGGTGATGCTCGTTATACTGATTACACTCCGTG : 420
TrFMTa2  : -------AGGCTAAGGTGTTTAAACCGTGTGATGCTCGTTATACGGATTACACTCCGTG :  52
TrFMTa3  : ---------------GTGTTTAAACCGTGTGATGCTCGTTATACGGATTACACTCCGTG :  44
TrFMTa4  : ------------------------------------------------------------ :   -
TrFMTa5  : ------------------------------------------------------------ :   -
TrFMTa6  : ------------------------------------------------------------ :   -
TrFMTa7  : ------------------------------------------------------------ :   -
TrFMTa8  : ------------------------------------------------------------ :   -
           TGATTCAAAGGCTAAGGTGTTTAAACCGTGTGATGCTCGTTATACGGATTACACTCCGTG

*        440         *        460         *        480
TrFMTa1  : TCAAGATCAACGTCGTGCTATGACTTTTCCGAGAGAAAACATGAACTATAGAGAGAGACA : 480
TrFMTa2  : TCAAGATCAACGTCGTGCTATGACATTTCCTAGAGAAAACATGAACTATAGAGAGAGACA : 112
TrFMTa3  : TCAAGATCAACGTCGTGCTATGACATTTCCTAGAGAAAACATGAACTATAGAGAGAGACA : 104
TrFMTa4  : ------------------------------------------------------------ :   -
TrFMTa5  : ------------------------------------------------------------ :   -
TrFMTa6  : ------------------------------------------------------------ :   -
TrFMTa7  : ------------------------------------------------------------ :   -
TrFMTa8  : ------------------------------------------------------------ :   -
           TCAAGATCAACGTCGTGCTATGACATTTCCTAGAGAAAACATGAACTATAGAGAGAGACA

*        500         *        520         *        540
TrFMTa1  : TTGCCCTCCAGAGGAAGAGAAGTTACACTGTATGATCCCTGCACCAAAAGGGTATGTAAC : 540
TrFMTa2  : TTGCCCTCCAGAGGAAGAGAAGTTACACTGTATGATCCCTGCACCAAAAGGTTATGTAAC : 172
TrFMTa3  : TTGCCCTCCAGAGGAAGAGAAGTTACACTGTATGATCCCTGCACCAAAAGGTTATGTAAC : 164
TrFMTa4  : ------------------------------------------------------------ :   -
TrFMTa5  : ------------------------------------------------------------ :   -
TrFMTa6  : ------------------------------------------------------------ :   -
TrFMTa7  : ------------------------------------------------------------ :   -
TrFMTa8  : ------------------------------------------------------------ :   -
           TTGCCCTCCAGAGGAAGAGAAGTTACACTGTATGATCCCTGCACCAAAAGGTTATGTAAC

*        560         *        580         *        600
TrFMTa1  : ACCTTTTCCATGGCCTAAGAGTAGGGAT-------------------------------- : 568
TrFMTa2  : ACCTTTTCCATGGCCTAAGAGTAGGGATTATGTTCCTTATGCTAATGCACCCTACAAGAG : 232
TrFMTa3  : ACCTTTTCCATGGCCTAAGAGTAGGGATTATGTTCCTTATGCTAATGCACCCTACAAGAG : 224
TrFMTa4  : ------------------------------------------------------------ :   -
TrFMTa5  : ------------------------------------------------------------ :   -
TrFMTa6  : ------------------------------------------------------------ :   -
TrFMTa7  : ------------------------------------------------------------ :   -
TrFMTa8  : ------------------------------------------------------------ :   -
           ACCTTTTCCATGGCCTAAGAGTAGGGATTATGTTCCTTATGCTAATGCACCCTACAAGAG
```

FIGURE 3, cont'd

```
                     *         620         *         640         *         660
TrFMTa1 : ------------------------------------------------------------ :   -
TrFMTa2 : TCTCACAGTTGAGAAGGCCATTCAGAATTGGATCCAATATGAGGGAAATGTGTTAAGATT : 292
TrFMTa3 : TCTCACAGTTGAGAAGGCCATTCAGAATTGGATCCAATATGAGGGAAATGTGTTAAGATT : 284
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          TCTCACAGTTGAGAAGGCCATTCAGAATTGGATCCAATATGAGGGAAATGTGTTAAGATT

*         680         *         700         *         720
TrFMTa1 : ------------------------------------------------------------ :   -
TrFMTa2 : CCCTGGTGGTGGAACTCAATTTCCTCAAGGTGCTGATAAATATATTGATCAACTTGCATC : 352
TrFMTa3 : CCCTGGTGGTGGAACTCAATTTGCTCAAGGTGCTGATAAATATATTGATCAACTTGCATC : 344
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          CCCTGGTGGTGGAACTCAATTTCCTCAAGGTGCTGATAAATATATTGATCAACTTGCATC

*         740         *         760         *         780
TrFMTa1 : ------------------------------------------------------------ :   -
TrFMTa2 : TGTGGTTCCTATAGATGATGGGACGGTTAGGACGGCGCTTGACACCGGTTGTGGGGTTGC : 412
TrFMTa3 : TGTGGTTCCTATAGATGATGGGACGGTTAGGACGGCGCTTGACACC-------------- : 390
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          TGTGGTTCCTATAGATGATGGGACGGTTAGGACGGCGCTTGACACCGGTTGTGGGGTTGC

*         800         *         820         *         840
TrFMTa1 : ------------------------------------------------------------ :   -
TrFMTa2 : AAGTTGGGGTGCATATCTCTGGAGCAGAAATGTTGTTGCCATGTCGTTTGCACCAAGGGA : 472
TrFMTa3 : ------------------------------------------------------------ :   -
TrFMTa4 : ------------------------------------------------------------ :   -
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          AAGTTGGGGTGCATATCTCTGGAGCAGAAATGTTGTTGCCATGTCGTTTGCACCAAGGGA

*         860         *         880         *         900
TrFMTa1 : ------------------------------------------------------------ :   -
TrFMTa2 : CTCTCATGAAGCACAAGTGCAATTTGCTCTTGAAAGGGGTGTACCTGCTGTTATTGGTGT : 532
TrFMTa3 : ------------------------------------------------------------ :   -
TrFMTa4 : ------------------GTGCAATTTGCTCTTGAA-GGGGTGTACCTGCTGTTATTGGTGT :  43
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          CTCTCATGAAGCACAAGTGCAATTTGCTCTTGAAAGGGGTGTACCTGCTGTTATTGGTGT
```

FIGURE 3, cont'd

```
                        *         920         *         940         *         960
TrFMTa1 : ------------------------------------------------------------ :   -
TrFMTa2 : TCTTGGAACAATAAAGTTGCCATATCCATCTAGAGCCTTCGACATGG-------------- : 579
TrFMTa3 : ------------------------------------------------------------ :   -
TrFMTa4 : TCTTGGAACAATAAAGTTGCCATATCCATCTAGAGCCTTCGACATGGCTCATTGCTCTCG : 103
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          TCTTGGAACAATAAAGTTGCCATATCCATCTAGAGCCTTCGACATGGCTCATTGCTCTCG

*         980         *        1000         *        1020
TrFMTa1 : ------------------------------------------------------------ :   -
TrFMTa2 : ------------------------------------------------------------ :   -
TrFMTa3 : ------------------------------------------------------------ :   -
TrFMTa4 : CTGTTTGATTCCGTGGGGAGCAAATGCTGGAATATATATGATGGAAGTTGATAGAGTTCT : 163
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          CTGTTTGATTCCGTGGGGAGCAAATGCTGGAATATATATGATGGAAGTTGATAGAGTTCT

*        1040         *        1060         *        1080
TrFMTa1 : ------------------------------------------------------------ :   -
TrFMTa2 : ------------------------------------------------------------ :   -
TrFMTa3 : ------------------------------------------------------------ :   -
TrFMTa4 : AAGGCCTGGTGGTTATTGGGTGCTTTCTGGTCCTCCAATCAATTGGAAGGTCAACTACAA : 223
TrFMTa5 : ------------------------------------------------------------ :   -
TrFMTa6 : ------------------------------------------------------------ :   -
TrFMTa7 : ------------------------------------------------------------ :   -
TrFMTa8 : ------------------------------------------------------------ :   -
          AAGGCCTGGTGGTTATTGGGTGCTTTCTGGTCCTCCAATCAATTGGAAGGTCAACTACAA

*        1100         *        1120         *        1140
TrFMTa1 : ------------------------------------------------------------ :   -
TrFMTa2 : ------------------------------------------------------------ :   -
TrFMTa3 : ------------------------------------------------------------ :   -
TrFMTa4 : ACCATGGCAAAGACCAAAGGAGGAACTCGAGGAAGAACAAAGAAATATTGAAGAGGTTGC : 283
TrFMTa5 : ---------------------------------------------TTGAAGAGGTTGC :  13
TrFMTa6 : ------------------------------------------------------------ :   -
TrFMTa7 : ------------------------------------------------------------ :   -
TrFMTa8 : ------------------------------------------------------------ :   -
          ACCATGGCAAAGACCAAAGGAGGAACTCGAGGAAGAACAAAGAAATATTGAAGAGGTTGC

*        1160         *        1180         *        1200
TrFMTa1 : ------------------------------------------------------------ :   -
TrFMTa2 : ------------------------------------------------------------ :   -
TrFMTa3 : ------------------------------------------------------------ :   -
TrFMTa4 : TAAGAAACTTTGCTGGGAGAAGAAGTCTGAGAAGGCTGAAATTGCCATTTGGCAAAAGAC : 343
TrFMTa5 : TAAGAAACTTTCCTGGGAGAAGAAGTCTGAGAAGGCTGAAATTGCCATTTGGCAAAAGAC :  73
TrFMTa6 : ---GAAACTTTCCTGGGAGAAGAAGTCTGAGAAGGCTGAAATTGCCATTTGGCAAAAGAC :  57
TrFMTa7 : ------------------------------------------------------------ :   -
TrFMTa8 : ------------------------------------------------------------ :   -
          TAAGAAACTTTCCTGGGAGAAGAAGTCTGAGAAGGCTGAAATTGCCATTTGGCAAAAGAC
```

FIGURE 3, cont'd

```
                        *        1220         *        1240         *        1260
TrFMTa1 : ------------------------------------------------------------ :   -
TrFMTa2 : ------------------------------------------------------------ :   -
TrFMTa3 : ------------------------------------------------------------ :   -
TrFMTa4 : TACCGACTCTGAATCTTGTCGTAGCAGACAAGATGACTCCAGTGTAGAATTTTGTGAAGC : 403
TrFMTa5 : TACCGACTCTGAATCTTGTCGTAGCAGACAAGATGACTCCAGTGTAGAATTTTGTGAAGC : 133
TrFMTa6 : TACCGACTCTGAATCTTGTCGTAGCAGACAAGATGACTCCAGTGTAGAATTTTGTGAAGC : 117
TrFMTa7 : ------------------------------------------------------------ :   -
TrFMTa8 : ------------------------------------------------------------ :   -
          TACCGACTCTGAATCTTGTCGTAGCAGACAAGATGACTCCAGTGTAGAATTTTGTGAAGC

*        1280         *        1300         *        1320
TrFMTa1 : ------------------------------------------------------------ :   -
TrFMTa2 : ------------------------------------------------------------ :   -
TrFMTa3 : ------------------------------------------------------------ :   -
TrFMTa4 : ATCAGATCCTGATGAGGTCTGGTATAAGAAAATGGAGGCCTGTGTTACTCCAACACCTAA : 463
TrFMTa5 : ATCAGATCCTGATGATGTCTGGTATAAGAAAATGGAGGCCTGTGTTACTCCAACACCTAA : 193
TrFMTa6 : ATCAGATCCTGATGATGTCTGGTATAAGAAAATGGAGGCCTGTGTTACTCCAACACCTAA : 177
TrFMTa7 : ------------------------------------------------------------ :   -
TrFMTa8 : ------------------------------------------------------------ :   -
          ATCAGATCCTGATGATGTCTGGTATAAGAAAATGGAGGCCTGTGTTACTCCAACACCTAA

*        1340         *        1360         *        1380
TrFMTa1 : ------------------------------------------------------------ :   -
TrFMTa2 : ------------------------------------------------------------ :   -
TrFMTa3 : ------------------------------------------------------------ :   -
TrFMTa4 : AGTTTTGGGTGGTGATCTTAAACCATTTCCAAACAGGCTATATGCGATCCCTCCTAGAGT : 523
TrFMTa5 : AGTTTTGGGTGGTGATCTTAAACCATTTCCAAACAGGCTATATGCGATCCCTCCTAGAGT : 253
TrFMTa6 : AGTTTTGGGTGGTGATCTTAAACCATTTCCAAACAGGCTATATGCGATCCCTCCTAGAGT : 237
TrFMTa7 : ------------------------------------------------------------ :   -
TrFMTa8 : ------------------------------------------------------------ :   -
          AGTTTTGGGTGGTGATCTTAAACCATTTCCAAACAGGCTATATGCGATCCCTCCTAGAGT

*        1400         *        1420         *        1440
TrFMTa1 : ------------------------------------------------------------ :   -
TrFMTa2 : ------------------------------------------------------------ :   -
TrFMTa3 : ------------------------------------------------------------ :   -
TrFMTa4 : TTCTAGTGGTTCTATTCCTGGAGTTTCTTCTGAGACATACCAGAATGA------------ : 571
TrFMTa5 : TTCTAGTGGTTCTATTCCTGGAGTTTCTTCTGAGACATACCAGAATGATAACAAAGAGTG : 313
TrFMTa6 : TTCTAGTGGTTCTATTCCTGGAGTTTCTTCTGAGACATACCAGAATGATAACAAAGAGTG : 297
TrFMTa7 : ------------------------------------------------------------ :   -
TrFMTa8 : ------------------------------------------------------------ :   -
          TTCTAGTGGTTCTATTCCTGGAGTTTCTTCTGAGACATACCAGAATGATAACAAAGAGTG

*        1460         *        1480         *        1500
TrFMTa1 : ------------------------------------------------------------ :   -
TrFMTa2 : ------------------------------------------------------------ :   -
TrFMTa3 : ------------------------------------------------------------ :   -
TrFMTa4 : ------------------------------------------------------------ :   -
TrFMTa5 : GAAAAAGCATGTCAGTGCTTACAAGAAAATTAATTCACTCTTGGATTCCGGTAGATATCG : 373
TrFMTa6 : GAAAAAGCATGTCAGTGCTTACAAGAAAATTAATTCACTCTTGGATTCCGGTAGATATCG : 357
TrFMTa7 : ---------------------------------------------------TAGATATCG :   9
TrFMTa8 : -------------------------------------------------------TATCG :   5
          GAAAAAGCATGTCAGTGCTTACAAGAAAATTAATTCACTCTTGGATTCCGGTAGATATCG
```

FIGURE 3, cont'd

```
                 *        1520         *        1540         *        1560
TrFMTa1 : ------------------------------------------------------------ :   -
TrFMTa2 : ------------------------------------------------------------ :   -
TrFMTa3 : ------------------------------------------------------------ :   -
TrFMTa4 : ------------------------------------------------------------ :   -
TrFMTa5 : CAACATTATGGATATGAATGCTGGTTTGGGTAGTTTCGCTGCAGCTATTCATTCGTCGAA : 433
TrFMTa6 : CAACATTATGGATATGAATGCTGGTTTGGGTAGTTTCGCTGCAGCTATTCATTCGTCGAA : 417
TrFMTa7 : CAACATTATGGATATGAATGCTGGTTTGGGTAGTTTCGCTGCAGCTATTCATTCGTCGAA :  69
TrFMTa8 : CAACATTATGGATATGAATGCTGGTTTGGGTAGTTTCGCTGCAGCTATTCATTCGTCGAA :  65
          CAACATTATGGATATGAATGCTGGTTTGGGTAGTTTCGCTGCAGCTATTCATTCGTCGAA

*        1580         *        1600         *        1620
TrFMTa1 : ------------------------------------------------------------ :   -
TrFMTa2 : ------------------------------------------------------------ :   -
TrFMTa3 : ------------------------------------------------------------ :   -
TrFMTa4 : ------------------------------------------------------------ :   -
TrFMTa5 : ATCATGGGTCATGAATGTTGTGCCAACTATAGCTGAGAAAAGTACTCTCGGTGCGATATA : 493
TrFMTa6 : ATCATGGGTCATGAATGTTGTGCCAACTATAGCTGAGAAAAGTACTCTCGGTGCGATATA : 477
TrFMTa7 : AT-ATGGGTCATGAATGTTGTGCCAACTATAGCTGAGAAAAGTACTCTCGGTGCGATATA : 128
TrFMTa8 : ATCATGGGTCATGAATGTTGTGCCAACTATAGCTGAGAAAAGTACTCTCGGTGCGATATA : 125
          ATCATGGGTCATGAATGTTGTGCCAACTATAGCTGAGAAAAGTACTCTCGGTGCGATATA

*        1640         *        1660         *        1680
TrFMTa1 : ------------------------------------------------------------ :   -
TrFMTa2 : ------------------------------------------------------------ :   -
TrFMTa3 : ------------------------------------------------------------ :   -
TrFMTa4 : ------------------------------------------------------------ :   -
TrFMTa5 : TGAGCGAGGACTGATTGGCATCTATCATGATTGGTGTGAAGCCTTTTCCACATATCCAAG : 553
TrFMTa6 : TGAGCGAGGACTGATTGGCATCTATCATGATTGGTGTGAAGCCTTTTCCACATATCCAAG : 537
TrFMTa7 : TGAGCGAGGACTGATTGGCATCTATCATGATTGGTGTGAAGCCTTTTCCACATATCCAAG : 188
TrFMTa8 : TGAGCGAGGACTGATTGGCATCTATCATGATTGGTGTGAAGCCTTTTCCACATATCCAAG : 185
          TGAGCGAGGACTGATTGGCATCTATCATGATTGGTGTGAAGCCTTTTCCACATATCCAAG

*        1700         *        1720         *        1740
TrFMTa1 : ------------------------------------------------------------ :   -
TrFMTa2 : ------------------------------------------------------------ :   -
TrFMTa3 : ------------------------------------------------------------ :   -
TrFMTa4 : ------------------------------------------------------------ :   -
TrFMTa5 : AACATACGATCTCATTCATGCTAATGGCCTCTTTAGTCTGTACAAG-------------- : 599
TrFMTa6 : AACATACGATCTCATTCATGCTAATGGCCTCTTTAGTCTGTACAAGGATAAATG------ : 591
TrFMTa7 : AACATACGATCTCATTCATGCTAATGGCCTCTTTAGTCTGTACAAGGATAAATGCAATAC : 248
TrFMTa8 : AACATACGATCTCATTCATGCTAATGGCCTCTTTAGTCTGTACAAGGATAAATGCAATAC : 245
          AACATACGATCTCATTCATGCTAATGGCCTCTTTAGTCTGTACAAGGATAAATGCAATAC

*        1760         *        1780         *        1800
TrFMTa1 : ------------------------------------------------------------ :   -
TrFMTa2 : ------------------------------------------------------------ :   -
TrFMTa3 : ------------------------------------------------------------ :   -
TrFMTa4 : ------------------------------------------------------------ :   -
TrFMTa5 : ------------------------------------------------------------ :   -
TrFMTa6 : ------------------------------------------------------------ :   -
TrFMTa7 : AGAAGACATTCTTCTCGAAATGGACCGGATTTTGCGACCAGAAGGTGCTGTCATAATCCG : 308
TrFMTa8 : AGAAGACATTCTTCTCGAAATGGACCGGATTTTGCGACCAGAAGGTGCTGTCATAATCCG : 305
          AGAAGACATTCTTCTCGAAATGGACCGGATTTTGCGACCAGAAGGTGCTGTCATAATCCG
```

FIGURE 3, cont'd

```
                   *        1820         *        1840         *        1860
TrFMTa1  : ----------------------------------------------------------------- :  -
TrFMTa2  : ----------------------------------------------------------------- :  -
TrFMTa3  : ----------------------------------------------------------------- :  -
TrFMTa4  : ----------------------------------------------------------------- :  -
TrFMTa5  : ----------------------------------------------------------------- :  -
TrFMTa6  : ----------------------------------------------------------------- :  -
TrFMTa7  : CGACGAAGTCGATGTATTAATTCAGGTAAAGAAATTAATCGGAGGAATGAGATGGAATAT : 368
TrFMTa8  : CGACGAAGTCGATGTATTAATTCAGGTAAAGAAATTAATCGGAGGAATGAGATGGAATAT : 365
           CGACGAAGTCGATGTATTAATTCAGGTAAAGAAATTAATCGGAGGAATGAGATGGAATAT

*        1880         *        1900         *        1920
TrFMTa1  : ----------------------------------------------------------------- :  -
TrFMTa2  : ----------------------------------------------------------------- :  -
TrFMTa3  : ----------------------------------------------------------------- :  -
TrFMTa4  : ----------------------------------------------------------------- :  -
TrFMTa5  : ----------------------------------------------------------------- :  -
TrFMTa6  : ----------------------------------------------------------------- :  -
TrFMTa7  : GAAATTAGTTGATCATGAAGATGGTCCTCTTGTTCCTGAGAAAGTACTAATTGCTGTCAA : 428
TrFMTa8  : GAAATTAGTTGATCATGAAGATGGTCCTCTTGTTCCTGAGAAAGTACTAATTGCTGTCAA : 425
           GAAATTAGTTGATCATGAAGATGGTCCTCTTGTTCCTGAGAAAGTACTAATTGCTGTCAA

*        1940         *        1960         *        1980
TrFMTa1  : ----------------------------------------------------------------- :  -
TrFMTa2  : ----------------------------------------------------------------- :  -
TrFMTa3  : ----------------------------------------------------------------- :  -
TrFMTa4  : ----------------------------------------------------------------- :  -
TrFMTa5  : ----------------------------------------------------------------- :  -
TrFMTa6  : ----------------------------------------------------------------- :  -
TrFMTa7  : ACAGTATTGGGTTACTGATGGAAATTCCACATCAACACAATAATCACTGAAAAACAAGTT : 488
TrFMTa8  : ACAGTATTGGGTTACTGATGGAAATTCCACATCAACACAATAATCACTGAAAAACAAGTT : 485
           ACAGTATTGGGTTACTGATGGAAATTCCACATCAACACAATAATCACTGAAAAACAAGTT

*        2000         *        2020         *        2040
TrFMTa1  : ----------------------------------------------------------------- :  -
TrFMTa2  : ----------------------------------------------------------------- :  -
TrFMTa3  : ----------------------------------------------------------------- :  -
TrFMTa4  : ----------------------------------------------------------------- :  -
TrFMTa5  : ----------------------------------------------------------------- :  -
TrFMTa6  : ----------------------------------------------------------------- :  -
TrFMTa7  : GAATTTACATCCCTACCCTTATCTATATACAACAATAGTCAAAGAGTTCATATGGTTTTG : 548
TrFMTa8  : GAATTTACATCCCTACCCTTATCTATATACAACAATAGTCAAAGAGTTCATATGGT---- : 541
           GAATTTACATCCCTACCCTTATCTATATACAACAATAGTCAAAGAGTTCATATGGTTTTG

*
TrFMTa1  : ----------------- :  -
TrFMTa2  : ----------------- :  -
TrFMTa3  : ----------------- :  -
TrFMTa4  : ----------------- :  -
TrFMTa5  : ----------------- :  -
TrFMTa6  : ----------------- :  -
TrFMTa7  : TGTCATCATCACAACTA : 565
TrFMTa8  : ----------------- :  -
           TGTCATCATCACAACTA
```

FIGURE 4

```
                 *        20         *        40         *        60
TrUG3Ea : CATCATCTGCAACTGTTTATGGCACACCTGAAAAGATACCTTGTGAGGAGGATTTCAATT :  60

*        80         *       100         *       120
TrUG3Ea : TATAAGCCATGAATCCATATGGACGGACCAAGCTTTTCCTCGAAGAAATCGCACGAGATA : 120

*       140         *       160         *       180
TrUG3Ea : TTCAGAAAGCTGAGCCAGAATGGAGGATCATTTTACTGAGATACTTCAATCCAGTTGGGG : 180

*       200         *       220         *       240
TrUG3Ea : CCCATGAAAGCGGTAGACTCGGTGAAGATCCCAAGGGCATCCCAAATAATCTCATGCCTT : 240

*       260         *       280         *       300
TrUG3Ea : ATATACAGCGTGTAGCTGTTGAAAGATTACCCGAGCTCAATGTATATGGTCATGATTATC : 300

*       320         *       340         *       360
TrUG3Ea : CTACGAGGGATGGTTCTGCGATTCGGGACTATATCCATGTGATGGACTTAGCAGATGGTC : 360

*       380         *       400         *       420
TrUG3Ea : ACATTGCTGCATTGAGAAAGCTTTTCACAACAGAAAACATAGGTTGTGCTGCTTACAACT : 420

*       440         *       460         *       480
TrUG3Ea : TGGGAACTGGTCGTGGTACATCTGTACTTGAAATGGTTGATGCATTTGAGAAAGCTTCTG : 480

*       500         *       520         *       540
TrUG3Ea : GCAAGAAAATTCCAGTGAAATTGTGTCCACGAAGGGCGGGAGATGCTACGGAGGTTTATG : 540

*       560         *
TrUG3Ea : CATCTACAGAGAGAGCTGAGAAAGAACTTGG : 571
```

FIGURE 5

```
              *        20         *        40         *        60
TrUG3Ea : MNPYGRTKLFLEEIARDIQKAEPEWRIILLRYFNPVGAHESGRLGEDPKGIPNNLMPYIQ :  60

*        80         *       100         *       120
TrUG3Ea : RVAVERLPELNVYGHDYPTRDGSAIRDYIHVMDLADGHIAALRKLFTTENIGCAAYNLGT : 120

*       140         *       160
TrUG3Ea : GRGTSVLEMVDAFEKASGKKIPVKLCPRRAGDATEVYASTERAEKEL : 167
```

FIGURE 6

```
              *         20         *         40         *         60
TrUG3Ea1 : CATCATCTGCAACTGTTTATGGCACACCTGAAAAGATACCTTGTGAGGAGGATTTCAATT :  60
TrUG3Ea2 : --TCATCTGCAACTGTTTATGGCACACCTGAAAAGATACCTTGTGAGGAGGATTTCAATT :  58
           CATCATCTGCAACTGTTTATGGCACACCTGAAAAGATACCTTGTGAGGAGGATTTCAATT

*         80         *        100         *        120
TrUG3Ea1 : TATAAGCCATGAATCCATATGGACGGACCAAGCTTTTCCTCGAAGAAATCGCACGAGATA : 120
TrUG3Ea2 : TATAAGCCATGAATCCATATGGACGGACCAAGCTTTTCCTCGAAGAAATCGCACGAGATA : 118
           TATAAGCCATGAATCCATATGGACGGACCAAGCTTTTCCTCGAAGAAATCGCACGAGATA

*        140         *        160         *        180
TrUG3Ea1 : TTCAGAAAGCTGAGCCAGAATGGAGGATCATTTTACTGAGATACTTCAATCCAGTTGGGG : 180
TrUG3Ea2 : TTCAGAAAGCTGAGCCAGAATGGAGGATCATTTTACTGAGATACTTCAATCCAGTTGGGG : 178
           TTCAGAAAGCTGAGCCAGAATGGAGGATCATTTTACTGAGATACTTCAATCCAGTTGGGG

*        200         *        220         *        240
TrUG3Ea1 : CCCATGAAAGCGGTAGACTCGGTGAAGATCCCAAGGGCATCCCAAATAATCTCATGCCTT : 240
TrUG3Ea2 : CCCATGAAAGCGGTAGACTCGGTGAAGATCCCAAGGGCATCCCAAATAATCTCATGCCTT : 238
           CCCATGAAAGCGGTAGACTCGGTGAAGATCCCAAGGGCATCCCAAATAATCTCATGCCTT

*        260         *        280         *        300
TrUG3Ea1 : ATATACAGCGTGTAGCTGTTGAAAGATTACCCGAGCTCAATGTATATGGTCATGATTATC : 300
TrUG3Ea2 : ATATACAGCGTGTAGCTGTTGAAAGATTACCCGAGCTCAATGTATATGGTCATGATTATC : 298
           ATATACAGCGTGTAGCTGTTGAAAGATTACCCGAGCTCAATGTATATGGTCATGATTATC

*        320         *        340         *        360
TrUG3Ea1 : CTACGAGGGATGGTTCTGCGATTCGGGACTATATCCATGTGATGGACTTAGCAGATGGTC : 360
TrUG3Ea2 : CTACGAGGGATGGTTCTGCGATTCGGGACTATATCCATGTGATGGACTTAGCAGATGGTC : 358
           CTACGAGGGATGGTTCTGCGATTCGGGACTATATCCATGTGATGGACTTAGCAGATGGTC

*        380         *        400         *        420
TrUG3Ea1 : ACATTGCTGCATTGAGAAAGCTTTTCACAACAGAAAACATAGGTTGTGCTGCTTACAACT : 420
TrUG3Ea2 : ACATTGCTGCATTGAGAAAGCTTTTCACAACAGAAAACATAGGTTGTGCTGCTTACAACT : 418
           ACATTGCTGCATTGAGAAAGCTTTTCACAACAGAAAACATAGGTTGTGCTGCTTACAACT

*        440         *        460         *        480
TrUG3Ea1 : TGGGAACTGGTCGTGGTACATCTGTACTTGAAATGGTTGATGCATTTGAGAAAGCTTCTG : 480
TrUG3Ea2 : TGGGAACTGGTCGTGGTACATCTGTACTTGAAATGGTTGATGCATTTGAGAAAGCTTCTG : 478
           TGGGAACTGGTCGTGGTACATCTGTACTTGAAATGGTTGATGCATTTGAGAAAGCTTCTG

*        500         *        520         *        540
TrUG3Ea1 : GCAAGAAAATTCCAGTGAAATTGTGTCCACGAAGGGCGGGAGATGCTACGGAGGTTTATG : 540
TrUG3Ea2 : GCAAGAAAATTCCAGTGAAATTGTGTCCACGAAGGGCGGGAGATGCTACGGAGGTTTATG : 538
           GCAAGAAAATTCCAGTGAAATTGTGTCCACGAAGGGCGGGAGATGCTACGGAGGTTTATG

*        560         *
TrUG3Ea1 : CATCTACAGAGAGAGCTGAGAAAGAACTTGG : 571
TrUG3Ea2 : CATCT-------------------------- : 543
           CATCTACAGAGAGAGCTGAGAAAGAACTTGG
```

FIGURE 7

```
              *        20         *        40         *        60
TrGSTa : GAGTAATTCAACTTTCGATAATATATATATATCCTCCTTCTCTCTTGTTGAAACATAT :  60

*        80         *       100         *       120
TrGSTa : ATTTCCTTTTTTTTTTTCTTTTCAAAAGAAACCATGGTAGTGAAGGTGTATGGTCCTCA : 120

*       140         *       160         *       180
TrGSTa : CTGTGCCTCAACCAAAAGAGTGTTGGTTTGTCTTGTTGAGAAGGAAATAGAATTTGAGGT : 180

*       200         *       220         *       240
TrGSTa : TGTCCCTATTAATTTCTTAGAAGGAGAACAGAAGAATCCTGAGTACCTCAAATTACAGCC : 240

*       260         *       280         *       300
TrGSTa : TTTTGGAACTCTTCCTGTGATTCAAGATGGAGACTATACCCTTTATGAATCTCGTGCAAT : 300

*       320         *       340         *       360
TrGSTa : AATAAGATACTATGCTGAAAAATATAGATCTCAAGGGGTTGAATTACTTGGAAAGACAAT : 360

*       380         *       400         *       420
TrGSTa : AGAAGAAAAAGGTCTAGTGGAACAATGGTTAGAAGTTGAAGCACAAAACTTTAACCCATC : 420

*       440         *       460         *       480
TrGSTa : AGCATACAACTTGGCCCTTCATATATTATTTCCTTCACTACTAGCTGACAACACTCCAAA : 480

*       500         *       520         *       540
TrGSTa : TCCTAAGGTAATTGAAGAGAGTGAACCAAAACTTGTGAAGGTTTTGAACATTTATGAAGA : 540

*       560         *
TrGSTa : GAGGCTATCAAAGAGCAAGTATTTGGCTGGTGATTT : 576
```

FIGURE 8

```
              *        20         *        40         *        60
TrGSTa :  MVVKVYGPHCASTKRVLVCLVEKEIEFEVVPINFLEGEQKNPEYLKLQPFGTLPVIQDGD :  60

*        80         *       100         *       120
TrGSTa :  YTLYESRAIIRYYAEKYRSQGVELLGKTIEEKGLVEQWLEVEAQNFNPSAYNLALHILFP : 120

*       140         *       160
TrGSTa :  SLLADNTPNPKVIEESEPKLVKVLNIYEERLSKSKYLAGD : 160
```

FIGURE 9

```
                      *        20         *        40         *        60
TrGSTa1 : GAGTAATTCAACTTTCGATAATATATATATATATCCTCCTTCTCTCTTGTTGAAACATAT : 60
TrGSTa2 : ------TTCGACTTTCGATAATATATATATATATCCTCCTTCTCTCTTGTTGAAACATAT : 54
          GAGTAATTCAACTTTCGATAATATATATATATATCCTCCTTCTCTCTTGTTGAAACATAT

*        80         *       100         *       120
TrGSTa1 : ATTTCCTTTTTTTTTTTCTTTTCAAAAGAAACCATGGTAGTGAAGGTGTATGGTCCTCA : 120
TrGSTa2 : ATTTCCTTTTTTTTTTTTCTTTT-AAAAGAAACCATGGTAGTGAAGGTGTATGGTCCTCA : 113
          ATTTCCTTTTTTTTTTTCTTTTCAAAAGAAACCATGGTAGTGAAGGTGTATGGTCCTCA

*       140         *       160         *       180
TrGSTa1 : CTGTGCCTCAACCAAAAGAGTGTTGGTTTGTCTTGTTGAGAAGGAAATAGAATTTGAGGT : 180
TrGSTa2 : CTGTGCCTCAACCAAAAGAGTGTTGGTTTGTCTTGTTGAGAAGGAAATAGAATTTGAGGT : 173
          CTGTGCCTCAACCAAAAGAGTGTTGGTTTGTCTTGTTGAGAAGGAAATAGAATTTGAGGT

*       200         *       220         *       240
TrGSTa1 : TGTCCCTATTAATTTCTTAGAAGGAGAACAGAAGAATCCTGAGTACCTCAAATTACAGCC : 240
TrGSTa2 : TGTCCCTATTAATTTCTTAGAAGGAGAACAGAAGAATCCTGAGTACCTCAAATTACAGCC : 233
          TGTCCCTATTAATTTCTTAGAAGGAGAACAGAAGAATCCTGAGTACCTCAAATTACAGCC

*       260         *       280         *       300
TrGSTa1 : TTTTGGAACTCTTCCTGTGATTCAAGATGGAGACTATACCCTTTATGAATCTCGTGCAAT : 300
TrGSTa2 : TTTTGGAACTCTTCCTGTGATTCAAGATGGAGACTATACCCTTTATGAATCTCGTGCAAT : 293
          TTTTGGAACTCTTCCTGTGATTCAAGATGGAGACTATACCCTTTATGAATCTCGTGCAAT

*       320         *       340         *       360
TrGSTa1 : AATAAGATACTATGCTGAAAAATATAGATCTCAAGGGGTTGAATTACTTGGAAAGACAAT : 360
TrGSTa2 : AATAAGATACTATGCTGAAAAATATAGATCTCAAGGGGTTGAATTACTTGGAAAGACAAT : 353
          AATAAGATACTATGCTGAAAAATATAGATCTCAAGGGGTTGAATTACTTGGAAAGACAAT

*       380         *       400         *       420
TrGSTa1 : AGAAGAAAAAGGTCTAGTGGAACAATGGTTAGAAGTTGAAGCACAAAACTTTAACCCATC : 420
TrGSTa2 : AGAAGAAAAAGGTCTAGTGGAACAATGGTTAGAAGTTGAAGCACAAAACTTTAACCCATC : 413
          AGAAGAAAAAGGTCTAGTGGAACAATGGTTAGAAGTTGAAGCACAAAACTTTAACCCATC

*       440         *       460         *       480
TrGSTa1 : AGCATACAACTTGGCCCTTCATATATTATTTCCTTCACTACTAGCTGACAACACTCCAAA : 480
TrGSTa2 : AGCATACAACTTGGCCCTTCATATATTATTTCCTTCACTACTAGCTGACAACACTCCAAA : 473
          AGCATACAACTTGGCCCTTCATATATTATTTCCTTCACTACTAGCTGACAACACTCCAAA

*       500         *       520         *       540
TrGSTa1 : TCCTAAGGTAATTGAAGAGAGTGAACCAAAACTTGTGAAGGTTTTGAACATTTA------ : 534
TrGSTa2 : TCCTAAGGTAATTGAAGAGAGTGAAGCAAAACTTGTGAAGGTTTTGAACATTTATGAAGA : 533
          TCCTAAGGTAATTGAAGAGAGTGAACCAAAACTTGTGAAGGTTTTGAACATTTATGAAGA

*       560         *
TrGSTa1 : ------------------------------------ :   -
TrGSTa2 : GAGGCTATCAAAGAGCAAGTATTTGGCTGGTGATTT : 569
          GAGGCTATCAAAGAGCAAGTATTTGGCTGGTGATTT
```

FIGURE 10

```
                    *         20         *         40         *         60
TrOMTa : CACCTTGAGAATTATTGCGATCAAGATTGCAATGAAAATTTTGGATAAGGCCATCCCTCC :    60

*         80         *        100         *        120
TrOMTa : CTCCCCTCCTCTCTATATAAGTAGTTGGTTGGTTAGTGTCAATATAAGAAGAAAAACACA :   120

*        140         *        160         *        180
TrOMTa : AACCAAACCATATATATAGTATCAATATCAATTAAGCTAGCTATTTCCAAATCAACATGG :   180

*        200         *        220         *        240
TrOMTa : CTCCTTCAACAACTGAATCCAATAAACAACAAATCCCCAACGGAAAAGACAATCATCTAA :   240

*        260         *        280         *        300
TrOMTa : AACCACAACAACAAGAAGAAGATGATGATGCCCTCGAATTTGCCACACAAATAACAGGTT :   300

*        320         *        340         *        360
TrOMTa : CCATTGTTGTTCCATTGGCTTTGAGGTCAGCCATTGATCTTGGCATCTTTGACATCCTAG :   360

*        380         *        400         *        420
TrOMTa : CCAAAGCTGGCGAAGGTGCAGAACTCTCTGCACAAGACATTGCTGTTAAGATTGGAACCA :   420

*        440         *        460         *        480
TrOMTa : ACAACCCGGAAGCACCAACAATGTTGAATCGTCTTCTTAGGTTGTTGGCCAGTCACTCTA :   480

*        500         *        520         *        540
TrOMTa : TTCTAAACTCCTCTGTTCCTCAACAACATGATGATCAACAAATATTCTACAGCCTCTCCA :   540

*        560         *        580         *        600
TrOMTa : ATCGCTCCAAATATTTTGTCACCGATGCTGACGGCATCTCGTTGGGACCCACCTTGGCAT :   600

*        620         *        640         *        660
TrOMTa : TACTTCTCGACAATGTCTTCTACCAAAGCTGGTCGGAGCTGAAAGGAGCGATAGTGGAAG :   660

*        680         *        700         *        720
TrOMTa : GAGGAATACCGTTCAATAGAGTATATGGAATGCATGCCTTTGAGTACCCACGTGTGGATC :   720

*        740         *        760         *        780
TrOMTa : CAAGGTTCAATGATGTTTTCAACAAAGCTATGCTTAGTTCAACCACTATTAATATGAAGA :   780

*        800         *        820         *        840
TrOMTa : GAATTCTTGAATTTTATCAAGGTTTTGAGCATGTCACTAAGTTGGTTGACGTTGGTGGTG :   840
```

FIGURE 10, cont'd

```
              *         860         *         880         *         900
TrOMTa : GTCTTGGACATAACCTCAAATTGATCACAGCCAAATATTCCCATATTCATGGAATTAATT :  900

*         920         *         940         *         960
TrOMTa : TTGACTTGCCTCATGTGCTACAAAATGCTCCTAACTACCCAGGTGTTGAACACGTGGGAG :  960

*         980         *        1000         *        1020
TrOMTa : GAGATATGTTTGAGAGCGTTCCTACAGGGGATGCCATTTTTATGAAGTGGATACTTCATG : 1020

*        1040         *        1060         *        1080
TrOMTa : ATTGGAGTGATGAACACTGCTTGAAGCTGTTGAAAAATTGTTACAAAGCTATTCCTGAGA : 1080

*        1100         *        1120         *        1140
TrOMTa : ATGGAAAGGTTATTGTTGTGGACACAATCCTTCCCACCACGCCCGAGACAACAGGGAGCG : 1140

*        1160         *        1180         *        1200
TrOMTa : CAAAGTTTGGTTTCTCGTCTGATCTTTTAATGATGACTCAAAATCCAGGAGGAAAAGAGA : 1200

*        1220         *        1240         *        1260
TrOMTa : GAACTGAGCAGGAATTCATAAAATTGGCAAAAGGATCTGGATTCAGTGGCATCAAACCTA : 1260

*        1280
TrOMTa : TATGTTGTGTGTCTGGACTATGGGTTAT : 1288
```

FIGURE 11

```
              *        20         *        40         *        60
TrOMTa : MAPSTTESNKQQIPNGKDNHLKPQQQEEDDDALEFATQITGSIVVPLALRSAIDLGIFDI :  60

*        80         *       100         *       120
TrOMTa : LAKAGEGAELSAQDIAVKIGTNNPEAPTMLNRLLRLLASHSILNSSVPQQHDDQQIFYSL : 120

*       140         *       160         *       180
TrOMTa : SNRSKYFVTDADGISLGPTLALLLDNVFYQSWSELKGAIVEGGIPFNRVYGMHAFEYPRV : 180

*       200         *       220         *       240
TrOMTa : DPRFNDVFNKAMLSSTTINMKRILEFYQGFEHVTKLVDVGGGLGHNLKLITAKYSHIHGI : 240

*       260         *       280         *       300
TrOMTa : NFDLPHVLQNAPNYPGVEHVGGDMFESVPTGDAIFMKWILHDWSDEHCLKLLKNCYKAIP : 300

*       320         *       340         *       360
TrOMTa : ENGKVIVVDTILPTTPETTGSAKFGFSSDLLMMTQNPGGKERTEQEFIKLAKGSGFSGIK : 360

*
TrOMTa : PICCVSGLWV : 370
```

FIGURE 12

```
               *        20         *        40         *        60
TrOMTa1 : CACCTTGAGAATTATTGCGATCAAGATTGCAATGAAAATTTTGGATAAGGCCATCCCTCC :  60
TrOMTa2 : ------------------------------------------------CTGTCCCTCC :  10
TrOMTa3 : ------------------------------------------------------------ :   -
TrOMTa4 : ------------------------------------------------------------ :   -
TrOMTa5 : ------------------------------------------------------------ :   -
TrOMTa6 : ------------------------------------------------------------ :   -
TrOMTa7 : ------------------------------------------------------------ :   -
TrOMTa8 : ------------------------------------------------------------ :   -
TrOMTa9 : ------------------------------------------------------------ :   -
          CACCTTGAGAATTATTGCGATCAAGATTGCAATGAAAATTTTGGATAAGGCCATCCCTCC

*        80         *       100         *       120
TrOMTa1 : CTCCCCTCCTCTCTATATAAGTAGTTGGTTGGTTAGTGTCAATATAAGAAGAAAAACACA : 120
TrOMTa2 : CTCCCCTCCTCTCTATATAAGTAGTTGGTTGGTTAGTGTCAATATAAGAAGAAAAACACA :  70
TrOMTa3 : -----------------------------------------------------------A :   1
TrOMTa4 : ------------------------------------------------------------ :   -
TrOMTa5 : ------------------------------------------------------------ :   -
TrOMTa6 : ------------------------------------------------------------ :   -
TrOMTa7 : ------------------------------------------------------------ :   -
TrOMTa8 : ------------------------------------------------------------ :   -
TrOMTa9 : ------------------------------------------------------------ :   -
          CTCCCCTCCTCTCTATATAAGTAGTTGGTTGGTTAGTGTCAATATAAGAAGAAAAACACA

*       140         *       160         *       180
TrOMTa1 : AACCAAACCATATATATAGTATCAATATCAATTAAGCTAGCTATTTCCAAATCAACATGG : 180
TrOMTa2 : AACCAAACCATATATATAGTATCAATATCAATTAAGCTAGCTATTTCCAAATCAACATGG : 130
TrOMTa3 : AACCAAACCATATATATAGTATCAATATCAATTAAGCTAGCTATTTCCAAATCAACATGG :  61
TrOMTa4 : -----AACCATATATATAGTATCAATATCAATTAAGCTAGCTATTTCCAAATCAACATGG :  55
TrOMTa5 : -------------------------------TTAAGCTAGCTATTTCCAAA-CAACATGG :  28
TrOMTa6 : -------------------------------------------------------CATGG :   5
TrOMTa7 : ------------------------------------------------------------ :   -
TrOMTa8 : ------------------------------------------------------------ :   -
TrOMTa9 : ------------------------------------------------------------ :   -
          AACCAAACCATATATATAGTATCAATATCAATTAAGCTAGCTATTTCCAAATCAACATGG

*       200         *       220         *       240
TrOMTa1 : CTCCTTCAACAACTGAATCCAATAAACAACAAATCCCCAACGGAAAAGACAATCATCTAA : 240
TrOMTa2 : CTCCTTCAACAACTGAATCCAATAAACAACAAATCCCCAACGGAAAAGACAATCATCTAA : 190
TrOMTa3 : CTCCTTCAACCCTGCCCCAATAAACAACAAATCCCCAACGGAAAAGACAATCATCTAA   : 121
TrOMTa4 : CTCCTTCAACAACTGAATCCAATAAACAACAAATCCCCAACGGAAAAGACAATCATCTAA : 115
TrOMTa5 : CTCCTTCAACAACTGAATCC-ATAAACAACAAATCCCCAACGGAAAAGACAATCATCTAA :  87
TrOMTa6 : CTCCTT-AACAACTGAATCCAATAAACAACAAATCCCCAACGGAAAAGACA-TCATCTAA :  63
TrOMTa7 : ------------------------------------------------------------ :   -
TrOMTa8 : ------------------------------------------------------------ :   -
TrOMTa9 : ------------------------------------------------------------ :   -
          CTCCTTCAACAACTGAATCCAATAAACAACAAATCCCCAACGGAAAAGACAATCATCTAA
```

FIGURE 12, cont'd

```
              *         260         *         280         *         300
TrOMTa1  :  AACCACAACAACAAGAAGAAGATGATGATGCCCTCGAATTTGCCACACAAATAACAGGTT  : 300
TrOMTa2  :  AACCACAACAACAAGAAGAAGATGATGATGCCCTCGAATTTGCCACACAAATAACAGGTT  : 250
TrOMTa3  :  AACCACAACAACAAGAAGAAGATGATGATGCCCTCGAATTTGCCACACAAATAACAGGGT  : 181
TrOMTa4  :  AACCACAACAACAAGAAGAAGATGATGATGCCCTCGAATTTGCCACACAAATAACAGGTT  : 175
TrOMTa5  :  AACCACAACAACAAGAAGAAGATGATGATGCCCTCGAATTTGCCACACAAATAACAGGTT  : 147
TrOMTa6  :  AACCACAACAACAAGAAGAAGATGATGATGCCCTCGAATTTGCCACACAAATAACAGGTT  : 123
TrOMTa7  :  ------------------------------------------------------------  :   -
TrOMTa8  :  ------------------------------------------------------------  :   -
TrOMTa9  :  ------------------------------------------------------------  :   -
            AACCACAACAACAAGAAGAAGATGATGATGCCCTCGAATTTGCCACACAAATAACAGGTT

*         320         *         340         *         360
TrOMTa1  :  CCATTGTTGTTCCATTGGCTTTGAGGTCAGCCATTGATCTTGGCATCTTTGACATCCTAG  : 360
TrOMTa2  :  CCATTGTTGTTCCATTGGCTTTGAGGTCAGCCATTGATCTTGGCATCTTTGACATCCTAG  : 310
TrOMTa3  :  CCATTGTTGTTCCATTGGCTTTGAGGCCAGCCATTGATCTTGGCATGGGCGGATCCTAN  : 241
TrOMTa4  :  CCATTGTTGTTCCATTGGCTTTGAGGTCAGCCATTGATCTTGGCATCTTTGACATCCTAG  : 235
TrOMTa5  :  CCATTGTTGTTCCATTGGCTTTGAGGTCAGCCATTGATCTTGGCATCTTTGACATCCTAG  : 207
TrOMTa6  :  CCATTGTTGTTCCATTGGCTTTGAGGTCAGCCATTGATCTTGGCATCTTTGACATCCTAG  : 183
TrOMTa7  :  ------------------------------------------------------------  :   -
TrOMTa8  :  ------------------------------------------------------------  :   -
TrOMTa9  :  ------------------------------------------------------------  :   -
            CCATTGTTGTTCCATTGGCTTTGAGGTCAGCCATTGATCTTGGCATCTTTGACATCCTAG

*         380         *         400         *         420
TrOMTa1  :  CCAAAGCTGGCGAAGGTGCAGAACTCTCTGCACAAGACATTGCTGTTAAGATTGGAACCA  : 420
TrOMTa2  :  CCAAAGCTGGCGAAGGTGCAGAACTCTCTGCACAAGACATTGCTGTTAAGATTGGAACCA  : 370
TrOMTa3  :  CCAAAGCTGGCGAAGGTGCAAAACTCTCTGCACAAGACATTGCTGTTAAGATTGGAACCA  : 301
TrOMTa4  :  CCAAAGCTGGCGAAGGTGCAGAACTCTCTGCACAAGACATTGCTGTTAAGATTGGAACCA  : 295
TrOMTa5  :  CCAAAGCTGGCGAAGGTGCAGAACTCTCTGCACAAGACATTGCTGTTAAGATTGGAACCA  : 267
TrOMTa6  :  CCAAAGCTGGCGAAGGTGCAGAACTCTCTGCACAAGACATTGCTGTTAAGATTGGAACCA  : 243
TrOMTa7  :  ------------------------------------------------------------  :   -
TrOMTa8  :  ------------------------------------------------------------  :   -
TrOMTa9  :  ------------------------------------------------------------  :   -
            CCAAAGCTGGCGAAGGTGCAGAACTCTCTGCACAAGACATTGCTGTTAAGATTGGAACCA

*         440         *         460         *         480
TrOMTa1  :  ACAACCCGGAAGCACCAACAATGTTGAATCGTCTTCTTAGGTTGTTGGCCAGTCACTCTA  : 480
TrOMTa2  :  ACAACCCGGAAGCACCAACAATGTTGAATCGTCTTCTTAGGTTGTTGGCCAGTCACTCTA  : 430
TrOMTa3  :  ACAACCCGGAAGCACCAACAATGTTGAATCGTCTTCTTAGGTTGTTGGCCAGTCACTCTA  : 361
TrOMTa4  :  ACAACCCGGAAGCACCAACAATGTTGAATCGTCTTCTTAGGTTGTTGGCCAGTCACTCTA  : 355
TrOMTa5  :  ACAACCCGGAAGCACCAACAATGTTGAATCGTCTTCTTAGGTTGTTGGCCAGTCACTCTA  : 327
TrOMTa6  :  ACAACCCGGAAGCACCAACAATGTTGAATCGTCTTCTTAGGTTGTTGGCCAGTCACTCTA  : 303
TrOMTa7  :  ------------------------------------------------------------  :   -
TrOMTa8  :  ------------------------------------------------------------  :   -
TrOMTa9  :  ------------------------------------------------------------  :   -
            ACAACCCGGAAGCACCAACAATGTTGAATCGTCTTCTTAGGTTGTTGGCCAGTCACTCTA

*         500         *         520         *         540
TrOMTa1  :  TTCTAAACTCCTCTGTTCCTCAACAACATGATGATCAACAAATATTCTACAGCCTCTCCA  : 540
TrOMTa2  :  TTCTAAACTCCTCTGTTCCTCAACAACATGATGATCAACAAATATTCTACAGCCTCTCCA  : 490
TrOMTa3  :  TTCTAAACTCCTCTGTTCCTCAACAACATGATGATCAACAAATATTCTACAGCCTCTCCA  : 421
TrOMTa4  :  TTCTAAACTCCTCTGTTCCTCAACAACATGATGATCAACAAATATTCTACAGCCTCTCCA  : 415
TrOMTa5  :  TTCTAAACTCCTCTGTTCCTCAACAACATGATGATCAACAAATATTCTACAGCCTCTCCA  : 387
TrOMTa6  :  TTCTAAACTCCTCTGTTCCTCAACAACATGATGATCAACAAATATTCTACAGCCTCTCCA  : 363
TrOMTa7  :  ---------------------------------------------------TCTCCA  :   6
TrOMTa8  :  ------------------------------------------------------------  :   -
TrOMTa9  :  ------------------------------------------------------------  :   -
            TTCTAAACTCCTCTGTTCCTCAACAACATGATGATCAACAAATATTCTACAGCCTCTCCA
```

FIGURE 12, cont'd

```
                    *         560         *         580         *         600
TrOMTa1 : ATCGCTCCAAATATTTTGTCACCGATGCTGACGGCATCTCGTT----------------- : 583
TrOMTa2 : ATCGCTCCAAATATTTTGTCACCGATGCTGACGGCATCTCGTTGGGACCCACCTT----- : 545
TrOMTa3 : ATCGCTCCAAATATTTTGTCACCGATGCTGAGGGCATCTCGTTGGGACCCACCTTGGCAT : 481
TrOMTa4 : ATCGCTCCAAATATTTTGTCACCGATGCTGACGGCATCTCGTTGGGACCCACCTTGGCAT : 475
TrOMTa5 : ATCGCTCCAAATATTTTGTCACCGATGCTGACGGCATCTCGTTGGGACCCACCTTGGCAT : 447
TrOMTa6 : ATCGCTCCAAATATTTTGTCACCGATGCTGACGGCATCTCGTTGGGACCCACCTTGGCAT : 423
TrOMTa7 : ATCGCTCCAAATATTTTGTCACCGATGCTGACGGCATCTCGTGGGACCCACCTTGGCAT  :  66
TrOMTa8 : ------------------------------------------------------------ :   -
TrOMTa9 : ------------------------------------------------------------ :   -
          ATCGCTCCAAATATTTTGTCACCGATGCTGACGGCATCTCGTTGGGACCCACCTTGGCAT

*         620         *         640         *         660
TrOMTa1 : ------------------------------------------------------------ :   -
TrOMTa2 : ------------------------------------------------------------ :   -
TrOMTa3 : TACTTCTCGACAATGTCTTCTACCAAAGCTGGTCGGAGCTGAAAGGAGCGATAGTGGAAG : 541
TrOMTa4 : TACTTCTCGACAATGTCTTCTACCAAAGCTGGTCGGAGCTGAAAGGAGCGATAGTGGAAG : 535
TrOMTa5 : TACTTCTCGACAATGTCTTCTACCAAAGCTGGTCGGAGCTGAAAGGAGCGATAGTGGAAG : 507
TrOMTa6 : TACTTCTCGACAATGTCTTCTACCAGAGCTGGTCGGAGCTGAAAGGAGCGATAGTGGAAG : 483
TrOMTa7 : TACTTCTCGACAATGTCTTCTACCAAAGCTGGTCGGAGCTGAAAGGAGCGATAGTGGAAG : 126
TrOMTa8 : --------------------------------------------------AGTGGAAG   :   8
TrOMTa9 : ------------------------------------------------------------ :   -
          TACTTCTCGACAATGTCTTCTACCAAAGCTGGTCGGAGCTGAAAGGAGCGATAGTGGAAG

*         680         *         700         *         720
TrOMTa1 : ------------------------------------------------------------ :   -
TrOMTa2 : ------------------------------------------------------------ :   -
TrOMTa3 : GAGGAATACCGTTCAATAGAGTATATGGAATGCATGCCTTTGAGTACCCACGTGTGGATC : 601
TrOMTa4 : GAGGAATACCGTTCAATAGAGTATATGGAATGCATGCCTTTGAGTACCCACGTGTGGATC : 595
TrOMTa5 : GAGGAATACCGT------------------------------------------------ : 519
TrOMTa6 : GAGGAATACCGTTCAATAGAGTATATGGAATGCATGCCTTT------------------- : 524
TrOMTa7 : GAGGAATACCGTTCAATAGAGTATATGGAATGCATGCCTTTGAGTACCCACGTGTGGATC : 186
TrOMTa8 : GGGGAATACCGTTCAATAGAGTATATGGAATGCATGCCTTTGAGTACCCACGTGTGGATC :  68
TrOMTa9 : ------------------GGAATGCATGCCTTTGAGTACC-CGTGTGGATC          :  33
          GAGGAATACCGTTCAATAGAGTATATGGAATGCATGCCTTTGAGTACCCACGTGTGGATC

*         740         *         760         *         780
TrOMTa1 : ------------------------------------------------------------ :   -
TrOMTa2 : ------------------------------------------------------------ :   -
TrOMTa3 : CAAGGTTCAATGATGTTTTCAACAAAGCTATGCTTAGTTCAACCACTATTAATATGAAGA : 661
TrOMTa4 : CAAGGTTCAATGATGTTT------------------------------------------ : 613
TrOMTa5 : ------------------------------------------------------------ :   -
TrOMTa6 : ------------------------------------------------------------ :   -
TrOMTa7 : CA---------------------------------------------------------- : 188
TrOMTa8 : CAAGGTTCAATGATGTTTTCAACAAAGCTATGCTTAGTTCAACCACTATTAATATGAAGA : 128
TrOMTa9 : CA-GGTTCAATGATGTTTT-AACAAAGCTATGCTTAGTTCAACCACTATTAATATGAAGA :  91
          CAAGGTTCAATGATGTTTTCAACAAAGCTATGCTTAGTTCAACCACTATTAATATGAAGA

*         800         *         820         *         840
TrOMTa1 : ------------------------------------------------------------ :   -
TrOMTa2 : ------------------------------------------------------------ :   -
TrOMTa3 : GAATTCTTGAATTTTATCAAGGTTT-GAGCATGTCACTA--------------------- : 699
TrOMTa4 : ------------------------------------------------------------ :   -
TrOMTa5 : ------------------------------------------------------------ :   -
TrOMTa6 : ------------------------------------------------------------ :   -
TrOMTa7 : ------------------------------------------------------------ :   -
TrOMTa8 : GAATTCTTGAATTTTATCAAGGTTTTGAGCATGTCACTAAGTTGGTTGACGTTGGTGGTG : 188
TrOMTa9 : GCATTCTTGAATTTTAT-AAGGTTTTGAGCATGTCACTAAGTTGGTTGACGTTGGTGGTG : 150
          GAATTCTTGAATTTTATCAAGGTTTTGAGCATGTCACTAAGTTGGTTGACGTTGGTGGTG
```

FIGURE 12, cont'd

```
               *         860         *         880         *         900
TrOMTa1  : ------------------------------------------------------------ :   -
TrOMTa2  : ------------------------------------------------------------ :   -
TrOMTa3  : ------------------------------------------------------------ :   -
TrOMTa4  : ------------------------------------------------------------ :   -
TrOMTa5  : ------------------------------------------------------------ :   -
TrOMTa6  : ------------------------------------------------------------ :   -
TrOMTa7  : ------------------------------------------------------------ :   -
TrOMTa8  : GTCTTGGACATAACCTCAAATTGATCACAGCCAAATATTCTCATATTCATGGAATTAATT : 248
TrOMTa9  : GTCTTGGACATAACCTCAAATTGATCACAGCCAAATATTCCCATATTCATGGAATTAATT : 210
           GTCTTGGACATAACCTCAAATTGATCACAGCCAAATATTCCCATATTCATGGAATTAATT

*         920         *         940         *         960
TrOMTa1  : ------------------------------------------------------------ :   -
TrOMTa2  : ------------------------------------------------------------ :   -
TrOMTa3  : ------------------------------------------------------------ :   -
TrOMTa4  : ------------------------------------------------------------ :   -
TrOMTa5  : ------------------------------------------------------------ :   -
TrOMTa6  : ------------------------------------------------------------ :   -
TrOMTa7  : ------------------------------------------------------------ :   -
TrOMTa8  : TTGACTTGCCTCATGTGCTACAAAATGCTCCTAACTACCCAGGTGTTGAACACGTGGGAG : 308
TrOMTa9  : TTGACTTGCCTCATGTGCTACAAAATGCTCCTAACTACCCAGGTGTTGAACACGTGGGAG : 270
           TTGACTTGCCTCATGTGCTACAAAATGCTCCTAACTACCCAGGTGTTGAACACGTGGGAG

*         980         *        1000         *        1020
TrOMTa1  : ------------------------------------------------------------ :   -
TrOMTa2  : ------------------------------------------------------------ :   -
TrOMTa3  : ------------------------------------------------------------ :   -
TrOMTa4  : ------------------------------------------------------------ :   -
TrOMTa5  : ------------------------------------------------------------ :   -
TrOMTa6  : ------------------------------------------------------------ :   -
TrOMTa7  : ------------------------------------------------------------ :   -
TrOMTa8  : GAGATATGTTTGAGAGCGTTCCTACAGGGGATGCCATTTTTATGAAGTGGATACTTCATG : 368
TrOMTa9  : GAGATATGTTTGAGAGCGTTCCTACAGGGGATGCCATTTTTATGAAGTGGATACTTCATG : 330
           GAGATATGTTTGAGAGCGTTCCTACAGGGGATGCCATTTTTATGAAGTGGATACTTCATG

*        1040         *        1060         *        1080
TrOMTa1  : ------------------------------------------------------------ :   -
TrOMTa2  : ------------------------------------------------------------ :   -
TrOMTa3  : ------------------------------------------------------------ :   -
TrOMTa4  : ------------------------------------------------------------ :   -
TrOMTa5  : ------------------------------------------------------------ :   -
TrOMTa6  : ------------------------------------------------------------ :   -
TrOMTa7  : ------------------------------------------------------------ :   -
TrOMTa8  : ATTGGAGTGATGAACACTGCTTGAAGCTGTTGAAAAATTGTTACAAAGCTATTCCTGAGA : 428
TrOMTa9  : ATTGGAGTGATGAACACTGCTTGAAGCTGTTGAAAAATTGTTACAAAGCTATTCCTGAGA : 390
           ATTGGAGTGATGAACACTGCTTGAAGCTGTTGAAAAATTGTTACAAAGCTATTCCTGAGA

*        1100         *        1120         *        1140
TrOMTa1  : ------------------------------------------------------------ :   -
TrOMTa2  : ------------------------------------------------------------ :   -
TrOMTa3  : ------------------------------------------------------------ :   -
TrOMTa4  : ------------------------------------------------------------ :   -
TrOMTa5  : ------------------------------------------------------------ :   -
TrOMTa6  : ------------------------------------------------------------ :   -
TrOMTa7  : ------------------------------------------------------------ :   -
TrOMTa8  : ATGGAAAGGTTATTGTTGTGGACACAATCCTTCCCACCATGCCCGAGACAACAGGGAGCG : 488
TrOMTa9  : ATGGAAAGGTTATTGTTGTGGACACAATCCTTCCCACCACGCCCGAGACAACAGGGAGCG : 450
           ATGGAAAGGTTATTGTTGTGGACACAATCCTTCCCACCACGCCCGAGACAACAGGGAGCG
```

FIGURE 12, cont'd

```
              *         1160        *         1180        *         1200
TrOMTa1 : ------------------------------------------------------------ :   -
TrOMTa2 : ------------------------------------------------------------ :   -
TrOMTa3 : ------------------------------------------------------------ :   -
TrOMTa4 : ------------------------------------------------------------ :   -
TrOMTa5 : ------------------------------------------------------------ :   -
TrOMTa6 : ------------------------------------------------------------ :   -
TrOMTa7 : ------------------------------------------------------------ :   -
TrOMTa8 : CANAGTTTGGTTTCTCGTCTGATCTTTTAATGATGACTCAAAATCCAGGAGGAAAAGAGA : 548
TrOMTa9 : CAAAGTTTGGTTTCTCGTCTGATCTTTTAATGATGACTCAAAATCCAGGAGGAAAAGAGA : 510
          CAAAGTTTGGTTTCTCGTCTGATCTTTTAATGATGACTCAAAATCCAGGAGGAAAAGAGA

*         1220        *         1240        *         1260
TrOMTa1 : ------------------------------------------------------------ :   -
TrOMTa2 : ------------------------------------------------------------ :   -
TrOMTa3 : ------------------------------------------------------------ :   -
TrOMTa4 : ------------------------------------------------------------ :   -
TrOMTa5 : ------------------------------------------------------------ :   -
TrOMTa6 : ------------------------------------------------------------ :   -
TrOMTa7 : ------------------------------------------------------------ :   -
TrOMTa8 : GAACTGAGCAGGAATTCATAAAATTGGCAAAAGGATCTGG-------------------- : 588
TrOMTa9 : GAAVTGAGCAGGAATTCATAAAATTGGCAAAAGGATCTGGATTCAGTGGCATCAAACCTA : 570
          GAACTGAGCAGGAATTCATAAAATTGGCAAAAGGATCTGGATTCAGTGGCATCAAACCTA

*         1280
TrOMTa1 : --------------------------- :   -
TrOMTa2 : --------------------------- :   -
TrOMTa3 : --------------------------- :   -
TrOMTa4 : --------------------------- :   -
TrOMTa5 : --------------------------- :   -
TrOMTa6 : --------------------------- :   -
TrOMTa7 : --------------------------- :   -
TrOMTa8 : --------------------------- :   -
TrOMTa9 : TATGTTGTGTGTCTGGACTATGGGTTAT : 598
          TATGTTGTGTGTCTGGACTATGGGTTAT
```

FIGURE 13

```
                  *        20         *        40         *        60
TrRTa : TTGTGGATAAAAGAGTGGTTGGACAAGCAACCACGTAGCACGGTATTATATGTGGCTTTT :  60

*        80         *       100         *       120
TrRTa : GGTAGTGAAGCAAAACCAAGTCAAGAAGAAGTCACTAAGATAGCTTTTGGGTTGGAGGAA : 120

*       140         *       160         *       180
TrRTa : TCAAAGATTCCGTTCTTTTGGGTCCTTAGGGTTCAGCGTGGACCAACTGACAATGTGGTG : 180

*       200         *       220         *       240
TrRTa : TTGCAGCTGCCAGAAGGGTTTGAGGAGCGAAACAAGGGGCGCGGAGTGGTATGCACTGAT : 240

*       260         *       280         *       300
TrRTa : TGGGCTCCGCAAGTGAAAATAATGGGTCACGTGGCAGTTGGTGGGTTCTTGACTCATGCT : 300

*       320         *       340         *       360
TrRTa : GGTTGGACATCAGTTGTGGAGGCTGTTCAAAATGAAAAGCCACTTGTGCTACTAACATTT : 360

*       380         *       400         *       420
TrRTa : CTTGCAGATCAAGGAATAAATGCGAGGGTGTTGGAGGAAAAGAAGATGGGTTACTCAGTG : 420

*       440         *       460         *       480
TrRTa : CCTAGGGATGAACGAGATGGGTCATTCACAAGTGACTCGGTGGCTGCTTCGATTAGACTA : 480

*       500         *       520         *       540
TrRTa : GTTATGCTTGAAGAAGAGGGAAGAATCTACAAGGAAAAGATTAAAGAGATGAAGGACTTG : 540

TrRTa : TTCG : 544
```

FIGURE 14

```
              *        20         *        40         *        60
TrRTa : LWIKEWLDKQPRSTVLYVAFGSEAKPSQEEVTKIAFGLEESKIPFFWVLRVQRGPTDNVV :  60

*        80         *       100         *       120
TrRTa : LQLPEGFEERNKGRGVVCTDWAPQVKIMGHVAVGGFLTHAGWTSVVEAVQNEKPLVLLTF : 120

*       140         *       160         *       180
TrRTa : LADQGINARVLEEKKMGYSVPRDERDGSFTSDSVAASIRLVMLEEEGRIYKEKIKEMKDL : 180

TrRTa : F : 181
```

FIGURE 15

```
                    *        20         *        40         *        60
TrCYTb5a : TAATAACATTATTATTATTGCTCCTCTAAAGCTCAAACCTCATTTACAACCATGGCAAAT :  60

*        80         *       100         *       120
TrCYTb5a : CAAAAGGTTTTCACCCTCTCACAAATCTCCCAACACAAGTCCAACAAAAACTGTTGGCTT : 120

*       140         *       160         *       180
TrCYTb5a : GTAATCAACGACAGAGTGTTGAACGTGACAAAGTTTTTGGAGGAACATCCAGGAGGAGAA : 180

*       200         *       220         *       240
TrCYTb5a : GAGGTAATTCTAGAGGTTGCAGGGAAAGATGCCACAAAGGAGTTTGATGATATTGGACAT : 240

*       260         *       280         *       300
TrCYTb5a : AGTAAAGCAGCTCAAAATTTAGTCCTCAAATATCAAGTTGGTGTACTTGAAGGTGCCAAG : 300

*       320         *       340         *       360
TrCYTb5a : GTTGAAAAGATTGATAATATGGATTTTGTTGAGGACAAGGAGTCCAAGAGCAAAGAAATG : 360

*       380         *       400         *       420
TrCYTb5a : AGTGCTTTTGTTGTCAAAGAGGATACTAGTTCCAAAACTGCAACATTTTTAGAGTTGTTT : 420

*       440         *       460         *       480
TrCYTb5a : GTGCCATTTCTTTTTGCTTTTATCTATTTTGGTTACAGTGTCATCACCAGAGCAGACACT : 480

*       500         *       520
TrCYTb5a : GTTGGTTACTAAATCATGGGGGATGTCTAGACCTTGGTCTGTG : 523
```

FIGURE 16

```
                *         20         *         40         *         60
TrCYTb5a : HYYYCSSKAQTSFTTMANQKVFTLSQISQHKSNKNCWLVINDRVLNVTKFLEEHPGGEEV :  60

*         80         *        100         *        120
TrCYTb5a : ILEVAGKDATKEFDDIGHSKAAQNLVLKYQVGVLEGAKVEKIDNMDFVEDKESKSKEMSA : 120

*        140         *        160
TrCYTb5a : FVVKEDTSSKTATFLELFVPFLFAFIYFGYSVITRADTVGY : 161
```

FIGURE 17

```
              *        20         *         40         *
TrLACa : CATAGAAGAAGCTCTATAGCAACATTTCTTTGTTGAGTAGAGGTATATAACTCAAAAG : 58

60         *         80         *        100         *
TrLACa : GGTTGCTATGGCCACGGCGCAATTTCGAATTATACTATTGTTGGTAGCATGTTTGCTT : 116

120         *        140         *        160         *
TrLACa : CCATTTTCTGTTGATGCTACGGTTCGACACTACAAGTTCAATGTTGTGTTGAAAAATG : 174

180         *        200         *        220         *
TrLACa : CCACAAGATTGTGTTCAACCAAACCAATTGTAACCATAAATGGAAAATCCCCAGGTCC : 232

240         *        260         *        280         *
TrLACa : CACCATCTATGCTAGAGAAGATGACAATGTTCTAATTAAGGTTGTCAACCATGTCAAA : 290

300         *        320         *        340
TrLACa : TACAATGTTAGCATACACTGGCATGGTGTCAAACAACTAAGAACGGGTTGGGCCGACG : 348

*        360         *        380         *        400
TrLACa : GGCCAGCATACATAACCCAATGTCCAATTCAACCGGGTCAGGCCTATGTTTACAACTT : 406

*        420         *        440         *        460
TrLACa : CACTCTTACAGGCCAGAGAGGCACACTTTGGTGGCATGCTCATATTCTTTGGCTTAGA : 464

*        480         *        500         *        520
TrLACa : GCCACTGTCCATGGTGCCTTGGTCATTTTACCAAAGCTTGGAGTTCCTTACCCTTTTC : 522

*        540         *
TrLACa : CCAAACCTCATATGGAACAAGTTATTGTATTAGGT : 557
```

FIGURE 18

```
            *        20         *        40         *        60
TrLACa : MATAQFRIILLLVACLLPFSVDATVRHYKFNVVLKNATRLCSTKPIVTINGKSPGPTIYA :  60

*        80         *       100         *       120
TrLACa : REDDNVLIKVVNHVKYNVSIHWHGVKQLRTGWADGPAYITQCPIQPGQAYVYNFTLTGQR : 120

*       140         *       160
TrLACa : GTLWWHAHILWLRATVHGALVILPKLGVPYPFPKPHMEQVIVLG : 164
```

FIGURE 20

```
            *         20         *         40         *
TrLACa : TAAGCAGTGGTAACAACGCAGAGTACGCGGGGATTGCATTGCATTTTCAAGAGAGTGA :   58

60         *         80         *        100         *
TrLACa : TCACTAGCCAGCATAGAAGAAGCTCTATAGCAACATTTCTTTGTTGAGTAGAGGTATA :  116

120         *        140         *        160         *
TrLACa : TAACTCAAAAGGGTTGCTATGGCCACGGCGCAATTTCGAATTATACTATTGTTGGTAG :  174

180         *        200         *        220         *
TrLACa : CATGTTTGCTTCCATTTTCTGTTGATGCTACGGTTCGACACTACAAGTTCAATGTTGT :  232

240         *        260         *        280         *
TrLACa : GTTGAAAAATGCCACAAGATTGTGTTCAACCAAACCAATTGTAACCATAAATGGAAAA :  290

300         *        320         *        340
TrLACa : TCCCCAGGTCCCACCATCTATGCTAGAGAAGATGACAATGTTCTAATTAAGGTTGTCA :  348

*        360         *        380         *        400
TrLACa : ACCATGTCAAATACAATGTTAGCATACACTGGCATGGTGTCAAACAACTAAGAACGGG :  406

*        420         *        440         *        460
TrLACa : TTGGGCCGACGGGCCAGCATACATAACCCAATGTCCAATTCAACCGGGTCAGGCCTAT :  464

*        480         *        500         *        520
TrLACa : GTTTACAACTTCACTCTTACAGGCCAGAGAGGCACACTTTGGTGGCATGCTCATATTC :  522

*        540         *        560         *        580
TrLACa : TTTGGCTTAGAGCCACTGTCCATGGTGCCTTGGTCATTTTACCAAAGCTTGGAGTTCC :  580

*        600         *        620         *
TrLACa : TTACCCTTTTCCCAAACCTCATATGGAACAAGTTATTGTATTAGGTGAATGGTGGAAA :  638

640         *        660         *        680         *
TrLACa : TCAGATACCGAGGCTATAATAAATGAAGCTTTAAAATCTGGATTAGCTCCAAATATTT :  696

700         *        720         *        740         *
TrLACa : CTGATGCTCACACAATCAATGGTCTTCCAGGGTCTGGCCAAGGTTGTGCTTCACAAGA :  754

760         *        780         *        800         *
TrLACa : TGGATTCTCATTGGAAGTTCAACAAAAAAAAACCTACTTACTAAGAATCATCAATGCT :  812

820         *        840         *        860         *
TrLACa : GCACTCAATGAAGAACTCTTTTTCAAAATTGCAAACCATCAATTAACTGTTGTTGAAG :  870

880         *        900         *        920
TrLACa : TTGATGCAACTTATGTAAAACCATTCAAAACTGACACAATTGTTATAGCACCTGGCCA :  928

*        940         *        960         *        980
TrLACa : AACCACAAACGTGCTTTTAGAAACCAAACAAGCACTAGGAAACTACTTAATTGCAGCT :  986

*       1000         *       1020         *       1040
TrLACa : TCTCCTTTCATGGATGCACCAATTGTTGTTGACAACAAAACTGCCATTGCCACATTAC : 1044

*       1060         *       1080         *       1100
TrLACa : ACTATTCAAACACACTTGGTTCCACAGTCACTTCCTTAACTTCTTTACCTCCAAAAAA : 1102

```
TrLACa : TGCTACTCCAATTGCTAATACTTTCACAGATTCTCTTAGAGGCTTAAACTCGAAAAAA : 1160

*         1180         *         1200         *
TrLACa : TATCCGGCTAATGTTCCTTTAAAGATTGATAATAAATTATTATTCACTGTTTCTCTTG : 1218

1220         *         1240         *         1260         *
TrLACa : GTATTAATCCTTGTCCTACATGTGTCAATAATAGTCGCGTCGTAGCTGATTTCAACAA : 1276

1280         *         1300         *         1320         *
TrLACa : TGTTACATTCGTGATGCCGAAAACCGCGCTTATTCAAGCACATTTTTTAAGATTAAA : 1334

1340         *         1360         *         1380         *
TrLACa : GGAGTTTTTAGTGATGATTTTCCTGGAAATCCTCCTGTGGTGTATAATTTTACTGGGA : 1392

1400         *         1420         *         1440         *
TrLACa : CACAGTTGACAAATTTTGGGACTACTAAAGGGACAAGGCTTTATAGACTTGCTTATAA : 1450

1460         *         1480         *         1500
TrLACa : TTCTACTGTTGAATTGGTTTTGCAAGATACTGGAATGATAACACCTGAGAATCATCCT : 1508

*         1520         *         1540         *         1560
TrLACa : ATTCATCTTCATGGATTCAATTTCTTTGTAGTTGGTAGTGGTAAAGGGAACTTGATT : 1566

*         1580         *         1600         *         1620
TrLACa : CTAAAAAAGATGCAAAAAAGTTTAATCTTGTTGATCCTGTTGAGAGGAATACTGTTGG : 1624

*         1640         *         1660         *         1680
TrLACa : TGTTCCGGCCGGAGGTTGGACTGCTATCAGATTCAGGGCTGATAATCCAGGGGTGTGG : 1682

*         1700         *         1720         *         1740
TrLACa : TTTATGCATTGTCATTTGGAGATTCATACAACATGGGGACTAAAGATGGCTTTTGTTG : 1740

*         1760         *         1780         *
TrLACa : TGGACAATGGTAAAGGCCCAAATGAATCTCTATTACCACCTCCAAGTGACCTTCCTAA : 1798

1800         *         1820         *         1840         *
TrLACa : GTGTTGAGGAAAGTACCAATTAACATTCAATGTTATTTGAAGAGAACAACATATTTTA : 1856

1860         *         1880         *         1900         *
TrLACa : ATGGAAGGATTAAACAAGGCAAATGACAAGATTTTCTTGGAATATGGAAAGAATAAGA : 1914

1920         *         1940         *         1960         *
TrLACa : TGTCCAATTTTCTTATAAAAAAAAAATGTCCAATTGACATTTATTGGTATATTTTAAT : 1972

1980         *         2000         *         2020         *
TrLACa : TCCTTTTAGTTGTATTATTTTCATTGTTTGTACCCATCTTTCTTCTTCTTGAAAGATA : 2030

2040         *         2060         *         2080
TrLACa : TTTTAGGGTTAATCAAAATTTTAAGAATTTTTAAGAAATCTTTTCTTTTGTTGCC : 2085
```

FIGURE 21

```
              *        20         *        40         *        60
TrLACa : MATAQFRIILLLVACLLPFSVDATVRHYKFNVVLKNATRLCSTKPIVTINGKSPGPTIYA :  60

*        80         *       100         *       120
TrLACa : REDDNVLIKVVNHVKYNVSIHWHGVKQLRTGWADGPAYITQCPIQPGQAYVYNFTLTGQR : 120

*       140         *       160         *       180
TrLACa : GTLWWHAHILWLRATVHGALVILPKLGVPYPFPKPHMEQVIVLGEWWKSDTEAIINEALK : 180

*       200         *       220         *       240
TrLACa : SGLAPNISDAHTINGLPGSGQGCASQDGFSLEVQQKKTYLLRIINAALNEELFFKIANHQ : 240

*       260         *       280         *       300
TrLACa : LTVVEVDATYVKPFKTDTIVIAPGQTTNVLLETKQALGNYLIAASPFMDAPIVVDNKTAI : 300

*       320         *       340         *       360
TrLACa : ATLHYSNTLGSTVTSLTSLPPKNATPIANTFTDSLRGLNSKKYPANVPLKIDNKLLFTVS : 360

*       380         *       400         *       420
TrLACa : LGINPCPTCVNNSRVVADFNNVTFVMPKTALIQAHFFKIKGVFSDDFPGNPPVVYNFTGT : 420

*       440         *       460         *       480
TrLACa : QLTNFGTTKGTRLYRLAYNSTVELVLQDTGMITPENHPIHLHGFNFFVVGSGKGNFDSKK : 480

*       500         *       520         *       540
TrLACa : DAKKFNLVDPVERNTVGVPAGGWTAIRFRADNPGVWFMHCHLEIHTTWGLKMAFVVDNGK : 540

*
TrLACa : GPNESLLPPPSDLPKC : 556
```

FIGURE 22
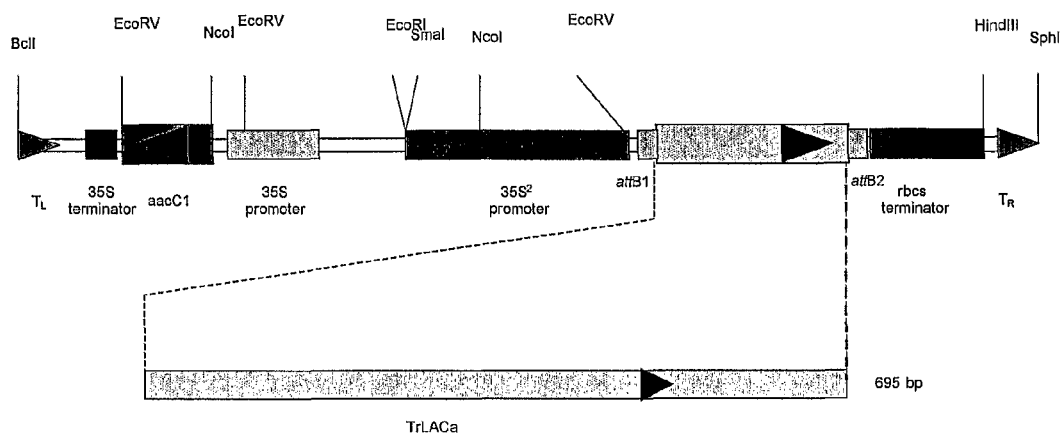
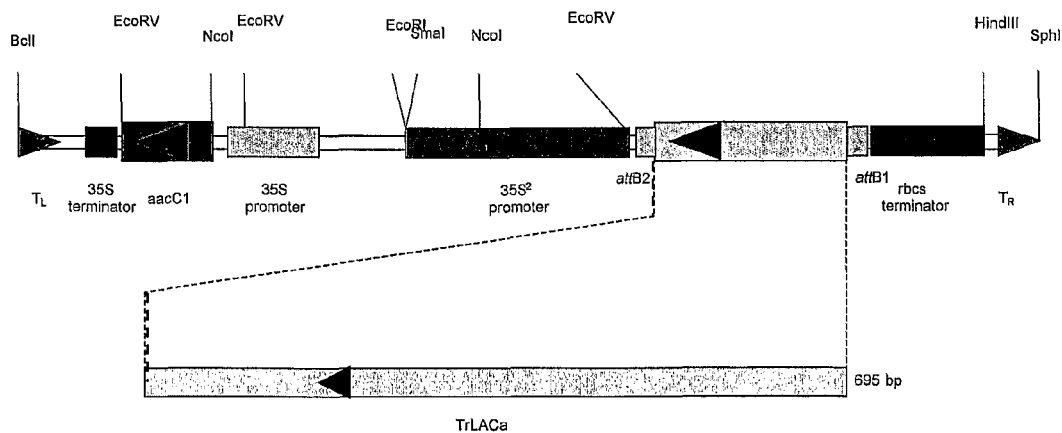

FIGURE 23

```
                    *        20         *        40         *        60
TrMADSa : AGAGAAATGGGAAGAGGAAGAGTTGAATTGAAGAGAATTGAGAACAAAATCAACAGACAA :  60

*        80         *       100         *       120
TrMADSa : GTTACCTTTGCAAAACGAAGAAATGGTCTTTTGAAGAAAGCTTATGAACTTTCTGTTCTT : 120

*       140         *       160         *       180
TrMADSa : TGTGATGCTGAGGTTGCTCTCATCGTCTTCTCCAATAGAGGAAAACTCTATGAGTTTTGC : 180

*       200         *       220         *       240
TrMADSa : AGCACTTCTAGCATGCTCAAAACTCTTGAGAGGTATCAGAAATGCAACTATGGAGCACCT : 240

*       260         *       280         *       300
TrMADSa : GAAGCTAATGTGACATCAAAGGAAGCTTTGGTATTGGAATTAAGCAGTCAACAAGAATAC : 300

*       320         *       340         *       360
TrMADSa : TTGAAGCTTAAGGCACGTTATGAATCTCTTCAACGCTCGCAAAGGAATCTTATGGGAGAA : 360

*       380         *       400         *       420
TrMADSa : GATCTTGGCCCTCTAAGTAGCAAAGATCTTGAACCACTTGAAAGGCAGCTAGATTCGTCC : 420

*       440         *       460         *       480
TrMADSa : TTGAAGCAAATCAGATCCACAAGGACCCAATTCATGCTGGATCAGCTTGGTGATCTTCAA : 480

*       500         *       520         *       540
TrMADSa : CGTAAGGAACACTTGCTATGTGAAGCAAACAGAGCTCTCAGACAAAGGATGGAAGGGTAT : 540

*       560         *       580         *       600
TrMADSa : CAAATAAATTCTCTCCAACTGAATCTGAGTGCTGAAGATATGGGATATGGTCGTCATCAT : 600

*       620         *       640         *       660
TrMADSa : CCAGTTCACACCCAGGGTGATGAACTATTTCAACCAATTGAGTGCGAACCAACCTTACAA : 660

*       680         *       700         *       720
TrMADSa : ATTGGATATCAAGCTGATCCAGGATCAGTGGTGACAGCAGGCCCAAGCATGAATAATTTC : 720

*       740         *       760         *       780
TrMADSa : ATGGGTGGATGGTTACCATGATGATGTTAAAGTTATATATTGAGAACGAGTGTGAAGCAT : 780

*       800         *       820         *       840
TrMADSa : GCATAAAGATCAAATGAAAATTTGTAATACTAGCATGTTATATAATGGACTACACTAAAC : 840

*       860         *       880
TrMADSa : TATGTATTAGTGTCTACTTACTATGTAGGCAAAATAATATAGTAA : 885
```

FIGURE 24

```
                 *        20         *        40         *        60
TrMADSa : MGRGRVELKRIENKINRQVTFAKRRNGLLKKAYELSVLCDAEVALIVFSNRGKLYEFCST :  60

*        80         *       100         *       120
TrMADSa : SSMLKTLERYQKCNYGAPEANVTSKEALVLELSSQQEYLKLKARYESLQRSQRNLMGEDL : 120

*       140         *       160         *       180
TrMADSa : GPLSSKDLEPLERQLDSSLKQIRSTRTQFMLDQLGDLQRKEHLLCEANRALRQRMEGYQI : 180

*       200         *       220         *       240
TrMADSa : NSLQLNLSAEDMGYGRHHPVHTQGDELFQPIECEPTLQIGYQADPGSVVTAGPSMNNFMG : 240

TrMADSa : GWLP : 244
```

FIGURE 25

```
              *         20         *         40         *         60
TrMADSa1 : AGAGAAATGGGAAGAGGAAGAGTTGAATTGAAGAGAATTGAGAACAAAATCAACAGACAA :  60
TrMADSa2 : AGAGAAATGGGAAGAGGAAGAGTTGAATTGAAGAGAATTGAGAACAAAATCAACAGACAA :  60
TrMADSa3 : ------------------------------------------------------------ :   -
TrMADSa4 : ------------------------------------------------------------ :   -
           AGAGAAATGGGAAGAGGAAGAGTTGAATTGAAGAGAATTGAGAACAAAATCAACAGACAA

*         80         *        100         *        120
TrMADSa1 : GTTACCTTTGCAAAACGAAGAAATGGTCTTTTGAAGAAAGCTTATGAACTTTCTGTTCTT : 120
TrMADSa2 : GTTACCTTTGCAAAACGAAGAAATGGTCTTTTGAAGAAAGCTTATGAACTTTCTGTTCTT : 120
TrMADSa3 : ------------------------------------------------------------ :   -
TrMADSa4 : ------------------------------------------------------------ :   -
           GTTACCTTTGCAAAACGAAGAAATGGTCTTTTGAAGAAAGCTTATGAACTTTCTGTTCTT

*        140         *        160         *        180
TrMADSa1 : TGTGATGCTGAGGTTGCTCTCATCGTCTTCTCCAATAGAGGAAAACTCTATGAGTTTTGC : 180
TrMADSa2 : TGTGATGCTGAGGTTGCTCTCATCGTCTTCTCCAATAGAGGAAAACTCTATGAGTTTTGC : 180
TrMADSa3 : ------------------------------------------------------------ :   -
TrMADSa4 : ------------------------------------------------------------ :   -
           TGTGATGCTGAGGTTGCTCTCATCGTCTTCTCCAATAGAGGAAAACTCTATGAGTTTTGC

*        200         *        220         *        240
TrMADSa1 : AGCACTTCTAGCATGCTCAAAACTCTTGAGAGGTATCAGAAATGCAACTATGGAGCACCT : 240
TrMADSa2 : AGCACTTCTAGCATGCTCAAAACTCTTGAGAGGTATCAGAAATGCAACTATGGAGCACCT : 240
TrMADSa3 : ------------------------------------------------------------ :   -
TrMADSa4 : ------------------------------------------------------------ :   -
           AGCACTTCTAGCATGCTCAAAACTCTTGAGAGGTATCAGAAATGCAACTATGGAGCACCT

*        260         *        280         *        300
TrMADSa1 : GAAGCTAATGTGACATCAAAGGAAGCTTTGGTATTGGAATTAAGCAGTCAACAAGAATAC : 300
TrMADSa2 : GAAGCTAATGTGACATCAAAGGAAGCTTTGGTATTGGAATTAAGCAGTCAACAAGAATAC : 300
TrMADSa3 : -----------------------------------------------------GAATAC :   6
TrMADSa4 : ------------------------------------------------------------ :   -
           GAAGCTAATGTGACATCAAAGGAAGCTTTGGTATTGGAATTAAGCAGTCAACAAGAATAC

*        320         *        340         *        360
TrMADSa1 : TTGAAGCTTAAGGCACGTTATGAATCTCTTCAACGCTCGCAAAGGAATCTTATGGGAGAA : 360
TrMADSa2 : TTGAAGCTTAAGGCACGTTATGAATCTCTTCAACGCTCGCAAAGGAATCTTATGGGAGAA : 360
TrMADSa3 : TTGAAGCTTAAGGCACGTTATGAATCTCTTCAACGCTCGCAAAGGAATCTTATGGGAGAA :  66
TrMADSa4 : ---------------GTTATGAATCTCTTCAACGCTCGCAAAGGAATCTTATGGGAGAA :  44
           TTGAAGCTTAAGGCACGTTATGAATCTCTTCAACGCTCGCAAAGGAATCTTATGGGAGAA

*        380         *        400         *        420
TrMADSa1 : GATCTTGGCCCTCTAAGTAGCAAAGATCTTGAACCACTTGAAAGGCAGCTAGATTCGTCC : 420
TrMADSa2 : GATCTTGGCCCTCTAAGTAGCAAAGATCTTGAACCACTTGAAAGGCAGCTAGATTCGTCC : 420
TrMADSa3 : GATCTTGGCCCTCTAAGTAGCAAAGATCTTGAACCACTTGAAAGGCAGCTAGATTCGTCC : 126
TrMADSa4 : GATCTTGGCCCTCTAAGTAGCAAAGATCTTGAACCACTTGAAAGGCAGCTAGATTCGTCC : 104
           GATCTTGGCCCTCTAAGTAGCAAAGATCTTGAACCACTTGAAAGGCAGCTAGATTCGTCC

*        440         *        460         *        480
TrMADSa1 : TTGAAGCAAATCAGATCCACAAGGACCCAATTCATGCTGGATCAGCTTGGTGATCTTCAA : 480
TrMADSa2 : TTGAAGCAAATCAGATCCACAAGGACCCAATTCATGCTGGATCAGCTTGGTGATCTTCAA : 480
TrMADSa3 : TTGAAGCAAATCAGATCCACAAGGACCCAATTCATGCTGGATCAGCTTGGTGATCTTCAA : 186
TrMADSa4 : TTGAAGCAAATCAGATCCACAAGGACCCAATTCATGCTGGATCAGCTTGGTGATCTTCAA : 164
           TTGAAGCAAATCAGATCCACAAGGACCCAATTCATGCTGGATCAGCTTGGTGATCTTCAA
```

FIGURE 25, cont'd

```
                   *         500         *         520         *         540
TrMADSa1 : CGTAAGGAACACTTGCTATGTGAAGCAAACAGAGCTCTCAGACAAAGGATGGAAGGGTAT : 540
TrMADSa2 : CGTAAGGAACACTTGCTATGTGAAGCAAACAGAGCTCTCAGACAAAGGATGGAAGGGTAT : 540
TrMADSa3 : CGTAAGGAACACTTGCTATGTGAAGCAAACAGAGCTCTCAGACAAAGGATGGAAGGGTAT : 246
TrMADSa4 : CGTAAGGAACACTTGCTATGTGAAGCAAACAGAGCTCTCAGACAAAGGATGGAAGGGTAT : 224
           CGTAAGGAACACTTGCTATGTGAAGCAAACAGAGCTCTCAGACAAAGGATGGAAGGGTAT

*         560         *         580         *         600
TrMADSa1 : CAAATAAATTCTCTCCAACTGAATCTGAGTGCTGAA------------------------ : 576
TrMADSa2 : CAAATAAATTCTCTCCAACTGAATCTGAGTGCTGAAGATATGG----------------- : 583
TrMADSa3 : CAAATAAATTCTCTCCAACTGAATCTGAGTGCTGAAGATATGGGATATGGTCGTCATCAT : 306
TrMADSa4 : CAAATAAATTCTCTCCAACTGAATCTGAGTGCTGAAGATATGGGATATGGTCGTCATCAT : 284
           CAAATAAATTCTCTCCAACTGAATCTGAGTGCTGAAGATATGGGATATGGTCGTCATCAT

*         620         *         640         *         660
TrMADSa1 : ------------------------------------------------------------ : -
TrMADSa2 : ------------------------------------------------------------ : -
TrMADSa3 : CCAGTTCACACCCAGGGTGATGAACTATTTCAACCAATTGAGTGCGAACCAACCTTACAA : 366
TrMADSa4 : CCAGTTCACACCCAGGGTGATGAACTATTTCAACCAATTGAGTGCGAACCAACCTTACAA : 344
           CCAGTTCACACCCAGGGTGATGAACTATTTCAACCAATTGAGTGCGAACCAACCTTACAA

*         680         *         700         *         720
TrMADSa1 : ------------------------------------------------------------ : -
TrMADSa2 : ------------------------------------------------------------ : -
TrMADSa3 : ATTGGATATCAAGCTGATCCAGGATCAGTGGTGACAGCAGGCCCAAGCATGAATAATTTC : 426
TrMADSa4 : ATTGGATATCAAGCTGATCCAGGATCAGTGGTGACAGCAGGCCCAAGCATGAATAATTTC : 404
           ATTGGATATCAAGCTGATCCAGGATCAGTGGTGACAGCAGGCCCAAGCATGAATAATTTC

*         740         *         760         *         780
TrMADSa1 : ------------------------------------------------------------ : -
TrMADSa2 : ------------------------------------------------------------ : -
TrMADSa3 : ATGGGTGGATGGTTACCATGATGATGTTAAAGTTATATATTGAGAACGAGTGTGAAGCAT : 486
TrMADSa4 : ATGGGTGGATGGTTACCATGATGATGTTAAAGTTATATATTGAGAACGAGTGTGAAGCAT : 464
           ATGGGTGGATGGTTACCATGATGATGTTAAAGTTATATATTGAGAACGAGTGTGAAGCAT

*         800         *         820         *         840
TrMADSa1 : ------------------------------------------------------------ : -
TrMADSa2 : ------------------------------------------------------------ : -
TrMADSa3 : GCATAAAGATCAAATGAAAATTTGTAATACTAGCATGTTATATAATGGACTACACTAAAC : 546
TrMADSa4 : GCATAAAGATCAAATGAAAATTTGTAATACTAGCATGTTATATAATGGACTACACTAAAC : 524
           GCATAAAGATCAAATGAAAATTTGTAATACTAGCATGTTATATAATGGACTACACTAAAC

*         860         *         880
TrMADSa1 : --------------------------------------- : -
TrMADSa2 : --------------------------------------- : -
TrMADSa3 : TATGTATTAGTGTCTACTTACTATG-------------- : 571
TrMADSa4 : TATGTATTAGTGTCTACTTACTATGTAGGCAAAATAATATAGTAA : 569
           TATGTATTAGTGTCTACTTACTATGTAGGCAAAATAATATAGTAA
```

FIGURE 26

```
              *         20         *         40         *         60
TrWRKYa : ATCTTCAAAAGATGCTTCTCATATTGATGTTAAACCCGGTAATGCCTCTAATATTCATGT :  60

*         80         *        100         *        120
TrWRKYa : TAAAAAGGCAGAGTTATTTCTAAAAACTATAAGGAAGGATACATCAAAGCAGAAAGGTAG : 120

*        140         *        160         *        180
TrWRKYa : CAAAGAAATCATGAAGCACAAATATGTATTTCAAACAAGGAGTCAGATCGATATACTAGA : 180

*        200         *        220         *        240
TrWRKYa : CGATGGGTTCCGATGGAGAAAGTACGGGGAAAAGTTGGTGAAAAACAACAAATATCCTAG : 240

*        260         *        280         *        300
TrWRKYa : AAGTTATTACAAATGCACTTATCCAGGCTGCAATGCAAAGAAACAAATCCAAAGGAATTC : 300

*        320         *        340         *        360
TrWRKYa : CAAACAGGATCATATTGTATAAACAACTTACGAGGGAATGCATATTCACCCTGTCCAGAA : 360

TrWRKYa : CTCAACTG : 368
```

FIGURE 27

```
                  *         20         *         40         *         60
TrWRKYa : SSKDASHIDVKPGNASNIHVKKAELFLKTIRKDTSKQKGSKEIMKHKYVFQTRSQIDILD :  60

*         80         *        100
TrWRKYa : DGFRWRKYGEKLVKNNKYPRSYYKCTYPGCNAKKQIQRNSKQDHIV : 106
```

FIGURE 28

```
                *        20         *        40         *        60
TrMYCa : CCTCTCTCTCTCTCTCTCCCCCACTCCATTATCACCACCACACGGTCTCTTCTTCCTAAC :  60

*        80         *       100         *       120
TrMYCa : TTTCTCTTCTTCTCTTTCTTTTCCCTAATTTACCTCCAAAATTAACCAAAAATAAATAAT : 120

*       140         *       160         *       180
TrMYCa : AAAAATTCCATTTCATGAATCTTTGGAGCGACGAGAACTCATCAGTGATGGAGGCTTTTA : 180

*       200         *       220         *       240
TrMYCa : TGACCTCATCCGATTTATCAACCTTATGGCCATCACAACCACAGCCGCCGTCGTCACAAC : 240

*       260         *       280         *       300
TrMYCa : CACCACAAACCACCACCGGATTCAACCAAGACACACTCCAACAACGTCTTCAAGCTTTAA : 300

*       320         *       340         *       360
TrMYCa : TCGAAGGCGCTTCCGAAATCTGGACTTACGCTATCTTCTGGCAACCTTCTTACGACTATT : 360

*       380         *       400         *       420
TrMYCa : CCGGCTCTTCTCTTCTCGGTTGGGGTGACGGTTATTACAAAGGCGAAGAAGACAAATCAA : 420

*       440         *       460         *       480
TrMYCa : AATCAAAATCCAAAGCTACTTCACCAGCTGAACAAGAACACCGTAGAAAAGTTCTCCGAG : 480

*       500         *       520         *       540
TrMYCa : AACTTAATTCTTTAATCTCCGGTAATCCAGCACCGGAAGAATCTTCCGTCGATGAAGAAG : 540

*       560         *       580         *       600
TrMYCa : TTACAGATACGGAATGGTTTTTTTTTAGTTTCTATGACTCAATCTTTTGTTAACGGAAGT : 600

*       620         *
TrMYCa : GGACTTCCTGGACAAGCTTATTTTAATTCAAC : 632
```

FIGURE 29

```
              *         20         *         40         *         60
TrMYCa : MNLWSDENSSVMEAFMTSSDLSTLWPSQPQPPSSQPPQTTTGFNQDTLQQRLQALIEGAS :  60

*         80         *        100         *        120
TrMYCa : EIWTYAIFWQPSYDYSGSSLLGWGDGYYKGEEDKSKSKSKATSPAEQEHRRKVLRELNSL : 120

*        140         *
TrMYCa : ISGNPAPEESSVDEEVTDTEWFFFSFYDSIFC : 152
```

FIGURE 30

```
                      *        20         *        40         *        60
TrMYCa1 : CCTCTCTCTCTCTCTCTCCCCCACTCCATTATCACCACCACACGGTCTCTTCTTCCTAAC :  60
TrMYCa2 : ------------------------------------------------------------ :   -
          CCTCTCTCTCTCTCTCTCCCCCACTCCATTATCACCACCACACGGTCTCTTCTTCCTAAC

*        80         *       100         *       120
TrMYCa1 : TTTCTCTTCTTCTCTTTCTTTTCCCTAATTTACCTCCAAAATTAACCAAAAATAAATAAT : 120
TrMYCa2 : ------------------------------------------------------------ :   -
          TTTCTCTTCTTCTCTTTCTTTTCCCTAATTTACCTCCAAAATTAACCAAAAATAAATAAT

*       140         *       160         *       180
TrMYCa1 : AAAAATTCCATTTCATGAATCTTTGGAGCGACGAGAACTCATCAGTGATGGAGGCTTTTA : 180
TrMYCa2 : -------------------------------------------TGATGGAGGCTTTTA :  15
          AAAAATTCCATTTCATGAATCTTTGGAGCGACGAGAACTCATCAGTGATGGAGGCTTTTA

*       200         *       220         *       240
TrMYCa1 : TGACCTCTTCCGATTTATCAACCTTATGGCCATCACAACCACAGCCGCCGTCGTCACAAC : 240
TrMYCa2 : TGACCTCATCCGATTTATCAACCTTATGGCCATCACAACCACAGCCGCCGTCGTCACAAC :  75
          TGACCTCATCCGATTTATCAACCTTATGGCCATCACAACCACAGCCGCCGTCGTCACAAC

*       260         *       280         *       300
TrMYCa1 : CACCACAAACCACCACCGGATTCAACCAAGACACACTCCAACAACGTCTTCAAGCTTTAA : 300
TrMYCa2 : CACCACAAACCACCACCGGATTCAACCAAGACACACTCCAACAACGTCTTCAAGCTTTAA : 135
          CACCACAAACCACCACCGGATTCAACCAAGACACACTCCAACAACGTCTTCAAGCTTTAA

*       320         *       340         *       360
TrMYCa1 : TCGAAGGCGCTTCCGAAATCTGGACTTACGCTATCTTCTGGCAACCTTCTTACGACTATT : 360
TrMYCa2 : TCGAAGGCGCTTCCGAAATCTGGACTTACGCTATCTTCTGGCAACCTTCTTACGACTATT : 195
          TCGAAGGCGCTTCCGAAATCTGGACTTACGCTATCTTCTGGCAACCTTCTTACGACTATT

*       380         *       400         *       420
TrMYCa1 : CCGGCTCTTCTCTTCTCGGTTGGGGTGACGGTTATTACAAAGGCGAAGAAGACAAATCAA : 420
TrMYCa2 : CCGGCTCTTCTCTTCTCGGTTGGGGTGACGGTTATTACAAAGGCGAAGAAGACAAATCAA : 255
          CCGGCTCTTCTCTTCTCGGTTGGGGTGACGGTTATTACAAAGGCGAAGAAGACAAATCAA

*       440         *       460         *       480
TrMYCa1 : AATCAAAATCCAAAGCTACTTCACCAGCTGAACAAGAACACCGTAGAAAAGTTCTCCGAG : 480
TrMYCa2 : AATCAAAATCCAAAGCTACTTCACCAGCTGAACAAGAACACCGTAGAAAAGTTCTCCGAG : 315
          AATCAAAATCCAAAGCTACTTCACCAGCTGAACAAGAACACCGTAGAAAAGTTCTCCGAG

*       500         *       520         *       540
TrMYCa1 : AACTTAATTCTTTAATCTCCGGTAATCCGGCACCGGAAGAATCTTCCGTCGATGAAGAAG : 540
TrMYCa2 : AACTTAATTCTTTAATCTCCGGTAATCCAGCACCGGAAGAATCTTCCGTCGATGAAGAAG : 375
          AACTTAATTCTTTAATCTCCGGTAATCCAGCACCGGAAGAATCTTCCGTCGATGAAGAAG

*       560         *       580         *       600
TrMYCa1 : TTACAGATACGGAATGG-TTTTTTTTAGTTTCTATGACTCAATCTT-------------- : 585
TrMYCa2 : TTACAGATACGGAGTGGTTTTTTTTTAGTTTCTATGACTCAATCTTTTGTTAACGGAAGT : 435
          TTACAGATACGGAATGGTTTTTTTTTAGTTTCTATGACTCAATCTTTTGTTAACGGAAGT

*       620         *
TrMYCa1 : ------------------------------- :   -
TrMYCa2 : GGACTTCCTGGACAAGCTTATTTTAATTCAAC : 467
          GGACTTCCTGGACAAGCTTATTTTAATTCAAC
```

FIGURE 32

```
                  *        20         *        40         *        60
TrMYCa : TAAGCAGTGGTAACAACGCAGAGTACGCGGGGATTCGTCTCTTTCTTCCTCTCTCTCT :  60

*        80         *       100         *       120
TrMYCa : CTCTCCCCCAATCCATTATCACCACCACACGGTCTCTTCTTCCTAACTTTCTCTTCTTCT : 120

*       140         *       160         *       180
TrMYCa : CTTTCTTTTCCCTAATTTACCTCCAAAATTAACCAAAAATAAATAATAAAAATTCCATTT : 180

*       200         *       220         *       240
TrMYCa : CATGAATCTTTGGAGCGACGAGAACTCATCAGTGATGGAGGCTTTTATGACCTCTTCCGA : 240

*       260         *       280         *       300
TrMYCa : TTTATCAACCTTATGGCCATCACAACCACAGCCGCCGTCGTCACAACCACCACAAACCAC : 300

*       320         *       340         *       360
TrMYCa : CACCGGATTCAACCAAGACACACTCCAACAACGTCTTCAAGCTTTAATCGAAGGCGCTTC : 360

*       380         *       400         *       420
TrMYCa : CGAAATCTGGACTTACGCTATCTTCTGGCAACCTTCTTACGACTATTCCGGCTCTTCTCT : 420

*       440         *       460         *       480
TrMYCa : TCTCGGTTGGGGTGACGGTTATTACAAAGGCGAAGAAGACAAATCGAAATCAAAATCCAA : 480

*       500         *       520         *       540
TrMYCa : AGCTACTTCACCAGCTGAACAAGAACACCGTAGAAAAGTTCTCCGAGAACTTAATTCTTT : 540

*       560         *       580         *       600
TrMYCa : AATCTCCGGTAATCCGGCACCGGAAGAATCTTCCGTCGATGAAGAAGTTACAGATACGGA : 600

*       620         *       640         *       660
TrMYCa : ATGGTTTTTTTTAGTTTCTATGACTCAATCTTTTGTTAACGGAAGTGGACTTCCTGGACA : 660

*       680         *       700         *       720
TrMYCa : AGCTTATTTTAATTCAACTCCGGTGTGGTTAGTCGGAGGTGAGAATCTCGCCCTCTCGGT : 720

*       740         *       760         *       780
TrMYCa : TTGCGAGAGGGCGAGACAAGGTCATGAACATGGTTTACAGACGCTGACGTGTATACCGTC : 780

*       800         *       820         *       840
TrMYCa : GGCGAACGGTGTTTTAGAGCTTGGATCTACTGAATTGATTTATCAGAATAACGATCTGAT : 840

*       860         *       880         *       900
TrMYCa : GAATAAAGTTAAGATGTTGTTTAATTTTAATAATAATTCTGATTTTGGATCTTCTTGGCA : 900
```

FIGURE 32, cont'd

```
                    *         920         *         940         *         960
TrMYCa : ATTAGGTAGTAATTCTACTGTAATTACTCATCAAGGTGAAAATGATCTTTCTTCAATTTG :  960

*         980         *        1000         *        1020
TrMYCa : GCTTAATGATCCTGAAACTAGAGATTCTGTTGATAATAATTCTCTTGCTGCAGCAACAAC : 1020

*        1040         *        1060         *        1080
TrMYCa : AACAACAACGACAACAAACACTTCAATTTCAATTCCAAGTCATCATCAGCAACAGCAACA : 1080

*        1100         *        1120         *        1140
TrMYCa : GCACCAGAACAATAGTAATAATCAGAGTTTGAGTGTGACGAAAACGATTCAATTTGAAAC : 1140

*        1160         *        1180         *        1200
TrMYCa : GCGTGGTTCAAGTACTTTAACAGAAGCTCCTAGTGTTGTTCATGTTTCAAGTAAGCAAAA : 1200

*        1220         *        1240         *        1260
TrMYCa : TCAACAAGGATTGTTTTCTAAAGAAATGAATCTTTTGGAGTACGGTGGGGGTAATAGTCA : 1260

*        1280         *        1300         *        1320
TrMYCa : GCAGCGTTCGTTGAAGCCGGAATCTGGTGAGATTTTGAGTTTTGGTGGTGAGAGTAAAAA : 1320

*        1340         *        1360         *        1380
TrMYCa : GAGTTCTTATGTTGCTAATAATGGAAATTCGAATTCGAATTTTTCTCTGGTCAATCACA : 1380

*        1400         *        1420         *        1440
TrMYCa : GTTAGTTTCAGTTGCTGAGGAGAATGGGAATGGAAATGGAAATGGGAAGAGGAGGTCTCC : 1440

*        1460         *        1480         *        1500
TrMYCa : GAATTCGAGAGGAAGCAATAATGATGATGGAATGCTATCTTTTACTTCTGGTGTAATTGT : 1500

*        1520         *        1540         *        1560
TrMYCa : TCCACCGGTGAATTTGAAATTCTCTGGTGGTACTGGTGGTGGTGATTCCGACCATTCGGA : 1560

*        1580         *        1600         *        1620
TrMYCa : TCTTGAAGCTTCGGTGGTGAAGGAAGTGGATAGTAGTCGTGTGGTGCAGCCGGAGAAGAA : 1620

*        1640         *        1660         *        1680
TrMYCa : GCCGAGGAAGAGAGGGAGGAAACCGGCGAATGGAAGAGAGGAACCGTTGAATCATGTTGA : 1680

*        1700         *        1720         *        1740
TrMYCa : AGCCGAGAGACAACGAAGAGAGAAGCTGAATCAGAGATTCTATGCTCTTCGTGCAGTTGT : 1740

*        1760         *        1780         *        1800
TrMYCa : TCCTAATGTTTCAAAGATGGATAAAGCTTCACTTTTGGGTGATGCTATATCATACATTAC : 1800
```

FIGURE 32, cont'd

```
                    *         1820         *         1840         *         1860
TrMYCa : TGAGCTGAAAACAAAGCTTGTGAAAACTGAATCCGATAAAGATGAATTAGAAAAACAACT : 1860

*         1880         *         1900         *         1920
TrMYCa : TGATGCAGTGAAGAATGAGCTTCAGAAAGTCAATGAAAACTCGTCTCATCCACCGCCTCA : 1920

*         1940         *         1960         *         1980
TrMYCa : ACCTCAACAACTACAACAACAACAACAAGTACCCGATAAACCCTCTTCCAATCAAGCTTT : 1980

*         2000         *         2020         *         2040
TrMYCa : AATCGATTTAGATATTGATGTGAAGATTATAGGTTGGGATGCAATGATAAGGGTCCAATG : 2040

*         2060         *         2080         *         2100
TrMYCa : CAGTAAGAAAAACCACCCTGCAGCGAAGTTGATGGCGGCGTTGATGGAGCTTGACCTAGA : 2100

*         2120         *         2140         *         2160
TrMYCa : AGTGCACCACGCAAGTGTTTCCGTGGTGAATGATTTGATGATACAACAAGCAACCGTGAA : 2160

*         2180         *         2200         *         2220
TrMYCa : GATGGGGGGTCGTTTTTACACCCAGGAGCAGCTTCGGGCAGCATTGTCCTCTAAAGTTGG : 2220

*         2240         *         2260         *         2280
TrMYCa : GGATGTTCAATAAAGTCTGTAAATTGCTGCAATGTGAAATTAATTGGGAATGTTATGTAT : 2280

*         2300         *         2320         *         2340
TrMYCa : GTAAATTTCTCATTCCTCCATAATTTTGGGGCTCTGGGATATTTACTGATTCCCGGTAA : 2340

*         2360         *         2380         *         2400
TrMYCa : CTATGTAAACTAGAAGTGTCTTTGTTTTTGGTAGCTTAGTATGAATTTTGAGGTAATTTT : 2400

*         2420         *         2440         *         2460
TrMYCa : ATTTGGGAATTTGTATGGAGATGAAGTACTAGAACTAGAGGTAGCGTCGATGAAGTAAGT : 2460

*         2480         *         2500         *         2520
TrMYCa : AAAAACTAAGTGTAATTTCTCCGCAATGCGTGCCCGTGTGTGTATATAGATGTTGTTGTA : 2520

*         2540         *         2560         *
TrMYCa : TAATTCTCATAAATGGGTAACATGGTGAAAATTCTGAATATTATTATTCTCAGCTTACC : 2579
```

FIGURE 33

```
              *        20         *        40         *        60
TrMYCa : MNLWSDENSSVMEAFMTSSDLSTLWPSQPQPPSSQPPQTTTGFNQDTLQQRLQALIEGAS :  60

*        80         *       100         *       120
TrMYCa : EIWTYAIFWQPSYDYSGSSLLGWGDGYYKGEEDKSKSKSKATSPAEQEHRRKVLRELNSL : 120

*       140         *       160         *       180
TrMYCa : ISGNPAPEESSVDEEVTDTEWFFLVSMTQSFVNGSGLPGQAYFNSTPVWLVGGENLALSV : 180

*       200         *       220         *       240
TrMYCa : CERARQGHEHGLQTLTCIPSANGVLELGSTELIYQNNDLMNKVKMLFNFNNNSDFGSSWQ : 240

*       260         *       280         *       300
TrMYCa : LGSNSTVITHQGENDLSSIWLNDPETRDSVDNNSLAAATTTTTTNTSISIPSHHQQQQQ : 300

*       320         *       340         *       360
TrMYCa : HQNNSNNQSLSVTKTIQFETRGSSTLTEAPSVVHVSSKQNQQGLFSKEMNLLEYGGGNSQ : 360

*       380         *       400         *       420
TrMYCa : QRSLKPESGEILSFGGESKKSSYVANNGNSNSNFFSGQSQLVSVAEENGNGNGNGKRRSP : 420

*       440         *       460         *       480
TrMYCa : NSRGSNNDDGMLSFTSGVIVPPVNLKFSGGTGGGDSDHSDLEASVVKEVDSSRVVEPEKK : 480

*       500         *       520         *       540
TrMYCa : PRKRGRKPANGREEPLNHVEAERQRREKLNQRFYALRAVVPNVSKMDKASLLGDAISYIT : 540

*       560         *       580         *       600
TrMYCa : ELKTKLVKTESDKDELEKQLDAVKNELQKVNENSSHPPPQPQQLQQQQQVPDKPSSNQAL : 600

*       620         *       640         *       660
TrMYCa : IDLDIDVKIIGWDAMIRVQCSKKNHPAAKLMAALMELDLEVHHASVSVVNDLMIQQATVK : 660

*       680
TrMYCa : MGGRFYTQEQLRAALSSKVGDVQ : 683
```

FIGURE 34
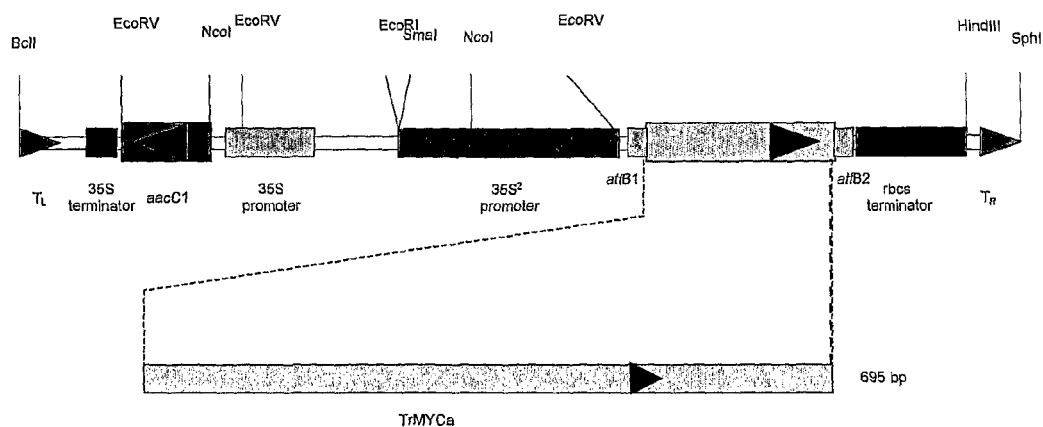
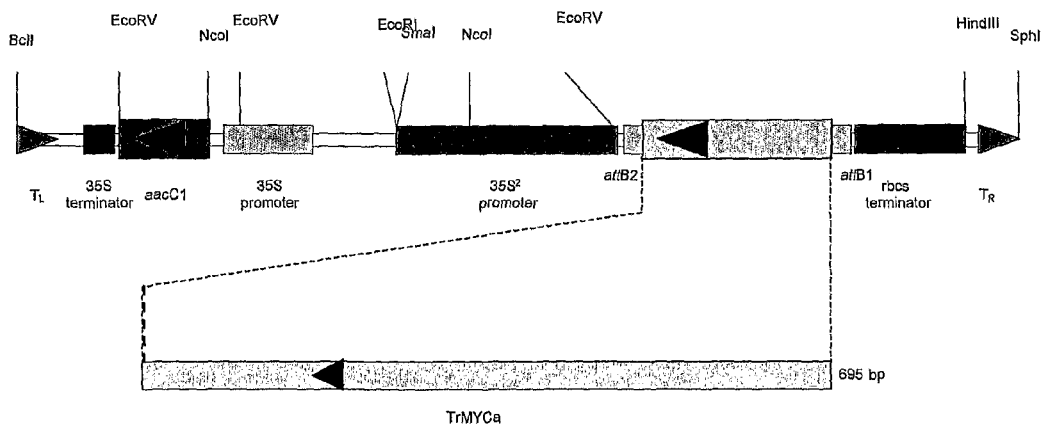

FIGURE 35

```
              *        20         *        40         *        60
TrTT1a : ATAAACCCTTTCTAGGGAGAGACTAATTGAATATATTGCACAAATCTAGGGACTCTATCT :  60

*        80         *       100         *       120
TrTT1a : CACTCTAAAACTAAGATGGGGGGAGAGATAAGTGCAATGTAAAAGACAAGAATTTATAT  : 120

*       140         *       160         *       180
TrTT1a : CTTCAAACCCCAACTTTCATTGAATGGCTCAAACCTTCTTCATCACTTTCATCTTCTCCT : 180

*       200         *       220         *       240
TrTT1a : TCATCATCTTTAACTCATCAACAAGAAATATCTCAAGAAACTTTTCAGTTTTTACCCATC : 240

*       260         *       280         *       300
TrTT1a : TATAGTGGAATTAAGTCCTTTGAGGAAAACCATGGGATGCAAAAGGAAGATTTAGAAGTA : 300

*       320         *       340         *       360
TrTT1a : AAAGAAGAGAAAGTGGAAAAAGTAACTGTGGCTTTGCACATTGGATTGCCTAACATAGGA : 360

*       380         *       400         *       420
TrTT1a : GGAGGTGAATCTTATGATCATGAAGAGAAGAATAAGGTTTTTGATGAGAACAATAAAGTT : 420

*       440         *       460         *       480
TrTT1a : AATGAAAAAGAATTAAAGAAAAACTTGCATGGTTTTTGTTTTAAGGAAGAAAGAAGGTTT : 480

*       500         *       520         *       540
TrTT1a : TGGATACCAACTCCTGCTCAGATCCTTGTTGGACCTATGCAATTTGCTTGCTCCATATGC : 540

*       560         *       580         *       600
TrTT1a : AACAAGACTTTCAATAGATACAACAATATGCAGATGCATATGTGGGGACATGGATCAGAA : 600

TrTT1a : T : 601
```

FIGURE 36

```
            *         20         *         40         *         60
TrTT1a : MGGRDKCNVKDKNLYLQTPTFIEWLKPSSSLSSSPSSSLTHQQEISQETFQFLPIYSGIK :  60

*         80         *        100         *        120
TrTT1a : SFEENHGMQKEDLEVKEEKVEKVTVALHIGLPNIGGGESYDHEEKNKVFDENNKVNEKEL : 120

*        140         *        160         *
TrTT1a : KKNLHGFCFKEERRFWIPTPAQILVGPMQFACSICNKTFNRYNNMQMHMWGHGSE : 175
```

FIGURE 37

```
              *         20         *         40         *         60
TrTT1a1 : ATAAACCCTTTCTAGGGAGAGACTAATTGAATATATTGCACAAATCTAGGGACTCTATCT :  60
TrTT1a2 : -TAAACCCTTTCTAGGGAGAGACTAATTGAATATATTGCACAAATCTAGGGACTCTATCT :  59
          ATAAACCCTTTCTAGGGAGAGACTAATTGAATATATTGCACAAATCTAGGGACTCTATCT

*         80         *        100         *        120
TrTT1a1 : CACTCTAAAACTAAGATGGGTTGGAGAGATAAGTGCAATGTAAAAGACAAGAATTTATAT : 120
TrTT1a2 : CACTCTAAAACTAANATGGGGGGGAGAGATAAGTGCAATGTAGAAGACAAGAATTTATAT : 119
          CACTCTAAAACTAAGATGGGGGGGAGAGATAAGTGCAATGTAAAAGACAAGAATTTATAT

*        140         *        160         *        180
TrTT1a1 : CTTCAAACCCCAACTTTCATTGAATGGCTCAAACCTTCTTCATCACTTTCATCTTCTCCT : 180
TrTT1a2 : CTTCAAACCCCAACTTTCATTGAATGGCTCAAACCTTCTTCATCACTTTCATCTTCTCCT : 179
          CTTCAAACCCCAACTTTCATTGAATGGCTCAAACCTTCTTCATCACTTTCATCTTCTCCT

*        200         *        220         *        240
TrTT1a1 : TCATCATCTTTAACTCATCAACAAGAAATATCTCAAGAAACTTTTCAGTTTTTACCCATC : 240
TrTT1a2 : TCATCATCTTTAACTCATCAACAAGAAATATCTCAAGAAACTTTTCAGTTTTTACCCATC : 239
          TCATCATCTTTAACTCATCAACAAGAAATATCTCAAGAAACTTTTCAGTTTTTACCCATC

*        260         *        280         *        300
TrTT1a1 : TATAGTGGAATTAAGTCCTTTGAGGAAAACCATGGGATGCAAAAGGAAGATTTAGAAGTA : 300
TrTT1a2 : TATAGTGGAATTAAGTCCTTTGAGGAAAACCATGGGATGCAAAAGGAAGATTTAGAAGTA : 299
          TATAGTGGAATTAAGTCCTTTGAGGAAAACCATGGGATGCAAAAGGAAGATTTAGAAGTA

*        320         *        340         *        360
TrTT1a1 : AAAGAAGAGAAAGTGGAAAAAGTAACTGTGGCTTTGCACATTGGATTGCCTAACATAGGA : 360
TrTT1a2 : AAAGAAGAGAAAGTGGAAAAAGTAACTGTGGCTTTGCACATTGGATTGCCTAACATAGGA : 359
          AAAGAAGAGAAAGTGGAAAAAGTAACTGTGGCTTTGCACATTGGATTGCCTAACATAGGA

*        380         *        400         *        420
TrTT1a1 : GGAGGTGAATCTTATGATCATGAAGAGAAGAATAAGGTTTTTGATGAGAACAATAAAGTT : 420
TrTT1a2 : GGAGGTGAATCTTATGATCATGAAGAGAAGAATAAGGTTTTTGATGAGAACAATAAAGTT : 419
          GGAGGTGAATCTTATGATCATGAAGAGAAGAATAAGGTTTTTGATGAGAACAATAAAGTT

*        440         *        460         *        480
TrTT1a1 : AATGAAAAAGAATTAAAGAAAAACTTGCATGGTTTTTGTTTTAAGGAAGAAAGAAGGTTT : 480
TrTT1a2 : AATGAAAAAGAATTAAAGAAAAACTTGCATGGTTTTTGTTTTAAGGAAGAAAGAAGGTTT : 479
          AATGAAAAAGAATTAAAGAAAAACTTGCATGGTTTTTGTTTTAAGGAAGAAAGAAGGTTT

*        500         *        520         *        540
TrTT1a1 : TGGATACCAACTCCTGCTCAGATCCTTGTTGGACCTATGCAATTTGCTTGCTCCATATGC : 540
TrTT1a2 : TGGATACCAACTCCTGCTCAGATCCTTGTTGGACCTATGCAATTTGCTTGCTCCATATGC : 539
          TGGATACCAACTCCTGCTCAGATCCTTGTTGGACCTATGCAATTTGCTTGCTCCATATGC

*        560         *        580         *        600
TrTT1a1 : AACAAGACTTTCAATAGATACAACAATATGCAGATGCATATGTGGGACATGGATCAGAA : 600
TrTT1a2 : AACAAGACTTTCAATAGATACAACAATATGCAGATGCATATGTGGGACATG-------- : 591
          AACAAGACTTTCAATAGATACAACAATATGCAGATGCATATGTGGGACATGGATCAGAA

TrTT1a1 : T : 601
TrTT1a2 : - : -
          T
```

FIGURE 38

```
              *        20         *        40         *        60
TrHLHa :  TACACACACAACAAACAATATGGACATGGATTCAACAGGTGGTTCTTCTTGTTGGCTCTA  :  60

*        80         *       100         *       120
TrHLHa :  TGATTATGGCTATGATATTTCTGTTCCTGCACCTGATTTCATGCCTTCTGATCATCACTC  :  120

*       140         *       160         *       180
TrHLHa :  TCCTGCTTCTGTTTTCACCTGGAATATGCCTCAGACTCATATCATCAAGCCTCCTTCCTC  :  180

*       200         *       220         *       240
TrHLHa :  CAATATCAGCTTGGAAATGGAATACTCACTGGACTCAACTGTACTGGAAAGTGGTCCTTC  :  240

*       260         *       280         *       300
TrHLHa :  ATCAAAGCGCTTGGAAATGGAATACTCACTGGATTCAACTGTACTGGAAAATGGCCCTTC  :  300

*       320         *       340         *       360
TrHLHa :  AAAGCGGTTAAAGACAGAATCATGTGCATCTGGCTCCAAGGCATGTCGCGAGAAACAGCG  :  360

*       380         *       400         *       420
TrHLHa :  CAGGGATAAACTGAATGACAAGTTTATGGAATTGAGTTCTGTCTTAGAGCCTGATACACT  :  420

*       440         *       460         *       480
TrHLHa :  GCCCAAAACAGACAAAGTTACCTTATTAAATGACGCGGTTCGTGTGGTTACACAATTAAG  :  480

*       500         *       520         *       540
TrHLHa :  AAATGAAGCAGAAAGGCTGAAGGAAAGGAATGACGAATTGCGCGAAAAAGTTAAAGAACT  :  540

*       560         *       580         *       600
TrHLHa :  TAAGACTGAGAAAAATGAGCTTCGCGATGAGAAAAATAAGCTGAAGTTAGACAAAGAAAA  :  600

*       620         *       640         *       660
TrHLHa :  GTTGGAACAGCAAGTGAAATTAACAAGTGTACAGTCCAGCATCCTCTCGAATGCCATGGC  :  660

*       680         *       700         *       720
TrHLHa :  GGCTAAAGGACAATCTGCTGCTAACCACAAGCTGATGCCTTTCATTGGTTATCCTGGAAT  :  720

*       740         *       760
TrHLHa :  TTCGGTGTGGCAGTTTATGTCACCTGCTACAGTTGATACATCACAGGA  :  768
```

FIGURE 39

```
                *        20         *        40         *        60
TrHLHa : THTTNNMDMDSTGGSSCWLYDYGYDISVPAPDFMPSDHHSPASVFTWNMPQTHIIKPPSS :  60

*        80         *       100         *       120
TrHLHa : NISLEMEYSLDSTVLESGPSSKRLEMEYSLDSTVLENGPSKRLKTESCASGSKACREKQR : 120

*       140         *       160         *       180
TrHLHa : RDKLNDKFMELSSVLEPDTLPKTDKVTLLNDAVRVVTQLRNEAERLKERNDELREKVKEL : 180

*       200         *       220         *       240
TrHLHa : KTEKNELRDEKNKLKLDKEKLEQQVKLTSVQSSILSNAMAAKGQSAANHKLMPFIGYPGI : 240

*
TrHLHa : SVWQFMSPATVDTSQ : 255
```

FIGURE 40

```
              *        20         *        40         *        60
TrHLHa1 : TACACACACAACAAACAATATGGACATGGATTCAACAGGTGGTTCTTCTTGTTGGCTCTA : 60
TrHLHa2 : ----ACACAACAAACAATATGGACATGGATTCCACAGGTGGTTCTTCTTGTTGGCTCTA : 55
          TACACACACAACAAACAATATGGACATGGATTCAACAGGTGGTTCTTCTTGTTGGCTCTA

*        80         *       100         *       120
TrHLHa1 : TGATTATGGCTATGATATTTCTGTTCCTGCACCTGATTTCATGCCTTCTG---ATCACTC : 117
TrHLHa2 : TGATTGTGGCTATGATATTTCTGTTCCTGCACCTGATTTCATGCCTTCTGATCATCACTC : 115
          TGATTATGGCTATGATATTTCTGTTCCTGCACCTGATTTCATGCCTTCTGATCATCACTC

*       140         *       160         *       180
TrHLHa1 : TCCTGCTTCTGTTTTCACCTGGAATATGCCTCAGACTCATATCATCAAGCCTCCTTCCTC : 177
TrHLHa2 : TCCTGCTTCTGTTTTCACCTGGAATATGCCTCAGACTCATATCATCAAGCCTCCTTCCTC : 175
          TCCTGCTTCTGTTTTCACCTGGAATATGCCTCAGACTCATATCATCAAGCCTCCTTCCTC

*       200         *       220         *       240
TrHLHa1 : CAATATCAGCTTGGAAATGGAATACTCACTGGACTCAACTGTACTGGAAAGTGGTCCTTC : 237
TrHLHa2 : CAATATCAGCTTGGAAATGGAATACTCACTGGACTCAACTGTATTGGAAAGTGGTCCTTC : 235
          CAATATCAGCTTGGAAATGGAATACTCACTGGACTCAACTGTACTGGAAAGTGGTCCTTC

*       260         *       280         *       300
TrHLHa1 : ATCAAAGCGCTTGGAAATGGAATACTCACTGGATTCAACTGTACTGGAAAATGGCCCTTC : 297
TrHLHa2 : A---AAGCGCTTGGAAATGGAATACTCACTGGATTCAACTGTACTGGAAAATGGCCCTTC : 292
          ATCAAAGCGCTTGGAAATGGAATACTCACTGGATTCAACTGTACTGGAAAATGGCCCTTC

*       320         *       340         *       360
TrHLHa1 : AAAGCGGTTAAAGACAGAATCATGTGCATCTGGCTCCAAGGCATGTCGCGAGAAACAGCG : 357
TrHLHa2 : AAAGCGGTTAAAGACAGAATCATGTGCATCTGGCTCCAAGGCATGTCGCGAGAAACAGCG : 352
          AAAGCGGTTAAAGACAGAATCATGTGCATCTGGCTCCAAGGCATGTCGCGAGAAACAGCG

*       380         *       400         *       420
TrHLHa1 : CAGGGATAAACTGAATGACAAGTTTATGGAATTGAGTTCTGTCTTAGAGCCTGATACACT : 417
TrHLHa2 : CAGGGATAAACTGAATGACAAGTTTGTGGAATTGAGTTCTGTCTTAGAGCCTGATACACT : 412
          CAGGGATAAACTGAATGACAAGTTTATGGAATTGAGTTCTGTCTTAGAGCCTGATACACT

*       440         *       460         *       480
TrHLHa1 : GCCCAAAACAGACAAAGTTACTTTATTAAATGACGCGGTTCGTGTGGTTACACAATTAAG : 477
TrHLHa2 : GCCCAAAACAGACAAAGTTACCTTATTAAATGACGCGGTTCGTGTGGTTACACAATTAAG : 472
          GCCCAAAACAGACAAAGTTACCTTATTAAATGACGCGGTTCGTGTGGTTACACAATTAAG

*       500         *       520         *       540
TrHLHa1 : AAATGAAGCAGAAAGGCTGAAGGAAAGGAATGACGAATTGCGCGAAAAAGTTAAAGAACT : 537
TrHLHa2 : AAATGAAGCAGAAAGGCTGAAGGAAAGGAATGATGAATTGCGCGAAAAAGTTAAAGAACT : 532
          AAATGAAGCAGAAAGGCTGAAGGAAAGGAATGACGAATTGCGCGAAAAAGTTAAAGAACT

*       560         *       580         *       600
TrHLHa1 : TAAGCCTGAGAAAAATGAGCTTCGCGATGAGAAAAATAAGCTGAAGTTAGACAAAGAAAA : 597
TrHLHa2 : TAAGACTGAGAAAATGAGCTTCGCGATGAGAAAAATAAGCTGAAGTTAGACAAAGAAAA : 592
          TAAGACTGAGAAAAATGAGCTTCGCGATGAGAAAAATAAGCTGAAGTTAGACAAAGAAAA

*       620         *       640         *       660
TrHLHa1 : GTTGGAACAGCAAGTGAAATTAACAAGTGTACAGTCCAGCTTCCTCTCGAATGCCATGGC : 657
TrHLHa2 : GTTGGAACAGCAAGTGAAATTAACAAGTGTACAGTCCAGCATCCTCTCGAATGCCATGGC : 652
          GTTGGAACAGCAAGTGAAATTAACAAGTGTACAGTCCAGCATCCTCTCGAATGCCATGGC
```

FIGURE 40, cont'd

```
              *        680         *        700         *        720
TrHLHa1 : G------------------------------------------------------- :  658
TrHLHa2 : GGCTAAAGGACAATCTGCTGCTAACCACAAGCTGATGCCTTTCATTGGTTATCCTGGAAT :  712
          GGCTAAAGGACAATCTGCTGCTAACCACAAGCTGATGCCTTTCATTGGTTATCCTGGAAT

*        740         *        760
TrHLHa1 : ------------------------------------------------- :    -
TrHLHa2 : TTCGGTGTGGCAGTTTATGTCACCTGCTACAGTTGATACATCACAGGA  :  760
          TTCGGTGTGGCAGTTTATGTCACCTGCTACAGTTGATACATCACAGGA
```

FIGURE 41

```
               *        20         *        40         *        60
TrMYB24a : TGAGAGAGAGAGAGAGAGAGAGAGAGGCTATGGGAAGCAGCTCCTTGTTGTGACAAAGAC :  60

*        80         *       100         *       120
TrMYB24a : AAAGTTAAGAGAGGACCATGGTCTCCTGATGAAGATGCAAAACTCAAGAATTATTTAGCA : 120

*       140         *       160         *       180
TrMYB24a : ATTCATGGCACTGTTGGAAATTGGATTGCATTGCCTAAAAAAGCTGGCCTTAAGCGGTGT : 180

*       200         *       220         *       240
TrMYB24a : GGAAAGAGTTGTCGTCTAAGGTGGCTGAATTATCTTAGGCCTGACATCAAACATGGAAGC : 240

*       260         *       280         *       300
TrMYB24a : TTTACTGAGGAAGAAGATACCATCATTTGTACCCTCTATGCTCAAATGGGTAGCAGATGG : 300

*       320         *       340         *       360
TrMYB24a : TCTGCCATAGCATCAAAACTACCTGGGAGAACAGACAATGATGTAAAAAACTATTGGAAC : 360

*       380         *       400         *       420
TrMYB24a : ACAAAACTGAAGAAGAAAATTATGGCAGGAAAAGTTGGCCTCAAATCATTGACTGAAAAT : 420

*       440         *       460         *       480
TrMYB24a : GACAATACTGTCCCTTCAACCCCATCAGTGACTCAAAATTGCAACATTATGTTAGACAAT : 480

*       500         *       520         *       540
TrMYB24a : AATTTTGATGCTAGTTATGGATTCAAGAATAATGAAAAAAACATTGGTTTTGATCAAATT : 540

*       560         *       580         *
TrMYB24a : CATGATGTTGGTGTCTCAGAAATTGGTGCAAGTAACAACAATATTGATATTAAT : 594
```

FIGURE 42

```
                    *        20         *        40         *        60
TrMYB24a : ERERERERLWEAAPCCDKDKVKRGPWSPDEDAKLKNYLAIHGTVGNWIALPKKAGLKRCG :  60

*        80         *       100         *       120
TrMYB24a : KSCRLRWLNYLRPDIKHGSFTEEEDTIICTLYAQMGSRWSAIASKLPGRTDNDVKNYWNT : 120

*       140         *       160         *       180
TrMYB24a : KLKKKIMAGKVGLKSLTENDNTVPSTPSVTQNCNIMLDNNFDASYGFKNNEKNIGFDQIH : 180

*
TrMYB24a : DVGVSEIGASNNNIDIN : 197
```

FIGURE 43

```
                    *         20         *         40         *         60
TrMYB24a1  : TGAGAGAGAGAGAGAGAGAGAGAGGCTATGGGAAG-AGCTCCTTGTTGTGACAAAGACA :
             60
TrMYB24a2  : ------------GAGAGAGAGAGAGGCTATGGGAAGCAGCTCCTTGTTGTGACAAAGACA :
             48
             TGAGAGAGAGAGAGAGAGAGAGAGGCTATGGGAAGCAGCTCCTTGTTGTGACAAAGACA

*         80         *        100         *        120
TrMYB24a1  : AAGTTAAGAGAGGACCATGGTCTCCTGATGAAGATGCAAAACTCAAGAATTATTTAGCAAT :
             121
TrMYB24a2  : AAGTTAAGAGAGGACCATGGTCTCCTGATGAAGATGCAAAACTCAAGAATTATTTAGCAAT :
             109
             AAGTTAAGAGAGGACCATGGTCTCCTGATGAAGATGCAAAACTCAAGAATTATTTAGCAAT

*        140         *        160         *        180
TrMYB24a1  : TCATGGCACTGTTGGAAATTGGATTGCATTGCCTAAAAAAGCTGGCCTTAAGCGGTGTGGA :
             182
TrMYB24a2  : TCATGGCACTGTTGGAAATTGGATTGCATTGCCTAAAAAAGCTGGCCTTAAGCGGTGTGGA :
             170
             TCATGGCACTGTTGGAAATTGGATTGCATTGCCTAAAAAAGCTGGCCTTAAGCGGTGTGGA

*        200         *        220         *        240
TrMYB24a1  : AAGAGTTGTCGTCTAAGGTGGCTGAATTATCTTAGGCCTGACATCAAACATGGAAGCTTTA :
             243
TrMYB24a2  : AAGAGTTGTCGTCTAAGGTGGCTGAATTATCTTAGGCCTGACATCAAACATGGAAGCTTTA :
             231
             AAGAGTTGTCGTCTAAGGTGGCTGAATTATCTTAGGCCTGACATCAAACATGGAAGCTTTA

*        260         *        280         *        300
TrMYB24a1  : CTGAGGAAGAAGATACCATCATTTGTACCCTCTATGCTCAAATGGGTAGCAGATGGTCTGC :
             304
TrMYB24a2  : CTGAGGAAGAAGATACCATCATTTGTACCCTCTATGCTCAAATGGGTAGCAGATGGTCTGC :
             292
             CTGAGGAAGAAGATACCATCATTTGTACCCTCTATGCTCAAATGGGTAGCAGATGGTCTGC

*        320         *        340         *        360
TrMYB24a1  : CATAGCATCAAAACTACCTGGGAGAACAGACAATGATGTAAAAAACTATTGGAACACAAAA :
             365
TrMYB24a2  : CATAGCATCAAAACTACCTGGGAGAACAGACAATGATGTAAAAAACTATTGGAACACAAAA :
             353
             CATAGCATCAAAACTACCTGGGAGAACAGACAATGATGTAAAAAACTATTGGAACACAAAA

*        380         *        400         *        420
TrMYB24a1  : CTGAAGAAGAAAATTATGGCAGGAAAAGTTGGCCTCAAATCATTGACTGAAAATGACAATA :
             426
TrMYB24a2  : CTGAAGAAGAAAATTATGGCAGGAAAAGTTGGCCTCAAATCATTGACTGAAAATGACAATA :
             414
             CTGAAGAAGAAAATTATGGCAGGAAAAGTTGGCCTCAAATCATTGACTGAAAATGACAATA

*        440         *        460         *        480
TrMYB24a1  : CTGTCCCTTCAACCCCATCAGTGACTCAAAATTGCAACATTATGTTAGACAATAATTTTGA :
             487
TrMYB24a2  : CTGTCCCTTCAACCCCATCAGTGACTCAAAATTGCAACATTATGTTAGACAATAATTTTGA :
             475
             CTGTCCCTTCAACCCCATCAGTGACTCAAAATTGCAACATTATGTTAGACAATAATTTTGA
```

FIGURE 43, cont'd

```
              *         500         *         520         *         540
TrMYB24a1 : TGCTAGTTATGGATTCAAGAATAATGAAAAAAACATTGGTTTTGATCAAATTCATGATGTT :
548
TrMYB24a2 : TGCTAGTTATGGATTCAAGAATAATGAAAAAAACATTGGTTTTGATCAAATTCATGATGTT :
536
            TGCTAGTTATGGATTCAAGAATAATGAAAAAAACATTGGTTTTGATCAAATTCATGATGTT

*         560         *         580         *
TrMYB24a1 : GGTGTCTCAGAAATTGGTGC---------------------------- : 568
TrMYB24a2 : GGTGTCTCAGAAATTGGTGCAAGTAACAACAATATTGATATTAAT : 581
            GGTGTCTCAGAAATTGGTGCAAGTAACAACAATATTGATATTAAT
```

FIGURE 45

```
                    *        20         *        40         *        60
TrMYB24a : TAAGCAGTGGTAACAACGCAGAGTACGCGGGGGAGTGAGAGAGAGAGAGAGAGAGAGA : 60

*        80         *       100         *       120
TrMYB24a : GGCTATGGGAAGAGCTCCTTGTTGTGACAAAGACAAAGTTAAGAGAGGACCATGGTCTCC :120

*       140         *       160         *       180
TrMYB24a : TGATGAAGATGCAAAACTCAAGAATTATTTAGCAATTCATGGCACTGTTGGAAATTGGAT :180

*       200         *       220         *       240
TrMYB24a : TGCATTGCCTAAAAAAGCTGGCCTTAAGCGGTGTGGAAAGAGTTGTCGTCTAAGGTGGCT :240

*       260         *       280         *       300
TrMYB24a : GAATTATCTTAGGCCTGACATCAAACATGGAAGCTTTACTGAGGAAGAAGATACCATCAT :300

*       320         *       340         *       360
TrMYB24a : TTGTACCCTCTATGCTCAAATGGGTAGCAGATGGTCTGCCATAGCATCAAAACTACCTGG :360

*       380         *       400         *       420
TrMYB24a : GAGAACAGACAATGATGTAAAAAACTATTGGAACACAAAACTGAAGAAGAAAATTATGGC :420

*       440         *       460         *       480
TrMYB24a : AGGAAAAGTTGGCCTCAAATCATTGACTGAAAATGACAATACTGTCCCTTCAACCCCATC :480

*       500         *       520         *       540
TrMYB24a : AGTGACTCAAAATTGCAACATTATGTTAGACAATAATTTTGATGCTAGTTATGGATTCAA :540

*       560         *       580         *       600
TrMYB24a : GAATAATGAAAAAAACATTGGTTTTGATCAAATTCATGATGTTGGTGTCTCAGAAATTGG :600

*       620         *       640         *       660
TrMYB24a : TGCAAGTAACAACAATATTGATATTAATCCTATGGTGTCAATATCTCAAGACAATTCAAG :660

*       680         *       700         *       720
TrMYB24a : CATTGGAGTGAACAACAATTGTGTATCACTTCAAGATCAAGCTGGTGATGAATCTTTGGA :720

*       740         *       760         *       780
TrMYB24a : ACCACTAATGGATTTTGGCTTTGGAGTTGGTAGTGATTTTGCTTCAAGTTGTTGCTTTCC :780

*       800         *       820         *       840
TrMYB24a : TGAGTGGGTTGATTTTAGTTATGCTGACATTAAGACAAATTGACTGGTTCAAAATCTTGC :840
```

FIGURE 45, cont'd

```
                  *       860         *       880         *       900
TrMYB24a : ATTGTCTAGTTCTAGTAATTAAATATGGGATTAATTAATTATGTAATAGCAAAATTACAT :900

*       920         *       940         *       960
TrMYB24a : TACATAGGTGAAATATTTTTAGTTTTGCTAAGTATTAAATTTAATTTTTCTTCCAACAAT :960

*       980         *       1000        *       1020
TrMYB24a : AAATTGGTCTGAGTGATAAACATTTTAAGTCCCTTAAGCAGTTAGTCGGGGATTGCAAGT :1020

*       1040
TrMYB24a : TCTTCAACAAAATTTATTCATCATT : 1045
```

FIGURE 46

```
                  *        20         *        40         *        60
TrMYB24a : MGRAPCCDKDKVKRGPWSPDEDAKLKNYLAIHGTVGNWIALPKKAGLKRCGKSCRLRWLN :  60

*        80         *       100         *       120
TrMYB24a : YLRPDIKHGSFTEEEDTIICTLYAQMGSRWSAIASKLPGRTDNDVKNYWNTKLKKKIMAG : 120

*       140         *       160         *       180
TrMYB24a : KVGLKSLTENDNTVPSTPSVTQNCNIMLDNNFDASYGFKNNEKNIGFDQIHDVGVSEIGA : 180

*       200         *       220         *       240
TrMYB24a : SNNNIDINPMVSISQDNSSIGVNNNCVSLQDQAGDESLEPLMDFGFGVGSDFASSCCFPE : 240

*
TrMYB24a : WVDFSYADIKTN : 252
```

FIGURE 47
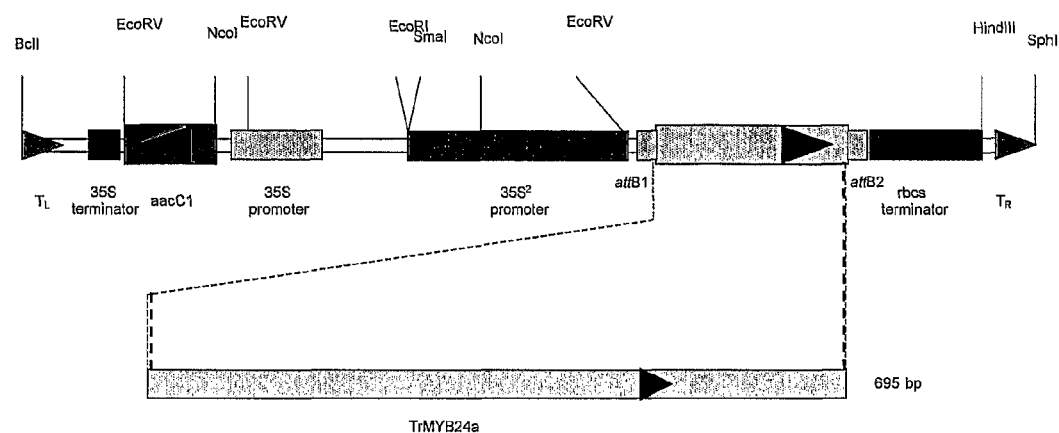
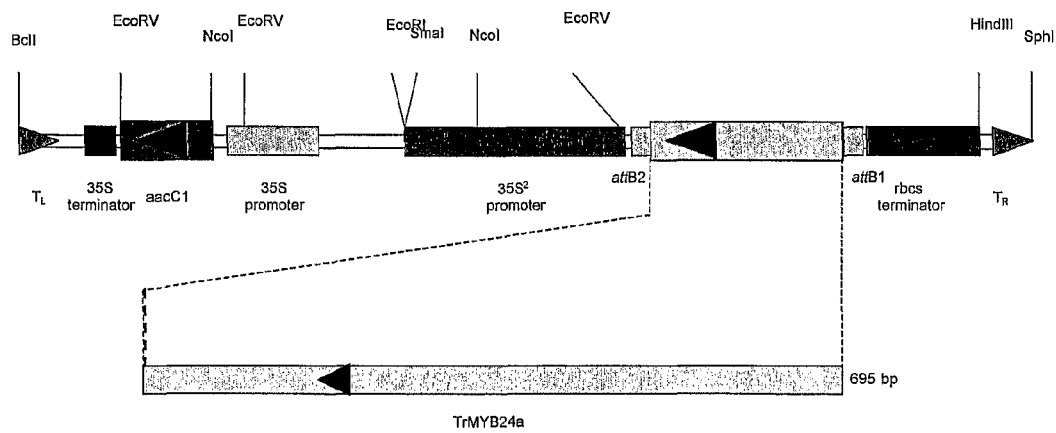

FIGURE 48

```
               *        20         *        40         *        60
TrABCa : AGCTGCATGGAAAATTGCCGATAAGTCTCCTCCTCAGAATTGGCCGAGTCATGGCACTAT :  60

*        80         *       100         *       120
TrABCa : AGAGTTAAATAATTTACAGGTTAGGTACAGGCCAAACACTCCTCTAGTTCTTAAGGGAAT : 120

*       140         *       160         *       180
TrABCa : CTCTCTAACCATTGAAGGTGGAGAAAAAGTTGGTGTCGTTGGTCGTACAGGAAGTGGAAA : 180

*       200         *       220         *       240
TrABCa : ATCAACACTTATTCAAGTGTTATTTAGATTAATTGAGCCTTCAGCTGGTAAAATTATTAT : 240

*       260         *       280         *       300
TrABCa : TGATGGTATCAATATTTCCAATATTGGCCTTCATGATTTAAGGTCACGTTTTGGAATTAT : 300

*       320         *       340         *       360
TrABCa : ACCACAAGAGCCTGTCCTCTTTCAAGGAACAGTAAGAACCAATATTGACCCTCTTGGAGT : 360

*       380         *       400         *       420
TrABCa : ATATTCAGAAGAAGAAATTTGGAAGAGTCTCGAGCGCTGCCAATTGAAAGAAGTGGTGGC : 420

*       440         *       460         *       480
TrABCa : TGCAAAGCCTGAGAAACTCGAGGCTTCAGTGGTTGATGGTGGAGACAATTGGAGTGTGGG : 480

*       500         *       520         *       540
TrABCa : ACAAAGACAGCTTCTATGCTTAGGAAGGATCATGCTAAAACGAAGCCAAATACTATTCAT : 540

*       560         *       580
TrABCa : GGACGAAGCAACAGCATCTGTCGATTCACAAACTGATGCTGTAATACAA : 589
```

FIGURE 49

```
              *        20         *        40         *        60
TrABCa : AAWKIADKSPPQNWPSHGTIELNNLQVRYRPNTPLVLKGISLTIEGGEKVGVVGRTGSGK :  60

*        80         *       100         *       120
TrABCa : STLIQVLFRLIEPSAGKIIIDGINISNIGLHDLRSRFGIIPQEPVLFQGTVRTNIDPLGV : 120

*       140         *       160         *       180
TrABCa : YSEEEIWKSLERCQLKEVVAAKPEKLEASVVDGGDNWSVGQRQLLCLGRIMLKRSQILFM : 180

*
TrABCa : DEATASVDSQTDAVIQ : 196
```

Figure 53
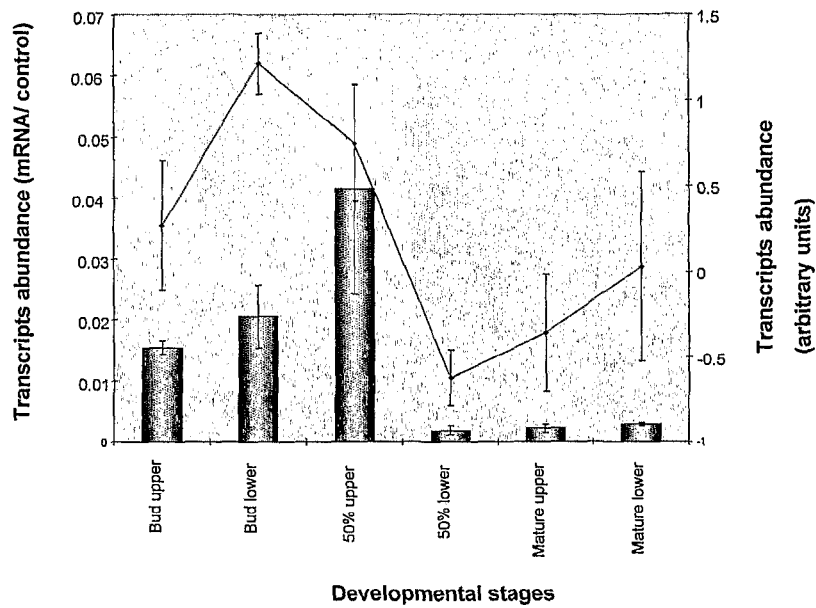
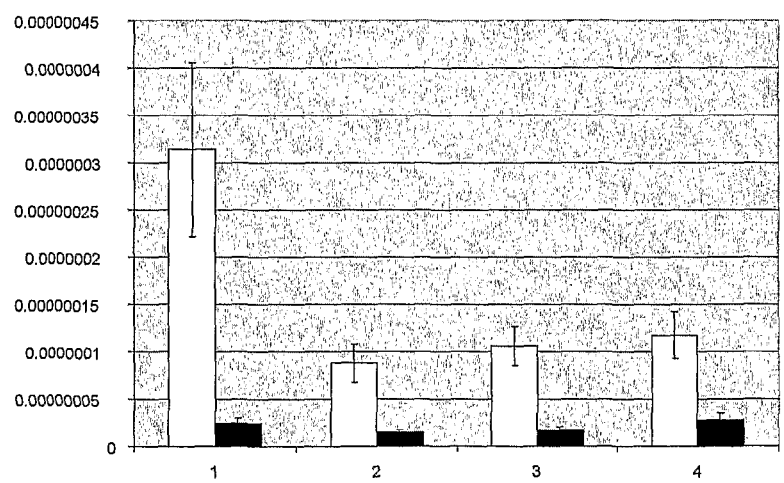
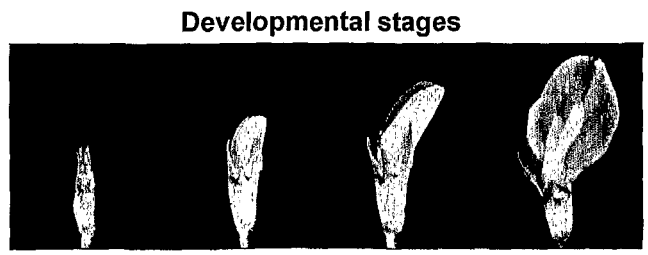

FIGURE 54

```
TrMYB24a     : VKRGPWSPDEDAKLKNYLAIHGTVGNWIALPKKAGLKRCGKSCRLRWLNYL : 62
PhMYB1_Z13   : LKKGPWTPEEDQKLLAYIEEHG-HGSWRALPAKAGLQRCGKSCRLRWTNYL : 61
AmMIXTA_CA   : VKKGPWTVDEDQKLLAYIEEHG-HGSWRSLPLKAGLQRCGKSCRLRWANYL : 61
AtGL1_P279   : MKKGLWTVEEDNILMDYVLNHC-TGQWNRIVRKTGLKRCGKSCRLRWMNYL : 63
AtWER_CAC0   : MKKGLWTVEEDKILMDYVKAHG-KGHWNRIAKKTGLKRCGKSCRLRWMNYL : 65
AtTT2_Q9FJ   : LNRGAWTDHEDKILRDYITTHG-EGKWSTLPNQAGLKRCGKSCRLRWKNYL : 63
VvMYBPA1_A   : LHRGSWTAREDILLTKYIQAHG-EHWSTLPKKAGLLRCGKSCRLRWMNYL : 61
AtMYB111_A   : LKRGRWTAEEDEILTKYIQTNG-EGSWRSLPKKAGLLRCGKSCRLRWINYL : 61
ZmP_P27898   : LKRGRWTAEEDQLLANYIAEHG-EGSWRSLPKNAGLLRCGKSCRLRWINYL : 61
ZmC1_AAA33   : VKRGAWTSKEDDALAAYVKAHG-EGKWREVPQKAGLRRCGKSCRLRWLNYL : 61
VvMYB5A_AA   : LKRGPWTPEEDELLANYVKREG-EGRWRTLPKRAGLLRCGKSCRLRWMNYL : 69
VvMYB5B_Q5   : LKRGPWTPEEDEVLANYIKKEG-EGRWRTLPKRAGLLRCGKSCRLRWMNYL : 74
PH4_AAY513   : LKRGPWTPEEDEILTNYINKEG-EGRWRTLPKKAGLLRCGKSCRLRWMNYL : 72
AtMYB5_U26   : MKRGPWTVEEDEILVSFIKKEG-EGRWRSLPKRAGLLRCGKSCRLRWMNYL : 72
OsMYB4_D88   : LKRGPWTPEEDEVLAFFVAREG-CDRWRTLPRRAGLLRCGKSCRLRWMNYL : 69
VvMYBA1_BA   : VRKGAWIQEEDVLLRKCIEKYG-EGKWHLVPLRAGLNRCKKSCRLRWLNYL : 55
VvMYBA2_BA   : VRKGAWTQEEDVLLRKCIEKYG-EGKWHLVPLRAGLNRCLKSCRLRWLNYL : 55
PhAN2_AAF6   : VRKGAWTEEEDLLLRECIDKYG-EGKWHLVPVRAGLNRCKKSCRLRWLNYL : 60
LeANT1_AAQ   : VRKGSWTDEEDFLLRKGIDKYG-EGKWHLVPIRAGLNRCRKSCRLRWLNYL : 60
AtPAP1_AAG   : LRKGAWTTEEDSLLRQCINKYG-EGKWHQVPVRAGLNRCRKSCRLRWLNYL : 57
AtPAP2_AAG   : LRKGAWTAEEDSLLRLGIDKYG-EGKWHQVPLRAGLNRCRKSCRLRWLNYL : 57
PmMBF1_AAA   : LNKGAWSAEEDSLLGKYIQTHG-EGNWRSLPKKAGLRRCGKSCRLRWLNYL : 61
               644GP53P2E126L615624HG3EG4WR36P44AG64RCGKSCR6RW6NYL

TrMYB24a     : RPDIKHGSFTEEEDTIIGTLVAQMGSRWSAIASKLPGRTDNDVKNYWNTKLKKK : 116
PhMYB1_Z13   : RPDIKRGKFTLQEEQIIIQLHALLGNRWSAIATHLPKRTDNEIKNYWNTHLKKR : 115
AmMIXTA_CA   : RPDIKRGPFSLQEEQIIQLHALLGNRWSAIASHLPKRTDNEIKNYWNTHLKKR : 115
AtGL1_P279   : SPNVKGNFTEQEEDLIIRLHKLLGNRWSLIAKRVPGRTDNQVKNYWNTHLSKK : 117
AtWER_CAC0   : SPNVKRGNFTEGEEDLIIRLHKLLGNRWSLIAKRVPGRTDNQVKNYWNTHLSKK : 119
AtTT2_Q9FJ   : RPCIKRGNISSDEEELIIRLHNLLGNRWSLIAGRLPGRTDNEIKNHWNSNLRKR : 117
VvMYBPA1_A   : RPDIKRGNITPDEDDLIIRLHSLLGNRWSLIAGRLPGRTDNEIKNYWNTHLSKK : 115
AtMYB111_A   : RRDLKRGNITSDEEEIIVKLHSLLGNRWSLIATHLPGRTDNEIKNYWNSHLSRK : 115
ZmP_P27898   : RADVKRGNISKEEEDIIIKLHATLGNRWSLIASHLPGRTDNEIKNYWNSHLSRQ : 115
ZmC1_AAA33   : RPNIRRGNISYDEEDLIIRLHRLLGNRWSLIAGRLPGRTDNEIKNYWNSTLGRR : 115
VvMYB5A_AA   : RPSVKRGQIAPDEEDLILRLHRLLGNRWSLIAGRIPGRTDNEIKNYWNTHLSKK : 123
VvMYB5B_Q5   : RPSVKRGQIAPDEEDLILRLHRLLGNRWALIAGRIPGRTDNEIKNYWNTHLSKK : 128
PH4_AAY513   : RPSVKRGHIAPDEEDLILRLHRLLGNRWSLIAGRIPGRTDNEIKNYWNTHLSKK : 126
AtMYB5_U26   : RPSVKRGGITSDEEDLILRLHRLLGNRWSLIAGRIPGRTDNEIKNYWNTHLRKK : 126
OsMYB4_D88   : RPDIKRCPIADDEEDLILRLHRLLGNRWSLIAGRLPGRTDNEIKNYWNSHLSKK : 123
VvMYBA1_BA   : KPDIKRGEFALDEVVDLMIRLHNLLGNRWSLIAGRLPGRTANDVKNYWHSHPFKK : 109
VvMYBA2_BA   : KPDIKRGEFALDEVVDLMIRLHNLLGNRWSLIAGRLPGRTANDVKNYWHGHHLKK : 109
PhAN2_AAF6   : RPHIKRGDFSLDEVDLILRLHNLLGNRWSLIAGRLPGRTANDVKNYWNTHLRKK : 114
LeANT1_AAQ   : RPHIKRGDFEQDEVDLILRLHKLLGNRWSLIAGRLPGRTANDVKNYWNTNLLRK : 114
AtPAP1_AAG   : KPSIKRGKLSSDEVDLLLRLHRLLGNRWSLIAGRLPGRTANDVKNYWNTHLSKK : 111
AtPAP2_AAG   : KPSIKRGRLSNDEVDLLLRLHKLLGNRWSLIAGRLPGRTANDVKNYWNTHLSKK : 111
PmMBF1_AAA   : RPCIKRGNITADEEHLIIRMHALLGNRWSIIAGRVPGRTDNEIKNYWNTNLSKK : 115
               4P1644G163PDE2166646H466G14WS66AG46PGR3DN26KN55N3H6SRQ
```

MODIFICATION OF PLANT FLAVONOID METABOLISM

The present invention relates to nucleic acid fragments encoding amino acid sequences for flavonoid biosynthetic enzymes in plants, and the use thereof for the modification of flavonoid biosynthesis in plants.

Flavonoids constitute a relatively diverse family of aromatic molecules that are derived from phenyalanine and malonyl-coenzyme A (CoA, via the fatty acid pathway). These compounds include six major subgroups that are found in most higher plants: the chalcones, flavones, flavonols, flavandiols, anthocyanins and condensed tannins (or proanthocyanidins). A seventh group, the aurones, is widespread, but not ubiquitous.

Some plant species also synthesize specialised forms of flavonoids, such as the isoflavonoids that are found in legumes and a small number of non-legume plants. Similarly, sorghum, maize and gloxinia are among the few species known to synthesize 3-deoxyanthocyanins (or phlobaphenes in the polymerised form). The stilbenes, which are closely related to flavonoids, are synthesised by another group of unrelated species that includes grape, peanut and pine.

Besides providing pigmentation to flowers, fruits, seeds, and leaves, flavonoids also have key roles in signalling between plants and microbes, in male fertility of some plant species, in defense as antimicrobial agents and feeding deterrents, and in UV protection.

Flavonoids also have significant activities when ingested by animals, and there is great interest in their potential health benefits, particularly for compounds such as isoflavonoids, which have been linked to anticancer benefits, and stilbenes that are believed to contribute to reduced heart disease.

The major branch pathways of flavonoid biosynthesis start with general phenylpropanoid metabolism and lead to the nine major subgroups: the colorless chalcones, aurones, isoflavonoids, flavones, flavonols, flavandiols, anthocyanins, condensed tannins, and phlobaphene pigments. The enzyme phenylalanine ammonia-lyase (PAL) of the general phenylpropanoid pathway will lead to the production of cinnamic acid. Cinnamate-4-hydroxylase (C4H) will produce p-coumaric acid which will be converted through the action of 4-coumaroyl:CoA-ligase (4CL) to the production of 4-coumaroyl-CoA and malonyl-CoA. Chalcone synthase (CHS) uses malonyl CoA and 4-coumaryl CoA as substrates. Chalcone reductase (CHR) balances the production of 5-hydroxy- or 5-deoxyflavonoids. The next enzyme, chalcone isomerase (CHI) catalyses ring closure to form a flavanone, but the reaction can also occur spontaneously. Further enzymes in the pathway are: flavanone 3-hydroxylase (F3H), dihydroflavonol 4-reductase (DFR), flavonoid 3'-hydroxylase (F3'H) and flavonoid 3', 5' hydroxylase (F3'5'H). A specific cytochrome b5 may act as an electron donor for F3'5'H enzymes.

In the branch of the phenylpropanoid pathway that is specific to condensed tannin and anthocyanin production, leucoanthocyanidins can be reduced to catechins by leucoanthocyanidin reductase (LAR) or to anthocyanidins by leucoanthocyanidin dioxygenase (LDOX). Anthocyanidins can be converted to anthocyanins by the addition of sugar groups, or to epicatechins by anthocyanidin reductase (ANR), encoded by the BANYULS gene. Catechins and epicatechins are the subunits of condensed tannins, which in *Arabidopsis* are thought to be transported into the vacuole by a multidrug secondary transporter-like protein, TRANSPARENT TESTA 12 (TT12), and polymerised by the activity of a laccase.

Enzymes in the flavonoid pathway have been found to be controlled by a range of transcription factors in *Arabidopsis*, maize and petunia. In *Arabidopsis*, condensed tannin biosynthesis requires the function of TRANSPARENT TESTA 2 (TT2), a R2R3 MYB family factor, TRANSPARENT TESTA 8 (TT8), a MYC/helix-loop-helix (bHLH) family factor and TRANSPARENT TESTA GLABRA 1 (TTG1), a WD40 family factor. These three proteins are thought to form a transcription complex that coordinately activates multiple flavonoid pathway enzymes in order to promote condensed tannin production in *Arabidopsis* seeds. Other myc and myb family transcription factors regulate distinct parts of the flavonoid pathway in maize, petunia and other plant species. Other transcription factors, including TRANSPARENT TESTA GLABRA 2 (TTG2) a WRKY box family member, TRANSPARENT TESTA 16 (TT16) a MADS box family member and TRANSPARENT TESTA 1 (TT1), a WIP family zinc finger factor, control the differentiation of condensed tannin-producing cells in the *Arabidopsis* seed coat. It is interesting that TTG2 also controls the development of trichomes in *Arabidopsis* and that glandular trichomes are the only sites of condensed tannin or monomer accumulation in vegetative organs of white clover.

A number of enzymes are involved in anthocyanin biosynthesis in plants. Anthocyanin biosynthesis begins in the cytoplasm with glycosylation and methylation of anthocyanidin molecules by flavonoid glycosyltransferases, rhamnosyltransferases and methyltransferases altering the hydrophilicity of their backbone as well as their stability and chemical properties. Addition of functional groups to flavonoids can also influence their intracellular transport and bioactivity. Expression of genes encoding glucosyltransferases has been shown to be critical for anthocyanin biosynthesis in some pigmented berries and in flower petals of some plants. Other sugar metabolism genes, including UDP glucose 4-epimerases, may be involved in the catabolism of complex carbohydrates to provide the sugar moieties used by glucosyltransferases and rhamnosyltransferases. Although anthocyanin biosynthesis occurs in the cytoplasm, anthocyanins accumulate in the vacuole of pigmented plant cells and there is evidence that specific glutathione-S-transferases and ATP-binding cassette (ABC) transporters of the multi-drug resistance-associated protein (MRP) family are involved in this subcellular transport.

While nucleic acid sequences encoding flavonoid methyltransferase (FMT), UDP glucose-3-epimerase (UG3E), glutathione-S-transferase (GST), O-methyltransferase (OMT), rhamnosyltransferase (RT), cytochrome b5 (CYTb5) and laccase-like enzymes, MADS box, WRKY, MYC, TT1, HLH and MYB transcription factors and ABC transporters, and like polypeptides, have been isolated for certain species of plants, there remains a need for materials useful in modifying flavonoid biosynthesis and metabolism; in modifying protein binding, metal chelation, anti-oxidation, and UV-light absorption; in modifying plant pigment production; in modifying plant defense to biotic stresses such as viruses, microorganisms, insects, fungal pathogens; in modifying forage quality, for example by disrupting protein foam and conferring protection from rumen pasture bloat, particularly in forage legumes, including alfalfa, medics and clovers, and for methods for their use.

It is an object of the present invention to overcome, or at least alleviate, one or more of the difficulties or deficiencies associated with the prior art.

In one aspect, the present invention provides a substantially purified or isolated nucleic acid or nucleic acid fragment encoding a polypeptide selected from the group consisting of flavonoid biosynthetic enzymes FMT, UG3E, GST, OMT, RT, CYTb5 and laccase, flavonoid biosynthesis-regulating transcription factors MADS box, WRKY, MYC, TT1, HLH and MYB, and an ABC transporter, from a clover (*Trifolium*) or medic (*Medicago*) species, complements thereof, sequences antisense thereto, and functionally active fragments and variants thereof.

The present invention also provides substantially purified or isolated nucleic acids or nucleic acid fragments encoding amino acid sequences for a class of proteins which are related to FMTs, UG3Es, GSTs, OMTs, RTs, CYTb5s and laccase enzymes, MADS box, WRKY, MYC, TT1, HLH and MYB transcription factors and ABC transporters, or functionally active fragments or variants thereof. Such proteins are referred to herein as FMT-like, UG3E-like, GST-like, OMT-like, RT-like, CYTb5-like and laccase-like, MADS box-like, WRKY-like, MYC-like, TT1-like, HLH-like and MYB-like and ABC transporter-like, respectively.

By a -like polypeptide is meant that either one of both of the following criteria apply: (i) the gene which encodes the -like polypeptide is expressed in a similar manner to the polypeptide, and (ii) the -like polypeptide has similar functional activity to the polypeptide. In a preferred embodiment, the -like polypeptide has at least approximately 70%, preferably at least approximately 80%, more preferably at least approximately 90% identity to the polypeptide.

Also provided are substantially purified or isolated nucleic acids or nucleic acid fragments complementary or antisense to nucleic acid fragments encoding -like polypeptides.

More particularly, the present invention provides a substantially purified or isolated nucleic acid or nucleic acid fragment encoding a polypeptide selected from the group consisting of flavonoid biosynthesis-regulating transcription factors MADS box, MADS box-like, WRKY, WRKY-like, MYC, MYC-like, TT1, TT1-like, HLH, HLH-like, MYB, and MYB-like; flavonoid biosynthetic enzymes FMT, FMT-like UG3E, UG3E-like, GST, GST-like, OMT, OMT-like, RT, RT-like, CYTb5, CYTb5-like, laccase and laccase-like; and flavonoid-related ABC transporter and ABC transporter-like protein; from a clover (Trifolium) or medic (Medicago) species; or a functionally active fragment or variant thereof.

The individual or simultaneous enhancement or otherwise manipulation of FMT, UG3E, GST, OMT, RT, CYTb5, laccase, MADS box, WRKY, MYC, TT1, HLH, MYB and ABC-type transporter or like gene activities in plants may enhance, reduce or otherwise alter flavonoid biosynthesis or metabolism; may enhance, reduce or otherwise alter the plant capacity for protein binding, metal chelation, anti-oxidation, and UV-light absorption; may enhance, reduce or otherwise alter plant pigment production.

The individual or simultaneous enhancement or otherwise manipulation of FMT, UG3E, GST, OMT, RT, CYTb5, laccase, MADS box, WRKY, MYC, TT1, HLH, MYB and ABC-type transporter or like gene activities in plants has significant consequences for a range of applications in, for example, plant production and plant protection. For example, it has applications in increasing plant tolerance and plant defense to biotic stresses such as viruses, microorganisms, insects and fungal pathogens; in improving plant forage quality, for example by disrupting protein foam and in conferring protection from rumen pasture bloat; in reducing digestion rates in the rumen and reducing parasitic load; in the production of plant compounds leading to health benefits, such as isoflavonoids, which have been linked to anticancer benefits, and stilbenes that are believed to contribute to reduced heart disease.

Methods for the manipulation of FMT, UG3E, GST, OMT, RT, CYTb5 and laccase, MADS box, WRKY, MYC, TT1, HLH and MYB and ABC-type transporter or like gene activities in plants, including legumes such as clovers (*Trifolium* species), lucerne (*Medicago sativa*) and medics (*Medicago* species) may facilitate the production of, for example, forage legumes and forage grasses and other crops with enhanced tolerance to biotic stresses such as viruses, microorganisms, insects and fungal pathogens; altered pigmentation in flowers; forage legumes with enhanced herbage quality and bloat-safety; crops with enhanced isoflavonoid content leading to health benefits.

The use of transcription factors to modify multiple product-specific enzymes in the flavonoid pathway may be a useful alternative strategy to cloning genes encoding many enzymes and modifying their expression in transgenic plants.

While Applicant does not wish to be restricted by theory, the down-regulation of gene(s) encoding proteins involved in the addition of functional groups to anthocyanins and their transport to the vacuole may block the anthocyanin-specific branch of the flavonoid pathway in plants by a negative feedback mechanism. This may upregulate the condensed tannin pathway, which significantly overlaps with anthocyanin biosynthesis until the biosynthesis of leucoanthocyanidins. A metabolic engineering approach that combines the down-regulation of anthocyanin-related genes with over-expression of key genes involved in condensed tannin biosynthesis, such as BAN and LAR and optionally genes involved in the general flavonoid pathway may activate the condensed tannin pathway in anthocyanin-producing cells in the foliage of pasture legumes, conferring bloat-safety.

The clover (*Trifolium*) or medic (*Medicago*) species may be of any suitable type, including white clover (*Trifolium repens*), red clover (*Trifolium pratense*), subterranean clover (*Trifolium subterraneum*) and alfalfa (*Medicago sativa*). Preferably, the species is white clover (*T. repens*) or alfalfa (*Medicago sativa*). White clover (*Trifolium repens*L.) and alfalfa (*Medicago sativa*) are key pasture legumes, in temperate climates throughout the world.

The nucleic acid or nucleic acid fragment may be of any suitable type and includes DNA (such as cDNA or genomic DNA) and RNA (such as mRNA) that is single- or double-stranded, optionally containing synthetic, non-natural or altered nucleotide bases, and combinations thereof.

Nucleic acids according to the invention may be full-length genes or part thereof, and are also referred to as "nucleic acid fragments" and "nucleotide sequences" in this specification. For convenience, the expression "nucleic acid or nucleic acid fragment" is used to cover all of these.

By 'substantially purified' is meant that the nucleic acid is free of the genes, which, in the naturally-occurring genome of the organism from which the nucleic acid of the invention is derived, flank the nucleic acid. The term therefore includes, for example, a nucleic acid which is incorporated into a vector; into an autonomously replicating plasmid or virus; or into the genomic DNA of a prokaryote or eukaryote; or which exists as a separate molecule (eg. a cDNA or a genomic or cDNA fragment produced by PCR or restriction endonuclease digestion) independent of other sequences. It also includes a nucleic acid which is part of a hybrid gene encoding additional polypeptide sequence. Preferably, the substantially purified nucleic acid is 90%, more preferably 95%, even more preferably 98% pure.

The term "isolated" means that the material is removed from its original environment (eg. the natural environment if it is naturally occurring). For example, a naturally occurring nucleic acid present in a living plant is not isolated, but the same nucleic acid separated from some or all of the coexisting materials in the natural system, is isolated. Such nucleic acids could be part of a vector and/or such nucleic acids could be part of a composition, and still be isolated in that such a vector or composition is not part of its natural environment.

Such nucleic acids or nucleic acid fragments could be assembled to form a consensus contig. As used herein, the term "consensus contig" refers to a nucleotide sequence that is assembled from two or more constituent nucleotide sequences that share common or overlapping regions of sequence homology. For example, the nucleotide sequence of two or more nucleic acids or nucleic acid fragments can be compared and aligned in order to identify common or overlapping sequences. Where common or overlapping sequences exist between two or more nucleic acids or nucleic acid fragments, the sequences (and thus their corresponding nucleic acids or nucleic acid fragments) can be assembled into a single contiguous nucleotide sequence.

In a preferred embodiment, the present invention provides a substantially purified or isolated nucleic acid or nucleic acid fragment encoding a polypeptide selected from the group consisting of FMT, UG3E, GST, OMT, RT, CYTb5, laccase, MADS box, WRKY, MYC, TT1, HLH, MYB and ABC-type transporter proteins, or complementary or antisense to a sequence encoding said polypeptide, and including a nucleotide sequence selected from the group consisting of (a) the sequences shown in FIGS. 1, 3, 4, 6, 7, 9, 10, 12, 13, 15, 17, 20, 23, 25, 26, 28, 30, 32, 35, 37, 38, 40, 41, 43 45 and 48 hereto; (b) the complements of the sequences recited in (a); (c) the sequences antisense to the sequences recited in (a) and (b); and (d) functionally active fragments and variants of the sequences recited in (a), (b) and (c).

By "functionally active" in relation to nucleic acids it is meant that the fragment or variant (such as an analogue, derivative or mutant) encodes a polypeptide which is capable of modifying flavonoid biosynthesis; in a plant. Such variants include naturally occurring allelic variants and non-naturally occurring variants. Additions, deletions, substitutions and derivatizations of one or more of the nucleotides are contemplated so long as the modifications do not result in loss of functional activity of the fragment or variant. Preferably the functionally active fragment or variant has at least approximately 80% identity to the relevant part of the nucleotide sequence upon which the fragment or variant is based, more preferably at least approximately 90% identity, even more preferably at least approximately 95% identity, most preferably at least approximately 98% identity. Such functionally active variants and fragments include, for example, those having conservative nucleic acid changes. By 'conservative nucleic acid changes' is meant nucleic acid substitutions that result in conservation of the same amino acid in the encoded protein, due to the degeneracy of the genetic code. Such functionally active variants and fragments also include, for example, those having nucleic acid changes which result in conservative amino acid substitutions of one or more residues in the corresponding amino acid sequence. By 'conservative amino acid substitutions' is meant the substitution of an amino acid by another one of the same class, the classes being as follows:

```
Nonpolar: Ala, Val, Leu, Ile, Pro, Met Phe, Trp
Uncharged polar: Gly, Ser, Thr, Cys, Tyr, Asn, Gln
Acidic: Asp, Glu
Basic: Lys, Arg, His
```

Other conservative amino acid substitutions may also be made as follows:

```
Aromatic: Phe, Tyr, His
Proton Donor: Asn, Gln, Lys, Arg, His, Trp
Proton Acceptor: Glu, Asp, Thr, Ser, Tyr, Asn, Gln
```

Preferably the fragment has a size of at least 30 nucleotides, more preferably at least 45 nucleotides, more preferably at least 60 nucleotides, more preferably at least 100 nucleotides, even more preferably at least 150 nucleotides.

In a preferred embodiment, the present invention provides a substantially purified or isolated nucleic acid or nucleic acid fragment encoding an FMT or FMT-like protein, or complementary or antisense to a sequence encoding an FMT or FMT-like protein, and including a nucleotide sequence selected from the group consisting of (a) the sequences shown in FIGS. 1 and 3 hereto (Sequence ID Nos: 1 and 3-10); (b) the complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a UG3E or UG3E-like protein, or complementary or antisense to a sequence encoding a UG3E or UG3E-like protein, and including a nucleotide sequence selected from the group consisting of (a) the sequences shown in FIGS. 4 and 6 hereto (Sequence ID Nos: 11, 13 and 14); (b) the complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a GST or GST-like protein, or complementary or antisense to a sequence encoding a GST or GST-like protein, and including a nucleotide sequence selected from the group consisting of (a) the sequences shown in FIGS. 7 and 9 hereto (Sequence ID Nos: 15, 17 and 18); (b) the complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding an OMT or OMT-like protein, or complementary or antisense to a sequence encoding an OMT or OMT-like protein, and including a nucleotide sequence selected from the group consisting of (a) the sequences shown in FIGS. 10 and 12 hereto (Sequence ID Nos: 19 and 21-29); (b) the complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding an RT or RT-like protein, or complementary or antisense to a sequence encoding a RT or RT-like protein, and including a nucleotide sequence selected from the group consisting of (a) the sequence shown in FIG. 13 hereto (Sequence ID No: 30); (b) the complement of the sequence recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a CYTb5 or CYTb5-like protein, or complementary or antisense to a sequence encoding a CYTb5 or CYTb5-like protein, and including a nucleotide sequence selected from the group consisting of (a) the sequence shown in FIG. 15 hereto (Sequence ID No: 32); (b) the complement of the sequence recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a laccase or laccase-like protein, or complementary or antisense to a sequence encoding a laccase or laccase-like protein, and including a nucleotide sequence selected from the group consisting of (a) sequences shown in FIGS. 17 and 20 hereto (Sequence ID Nos: 34 and 36, respectively); (b) complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a MADS box or MADS box-like protein, or complementary or antisense to a sequence encoding a MADS box or MADS box-like protein, and including a nucleotide sequence selected from the group consisting of (a) the sequences shown in FIGS. 23 and 25 hereto (Sequence ID Nos: 38 and 40-43); (b) the complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a WRKY or WRKY-like protein, or complementary or antisense to a sequence encoding a WRKY or WRKY-like protein, and including a nucleotide sequence selected from the group consisting of (a) the sequence shown in FIG. 26 hereto (Sequence ID No: 44); (b) the complement of the sequence recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a MYC or MYC-like protein, or complementary or antisense to a sequence encoding a MYC or MYC-like protein, and including a nucleotide sequence selected from the group consisting of (a) sequences shown in FIGS. 28, 30 and 32 hereto (Sequence ID Nos: 46, 48, 49 and 50); (b) complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a TT1 or TT1-like protein, or complementary or antisense to a sequence encoding a TT1 or TT1-like protein, and including a nucleotide sequence selected from the group consisting of (a) the sequences shown in FIGS. 35 and 37 hereto (Sequence ID Nos: 52, 54 and 55); (b) the complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding an HLH or HLH-like protein, or complementary or antisense to a sequence encoding an HLH or HLH-like protein, and including a nucleotide sequence selected from the group consisting of (a) the sequences shown in FIGS. 38 and 40 hereto (Sequence ID Nos: 5, 56, 58 and 59); (b) the complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding a MYB or MYB-like protein, or complementary or antisense to a sequence encoding a MYB or MYB-like protein, and including a nucleotide sequence selected from the group consisting of (a) sequences shown in FIGS. 41, 43 and 45 hereto (Sequence ID Nos: 60, 62, 63 and 64); (b) complements of the sequences recited in (a); (c) sequences antisense to the sequences recited in (a) and (b); and (d) functionally active fragments and variants of the sequences recited in (a), (b) and (c).

In a preferred embodiment, the present invention provides a substantially purified or isolated nucleic acid or nucleic acid fragment encoding an ABC transporter or ABC transporter-like protein, or complementary or antisense to a sequence encoding a ABC transporter or ABC transporter-like protein, and including a nucleotide sequence selected from the group consisting of (a) the sequence shown in FIG. 48 hereto (Sequence ID No: 66); (b) the complement of the sequence recited in (a); (c) sequences antisense to the sequences recited in (a) and (b); and (d) functionally active fragments and variants of the sequences recited in (a), (b) and (c).

In a particularly preferred embodiment, the present invention provides a substantially purified or isolated nucleic acid or nucleic acid fragment comprising a nucleotide sequence selected from the group consisting of the sequences shown in FIGS. 1, 3 4, 6 7, 9 10, 12, 13, 15, 17, 20, 23, 25, 26, 28, 30, 32, 35, 37, 38, 39, 41, 43, 45 and 48 hereto; and the sequences complementary and antisense thereto.

Nucleic acids or nucleic acid fragments encoding at least a portion of FMT, UG3E, GST, OMT, RT, CYTb5, laccase, MADS box, WRKY, MYC, TT1, HLH, MYB and ABC-type transporter orthologs have been isolated and identified. The nucleic acids or nucleic acid fragments of the present invention may be used to isolate cDNAs and genes encoding homologous proteins from the same or other plant species. Isolation of homologous genes using sequence-dependent protocols, such as methods of nucleic acid hybridisation, and methods of DNA and RNA amplification as exemplified by various uses of nucleic acid amplification technologies (e.g. polymerase chain reaction, ligase chain reaction), is well known in the art.

For example, genes encoding other FMT, UG3E, GST, OMT, RT, CYTb5, laccase, MADS box, WRKY, MYC, TT1, HLH, MYB and ABC-type transporter proteins, either as cDNAs or genomic DNAs, may be isolated directly by using all or a portion of the nucleic acids or nucleic acid fragments of the present invention as hybridisation probes to screen libraries from the desired plant employing the methodology well known to those skilled in the art. Specific oligonucleotide probes based upon the nucleic acid sequences of the present invention may be designed and synthesized by methods known in the art. Moreover, the entire sequences may be used directly to synthesize DNA probes by methods known to the skilled artisan such as random primer DNA labelling, nick translation, or end-labelling techniques, or RNA probes using available in vitro transcription systems. In addition, specific primers may be designed and used to amplify a part or all of the sequences of the present invention. The resulting amplification products may be labelled directly during amplification reactions or labelled after amplification reactions, and used as probes to isolate full-length cDNA or genomic fragments under conditions of appropriate stringency.

In addition, short segments of the nucleic acids or nucleic acid fragments of the present invention may be used in protocols to amplify longer nucleic acids or nucleic acid fragments encoding homologous genes from DNA or RNA. For example, polymerase chain reaction may be performed on a library of cloned nucleic acid fragments wherein the sequence of one primer is derived from the nucleic acid sequences of the present invention, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, those skilled in the art can follow the RACE protocol (Frohman et al. (1988) *Proc. Natl. Acad Sci. USA* 85:8998, the entire disclosure of which is incorporated herein by reference) to generate cDNAs by using PCR to amplify copies of the region between a single point in the transcript and the 3' or 5' end. Using commercially available 3' RACE and 5' RACE systems (BRL), specific 3' or 5' cDNA fragments may be isolated (Ohara et al. (1989) *Proc. Natl. Acad Sci USA* 86:5673; Loh et al. (1989) *Science* 243:217, the entire disclosures of which are incorporated herein by reference). Products generated by the 3' and 5' RACE procedures may be combined to generate full-length cDNAs.

In a second aspect of the present invention there is provided a substantially purified or isolated polypeptide from a clover (*Trifolium*) or medic (*Medicago*), species, selected from the group consisting of FMT, UG3E, GST, OMT, RT, CYTb5, laccase, MADS box, WRKY, MYC, TT1, HLH, MYB and ABC transporter and like proteins; and functionally active fragments and variants thereof.

The clover (*Trifolium*) or medic (*Medicago*) species may be of any suitable type, including white clover (*Trifolium repens*), red clover (*Trifolium pratense*), subterranean clover (*Trifolium subterraneum*) and alfalfa (*Medicago sativa*). Preferably, the species is white clover (*T. repens*) or alfalfa (*M. sativa*).

In a preferred embodiment, the present invention provides a substantially purified or isolated polypeptide selected from the group consisting of FMT, UG3E, GST, OMT, RT, CYTb5, laccase, MADS box, WRKY, MYC, TT1, HLH, MYB and ABC transporter polypeptides, said polypeptide including an amino acid sequence selected from the group consisting of sequences shown in FIGS. 2, 5, 8, 11, 14, 16, 18, 21, 24, 27, 29, 33, 36, 39, 42, 46 and 49 hereto, and functionally active fragments and variants thereof.

By "functionally active" in relation to polypeptides it is meant that the fragment or variant has one or more of the biological properties of the polypeptide upon which the fragment or variant is based. Additions, deletions, substitutions and derivatizations of one or more of the amino acids are contemplated so long as the modifications do not result in loss of functional activity of the fragment or variant. Preferably the functionally active fragment or variant has at least approximately 80% identity to the relevant part of the amino acid sequence upon which the fragment or variant is based, more preferably at least approximately 90% identity, even more preferably at least approximately 95% identity, most preferably at least approximately 98% identity. Such functionally active variants and fragments include, for example, those having conservative amino acid substitutions of one or more residues in the corresponding amino acid sequence. By 'conservative amino acid substitutions' is meant the substitution of an amino acid by another one of the same class, the classes being as follows:

Nonpolar: Ala, Val, Leu, Ile, Pro, Met Phe, Trp

Uncharged polar: Gly, Ser, Thr, Cys, Tyr, Asn, Gln

Acidic: Asp, Glu

Basic: Lys, Arg, His

Other conservative amino acid substitutions may also be made as follows:

Aromatic: Phe, Tyr, His

Proton Donor: Asn, Gln, Lys, Arg, His, Trp

Proton Acceptor: Glu, Asp, Thr, Ser, Tyr, Asn, Gln

Preferably the fragment has a size of at least 10 amino acids, more preferably at least 15 amino acids, more preferably at least 20 amino acids, more preferably at least 50 amino acids.

In a preferred embodiment, the present invention provides a substantially purified or isolated FMT or FMT-like polypeptide including an amino acid sequence shown in FIG. 2 hereto (Sequence ID No: 2); or a functionally active fragment or variant thereof.

In a preferred embodiment, the present invention provides a substantially purified or isolated UG3E or UG3E-like polypeptide including an amino acid sequence shown in FIG. 5 hereto (Sequence ID No: 12); or a functionally active fragment or variant thereof.

In a preferred embodiment, the present invention provides a substantially purified or isolated GST or GST-like polypeptide including an amino acid sequence shown in FIG. 8 hereto (Sequence ID No: 16); or a functionally active fragment or variant thereof.

In a preferred embodiment, the present invention provides a substantially purified or isolated OMT or OMT-like polypeptide including an amino acid sequence shown in FIG. 11 hereto (Sequence ID No: 20); or a functionally active fragment or variant thereof.

In a preferred embodiment, the present invention provides a substantially purified or isolated RT or RT-like polypeptide including an amino acid sequence shown in FIG. 14 hereto (Sequence ID No: 31); or a functionally active fragment or variant thereof.

In a preferred embodiment, the present invention provides a substantially purified or isolated CYTb5 or CYTb5-like polypeptide including an amino acid sequence shown in FIG. 16 hereto (Sequence ID No: 33); or a functionally active fragment or variant thereof.

In a preferred embodiment, the present invention provides a substantially purified or isolated laccase or laccase-like polypeptide including an amino acid sequence selected from the group consisting of sequences shown in FIGS. 18 and 21 hereto (Sequence ID Nos: 35 and 37, respectively); and functionally active fragments and variants thereof.

In a preferred embodiment, the present invention provides a substantially purified or isolated MADS box or MADS box-like polypeptide including an amino acid sequence shown in FIG. 24 hereto (Sequence ID No: 39); or a functionally active fragment or variant thereof.

In a preferred embodiment, the present invention provides a substantially purified or isolated WRKY or WRKY-like polypeptide including an amino acid sequence shown in FIG. 27 hereto (Sequence ID No: 45); or a functionally active fragment or variant thereof.

In a preferred embodiment, the present invention provides a substantially purified or isolated MYC or MYC-like polypeptide including an amino acid sequence selected from the group consisting of sequences shown in FIGS. 29 and 33 hereto (Sequence ID Nos: 47 and 51, respectively); and functionally active fragments and variants thereof.

In a preferred embodiment, the present invention provides a substantially purified or isolated TT1 or TT1-like polypeptide including an amino acid sequence shown in FIG. 36 hereto (Sequence ID No: 53); or a functionally active fragment or variant thereof.

In a preferred embodiment, the present invention provides a substantially purified or isolated HLH or HLH-like polypeptide including an amino acid sequence shown in FIG. 39 hereto (Sequence ID No: 57); or a functionally active fragment or variant thereof.

In a preferred embodiment, the present invention provides a substantially purified or isolated MYB or MYB-like polypeptide including an amino acid sequence selected from the group consisting of sequences shown in FIGS. 42 and 46 hereto (Sequence ID Nos: 61 and 65, respectively); and functionally active fragments and variants thereof.

In a preferred embodiment, the present invention provides a substantially purified or isolated ABC transporter or ABC transporter-like polypeptide including an amino acid sequence shown in FIG. 49 hereto (Sequence ID No: 67); or a functionally active fragment or variant thereof.

In a particularly preferred embodiment, the present invention provides a substantially purified or isolated polypeptide comprising an amino acid sequence selected from the group consisting of sequences shown in FIGS. 2, 5, 8, 11, 14, 16, 18, 21, 24, 27, 29, 33, 36, 39, 42, 46 and 49 hereto.

In a further embodiment of this aspect of the invention, there is provided a polypeptide recombinantly produced from a nucleic acid or nucleic acid fragment according to the present invention. Techniques for recombinantly producing polypeptides are known to those skilled in the art.

Availability of the nucleotide sequences of the present invention and deduced amino acid sequences facilitates immunological screening of cDNA expression libraries. Synthetic peptides representing portions of the instant amino acid sequences may be synthesized. These peptides may be used to immunise animals to produce polyclonal or monoclonal antibodies with specificity for peptides and/or proteins including the amino acid sequences. These antibodies may be then used to screen cDNA expression libraries to isolate full-length cDNA clones of interest.

In a still further aspect of the present invention there is provided a method of isolating a nucleic acid or nucleic acid fragment of the present invention said method including sequencing nucleic acid fragments from a nucleic acid library.

The nucleic acid library may be of any suitable type and is preferably a cDNA library.

The nucleic acid or nucleic acid fragment may be isolated from a recombinant plasmid or may be amplified, for example using polymerase chain reaction.

The sequencing may be performed by techniques known to those skilled in the art.

In a still further aspect of the present invention there is provided use of a nucleic acid or nucleic acid fragment of the present invention, and/or nucleotide sequence information thereof, as a molecular genetic marker.

More particularly, nucleic acids or nucleic acid fragments according to the present invention and/or nucleotide sequence information thereof may be used as a molecular genetic marker for quantitative trait loci (QTL) tagging, QTL mapping, DNA fingerprinting and in marker assisted selection, particularly in clovers, alfalfa and medics. Even more particularly, nucleic acids or nucleic acid fragments according to the present invention and/or nucleotide sequence information thereof may be used as molecular genetic markers in plant improvement in relation to plant tolerance to biotic stresses such as viruses, microorganisms, insects, fungal pathogens; in relation to forage quality; in relation to bloat safety; in relation to condensed tannin content; in relation to plant pigmentation. Even more particularly, sequence information revealing SNPs in allelic variants of the nucleic acids or nucleic acid fragments of the present invention and/or nucleotide sequence information thereof may be used as molecular genetic markers for QTL tagging and mapping and in marker assisted selection, particularly in clovers, alfalfa and medics.

In a still further aspect of the present invention there is provided a construct including a nucleic acid or nucleic acid fragment according to the present invention.

The term "construct" as used herein refers to an artificially assembled or isolated nucleic acid molecule which includes the gene of interest. In general a construct may include the gene or genes of interest, a marker gene which in some cases can also be the gene of interest and appropriate regulatory sequences. It should be appreciated that the inclusion of regulatory sequences in a construct is optional, for example, such sequences may not be required in situations where the regulatory sequences of a host cell are to be used. The term construct includes vectors but should not be seen as being limited thereto.

In a still further aspect of the present invention there is provided a vector including a nucleic acid or nucleic acid fragment according to the present invention.

The term "vector" as used herein encompasses both cloning and expression vectors. Vectors are often recombinant molecules containing nucleic acid molecules from several sources.

In a preferred embodiment of this aspect of the invention, the vector may include a regulatory element such as a promoter, a nucleic acid or nucleic acid fragment according to the present invention and a terminator; said regulatory element, nucleic acid or nucleic acid fragment and terminator being operatively linked.

By "operatively linked" is meant that said regulatory element is capable of causing expression of said nucleic acid or nucleic acid fragment in a plant cell and said terminator is capable of terminating expression of said nucleic acid or nucleic acid fragment in a plant cell. Preferably, said regulatory element is upstream of said nucleic acid or nucleic acid fragment and said terminator is downstream of said nucleic acid or nucleic acid fragment.

The vector may be of any suitable type and may be viral or non-viral. The vector may be an expression vector. Such vectors include chromosomal, non-chromosomal and synthetic nucleic acid sequences, eg. derivatives of plant viruses;

bacterial plasmids; derivatives of the Ti plasmid from *Agrobacterium tumefaciens*, derivatives of the Ri plasmid from *Agrobacterium rhizogenes*; phage DNA; yeast artificial chromosomes; bacterial artificial chromosomes; binary bacterial artificial chromosomes; vectors derived from combinations of plasmids and phage DNA. However, any other vector may be used as long as it is replicable, integrative or viable in the plant cell.

The regulatory element and terminator may be of any suitable type and may be endogenous to the target plant cell or may be exogenous, provided that they are functional in the target plant cell.

Preferably the regulatory element is a promoter. A variety of promoters which may be employed in the vectors of the present invention are well known to those skilled in the art. Factors influencing the choice of promoter include the desired tissue specificity of the vector, and whether constitutive or inducible expression is desired and the nature of the plant cell to be transformed (eg. monocotyledon or dicotyledon). Particularly suitable constitutive promoters include the Cauliflower Mosaic Virus 35S (CaMV 35S) promoter.

A variety of terminators which may be employed in the vectors of the present invention are also well known to those skilled in the art. The terminator may be from the same gene as the promoter sequence or a different gene. Particularly suitable terminators are polyadenylation signals, such as the CaMV 35S polyA and other terminators from the nopaline synthase (nos) and the octopine synthase (ocs) genes.

The vector, in addition to the regulatory element, the nucleic acid or nucleic acid fragment of the present invention and the terminator, may include further elements necessary for expression of the nucleic acid or nucleic acid fragment, in different combinations, for example vector backbone, origin of replication (ori), multiple cloning sites, spacer sequences, enhancers, introns (such as the maize Ubiquitin Ubi intron), antibiotic resistance genes and other selectable marker genes [such as the neomycin phosphotransferase (npt2) gene, the hygromycin phosphotransferase (hph) gene, the phosphinothricin acetyltransferase (bar or pat) gene], and reporter genes (such as beta-glucuronidase (GUS) gene (gusA)]. The vector may also contain a ribosome binding site for translation initiation. The vector may also include appropriate sequences for amplifying expression.

As an alternative to use of a selectable marker gene to provide a phenotypic trait for selection of transformed host cells, the presence of the vector in transformed cells may be determined by other techniques well known in the art, such as PCR (polymerase chain reaction), Southern blot hybridisation analysis, histochemical GUS assays, northern and Western blot hybridisation analyses.

Those skilled in the art will appreciate that the various components of the vector are operatively linked, so as to result in expression of said nucleic acid or nucleic acid fragment. Techniques for operatively linking the components of the vector of the present invention are well known to those skilled in the art. Such techniques include the use of linkers, such as synthetic linkers, for example including one or more restriction enzyme sites.

The vectors of the present invention may be incorporated into a variety of plants, including dicotyledons (such as *arabidopsis*, tobacco, clovers, medics, eucalyptus, potato, sugarbeet, canola, soybean, chickpea), monocotyledons (such as grasses from the genera *Lolium, Festuca, Paspalum, Pennisetum, Panicum* and other forage and turfgrasses, corn, oat, sugarcane, wheat and barley) and gymnosperms. In a preferred embodiment, the vectors may be used to transform dicotyledons, preferably forage legume species such as clovers (*Trifolium* species) and medics (*Medicago* species), more preferably white clover (*Trifolium repens*), red clover (*Trifolium pratense*), subterranean clover (*Trifolium subterraneum*) and alfalfa (*Medicago sativa*). Clovers, alfalfa and medics are key pasture legumes in temperate climates throughout the world.

Techniques for incorporating the vectors of the present invention into plant cells (for example by transduction, transfection or transformation) are well known to those skilled in the art. Such techniques include *Agrobacterium* mediated introduction, electroporation to tissues, cells and protoplasts, protoplast fusion, injection into reproductive organs, injection into immature embryos and high velocity projectile introduction to cells, tissues, calli, immature and mature embryos. The choice of technique will depend largely on the type of plant to be transformed.

Cells incorporating the vectors of the present invention may be selected, as described above, and then cultured in an appropriate medium to regenerate transformed plants, using techniques well known in the art. The culture conditions, such as temperature, pH and the like, will be apparent to the person skilled in the art. The resulting plants may be reproduced, either sexually or asexually, using methods well known in the art, to produce successive generations of transformed plants.

In a further aspect of the present invention there is provided a plant cell, plant, plant seed or other plant part, including, e.g. transformed with, a vector or construct, nucleic acid or nucleic acid fragment of the present invention.

The plant cell, plant, plant seed or other plant part may be from any suitable species, including dicotyledons, moncotyledons and gymnosperms. In a preferred embodiment the plant cell, plant, plant seed or other plant part may be from a dicotyledon, preferably forage legume species such as clovers (*Trifolium* species) and medics (*Medicago* species), more preferably white clover (*Trifolium* repens), red clover (*Trifolium pratense*), subterranean clover (*Trifolium subterraneum*) and alfalfa (*Medicago sativa*).

The present invention also provides a plant, plant seed or other plant part, or a plant extract derived from a plant cell or plant of the present invention and preferably including e.g. transformed with, a vector or construct, nucleic acid or nucleic acid fragment of the present invention.

In a further aspect of the present invention there is provided a method of modifying flavonoid biosynthesis or metabolism; of modifying protein binding, metal chelation, anti-oxidation or UV-light absorption; of modifying plant pigment production; of modifying plant defense to biotic stresses such as viruses, microorganisms, insects, fungal pathogens; or of modifying forage quality by disrupting protein foam and conferring protection from rumen pasture bloat; said method including introducing into said plant an effective amount of a nucleic acid or nucleic acid fragment, construct and/or vector according to the present invention.

By "an effective amount" it is meant an amount sufficient to result in an identifiable phenotypic trait in said plant, or a plant, plant seed or other plant part derived therefrom. Such amounts can be readily determined by an appropriately skilled person, taking into account the type of plant, the route of administration and other relevant factors. Such a person will readily be able to determine a suitable amount and method of administration. See, for example, Maniatis et al, Molecular Cloning: A Laboratory Manual, Cold Spring Harbor Laboratory, Cold Spring Harbor, the entire disclosure of which is incorporated herein by reference.

Using the methods and materials of the present invention, flavonoid biosynthesis or metabolism, protein binding, metal chelation, anti-oxidation, UV-light absorption, tolerance to biotic stresses such as viruses, microorganisms, insects and fungal pathogens; pigmentation in for example flowers and leaves; herbage quality and bloat-safety; isoflavonoid content leading to health benefits, may be increased, decreased or otherwise altered, in a transformed plant relative to an untransformed control plant, for example by incorporating additional copies of a sense nucleic acid or nucleic acid fragment of the present invention, preferably to overexpress the polypeptide or in sense suppression. They may be decreased or otherwise altered, for example by incorporating an antisense nucleic acid or nucleic acid fragment of the present invention.

One or more nucleic acids of the present invention may be used in the methods, constructs and vectors of the present invention, optionally in combination with one or more nucleic acids described in Applicant's earlier patent applications AU 2002333038, PCT/AU2006/001020 and PCT/AU2006/001590, the entire disclosures of which are incorporated herein by reference.

The present invention will now be more fully described with reference to the accompanying Examples and drawings. It should be understood, however, that the description following is illustrative only and should not be taken in any way as a restriction on the generality of the invention described above.

IN THE FIGURES

FIG. 1 shows the consensus nucleotide sequence of TrFMTa (SEQ ID No: 1)

FIG. 2 shows the deduced amino acid sequence of TrFMTa (SEQ ID No: 2).

FIG. 3 shows the nucleotide sequences of nucleic acid fragments contributing to the consensus sequence of TrFMTa (SEQ ID Nos: 3-10).

FIG. 4 shows the consensus nucleotide sequence of TrUG3Ea (SEQ ID No: 11).

FIG. 5 shows the deduced amino acid sequence of TrUG3Ea (SEQ ID No: 12).

FIG. 6 shows the nucleotide sequences of nucleic acid fragments contributing to the consensus sequence of TrUG3Ea (SEQ ID Nos: 13 and 14).

FIG. 7 shows the consensus nucleotide sequence of TrGSTa (SEQ ID No: 15).

FIG. 8 shows the deduced amino acid sequence of TrGSTa (SEQ ID No: 16).

FIG. 9 shows the nucleotide sequences of nucleic acid fragments contributing to the consensus sequence of TrGSTa (SEQ ID Nos: 17 and 18).

FIG. 10 shows the consensus nucleotide sequence of TrOMTa (SEQ ID No: 19).

FIG. 11 shows the deduced amino acid sequence of TrOMTa (SEQ ID No: 20).

FIG. 12 shows the nucleotide sequences of nucleic acid fragments contributing to the consensus sequence of TrOMTa (SEQ ID Nos: 21-29).

FIG. 13 shows the nucleotide sequence of TrRTa (SEQ ID No: 30).

FIG. 14 shows the deduced amino acid sequence of TrRTa (SEQ ID No: 31).

FIG. 15 shows the nucleotide sequence of TrCYTb5a (SEQ ID No: 32).

FIG. 16 shows the deduced amino acid sequence of TrCyTb5a (SEQ ID No: 33).

FIG. 17 shows the nucleotide sequence of TrLACa (SEQ ID No: 34).

FIG. 18 shows the deduced amino acid sequence of TrLACa (SEQ ID No: 35).

FIG. 20 shows the full nucleotide sequence of the white clover TrLACa cDNA (SEQ ID No: 36).

FIG. 21 shows the deduced amino acid sequence of the TrLACa cDNA (SEQ ID No: 37).

FIG. 22 shows plasmid maps of the cDNA encoding TrLACa in the sense and antisense orientations in the pPZP221 binary transformation vector FIG. 23 shows the consensus nucleotide sequence of TrMADSa (SEQ ID No: 38).

FIG. 24 shows the deduced amino acid sequence of TrMADSa (SEQ ID No: 39).

FIG. 25 shows the nucleotide sequences of nucleic acid fragments contributing to the consensus sequence of TrMADSa (SEQ ID Nos: 40-43).

FIG. 26 shows the nucleotide sequence of TrWRKYa (SEQ ID No: 44).

FIG. 27 shows the deduced amino acid sequence of TrWRKYa (SEQ ID No: 45).

FIG. 28 shows the consensus nucleotide sequence of TrMYCa (SEQ ID No: 46).

FIG. 29 shows the deduced amino acid sequence of TrMYCa (SEQ ID No: 47).

FIG. 30 shows the nucleotide sequences of nucleic acid fragments contributing to the consensus sequence of TrMYCa (SEQ ID Nos: 48-49).

FIG. 32 shows the full nucleotide sequence of the TrMYCa cDNA (SEQ ID No: 50).

FIG. 33 shows the deduced amino acid sequence of the TrMYCa cDNA (SEQ ID No: 51).

FIG. 34 shows plasmid maps of the cDNA encoding TrMYCa in the sense and antisense orientations in the pPZP221 binary transformation vector FIG. 35 shows the consensus nucleotide sequence of TrTT1a (SEQ ID No: 52).

FIG. 36 shows the deduced amino acid sequence of TrTT1a (SEQ ID No: 53).

FIG. 37 shows the nucleotide sequences of nucleic acid fragments contributing to the consensus sequence of TrTT1a (SEQ ID Nos: 54-55).

FIG. 38 shows the consensus nucleotide sequence of TrHLHa (SEQ ID No: 56).

FIG. 39 shows the deduced amino acid sequence of TrHLHa (SEQ ID No: 57).

FIG. 40 shows the nucleotide sequences of nucleic acid fragments contributing to the consensus sequence of TrHLHa (SEQ ID Nos: 58 and 59).

FIG. 41 shows the consensus nucleotide sequence of TrMYBa (SEQ ID No: 60).

FIG. 42 shows the deduced amino acid sequence of TrMYBa (SEQ ID No: 61).

FIG. 43 shows the nucleotide sequences of nucleic acid fragments contributing to the consensus sequence of TrMYBa (SEQ ID Nos: 62-63).

FIG. 45 shows the full nucleotide sequence of the TrMYBa cDNA (SEQ ID No: 64).

FIG. 46 shows the deduced amino acid sequence of the TrMYBa cDNA (SEQ ID No: 65).

FIG. 47 shows plasmid maps of the cDNA encoding TrMYBa in the sense and antisense orientations in the pPZP221 binary transformation vector FIG. 48 shows the nucleotide sequence of TrABCa (SEQ ID No: 66).

FIG. 49 shows the deduced amino acid sequence of TrABCa (SEQ ID No: 67).

Figure 51:
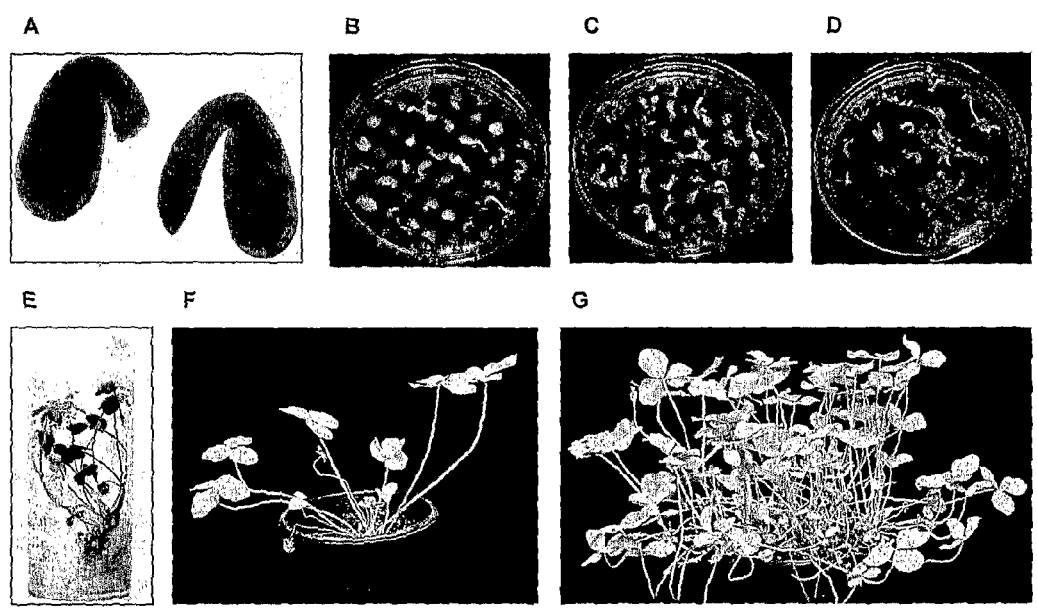
Figure 52:
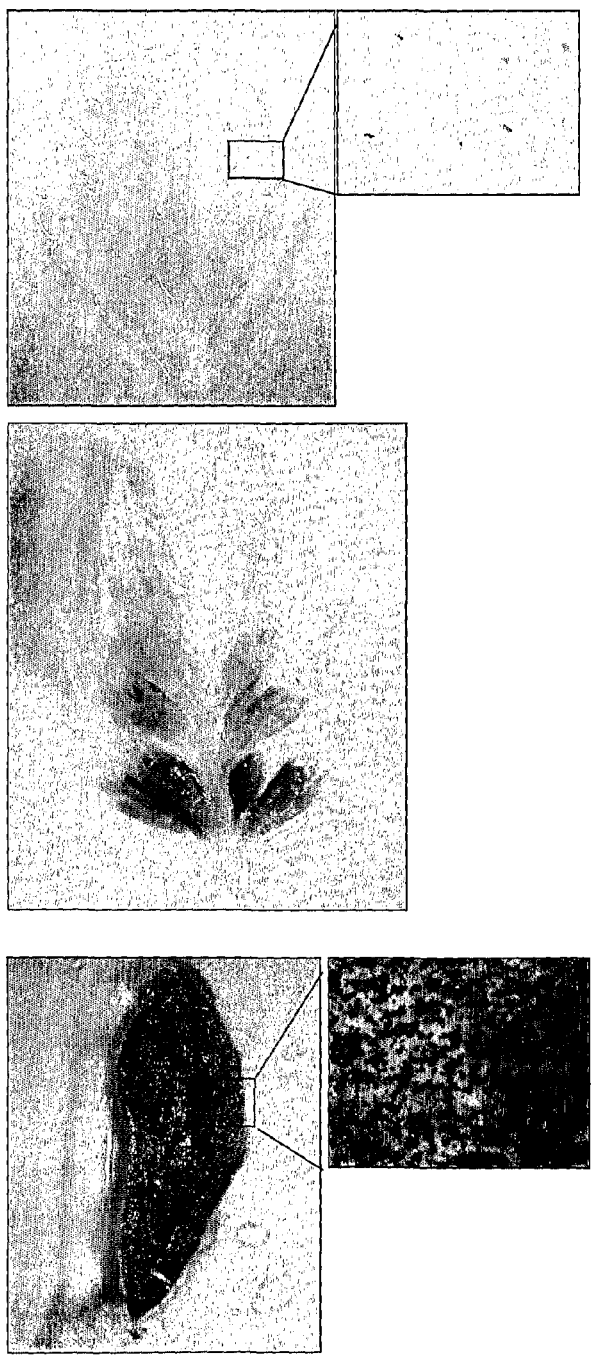

FIG. 51 shows the steps of selection during *Agrobacterium*-mediated white clover transformation FIG. 52 shows 4-dimethylaminocinnemaldehyde (DMACA) staining patterns in *Trifolium repens* (cv 'Mink') leaf and immature inflorescence tissue and in *Lotus corniculatus* (cv 'Draco') leaf tissue FIG. 53 shows the results of microarray (lines) and real-time RT-PCR (bars) analyses of TrMYB24a expression in upper and lower halves of white clover (cv Mink) inflorescences at three stages of development (upper panel). Real-time RT-PCR analysis was also used to test TrMYB24a expression in sepals (dark bars) or remaining floral organs (florets without sepals; light bars) from florets at 4 stages of development (lower panel). More particularly, the graphs show expression of TrMYB24a normalised against expression of the elongation factor 1 alpha (EF-1α) control gene. Complementary DNA from white clover (cv Mink) upper, lower and whole buds was tested by real-time RT-PCR using SYBR Green chemistry, primer sets designed using cDNA clones of flavonoid-related genes (Table 4). Microarray analysis was performed using custom-made 12K Combimatrix slides containing oligonucleotide probes based on white clover cDNA sequences. All experiments were performed in triplicate.

FIG. 54 shows an alignment of the conserved R2 and R3 MYB domains of TrMYB24a and corresponding regions of R2R3 MYB proteins from the plant species *Petunia hybrida, Antirrhinum majus, Arabidopsis thaliana, Vitus vinifera, Zea mays, Oryza sativa, Lycopersicon esculentum* and *Picea mariana*.

Figure 55:
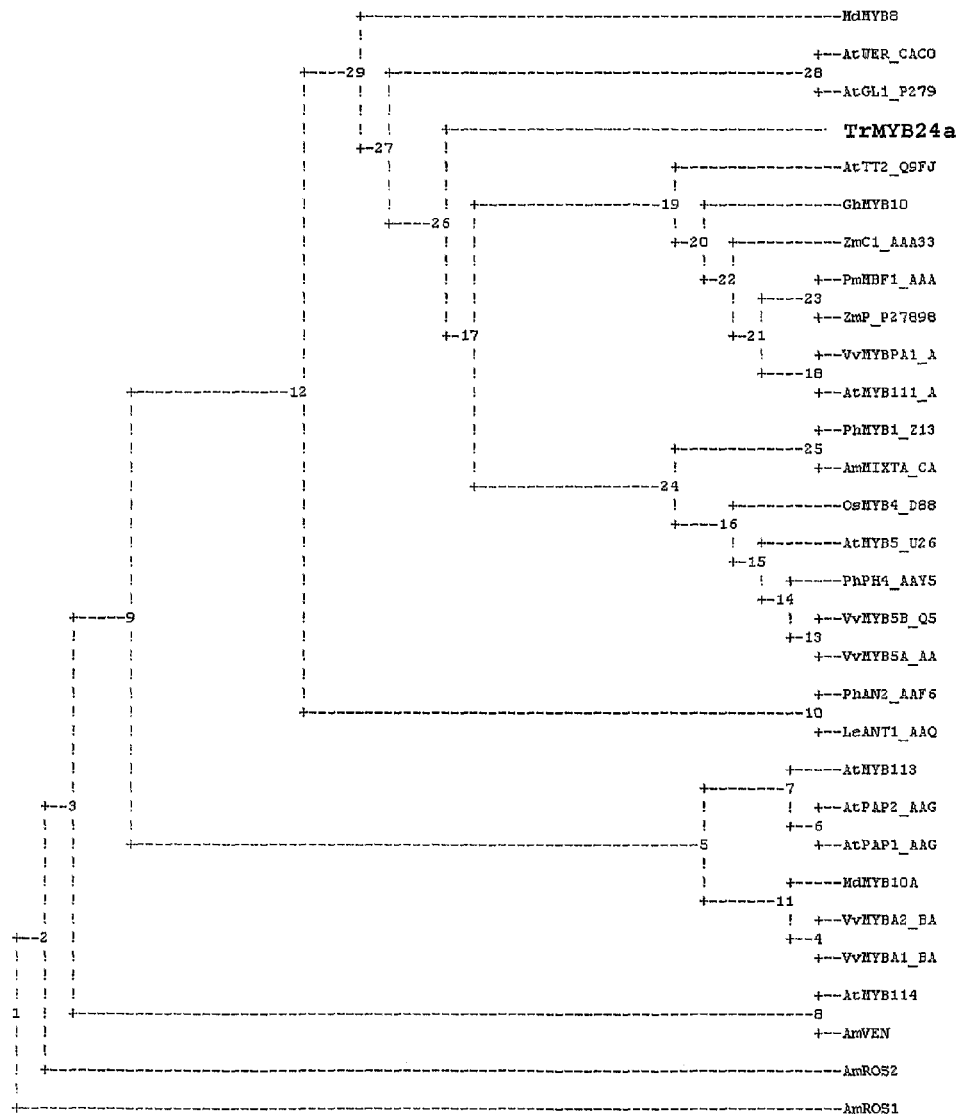

FIG. 55 shows a phylogenetic tree based on parsimony, comparing the amino acid sequences of TrMYB24a and R2R3 MYB proteins from the plant species *Malus domestica, Arabidopsis thaliana, Gossypium hirsutum, Zea mays, Petunia hybrida, Vitus vinifera, Antirrhinum majus, Oryza sativa, Lycopersicon esculentum* and *Antirrhinum majus*.

EXAMPLE 1

Preparation of cDNA Libraries, Isolation and Sequencing of cDNAs Coding for FMT, UG3E, GST, OMT, RT, CYTb5, laccase, MADS box, WRKY, MYC, TT1, HLH, MYB and ABC Transporter and Like Proteins from White Clover (*Trifolium repens*)

cDNA libraries representing mRNAs from various organs and tissues of white clover (*Trifolium repens*) were prepared. The characteristics of the white clover libraries are described below (Table 1).

TABLE 1 cDNA libraries from white clover (*Trifolium repens*)

| Library | Organ/Tissue |
|---|---|
| 01wc | Whole seedling, light grown |
| 02wc | Nodulated root 3, 5, 10, 14, 21 & 28 day old seedling |
| 03wc | Nodules pinched off roots of 42 day old *rhizobium* inoculated plants |
| 04wc | Cut leaf and stem collected after 0, 1, 4, 6 & 14 h after cutting |
| 05wc | Inflorescences: <50% open, not fully open and fully open |
| 06wc | Dark grown etiolated |
| 07wc | Inflorescence - very early stages, stem elongation, <15 petals, 15-20 petals |
| 08wc | seed frozen at −80° C., imbibed in dark overnight at 10° C. |
| 09wc | Drought stressed plants |
| 10wc | AMV infected leaf |
| 11wc | WCMV infected leaf |
| 12wc | Phophorus starved plants |
| 13wc | Vegetative stolon tip |
| 14wc | stolon root initials |
| 15wc | Senescing stolon |
| 16wc | Senescing leaf |

The cDNA libraries may be prepared by any of many methods available. For example, total RNA may be isolated using the Trizol method (Gibco-BRL, USA) or the RNeasy Plant Mini kit (Qiagen, Germany), following the manufacturers' instructions. cDNAs may be generated using the SMART PCR cDNA synthesis kit (Clontech, USA), cDNAs may be amplified by long distance polymerase chain reaction using the Advantage 2 PCR Enzyme system (Clontech, USA), cDNAs may be cleaned using the GeneClean spin column (Bio 101, USA), tailed and size fractionated, according to the protocol provided by Clontech. The cDNAs may be introduced into the pGEM-T Easy Vector system 1 (Promega, USA) according to the protocol provided by Promega. The cDNAs in the pGEM-T Easy plasmid vector are transfected into *Escherichia coli* Epicurian coli XL10-Gold ultra competent cells (Stratagene, USA) according to the protocol provided by Stratagene.

Alternatively, the cDNAs may be introduced into plasmid vectors for first preparing the cDNA libraries in Uni-ZAP XR vectors according to the manufacturer's protocol (Stratagene Cloning Systems, La Jolla, Calif., USA). The Uni-ZAP XR libraries are converted into plasmid libraries according to the protocol provided by Stratagene. Upon conversion, cDNA inserts will be contained in the plasmid vector pBluescript. In addition, the cDNAs may be introduced directly into precut pBluescript II SK(+) vectors (Stratagene) using T4 DNA ligase (New England Biolabs), followed by transfection into *E. coli* DH10B cells according to the manufacturer's protocol (GIBCO BRL Products).

Once the cDNA inserts are in plasmid vectors, plasmid DNAs are prepared from randomly picked bacterial colonies containing recombinant plasmids, or the insert cDNA sequences are amplified via polymerase chain reaction using primers specific for vector sequences flanking the inserted cDNA sequences. Plasmid DNA preparation may be performed robotically using the Qiagen QiaPrep Turbo kit (Qiagen, Germany) according to the protocol provided by Qiagen. Amplified insert DNAs are sequenced in dye-terminator sequencing reactions to generate partial cDNA sequences (expressed sequence tags or "ESTs"). The resulting ESTs are analyzed using an Applied Biosystems ABI 3700 sequence analyser.

EXAMPLE 2

DNA Sequence Analyses cDNA clones encoding FMT, UG3E, GST, OMT, RT, CYTb5, MADS, WRKY, MYC, TT1, HLH, MYB, ABC and -like proteins were identified by conducting a BLAST (Basic Local Alignment Search Tool; Altschul et al. (1993) *J. Mol. Biol.* 215:403-410) search. The DNA sequence was translated in all reading frames and compared for similarity to all publicly available protein sequences contained in the Uniprot protein sequence database using the BLASTx algorithm (v 2.0.1) (Gish and States (1993) *Nature Genetics* 3:266-272) provided by the NCBI.

EXAMPLE 3

Identification and Full-Length Sequencing of cDNAs Encoding White Clover FMT, UG3E, GST, OMT, RT, CYTb5, laccase, MADS box, WRKY, MYC, TT1, HLH, MYB and ABC Transporter and Like Proteins To fully characterise for the purposes of the generation of probes for hybridisation experiments and the generation of transformation vectors, a set of cDNAs encoding white clover FMT, UG3E, GST, OMT, RT, CYTb5, laccase, MADS box, WRKY, MYC, TT1, HLH, MYB and ABC transporter and like proteins are identified and fully sequenced by the following method.

Full-length or partial cDNAs were identified from our EST sequence database using relevant published sequences (NCBI databank) as queries for BLAST searches. Full-length cDNAs were identified by alignment of the query and hit sequences using Sequencher (Gene Codes Corp., Ann Arbor, Mich. 48108, USA). The original cDNA in the pGEM-T easy vector is then used to transform chemically competent DH5 alpha cells (Invitrogen, Carlsbad, USA). At least two colonies per transformation are picked for initial sequencing with M13F and M13R primers. The resulting sequences are aligned with the original EST sequence using Sequencher to confirm identity and one of the two clones is picked for full-length sequencing, usually the one with the best initial sequencing result.

Sequencing is completed by primer walking, i.e. oligonucleotide primers are designed to the initial sequence and used for further sequencing from the 5' end. In most instances, an extended poly-A tail necessitates the sequencing of the cDNA to be completed from the 5' end.

Contigs are then assembled in Sequencher. The contigs include at least the 5' end of the original EST sequence and extend to at least the poly-A tail at the 3' end of the cDNA.

Plasmid maps and the full cDNA sequences of white clover laccase, MYCa and MYB24a were obtained by this method (FIGS. 19, 20, 31, 44, 45 and Table 2).

Plasmid maps and full or partial cDNA sequences of white clover FMT, UG3E, GST, OMT, RT, CYTb5, MADS box, WRKY, TT1, HLH and ABC transporter and like genes in the pGEM-T Easy vector are obtained by this method.

TABLE 2

Primers used for sequencing of full-length cDNAs

| gene name | clone ID | sequencing primer | primer sequence (5'>3') | SEQ ID No: |
|---|---|---|---|---|
| TrLACa | 14wc1IsC08 | 14wc1IsC08.f1 | CAGCATACATAACCCAATG | 90 |
| TrLACa | 14wc1IsC08 | 14wc1IsC08.f2 | GAATGGTGGAAATCAGATAC | 91 |
| TrMYCa | 05wc1KsD09 | 05wc1KsD09.f1 | ACGACTATTCCGGCTCTT | 92 |
| TrMYCa | 05wc1KsD09 | 05wc1KsD09.f2 | CTGAACAAGAACACCGTAGA | 93 |
| TrMYCa | 05wc1KsD09 | 05wc1KsD09.f3a | GCAATTAGGTAGTAATTCTACT | 94 |
| TrMYCa | 05wc1KsD09 | 05wc1KsD09.f3b | CTACTGTAATTACTCATCAAG | 95 |
| TrMYCa | 05wc1KsD09 | 05wc1KsD09.f4 | GCTCCTAGTGTTGTTCATG | 96 |
| TrMYCa | 05wc1KsD09 | 05wc1KsD09.f5 | CTCCGAATTCGAGAGGAAG | 97 |
| TrMYCa | 05wc1KsD09 | 05wc1KsD09.f6 | ATCATACATTACTGAGCTG | 98 |
| TrMYCa | 05wc1KsD09 | 05wc1KsD09.r1 | GCTTGAAGACGTTGTTGG | 99 |
| TrMYB24a | 07wc3SsF02 | 07wc3SsF02.r1 | CAGGTAGTTTTGATGCTATG | 100 |

EXAMPLE 4

Development of Binary Transformation Vectors Containing Chimeric Genes with cDNA Sequences from White Clover FMT, UG3E, GST, OMT, RT, CYTb5, laccase, MADS box, WRKY, MYC, TT1, HLH, MYB and ABC Transporter and Like Proteins To alter the expression of the proteins involved in flavonoid biosynthesis or metabolism, protein binding, metal chelation, anti-oxidation, UV-light absorption, tolerance to biotic stresses such as viruses, micro-organisms, insects and fungal pathogens; pigmentation in for example flowers and leaves; herbage quality and bloat-safety and isoflavonoid content leading to health benefits, through antisense and/or sense suppression technology and for over-expression of these key proteins in transgenic plants, a set of sense and antisense binary transformation vectors is produced by the following method.

digestion with EcoRI, and the expression cassette cloned into the EcoRI site and the 3' T overhang restoring the HindIII site. This binary vector contains between the left and right border the plant selectable marker gene aaaC1 under the control of the 35S promoter and 35S terminator and the pKYLX71:35 S2-derived expression cassette with a CaMV 35S promoter with a duplicated enhancer region and an rbcS terminator. This vector was GATEWAY®-enabled by digesting it with XbaI and blunt-ended using Klenow DNA polymerase, allowing the RfA recombination cassette to be cloned in the sense or antisense orientation between the enhanced 35S promoter and the rbcS terminator.

The orientation of the constructs (sense or antisense) is checked by restriction enzyme digestion and sequencing. Transformation vectors containing chimeric genes using full-length open reading frame cDNAs in sense and antisense orientations under the control of the CaMV 35S2 promoter are generated (FIGS. 22, 34 and 47).

TABLE 3

List of primers used to PCR-amplify the open reading frames of flavonoid-related genes from white clover and expression cassettes used in binary transformation vectors

Figure 19:
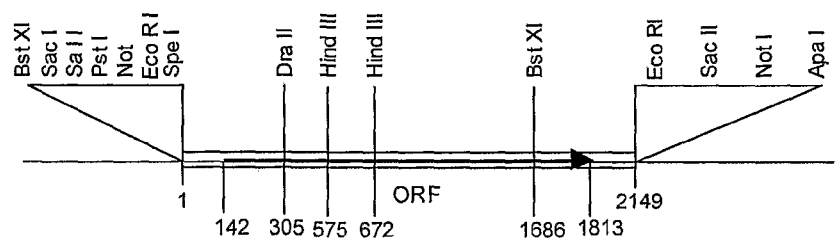
FIG. 19 shows a plasmid map of the cDNA encoding TrLACa.
Figure 31:
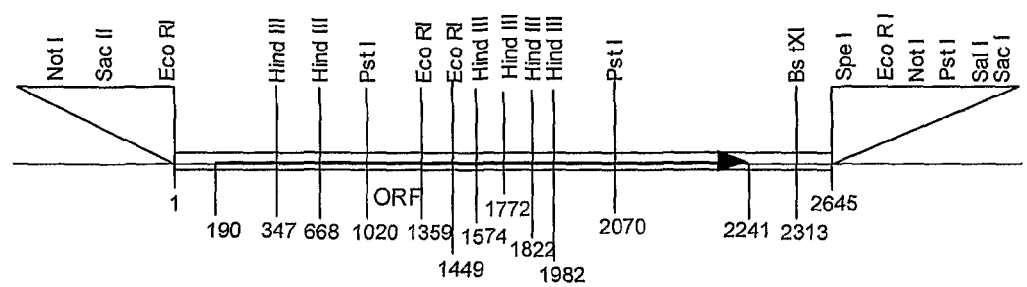
FIG. 31 shows a plasmid map of the cDNA encoding TrMYCa
Figure 44:
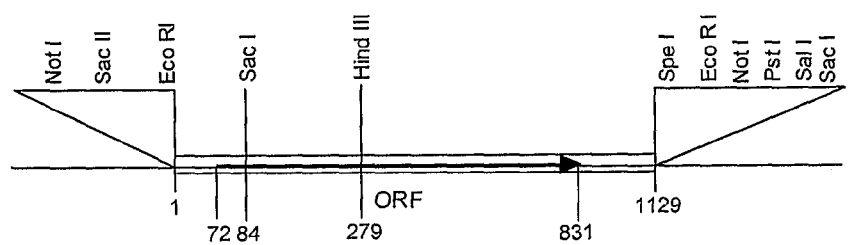
FIG. 44 shows a plasmid map of the cDNA encoding TrMYBa.
Figure 50:
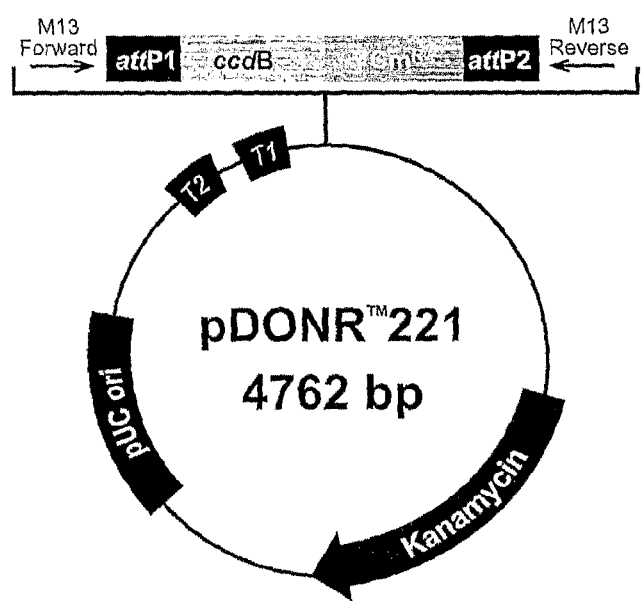
FIG. 50 shows a plasmid map of the pDONR221 GATEWAY entry vector (Invitrogen, Carlsbad, USA).

| gene name | clone ID | primer | primer sequence (5'->3') | SEQ ID No: |
|---|---|---|---|---|
| TrLACa | 14wc1IsC08 | TrLACa.attB1.f | GGGGACAAGTTTGTACAAAAAAGCAGGCTTCATGGCCACGGCGCAATTTCG | 101 |
| TrLACa | 14wc1IsC08 | TrLACa.attB2.r | GGGGACCACTTTGTACAAGAAAGCTGGGTCTCAACACTTAGGAAGGTCACTTGG | 102 |
| TrMYCa | 05wc1KsD09 | TrMYCa.attB1.f | GGGGACAAGTTTGTACAAAAAAGCAGGCTTCATGAATCTTTGGAGCGACGAGAACTC | 103 |
| TrMYCa | 05wc1KsD09 | TrMYCa.attB2.r | GGGGACCACTTTGTACAAGAAAGCTGGGTCTTATTGAACATCCCCAACTTTAGAGGAC | 104 |
| TrMYB24a | 07wc3SsF02 | TrMYB24a.attB1.f | GGGGACAAGTTTGTACAAAAAAGCAGGCTTCATGGGAAGAGCTCCTTGTTGTGAC | 105 |
| TrMYB24a | 07wc3SsF02 | TrMYB24a.attB2.r | GGGGACCACTTTGTACAAGAAAGCTGGGTCTCAATTTGTCTTAATGTCAGCATAAC | 106 | cDNA fragments are generated by high fidelity PCR using the original pGEM-T Easy plasmid cDNA as a template. The primers used contain attB1 and attB2 GATEWAY® recombination sites for directional cloning into the target vector. After PCR amplification and purification of the products, the cDNA fragments are cloned into the recombination site of the pDONR221™ vector (FIG. 50) using BP GATEWAY® technology (Invitrogen, Carlsbad, USA). The pPZP221 binary vector (Hajdukiewicz et al., 1994, The small versatile pPZP family of Agrobacterium binary vectors for plant transformation. Plant Mol. Biol. 25:989-994.) was modified to contain the 35S2 cassette from pKYLX71:35 S2 as follows. pKYLX71:35 S2 was cut with ClaI. The 5' overhang was filled in using Klenow and the blunt end was A-tailed with Taq polymerase. After cutting with EcoRI, the 2 kb fragment with an EcoRI-compatible and a 3'-A tail was gel-purified. pPZP221 was cut with HindIII and the resulting 5' overhang filled in and T-tailed with Taq polymerase. The remainder of the original pPZP221 multi-cloning site was removed by

EXAMPLE 5

Production and Analysis of Transgenic White Clover Plants Carrying Chimeric White Clover FMT, UG3E, GST, OMT, RT, CYTb5, laccase, MADS box, WRKY, MYC, HLH, MYB and ABC Transporter and Like Genes Involved in Flavonoid Biosynthesis Transgenic white clover plants carrying white clover genes involved in flavonoid biosynthesis or metabolism, protein binding, metal chelation, anti-oxidation, UV-light absorption, tolerance to biotic stresses such as viruses, micro-organisms, insects and fungal pathogens; pigmentation in for example flowers and leaves; herbage quality and bloat-safety and isoflavonoid content leading to health benefits, are produced by the following method.

pPZP221-based transformation vectors with cDNAs comprising the full open reading frame sequences in sense and antisense orientations under the control of the CaMV 35S promoter with duplicated enhancer region (35S2) are generated as detailed in Example 4.

*Agrobacterium*-mediated gene transfer experiments are performed using these transformation vectors.

Preparation of White Clover Cotyledonary Explants

White clover (cv 'Mink') seeds are rinsed for 5 minutes in running tap water and incubated twice, for 5 minutes in 70% v/v ethanol in a 120 ml tissue culture container with gentle shaking. The same container is used to incubate the seeds for 2 minutes in 1% sodium hypochlorite (1:3 ratio of Domestos™ bleach in water) with gentle shaking. The seeds are then rinsed six times in sterile water in a laminar flow hood and incubated for 18 hours at 4° C. in the dark. Cotyledonary explants are extracted using 10 ml syringes attached to 21 G needles (Terumo, Japan) under a dissecting microscope in a laminar flow hood. Both layers of the seed coat are peeled away, the end of the hypocotyl is cut off and the cotyledons with approximately 4 mm of hypocotyl are separated and transferred to a 90×90×20 mm petri dish containing MGL medium.

Preparation of *Agrobacterium*

*Agrobacterium tumefaciens* strain AGL-1 containing each PZP221-derived binary expression vector is streaked on LB medium containing 50 µg/ml rifampicin and 100 µg/ml spectinomycin and grown at 27° C. for 48 hours. A single colony is used to inoculate 5 ml of LB medium containing 50 µg/ml rifampicin and 100 µg/ml spectinomycin and grown over night at 27° C. and 250 rpm on an orbital shaker. The overnight culture is used as an inoculum for 40 ml of YEP medium containing 100 µg/ml spectinomycin and 40 mg/l acetosyringone. Incubation is over night at 27° C. and 250 rpm on an orbital shaker in a 250 ml Erlenmeyer flask.

The overnight cultures are centrifuged for 15 min at 5500×g and the supernatant discarded. The cells are resuspended in MGL media with 40 mg/l acetosyringone to a volume corresponding to an $OD_{600}$ reading of 0.4. The cells are then incubated at 27° C. and 250 rpm until the $OD_{600}$ reading reaches 0.8.

Cocultivation and Selection of White Clover Transformants

The MGL medium is removed from the petri dish containing white clover cotyledonary explants and replaced with the prepared *Agrobacterium* suspension using a sterile serological pipette. The petri dish is sealed with laboratory film, covered with aluminium foil and incubated with gentle shaking for 45 min. The dish is opened in the laminar flow hood and the *Agrobacterium* suspension removed with a pipette. The explants are then transferred to plates containing RM73 media with 40 mg/l acetosyringone (Table 1) and incubated for 3 days in a plant tissue culture room at 22° C. with a 16 hour photoperiod. After this, the explants are transferred, with the hypocotyl end in the media, to plates containing RM73 media with 75 mg/l gentamicin and 250 mg/l cefotaxime. The explants are transferred to fresh plates every two weeks for 6-8 weeks. Shoots are then transferred to 120 ml tissue culture vessels containing RIM media (Table 2) with 75 mg/l gentamicin and 250 mg/l cefotaxime. When roots develop, the plantlets are transferred to pots of soil and after 2 weeks of recovery in a misting bench, are grown under standard glasshouse conditions.

Preparation of Genomic DNA 1-2 leaflets of white clover plants recovered from the transformation process are harvested and freeze-dried. The tissue is homogenised on a Retsch MM300 mixer mill, then centrifuged for 10 min at 1700×g to collect cell debris. Genomic DNA is isolated from the supernatant using Wizard Magnetic 96 DNA Plant System kits (Promega) on a Biomek FX (Beckman Coulter). 5 µl of the sample (50 µl) is then analysed on an agarose gel to check the yield and the quality of the genomic DNA.

Analysis of DNA from Putative Transgenic Lines Using Real-Time PCR

Genomic DNA is analysed for the presence of the transgene by real-time PCR using SYBR Green chemistry. PCR primer pairs were designed to detect the aacC1 gentamycin resistance gene in the transferred T-DNA region using MacVector (Accelrys). The sequences of these primers are as follows:

(SEQ ID No: 107)
pPZPaacC1-1f 5'-TCAAGTATGGGCATCATTCGCAC-3'

(SEQ ID No: 108)
pPZPaacC1-1.r 5'-TGCTCAAACCGGGCAGAACG-3'

2.5 µl of each genomic DNA sample is run in a 25 µl PCR reaction including SYBR Green on an ABI (Applied Biosystems) together with samples containing DNA isolated from wild type white clover plants (cv 'Mink', negative control), samples containing buffer instead of DNA (buffer control) and samples containing the plasmid used for transformation (positive plasmid control).

TABLE 4

| Composition of RM73 tissue culture media, pH 5.75 | | |
|---|---|---|
| Component | [Stock] | For 1 litre |
| MS Macronutients | 10 x | 100 mL |
| MS Micronutrients | 100 x | 10 mL |
| MS Vitamins | 100 x | 10 mL |
| TDZ | 100 mM | 50 uL |
| NAA | 1 mM | 0.5 mL |
| Sucrose (BDH Chemicals) | — | 30 g |
| Agar | — | 8 g |

TABLE 5

| Composition of root-inducing tissue culture media (RIM73), pH 5.75 | | |
|---|---|---|
| Component | [Stock] | For 1 litre |
| MS macronutrients | 10 x | 100 mL |
| MS micronutrients | 100 x | 10 mL |
| MS vitamins | 100 x | 10 mL |
| Indole-3-butyric acid | 1 mM | 1.2 mL |
| Sucrose (BDH Chemicals) | — | 15 g |
| Agar (Becton-Dickinson) | — | 8 g |

EXAMPLE 6

Analysis of Condensed Tannins and their Monomers in the Leaves of Transgenic White Clover Plants Carrying Chimeric White Clover FMT, UG3E, GST, OMT, RT, CYTb5, laccase, MADS box, WRKY, MYC, TT1, HLH, MYB and ABC Transporter and Like Genes Involved in Flavonoid Biosynthesis Accumulation of condensed tannins and their monomers is analysed qualitatively in leaves of transgenic and wild type (cv 'Mink') white clover plants using 4-dimethylaminocinnemaldehyde (DMACA) staining according to the following method.

Two mature leaflets from each plant are decolourised in absolute ethanol in 6-well tissue culture plates for 3 hours with gentle shaking. The ethanol is removed and replaced with a 0.01% w/v solution of DMACA (Fluka), freshly made up in absolute ethanol with 2.4% v/v concentrated hydrochloric acid. After 1 hour of incubation with gentle shaking, the leaflets are rinsed with distilled water and mounted in 50% glycerol for analysis with a dissecting microscope (FIG. 52). Wild type white clover plants show blue staining in epidermal cells in the floral organs and in trichomes. *Lotus corniculatus* (cv 'Draco'), a forage legume with a 'bloat-safe' level of condensed tannins in the leaves, shows blue staining of approximately 50% of mesophyll cells in leaves. Achieving a level of condensed tannins in white clover leaves that is comparable to the level seen in leaves of *L. corniculatus* by metabolic engineering would be agronomically valuable.

DMACA staining can detect economically significant levels of condensed tannins and their monomers in the leaves of established bloat-safe forage legumes. However, the condensation of catechin monomers to form condensed tannins and their transport from the cytoplasm to the vacuole is poorly understood. Hence, modifying the regulation of known enzymes and transcription factors in the flavonoid pathway may up-regulate catechin levels but not increase condensed tannin levels, and therefore, bloat-safety. The PVPP-butanol-HCl assay detects only condensed tannins, relying on the ability of condensed tannins, but not their monomers to bind to PVPP. The detailed method is as follows.

Clover leaf and inflorescence (positive control) tissue is snap-frozen and ground to a fine powder in a mortar and pestle under liquid nitrogen. After grinding, 0.75 g of the powder from each sample is transferred to a 14 ml screw-cap centrifuge tube (Falcon), vortex-mixed with 1.5 ml of extraction buffer containing 80% v/v methanol in distilled water with 5.3 mM sodium bisulfite. Samples are mixed for 5 hours on a mixing wheel before centrifugation at 3000×g for 10 minutes. A 1 ml aliquot of each supernatant is transferred to a 1.5 ml microcentrifuge tube and reduced to 0.25 ml in a vacuum centrifuge. Equal volumes of the sample are added to each of two 1.5 ml microcentrifuge tubes containing 25 mg of polyvinyl polypyrrolidone (PVPP). Each mixture is vortex-mixed intermittently for 15 min and centrifuged for 1 min at maximum speed in a microcentrifuge. After removal of the supernatant, the pellet is washed four times with 1 ml of methanol, with a 1 min centrifugation step at maximum speed in a microcentrifuge between each wash. A freshly-made 70:30 (v/v) solution of butanol and concentrated hydrochloric acid is added to each pellet and one tube of the mixture is incubated for 1 hour at 70° C., whereas the other tube is incubated at ambient temperature. The difference in the absorbance (530 nm) between the two tubes from each plant sample is proportional to the level of condensed tannins in the sample. This assay can be quantitated with a condensed tannin of known concentration.

EXAMPLE 7

Analysis of the Temporal and Spatial Pattern of Flavonoid-Related Gene Expression Biochemical, molecular and microscopic analyses suggest that at least two proanthocyanidin (PA) and two anthocyanin (ANT) pathways are active in developing white clover florets. A PA pathway which is developmentally regulated in epidermal cells of IW with accumulation of flavan-3-ol monomers peaking at the stage 3 and sharply down-regulated at the later stages; another PA pathway is active in the trichomes located in sepals at all six developmental stages; an ANT pathway which is developmentally and light-regulated in epidermal cells of IW at the stages 4-6 and ANT pathway that is active at all stages in a small group of cells in sepals (FIG. 53).

We monitored the expression pattern of 12,000 *T. repens* genes at six stages of inflorescence development using custom-made CombiMatrix oligonucleotide arrays in order to identify flavonoid genes differentially expressed in developing white clover florets. Each gene was represented by a sequence-specific, 30-40 base pair oligonucleotide. This approach aimed to determine which flavonoid-related genes and isoforms are most likely to be involved in condensed tannin production, or in the production of other flavonoids, and could therefore be targeted for overexpression or down-regulation in the metabolic engineering of bloat-safe white clover. The expression of the TrMYB24a gene peaked at stage 3 (50% open inflorescence, upper half) and then declined (FIG. 53).

Real-time RT-PCR is a recently developed technique that allows more quantitative analyses of gene expression than Northern or conventional RT-PCR experiments. Essentially, real-time RT-PCR with SYBR Green chemistry and gene-specific primers involves the automatic measurement of the level of a fluorescent PCR product generated from a cDNA species over each cycle. The abundance of each template is proportional to the amplification rate. Therefore, a threshold corresponding to the start of the exponential phase of PCR allows the relative abundance of target genes to be standardised against a uniformly expressed 'housekeeping' gene in each tissue and compared to a negative control without a template. Real-time RT-PCR with SYBR Green chemistry has been used successfully by others in the field to quantify the expression of four flavonoid-related genes in *Lotus corniculatus* plants exposed to different light regimes (Paolocci et al., 2005, Light and an exogenous transcription factor qualitatively and quantitatively affect the biosynthetic pathway of condensed tannins in *Lotus corniculatus* leaves. J. Exp. Bot. 56: 1093-1103).

A Real-Time RT-PCR strategy involving with SYBR Green chemistry and absolute quantification was used to validate the microarray results. Real-time RT-PCR was also used to test whether expression of the TrMYB24a gene is restricted to the inner whorls (IW) of white clover florets at inflorescence stages 3, 4, 5 and 6, correlating with PA production.

The full-length cDNA sequences encoding TrMYB24a and TrEF1α were used as input data for the Primer Express (Applied Biosystems, Foster City, USA) primer design program, using the default settings, no 3' GC clamp and a predicted amplicon size of 50-150 base pairs. Primers close to the 3' ends of the input sequences are preferred, due to the likelihood of a large number of cDNA molecules derived from clover samples being incomplete at the 5' end.

The specificity of the primer sets was tested using 1 ul of plasmid DNA (0.01 ng/ul) from the original cDNA cloned into pGEM-T Easy or autoclaved, purified water, 12.5 ul 2×SYBR Green Master Mix (Applied Biosystems), 0.5 ul each of the forward and reverse primers (10 uM) and 10.5 ul of autoclaved, purified water (Sartorius AG, Goettingen, Germany). Real-time PCR was performed in 96-well optical PCR plates (Applied Biosystems) using the Stratagene MX3000P cycler and the following cycling parameters: 95° C. for 10 min, 40 cycles of 95° C. for 30 sec and 60° C. for 1 min, followed by 55° C. for 1 min and 95° C. for 1 min. Primer sets generally amplified a satisfactory level of products from the corresponding cDNA templates with a cycle threshold cut-off of 24 cycles. The primer sets were generally isoform-specific.

Total RNA was extracted from white clover tissues using a CTAB-based method (Chang, S., Puryear, J. and Cairney, J. (1993). A simple and efficient method for isolating RNA from pine trees. *Plant Mol Biol Rep* 11:113-116) and contaminating genomic DNA was digested on the column using the optional on-column DNAse digestion method from the RNeasy kit (QIAGEN GmbH, Hilden, Germany) according to the manufacturers' instructions. Complementary DNA (cDNA) is synthesised from 0.5 ug of total RNA using the Quantitect Reverse Transcriptase Kit (QIAGEN GmbH). Real-time RT-PCR reactions are set up and run as described earlier using 1 ul of cDNA, plasmid control DNA or autoclaved, purified water as the template.

Real-time RT-PCR results supported the expression profile of TrMYB24a seen in the microarray experiment. TrMYB24a was also found to be expressed at a significantly higher level in inner whorls than in sepals (FIG. 53).

TABLE 6

List of primers designed for Real-time RT-PCR analysis of condensed tannin-rich organs of white clover, based on the cDNA sequences of white clover genes

| Gene name | Clone ID | primer 1 (forward) | primer 2 (reverse) |
| --- | --- | --- | --- |
| TrEF-1α | 14wc2PsG04 | TCGAGAAGGAAGCTGCTGAAA (SEQ ID No. 109) | CCCAGGCATACTTGAATGACCT (SEQ ID No. 110) |
| TrMYB24a | 07wc3SsF02 | TGAATCTTTGGAACCACTAATGGA (SEQ ID No. 111) | AAGCAACAACTTGAAGCAAAATCA (SEQ ID No. 112) |

Finally, it is to be understood that various alterations, modifications and/or additions may be made without departing from the spirit of the present invention as outlined herein.

It will also be understood that the term "comprises" (or its grammatical variants) as used in this specification is equivalent to the term "includes" and should not be taken as excluding the presence of other elements or features.

Documents cited in this specification are for reference purposes only and their inclusion is not acknowledgment that they form part of the common general knowledge in the relevant art.

SEQUENCE LISTING

<160> NUMBER OF SEQ ID NOS: 112

<210> SEQ ID NO 1
<211> LENGTH: 2057
<212> TYPE: DNA
<213> ORGANISM: Trifolium repens

<400> SEQUENCE: 1

```
atctctcaac agttccttaa ccccattttc atatcattct taagtaacag atctcatctt      60
tcgatccatc atctaaattt tcttcctttc ttaatttgct taatattatt tttacgatcc     120
aaggttctag atggcaaaac caagtgctgc tgataatagg actagaagtt ctgtgcagat     180
ctttatagta gttggtttgt gctgtttctt ctatatattg ggagcgtggc aaagaagtgg     240
atttggaaaa ggagatagca tagcattaga gattaccaag aataatgctg aatgtgatgt     300
agttccaaat ttaagttttg attcacacca tgctggagaa gttagtcaaa tcgatgaatc     360
tgattcaaag gctaaggtgt ttaaaccgtg tgatgctcgt tatacggatt acactccgtg     420
tcaagatcaa cgtcgtgcta tgacatttcc tagagaaaac atgaactata gagagagaca     480
ttgccctcca gaggaagaga agttacactg tatgatccct gcaccaaaag gttatgtaac     540
accttttcca tggcctaaga gtagggatta tgttccttat gctaatgcac cctacaagag     600
tctcacagtt gagaaggcca ttcagaattg gatccaatat gagggaaatg tgttaagatt     660
ccctggtggt ggaactcaat ttcctcaagg tgctgataaa tatattgatc aacttgcatc     720
tgtggttcct atagatgatg ggacggttag gacggcgctt gacaccggtt gtggggttgc     780
```

```
aagttggggt gcatatctct ggagcagaaa tgttgttgcc atgtcgtttg caccaaggga    840
ctctcatgaa gcacaagtgc aatttgctct tgaaaggggt gtacctgctg ttattggtgt    900
tcttggaaca ataaagttgc catatccatc tagagccttc gacatggctc attgctctcg    960
ctgtttgatt ccgtggggag caaatgctgg aatatatatg atggaagttg atagagttct   1020
aaggcctggt ggttattggg tgctttctgg tcctccaatc aattggaagg tcaactacaa   1080
accatggcaa agaccaaagg aggaactcga ggaagaacaa agaaatattg aagaggttgc   1140
taagaaactt tcctgggaga agaagtctga gaaggctgaa attgccattt ggcaaaagac   1200
taccgactct gaatcttgtc gtagcagaca agatgactcc agtgtagaat tttgtgaagc   1260
atcagatcct gatgatgtct ggtataagaa aatggaggcc tgtgttactc caacacctaa   1320
agttttgggt ggtgatctta aaccatttcc aaacaggcta tatgcgatcc ctcctagagt   1380
ttctagtggt tctattcctg gagtttcttc tgagacatac cagaatgata caaagagtg    1440 gaaaagcat gtcagtgctt acaagaaaat taattcactc ttggattccg gtagatatcg   1500
caacattatg gatatgaatg ctggtttggg tagtttcgct gcagctattc attcgtcgaa   1560
atcatgggtc atgaatgttg tgccaactat agctgagaaa agtactctcg gtgcgatata   1620
tgagcgagga ctgattggca tctatcatga ttggtgtgaa gccttttcca catatccaag   1680
aacatacgat ctcattcatg ctaatggcct ctttagtctg tacaaggata aatgcaaatac  1740 agaagacatt cttctcgaaa tggaccggat tttgcgacca gaaggtgctg tcataatccg   1800
cgacgaagtc gatgtattaa ttcaggtaaa gaaattaatc ggaggaatga gatggaatat   1860
gaaattagtt gatcatgaag atggtcctct tgttcctgag aaagtactaa ttgctgtcaa   1920
acagtattgg gttactgatg gaaattccac atcaacacaa taatcactga aaaacaagtt   1980
gaatttacat ccctacccctt atctatatac aacaatagtc aaagagttca tatggttttg   2040
tgtcatcatc acaacta                                                   2057
```

<210> SEQ ID NO 2
<211> LENGTH: 610
<212> TYPE: PRT
<213> ORGANISM: Trifolium repens

<400> SEQUENCE: 2

```
Met Ala Lys Pro Ser Ala Ala Asp Asn Arg Thr Arg Ser Ser Val Gln
1               5                   10                  15

Ile Phe Ile Val Val Gly Leu Cys Cys Phe Phe Tyr Ile Leu Gly Ala
            20                  25                  30

Trp Gln Arg Ser Gly Phe Gly Lys Gly Asp Ser Ile Ala Leu Glu Ile
        35                  40                  45

Thr Lys Asn Asn Ala Glu Cys Asp Val Val Pro Asn Leu Ser Phe Asp
    50                  55                  60

Ser His His Ala Gly Glu Val Ser Gln Ile Asp Glu Ser Asp Ser Lys
65                  70                  75                  80

Ala Lys Val Phe Lys Pro Cys Asp Ala Arg Tyr Thr Asp Tyr Thr Pro
                85                  90                  95

Cys Gln Asp Gln Arg Arg Ala Met Thr Phe Pro Arg Glu Asn Met Asn
            100                 105                 110

Tyr Arg Glu Arg His Cys Pro Pro Glu Glu Lys Leu His Cys Met
        115                 120                 125

Ile Pro Ala Pro Lys Gly Tyr Val Thr Pro Phe Pro Trp Pro Lys Ser
    130                 135                 140
```

```
Arg Asp Tyr Val Pro Tyr Ala Asn Ala Pro Tyr Lys Ser Leu Thr Val
145                 150                 155                 160

Glu Lys Ala Ile Gln Asn Trp Ile Gln Tyr Glu Gly Asn Val Leu Arg
                165                 170                 175

Phe Pro Gly Gly Gly Thr Gln Phe Pro Gln Gly Ala Asp Lys Tyr Ile
            180                 185                 190

Asp Gln Leu Ala Ser Val Val Pro Ile Asp Asp Gly Thr Val Arg Thr
        195                 200                 205

Ala Leu Asp Thr Gly Cys Gly Val Ala Ser Trp Gly Ala Tyr Leu Trp
    210                 215                 220

Ser Arg Asn Val Val Ala Met Ser Phe Ala Pro Arg Asp Ser His Glu
225                 230                 235                 240

Ala Gln Val Gln Phe Ala Leu Glu Arg Gly Val Pro Ala Val Ile Gly
                245                 250                 255

Val Leu Gly Thr Ile Lys Leu Pro Tyr Pro Ser Arg Ala Phe Asp Met
            260                 265                 270

Ala His Cys Ser Arg Cys Leu Ile Pro Trp Gly Ala Asn Ala Gly Ile
        275                 280                 285

Tyr Met Met Glu Val Asp Arg Val Leu Arg Pro Gly Gly Tyr Trp Val
    290                 295                 300

Leu Ser Gly Pro Pro Ile Asn Trp Lys Val Asn Tyr Lys Pro Trp Gln
305                 310                 315                 320

Arg Pro Lys Glu Glu Leu Glu Glu Gln Arg Asn Ile Glu Glu Val
                325                 330                 335

Ala Lys Lys Leu Ser Trp Glu Lys Lys Ser Lys Ala Glu Ile Ala
                340                 345                 350

Ile Trp Gln Lys Thr Thr Asp Ser Glu Ser Cys Arg Ser Arg Gln Asp
                355                 360                 365

Asp Ser Ser Val Glu Phe Cys Glu Ala Ser Pro Asp Asp Val Trp
    370                 375                 380

Tyr Lys Lys Met Glu Ala Cys Val Thr Pro Thr Pro Lys Val Leu Gly
385                 390                 395                 400

Gly Asp Leu Lys Pro Phe Pro Asn Arg Leu Tyr Ala Ile Pro Pro Arg
                405                 410                 415

Val Ser Ser Gly Ser Ile Pro Gly Val Ser Ser Glu Thr Tyr Gln Asn
                420                 425                 430

Asp Asn Lys Glu Trp Lys Lys His Val Ser Ala Tyr Lys Lys Ile Asn
                435                 440                 445

Ser Leu Leu Asp Ser Gly Arg Tyr Arg Asn Ile Met Asp Met Asn Ala
    450                 455                 460

Gly Leu Gly Ser Phe Ala Ala Ala Ile His Ser Ser Lys Ser Trp Val
465                 470                 475                 480

Met Asn Val Val Pro Thr Ile Ala Glu Lys Ser Thr Leu Gly Ala Ile
                485                 490                 495

Tyr Glu Arg Gly Leu Ile Gly Ile Tyr His Asp Trp Cys Glu Ala Phe
            500                 505                 510

Ser Thr Tyr Pro Arg Thr Tyr Asp Leu Ile His Ala Asn Gly Leu Phe
    515                 520                 525

Ser Leu Tyr Lys Asp Lys Cys Asn Thr Glu Asp Ile Leu Leu Glu Met
    530                 535                 540

Asp Arg Ile Leu Arg Pro Glu Gly Ala Val Ile Ile Arg Asp Glu Val
545                 550                 555                 560

Asp Val Leu Ile Gln Val Lys Lys Leu Ile Gly Gly Met Arg Trp Asn
                565                 570                 575
```

```
Met Lys Leu Val Asp His Glu Asp Gly Pro Leu Val Pro Glu Lys Val
            580                 585                 590

Leu Ile Ala Val Lys Gln Tyr Trp Val Thr Asp Gly Asn Ser Thr Ser
        595                 600                 605

Thr Gln
    610

<210> SEQ ID NO 3
<211> LENGTH: 568
<212> TYPE: DNA
<213> ORGANISM: Trifolium repens

<400> SEQUENCE: 3
atctctcaac agttccttaa ccccattttc atatcattct taagtaacag atctcatctt      60
tcgatccatc atctaaattt tcttcctttc ttaatttgct taatattatt tttacgatcc     120
aaggttctag atggcaaaac caagtgctgc tgataatagg actagaagtt ctgtgcagat     180
ctttatagta gttggtttgt gctgtttctt ctatatattg ggagcgtggc aaagaagtgg     240
atttggaaaa ggagatagca tagcattaga gattaccaag aataatgctg aatgtgatgt     300
agttccaaat ttaagttttg attcacacca tgctggagaa gttagtcaaa tcgatgaatc     360
tgattcaaag gctaaggtgt ttaaaccgcg tgatgctcgt tatactgatt acactccgtg     420
tcaagatcaa cgtcgtgcta tgacgtttcc gagagaaaac atgaactata gagagagaca     480
ttgccctcca gaggaagaga agttacactg tatgatccct gcaccaaaag ggtatgtaac     540
accttttcca tggcctaaga gtagggat                                        568

<210> SEQ ID NO 4
<211> LENGTH: 579
<212> TYPE: DNA
<213> ORGANISM: Trifolium repens

<400> SEQUENCE: 4
aggctaaggt gtttaaaccg tgtgatgctc gttatacgga ttacactccg tgtcaagatc      60
aacgtcgtgc tatgacattt cctagagaaa acatgaacta tagagagaga cattgccctc     120
cagaggaaga gaagttacac tgtatgatcc ctgcaccaaa aggttatgta cacctttttc     180
catggcctaa gagtagggat tatgttcctt atgctaatgc accctacaag agtctcacag     240
ttgagaaggc cattcagaat tggatccaat atgagggaaa tgtgttaaga ttccctggtg     300
gtggaactca atttcctcaa ggtgctgata aatatattga tcaacttgca tctgtggttc     360
ctatagatga tgggacggtt aggacggcgc ttgacaccgg ttgtgggtt gcaagttggg      420 gtgcatatct ctggagcaga aatgttgttg ccatgtcgtt tgcaccaagg gactctcatg     480
aagcacaagt gcaatttgct cttgaaaggg gtgtacctgc tgttattggt gttcttggaa     540
caataaagtt gccatatcca tctagagcct tcgacatgg                            579

<210> SEQ ID NO 5
<211> LENGTH: 390
<212> TYPE: DNA
<213> ORGANISM: Trifolium repens

<400> SEQUENCE: 5
gtgtttaaac cgtgtgatgc tcgttatacg gattacactc cgtgtcaaga tcaacgtcgt      60
gctatgacat ttcctagaga aaacatgaac tatagagaga cattgccc tccagaggaa       120 gagaagttac actgtatgat ccctgcacca aaaggttatg taacaccttt tccatggcct     180
```

```
aagagtaggg attatgttcc ttatgctaat gcaccctaca agagtctcac agttgagaag      240
gccattcaga attggatcca atatgaggga aatgtgttaa gattccctgg tggtggaact      300
caatttgctc aaggtgctga taaatatatt gatcaacttg catctgtggt ttctatagat      360
gatgggacgg ttaggacggc gcttgacacc                                      390

<210> SEQ ID NO 6
<211> LENGTH: 571
<212> TYPE: DNA
<213> ORGANISM: Trifolium repens

<400> SEQUENCE: 6
gtgcaatttg ctcttgaagg ggtgtacctg ctgttattgg tgttcttgga acaataaagt       60
tgccatatcc atctagagcc ttcgacatgg ctcattgctc tcgctgtttg attccgtggg      120
gagcaaatgc tggaatatat atgatggaag ttgatagagt tctaaggcct ggtggttatt      180
gggtgctttc tggtcctcca atcaattgga aggtcaacta caaaccatgg caaagaccaa      240
aggaggaact cgaggaagaa caaagaaata ttgaagaggt tgctaagaaa ctttgctggg      300
agaagaagtc tgagaaggct gaaattgcca tttggcaaaa gactactgac tctgaatctt      360
gtcgtagcag acaagatgac tccagtgtag aattttgtga agcatcagat cctgatgacg      420
tctggtataa gaaatggag gcctgtgtta ctccaacacc taaagttttg ggtggtgatc        480
ttaaaccatt tccaaacagg ctatatgcga tccctcctag agtttctagt ggttctattc      540
ctggagtttc ttctgagaca taccagaatg a                                    571

<210> SEQ ID NO 7
<211> LENGTH: 599
<212> TYPE: DNA
<213> ORGANISM: Trifolium repens

<400> SEQUENCE: 7
ttgaagaggt tgctaagaaa ctttcctggg agaagaagtc tgagaaggct gaaattgcca       60
tttggcaaaa gactaccgac tctgaatctt gtcgtagcag acaagatgac tccagtgtag      120
aattttgtga agcatcagat cctgatgatg tctggtataa gaaatggag gcctgtgtta       180 ctccaacacc taaagttttg ggtggtgatc ttaaaccatt tccaaacagg ctatatgcga      240
tccctcctag agtttctagt ggttctattc ctggagtttc ttctgagaca taccagaatg      300
ataacaaaga gtggaaaaag catgtcagtg cttacaagaa aattaattca ctcttggatt      360
ccggtagata tcgcaacatt atggatatga atgctggttt gggtagtttc gctgcagcta      420
ttcattcgtc gaaatcatgg gtcatgaatg ttgtgccaac tatagctgag aaaagtactc      480
tcggtgcgat atatgagcga ggactgattg gcatctatca tgattggtgt gaagcctttt      540
ccacatatcc aagaacatac gatctcattc atgctaatgg cctctttagt ctgtacaag       599

<210> SEQ ID NO 8
<211> LENGTH: 591
<212> TYPE: DNA
<213> ORGANISM: Trifolium repens

<400> SEQUENCE: 8
gaaactttcc tgggagaaga agtctgagaa ggctgaaatt gccatttggc aaaagactac       60
cgactctgaa tcttgtcgta gcagacaaga tgactccagt gtagaatttt gtgaagcatc      120
agatcctgat gatgtctggt ataagaaaat ggaggcctgt gttactccaa cacctaaagt      180
tttgggtggt gatcttaaac catttccaaa caggctatat gcgatccctc ctagagtttc      240
```

```
tagtggttct attcctggag tttcttctga gacataccag aatgataaca aagagtggaa        300
aaagcatgtc agtgcttaca agaaaattaa ttcactcttg gattccggta gatatcgcaa        360
cattatggat atgaatgctg gtttgggtag tttcgctgca gctattcatt cgtcgaaatc        420
atgggtcatg aatgttgtgc caactatagc tgagaaaagt actctcggtg cgatatatga        480
gcgaggactg attggcatct atcatgattg gtgtgaagcc ttttccacat atccaagaac        540
atacgatctc attcatgcta atggcctctt tagtctgtac aaggataaat g                591

<210> SEQ ID NO 9
<211> LENGTH: 565
<212> TYPE: DNA
<213> ORGANISM: Trifolium repens

<400> SEQUENCE: 9
tagatatcgc aacattatgg atatgaatgc tggtttgggt agtttcgctg cagctattca         60
ttcgtcgaaa tatgggtcat gaatgttgtg ccaactatag ctgagaaaag tactctcggt        120
gcgatatatg agcgaggact gattggcatc tatcatgatt ggtgtgaagc cttttccaca        180
tatccaagaa catacgatct cattcatgct aatggcctct ttagtctgta caaggataaa        240
tgcaatacag aagacattct ctcgaaatg gaccggattt tgcgaccaga aggtgctgtc        300
ataatccgcg acgaagtcga tgtattaatt caggtaaaga aattaatcgg aggaatgaga        360
tggaatatga attagttga tcatgaagat ggtcctcttg ttcctgagaa agtactaatt        420
gctgtcaaac agtattgggt tactgatgga aattccacat caacacaata atcactgaaa        480
aacaagttga atttacatcc ctacccttat ctatatacaa caatagtcaa agagttcata        540
tggttttgtg tcatcatcac aacta                                              565

<210> SEQ ID NO 10
<211> LENGTH: 541
<212> TYPE: DNA
<213> ORGANISM: Trifolium repens

<400> SEQUENCE: 10
tatcgcaaca ttatggatat gaatgctggt ttgggtagtt tcgctgcagc tattcattcg         60
tcgaaatcat gggtcatgaa tgttgtgcca actatagctg agaaaagtac tctcggtgcg        120
atatatgagc gaggactgat tggcatctat catgattggt gtgaagcctt tccacatat         180 ccaagaacat acgatctcat tcatgctaat ggcctcttta gtctgtacaa ggataaatgc        240
aatacagaag acattcttct cgaaatggac cggattttgc gaccagaagg tgctgtcata        300
atccgcgacg aagtcgatgt attaattcag gtaaagaaat taatcggagg aatgagatgg        360
aatatgaaat tagttgatca tgaagatggt cctcttgttc ctgagaaagt actaattgct        420
gtcaaacagt attgggttac tgatggaaat tccacatcaa cacaataatc actgaaaaac        480
aagttgaatt tacatcccta cccttatcta tatacaacaa tagtcaaaga gttcatatgg        540
t                                                                        541

<210> SEQ ID NO 11
<211> LENGTH: 571
<212> TYPE: DNA
<213> ORGANISM: Trifolium repens

<400> SEQUENCE: 11
catcatctgc aactgtttat ggcacacctg aaaagatacc ttgtgaggag gatttcaatt         60
tataagccat gaatccatat ggacggacca agcttttcct cgaagaaatc gcacgagata        120
```

```
ttcagaaagc tgagccagaa tggaggatca ttttactgag atacttcaat ccagttgggg      180
cccatgaaag cggtagactc ggtgaagatc ccaagggcat cccaaataat ctcatgcctt      240
atatacagcg tgtagctgtt gaaagattac ccgagctcaa tgtatatggt catgattatc      300
ctacgaggga tggttctgcg attcgggact atatccatgt gatggactta gcagatggtc      360
acattgctgc attgagaaag cttttcacaa cagaaaacat aggttgtgct gcttacaact      420
tgggaactgg tcgtggtaca tctgtacttg aaatggttga tgcatttgag aaagcttctg      480
gcaagaaaat tccagtgaaa ttgtgtccac gaagggcggg agatgctacg gaggtttatg      540
catctacaga gagagctgag aaagaacttg g                                     571
```

<210> SEQ ID NO 12
<211> LENGTH: 167
<212> TYPE: PRT
<213> ORGANISM: Trifolium repens

<400> SEQUENCE: 12

```
Met Asn Pro Tyr Gly Arg Thr Lys Leu Phe Leu Glu Glu Ile Ala Arg
1               5                   10                  15

Asp Ile Gln Lys Ala Glu Pro Glu Trp Arg Ile Ile Leu Leu Arg Tyr
            20                  25                  30

Phe Asn Pro Val Gly Ala His Glu Ser Gly Arg Leu Gly Glu Asp Pro
        35                  40                  45

Lys Gly Ile Pro Asn Asn Leu Met Pro Tyr Ile Gln Arg Val Ala Val
    50                  55                  60

Glu Arg Leu Pro Glu Leu Asn Val Tyr Gly His Asp Tyr Pro Thr Arg
65                  70                  75                  80

Asp Gly Ser Ala Ile Arg Asp Tyr Ile His Val Met Asp Leu Ala Asp
                85                  90                  95

Gly His Ile Ala Ala Leu Arg Lys Leu Phe Thr Thr Glu Asn Ile Gly
            100                 105                 110

Cys Ala Ala Tyr Asn Leu Gly Thr Gly Arg Gly Thr Ser Val Leu Glu
        115                 120                 125

Met Val Asp Ala Phe Glu Lys Ala Ser Gly Lys Lys Ile Pro Val Lys
    130                 135                 140

Leu Cys Pro Arg Arg Ala Gly Asp Ala Thr Glu Val Tyr Ala Ser Thr
145                 150                 155                 160

Glu Arg Ala Glu Lys Glu Leu
                165
```

<210> SEQ ID NO 13
<211> LENGTH: 571
<212> TYPE: DNA
<213> ORGANISM: Trifolium repens

<400> SEQUENCE: 13

```
catcatctgc aactgtttat ggcacacctg aaaagatacc ttgtgaggag gatttcaatt       60
tataagccat gaatccatat ggacggacca agcttttcct cgaagaaatc gcacgagata      120
ttcagaaagc tgagccagaa tggaggatca ttttactgag atacttcaat ccagttgggg      180
cccatgaaag cggtagactc ggtgaagatc ccaagggcat cccaaataat ctcatgcctt      240
atatacagcg tgtagctgtt gaaagattac ccgagctcaa tgtatatggt catgattatc      300
ctacgaggga tggttctgcg attcgggact atatccatgt gatggactta gcagatggtc      360
acattgctgc attgagaaag cttttcacaa cagaaaacat aggttgtgct gcttacaact      420
tgggaactgg tcgtggtaca tctgtacttg aaatggttga tgcatttgag aaagcttctg      480
```

```
gcaagaaaat tccagtgaaa ttgtgtccac gaagggcggg agatgctacg gaggtttatg    540
catctacaga gagagctgag aaagaacttg g                                    571

<210> SEQ ID NO 14
<211> LENGTH: 543
<212> TYPE: DNA
<213> ORGANISM: Trifolium repens

<400> SEQUENCE: 14
tcatctgcaa ctgtttatgg cacacctgaa aagataccct tgtgaggagga tttcaattta    60 taagccatga atccatatgg acggaccaag cttttcctcg aagaaatcgc acagagatatt   120 cagaaagctg agccagaatg gaggatcatt ttactgagat acttcaatcc agttggggcc   180
catgaaagcg gtagactcgg tgaagatccc aagggcatcc caaataatct catgccttat   240
atacagcgtg tagctgttga aagattaccc gagctcaatg tatatggtca tgattatcct   300
acgagggatg gttctgcgat tcggactat atccatgtga tggacttagc agatggtcac    360
attgctgcat tgagaaagct tttcacaaca gaaaacatag gttgtgctgc ttacaacttg   420
ggaactggtc gtggtacatc tgtacttgaa atggttgatg catttgagaa agcttctggc   480
aagaaaattc cagtgaaatt gtgtccacga agggcgggag atgctacgga ggtttatgca   540
tct                                                                  543

<210> SEQ ID NO 15
<211> LENGTH: 576
<212> TYPE: DNA
<213> ORGANISM: Trifolium repens

<400> SEQUENCE: 15
gagtaattca actttcgata atatatatat atatcctcct tctctcttgt tgaaacatat    60
atttcctttt ttttttttct tttcaaaaga aaccatggta gtgaaggtgt atggtcctca   120
ctgtgcctca accaaaagag tgttggtttg tcttgttgag aaggaaatag aatttgaggt   180
tgtccctatt aatttcttag aaggagaaca gaagaatcct gagtacctca aattacagcc   240
ttttggaact cttcctgtga ttcaagatgg agactatacc ctttatgaat ctcgtgcaat   300
aataagatac tatgctgaaa atatagatc tcaagggggtt gaattacttg aaagacaat   360 agaagaaaaa ggtctagtgg aacaatggtt agaagttgaa gcacaaaact ttaacccatc   420
agcatacaac ttggcccttc atatattatt tccttcacta ctagctgaca acactccaaa   480
tcctaaggta attgaagaga gtgaaccaaa acttgtgaag gttttgaaca tttatgaaga   540
gaggctatca aagagcaagt atttggctgg tgatttt                             576

<210> SEQ ID NO 16
<211> LENGTH: 160
<212> TYPE: PRT
<213> ORGANISM: Trifolium repens

<400> SEQUENCE: 16

Met Val Val Lys Val Tyr Gly Pro His Cys Ala Ser Thr Lys Arg Val
 1               5                  10                  15

Leu Val Cys Leu Val Glu Lys Glu Ile Glu Phe Glu Val Val Pro Ile
                20                  25                  30

Asn Phe Leu Glu Gly Glu Gln Lys Asn Pro Glu Tyr Leu Lys Leu Gln
        35                  40                  45

Pro Phe Gly Thr Leu Pro Val Ile Gln Asp Gly Asp Tyr Thr Leu Tyr
    50                  55                  60
```

Glu Ser Arg Ala Ile Ile Arg Tyr Tyr Ala Glu Lys Tyr Arg Ser Gln
65                  70                  75                  80

Gly Val Glu Leu Leu Gly Lys Thr Ile Glu Glu Lys Gly Leu Val Glu
                85                  90                  95

Gln Trp Leu Glu Val Glu Ala Gln Asn Phe Asn Pro Ser Ala Tyr Asn
            100                 105                 110

Leu Ala Leu His Ile Leu Phe Pro Ser Leu Leu Ala Asp Asn Thr Pro
        115                 120                 125

Asn Pro Lys Val Ile Glu Glu Ser Glu Pro Lys Leu Val Lys Val Leu
    130                 135                 140

Asn Ile Tyr Glu Glu Arg Leu Ser Lys Ser Lys Tyr Leu Ala Gly Asp
145                 150                 155                 160

<210> SEQ ID NO 17
<211> LENGTH: 534
<212> TYPE: DNA
<213> ORGANISM: Trifolium repens

<400> SEQUENCE: 17
gagtaattca actttcgata atatatatat atatcctcct tctctcttgt tgaaacatat    60
atttcctttt ttttttttct tttcaaaaga aaccatggta gtgaaggtgt atggtcctca   120
ctgtgcctca accaaaagag tgttggtttg tcttgttgag aaggaaatag aatttgaggt   180
tgtccctatt aatttcttag aaggagaaca gaagaatcct gagtacctca aattacagcc   240
ttttggaact cttcctgtga ttcaagatgg agactatacc ctttatgaat ctcgtgcaat   300
aataagatac tatgctgaaa aatatagatc tcaaggggtt gaattacttg gaaagacaat   360
agaagaaaaa ggtctagtgg aacaatggtt agaagttgaa gcacaaaact taacccatc    420 agcatacaac ttggcccttc atatattatt ccttcacta ctagctgaca cactccaaa    480 tcctaaggta attgaagaga gtgaaccaaa acttgtgaag gttttgaaca ttta          534

<210> SEQ ID NO 18
<211> LENGTH: 569
<212> TYPE: DNA
<213> ORGANISM: Trifolium repens

<400> SEQUENCE: 18
ttccactttc gataatatat atatatatcc tccttctctc ttgttgaaac atatatttcc    60 ttttttttt tctttttaaa agaaaccatg gtagtgaagg tgtatggtcc tcactgtgcc   120
tcaaccaaaa gagtgttggt tgtcttgtt gagaaggaaa tagaatttga ggttgtccct   180
attaatttct tagaaggaga acagaagaat cctgagtacc tcaaattaca gccttttgga   240
actcttcctg tgattcaaga tggagactat acccttatg aatctcgtgc aataataaga   300
tactatgctg aaaaatatag atctcaaggg gttgaattac ttggaaagac aatagaagaa   360
aaaggtctag tggaacaatg gttagaagtt gaagcacaaa actttaaccc atcagcatac   420
aacttggccc ttcatatatt atttccttca ctactagctg acaacactcc aaatcctaag   480
gtaattgaag agagtgaagc aaaacttgtg aaggttttga acatttatga agagaggcta   540
tcaaagagca agtatttggc tggtgattt                                      569

<210> SEQ ID NO 19
<211> LENGTH: 1288
<212> TYPE: DNA
<213> ORGANISM: Trifolium repens

<400> SEQUENCE: 19

```
caccttgaga attattgcga tcaagattgc aatgaaaatt ttggataagg ccatccctcc      60
ctcccctcct ctctatataa gtagttggtt ggttagtgtc aatataagaa gaaaaacaca     120
aaccaaacca tatatatagt atcaatatca attaagctag ctatttccaa atcaacatgg     180
ctccttcaac aactgaatcc aataaacaac aaatccccaa cggaaaagac aatcatctaa     240
aaccacaaca acaagaagaa gatgatgatg ccctcgaatt tgccacacaa ataacaggtt     300
ccattgttgt tccattggct ttgaggtcag ccattgatct tggcatcttt gacatcctag     360
ccaaagctgg cgaaggtgca gaactctctg cacaagacat tgctgttaag attggaacca     420
acaacccgga agcaccaaca atgttgaatc gtcttcttag gttgttggcc agtcactcta     480
ttctaaactc ctctgttcct caacaacatg atgatcaaca atattctac agcctctcca      540
atcgctccaa atattttgtc accgatgctg acggcatctc gttgggaccc accttggcat     600
tacttctcga caatgtcttc taccaaagct ggtcggagct gaaaggagcg atagtggaag     660
gaggaatacc gttcaataga gtatatggaa tgcatgcctt tgagtaccca cgtgtggatc     720
caaggttcaa tgatgttttc aacaaagcta tgcttagttc aaccactatt aatatgaaga     780
gaattcttga attttatcaa ggttttgagc atgtcactaa gttggttgac gttggtggtg     840
gtcttggaca taacctcaaa ttgatcacag ccaaatattc ccatattcat ggaattaatt     900
ttgacttgcc tcatgtgcta caaaatgctc ctaactaccc aggtgttgaa cacgtgggag     960
gagatatgtt tgagagcgtt cctacagggg atgccatttt tatgaagtgg atacttcatg    1020
attggagtga tgaacactgc ttgaagctgt tgaaaaattg ttacaaagct attcctgaga    1080
atggaaaggt tattgttgtg gacacaatcc ttcccaccac gcccgagaca cagggagcg     1140
caaagtttgg tttctcgtct gatcttttaa tgatgactca aaatccagga ggaaaagaga    1200
gaactgagca ggaattcata aaattggcaa aaggatctgg attcagtggc atcaaaccta    1260
tatgttgtgt gtctggacta tgggttat                                        1288
```

<210> SEQ ID NO 20
<211> LENGTH: 370
<212> TYPE: PRT
<213> ORGANISM: Trifolium repens

<400> SEQUENCE: 20

```
Met Ala Pro Ser Thr Thr Glu Ser Asn Lys Gln Gln Ile Pro Asn Gly
1               5                   10                  15

Lys Asp Asn His Leu Lys Pro Gln Gln Gln Glu Glu Asp Asp Asp Ala
            20                  25                  30

Leu Glu Phe Ala Thr Gln Ile Thr Gly Ser Ile Val Val Pro Leu Ala
        35                  40                  45

Leu Arg Ser Ala Ile Asp Leu Gly Ile Phe Asp Ile Leu Ala Lys Ala
    50                  55                  60

Gly Glu Gly Ala Glu Leu Ser Ala Gln Asp Ile Ala Val Lys Ile Gly
65                  70                  75                  80

Thr Asn Asn Pro Glu Ala Pro Thr Met Leu Asn Arg Leu Leu Arg Leu
                85                  90                  95

Leu Ala Ser His Ser Ile Leu Asn Ser Ser Val Pro Gln Gln His Asp
            100                 105                 110

Asp Gln Gln Ile Phe Tyr Ser Leu Ser Asn Arg Ser Lys Tyr Phe Val
        115                 120                 125

Thr Asp Ala Asp Gly Ile Ser Leu Gly Pro Thr Leu Ala Leu Leu Leu
    130                 135                 140
```

```
Asp Asn Val Phe Tyr Gln Ser Trp Ser Glu Leu Lys Gly Ala Ile Val
145                 150                 155                 160

Glu Gly Gly Ile Pro Phe Asn Arg Val Tyr Gly Met His Ala Phe Glu
            165                 170                 175

Tyr Pro Arg Val Asp Pro Arg Phe Asn Asp Val Phe Asn Lys Ala Met
        180                 185                 190

Leu Ser Ser Thr Thr Ile Asn Met Lys Arg Ile Leu Glu Phe Tyr Gln
    195                 200                 205

Gly Phe Glu His Val Thr Lys Leu Val Asp Val Gly Gly Gly Leu Gly
210                 215                 220

His Asn Leu Lys Leu Ile Thr Ala Lys Tyr Ser His Ile His Gly Ile
225                 230                 235                 240

Asn Phe Asp Leu Pro His Val Leu Gln Asn Ala Pro Asn Tyr Pro Gly
                245                 250                 255

Val Glu His Val Gly Gly Asp Met Phe Glu Ser Val Pro Thr Gly Asp
            260                 265                 270

Ala Ile Phe Met Lys Trp Ile Leu His Asp Trp Ser Asp Glu His Cys
        275                 280                 285

Leu Lys Leu Leu Lys Asn Cys Tyr Lys Ala Ile Pro Glu Asn Gly Lys
    290                 295                 300

Val Ile Val Val Asp Thr Ile Leu Pro Thr Thr Pro Glu Thr Thr Gly
305                 310                 315                 320

Ser Ala Lys Phe Gly Phe Ser Ser Asp Leu Leu Met Met Thr Gln Asn
                325                 330                 335

Pro Gly Gly Lys Glu Arg Thr Glu Gln Glu Phe Ile Lys Leu Ala Lys
            340                 345                 350

Gly Ser Gly Phe Ser Gly Ile Lys Pro Ile Cys Cys Val Ser Gly Leu
        355                 360                 365

Trp Val
    370

<210> SEQ ID NO 21
<211> LENGTH: 583
<212> TYPE: DNA
<213> ORGANISM: Trifolium repens

<400> SEQUENCE: 21
caccttgaga attattgcga tcaagattgc aatgaaaatt ttggataagg ccatccctcc      60
ctcccctcct ctctatataa gtagttggtt ggttagtgtc aatataagaa gaaaaacaca     120
aaccaaacca tatatatagt atcaatatca attaagctag ctatttccaa atcaacatgg     180
ctccttcaac aactgaatcc aataaacaac aaatccccaa cggaaaagac aatcatctaa     240
aaccacaaca acaagaagaa gatgatgatg ccctcgaatt tgccacacaa ataacaggtt     300
ccattgttgt tccattggct ttgaggtcag ccattgatct tggcatcttt gacatcctag     360
ccaaagctgg cgaaggtgca gaactctctg cacaagacat tgctgttaag attggaacca     420
acaacccgga agcaccaaca atgttgaatc gtcttcttag gttgttggcc agtcactcta     480
ttctaaactc ctctgttcct caacaacatg atgatcaaca aatattctac agcctctcca     540
atcgctccaa atattttgtc accgatgctg acggcatctc gtt                       583

<210> SEQ ID NO 22
<211> LENGTH: 545
<212> TYPE: DNA
<213> ORGANISM: Trifolium repens

<400> SEQUENCE: 22
```

-continued

```
ctctccctcc ctccctcct ctctatataa gtagttggtt ggttagtgtc aatataagaa      60
gaaaaacaca aaccaaacca tatatatagt atcaatatca attaagctag ctatttccaa     120
atgaacatgg ctccttcaac aactgaatcc aataaacaac aaatccccaa cggaaaagac     180
aatcatctaa aaccacaaca acaagaagaa gatgatgatg ccctcgaatt tgccacacaa     240
ataacaggtt ccattgttgt tccattggct ttgaggtcag ccattgatct tggcatcttt     300
gacatcctag ccaaagctgg cgaaggtgca gaactctctg cacaagacat tgctgttaag     360
attggaacca acaacccgga agcaccaaca atgttgaatc gtcttcttag gttgttggcc     420
agtcactcta ttctaaactc ctctgttcct caacaacatg atgatcaaca aatattctac     480
agcctctcca atcgctccaa atattttgtc accgatgctg acggcatctc gtgggaccc     540 acctt                                                                545
```

<210> SEQ ID NO 23
<211> LENGTH: 699
<212> TYPE: DNA
<213> ORGANISM: Trifolium repens
<220> FEATURE:
<221> NAME/KEY: misc_feature
<222> LOCATION: (241)..(241)
<223> OTHER INFORMATION: n is a, c, g, or t

<400> SEQUENCE: 23

```
aaaccaaacc atatatatag tatcaatatc aattaagcta gctatttcca aatcaacatg      60
gctccttcaa cggctggggc gaataaacaa caaatcccca acggaaaaga caatcatcta     120
aaaccacaac aacaagaaga agatgatgat gccctcgaat tgccacaca aataacaggg     180 tccattgttg ttccattggc tttgagggca gccattgatc ttggcatggg ggggatccta     240
nccaaagctg gcgaaggtgc aaaactctct gcacaagaca ttgctgttaa gattggaacc     300
aacaacccgg aagcaccaac aatgttgaat cgtcttctta ggttgttggc cagtcactct     360
attctaaact cctctgttcc tcaacaacat gatgatcaac aaatattcta cagcctctcc     420
aatcgctcca aatattttgt caccgatgct gatggcatct cgtgggacc cacccttggca     480 ttacttctcg acaatgtctt ctaccaaagc tggtcggagc tgaaaggagc gatagtggaa     540
ggaggaatac cgttcaatag agtatatgga atgcatgcct ttgagtaccc acgtgtggat     600
ccaaggttca atgatttttt caacaaagct atgcttagtt caaccactat taatatgaag     660
agaattcttg aattttatca aggtttgagc atgtcacta                            699
```

<210> SEQ ID NO 24
<211> LENGTH: 613
<212> TYPE: DNA
<213> ORGANISM: Trifolium repens

<400> SEQUENCE: 24

```
aaccatatat atagtatcaa tatcaattaa gctagctatt tccaaatcaa catggctcct      60
tcaacaactg aatccaataa acaacaaatc cccaacggaa agacaatca tctaaaacca     120 caacaacaag aagaagatga tgatgccctc gaatttgcca cacaaataac aggttccatt     180
gttgttccat ggctttgag tcagccatt gatcttggca tctttgacat cctagccaaa     240
gctggcgaag gtgcagaact ctctgcacaa gacattgctg ttaagattgg aaccaacaac     300
ccggaagcac caacaatgtt gaatcgtctt cttaggttgt tggccagtca ctctattcta     360
aactcctctg ttcctcaaca acatgatgat caacaaatat tctacagcct ctccaatcgc     420
tccaaatatt ttgtcaccga tgctgacggc atctcgttgg gacccacctt ggcattactt     480
```

```
ctcgacaatg tcttctacca aagctggtcg gagctgaaag gagcgatagt ggaaggagga    540
ataccgttca atagagtata tggaatgcat gcctttgagt acccacgtgt ggatccaagg    600
ttcaatgatg ttt                                                        613

<210> SEQ ID NO 25
<211> LENGTH: 519
<212> TYPE: DNA
<213> ORGANISM: Trifolium repens

<400> SEQUENCE: 25
ttaagctagc tatttccaaa gaacatggct ccttcaacaa ctgaatccat aaacaacaaa     60
tccccaacgg aaaagacaat catctaaaac cacaacaaca acaagaagat gatgatgccc   120
tcgaatttgc cacacaaata acaggttcca ttgttgttcc attggctttg aggtcagcca   180
ttgatcttgg catctttgac atcctagcca aagctggcga aggtgcagaa ctctctgcac   240
aagacattgc tgttaagatt ggaaccaaca acccggaagc accaacaatg ttgaatcgtc   300
ttcttaggtt gttggccagt cactctattc taaactcctc tgttcctcaa caacatgatg   360
atcaacaaat attctacagc ctctccaatc gctccaaata ttttgtcacc gatgctgacg   420
gcatctcgtt gggacccacc ttggcattac ttctcgacaa tgtcttctac caaagctggt   480
cggagctgaa aggagcgata gtggaaggag aataccgt                            519

<210> SEQ ID NO 26
<211> LENGTH: 524
<212> TYPE: DNA
<213> ORGANISM: Trifolium repens

<400> SEQUENCE: 26
catggctcct taacaactga atccaataaa caacaaatcc ccaacggaaa agacatcatc     60
taaaaccaca acaacaagaa gaagatgatg atgccctcga atttgccaca caataacag    120 gttccattgt tgttccattg ctttgaggt cagccattga tcttggcatc tttgacatcc    180
tagccaaagc tggcgaaggt gcagaactct ctgcacaaga cattgctgtt aagattggaa   240
ccaacaaccc ggaagcacca acaatgttga atcgtcttct taggttgttg gccagtcact   300
ctattctaaa ctcctctgtt cctcaacaac atgatgatca acaaatattc tacagcctct   360
ccaatcgctc caaatatttt gtcaccgatg ctgacggcat ctcgttggga cccaccttgg   420
cattacttct cgacaatgtc ttctaccaga gctggtcgga gctgaaagga gcgatagtgg   480
aaggaggaat accgttcaat agagtatatg gaatgcatgc cttt                     524

<210> SEQ ID NO 27
<211> LENGTH: 188
<212> TYPE: DNA
<213> ORGANISM: Trifolium repens

<400> SEQUENCE: 27
tctccaatcg ctccaaatat tttgtcaccg atgctgacgg catctcgctg ggacccacct     60
tggcattact tctcgacaat gtcttctacc aaagctggtc ggagctgaaa ggagcgatag   120
tggaaggagg aataccgttc aatagagtat atggaatgca tgcctttgag tatccacgtg   180
tggatcca                                                             188

<210> SEQ ID NO 28
<211> LENGTH: 588
<212> TYPE: DNA
<213> ORGANISM: Trifolium repens
```

```
<220> FEATURE:
<221> NAME/KEY: misc_feature
<222> LOCATION: (491)..(491)
<223> OTHER INFORMATION: n is a, c, g, or t

<400> SEQUENCE: 28
agtggaaggg ggaataccgt tcaatagagt atatggaatg catgcctttg agtacccacg      60
tgtggatcca aggttcaatg atgttttcaa caaagctatg cttagttcaa ccactattaa     120
tatgaagaga attcttgaat tttatcaagg ttttgagcat gtcactaagt tggttgacgt     180
tggtggtggt cttggacata acctcaaatt gatcacagcc aaatattctc atattcatgg     240
aattaatttt gacttgcctc atgtgctaca aaatgctcct aactacccag gtgttgaaca     300
cgtgggagga gatatgtttg agagcgttcc tacaggggat gccattttta tgaagtggat     360
acttcatgat tggagtgatg aacactgctt gaagctgttg aaaaattgtt acaaagctat     420
tcctgagaat ggaaaggtta ttgttgtgga cacaatcctt cccaccatgc ccgagacaac     480
agggagcgca nagtttggtt tctcgtctga tcttttaatg atgactcaaa atccaggagg     540
aaaagagaga actgagcagg aattcataaa attggcaaaa ggatctgg                  588

<210> SEQ ID NO 29
<211> LENGTH: 598
<212> TYPE: DNA
<213> ORGANISM: Trifolium repens

<400> SEQUENCE: 29
ggaatgcatg cctttgagta tcccgtgtgg atccaggttc aatgatgttt taacaaagct      60
atgcttagtt caaccactat taatatgaag aggattcttg aattttataa ggttttgagc     120
atgtcactaa gttggttgac gttggtggtg gtcttggaca taacctcaaa ttgatcacag     180
ccaaatattc ccatattcat ggaattaatt ttgacttgtc tcatgtgcta caaaatgctc     240
ctaactaccc agtgtgttaa cacgtgggag gagatatgtt tgagagcgtt cctacagggg     300
atgccatttt tatgaagtgg atacttcatg attggagtga tgaacactgc ttgaagctgt     360
tgaaaaattg ttacaaagct attcctgaga atggaaaggt tattgttgtg gacacaatcc     420
ttcccaccac gcccgagaca acagggagcg caaagtttgg tttctcgtct gatcttttaa     480
tgatgactca aaatccagga ggaaaagaga gaagtgagca ggaattcata aaattggcaa     540
aaggatctgg attcagtggc atcaaaccta tatgttgtgt gtctggacta tgggttat      598

<210> SEQ ID NO 30
<211> LENGTH: 544
<212> TYPE: DNA
<213> ORGANISM: Trifolium repens

<400> SEQUENCE: 30
ttgtggataa aagagtggtt ggacaagcaa ccacgtagca cggtattata tgtggctttt      60
ggtagtgaag caaaaccaag tcaagaagaa gtcactaaga tagcttttgg gttggaggaa     120
tcaaagattc cgttcttttg ggtccttagg gttcagcgtg gaccaactga caatgtggtg     180
ttgcagctgc cagaagggtt tgaggagcga acaaggggc gcggagtggt atgcactgat      240
tgggctccgc aagtgaaaat aatgggtcac gtggcagttg gtgggttctt gactcatgct     300
ggttggacat cagttgtgga ggctgttcaa atgaaaagc cacttgtgct actaacatttt     360
cttgcagatc aaggaataaa tgcgagggtg ttggaggaaa agaagatggg ttactcagtg     420
cctagggatc aacgagatgg gtcattcaca agtgactcgg tggctgcttc gattagacta     480
gttatgcttg aagaagaggg aagaatctac aaggaaaaga ttaaagagat gaaggacttg     540
``` ttcg                                                                544

<210> SEQ ID NO 31
<211> LENGTH: 181
<212> TYPE: PRT
<213> ORGANISM: Trifolium repens

<400> SEQUENCE: 31

Leu Trp Ile Lys Glu Trp Leu Asp Lys Gln Pro Arg Ser Thr Val Leu
1               5                   10                  15

Tyr Val Ala Phe Gly Ser Glu Ala Lys Pro Ser Gln Glu Glu Val Thr
            20                  25                  30

Lys Ile Ala Phe Gly Leu Glu Glu Ser Lys Ile Pro Phe Phe Trp Val
        35                  40                  45

Leu Arg Val Gln Arg Gly Pro Thr Asp Asn Val Val Leu Gln Leu Pro
    50                  55                  60

Glu Gly Phe Glu Glu Arg Asn Lys Gly Arg Gly Val Val Cys Thr Asp
65                  70                  75                  80

Trp Ala Pro Gln Val Lys Ile Met Gly His Val Ala Val Gly Gly Phe
                85                  90                  95

Leu Thr His Ala Gly Trp Thr Ser Val Val Glu Ala Val Gln Asn Glu
            100                 105                 110

Lys Pro Leu Val Leu Leu Thr Phe Leu Ala Asp Gln Gly Ile Asn Ala
        115                 120                 125

Arg Val Leu Glu Glu Lys Lys Met Gly Tyr Ser Val Pro Arg Asp Glu
    130                 135                 140

Arg Asp Gly Ser Phe Thr Ser Asp Ser Val Ala Ala Ser Ile Arg Leu
145                 150                 155                 160

Val Met Leu Glu Glu Glu Gly Arg Ile Tyr Lys Glu Lys Ile Lys Glu
                165                 170                 175

Met Lys Asp Leu Phe
            180

<210> SEQ ID NO 32
<211> LENGTH: 523
<212> TYPE: DNA
<213> ORGANISM: Trifolium repens

<400> SEQUENCE: 32
taataacatt attattattg ctcctctaaa gctcaaacct catttacaac catggcaaat      60
caaaaggttt tcaccctctc acaaatctcc caacacaagt ccaacaaaaa ctgttggctt     120
gtaatcaacg acagagtgtt gaacgtgaca aagttttttgg aggaacatcc aggaggagaa    180
gaggtaattc tagaggttgc agggaaagat gccacaaagg agtttgatga tattggacat    240
agtaaagcag ctcaaaattt agtcctcaaa tatcaagttg gtgtacttga aggtgccaag    300
gttgaaaaga ttgataatat ggattttgtt gaggacaagg agtccaagag caaagaaatg    360
agtgcttttg ttgtcaaaga ggatactagt tccaaaactg caacattttt agagttgttt    420
gtgccatttc ttttgctttt tatctatttt ggttacagtg tcatcaccag agcagacact    480
gttggttact aaatcatggg ggatgtctag accttggtct gtg                      523

<210> SEQ ID NO 33
<211> LENGTH: 161
<212> TYPE: PRT
<213> ORGANISM: Trifolium repens

<400> SEQUENCE: 33

His Tyr Tyr Cys Ser Ser Lys Ala Gln Thr Ser Phe Thr Thr Met
1               5                   10                  15

Ala Asn Gln Lys Val Phe Thr Leu Ser Gln Ile Ser Gln His Lys Ser
            20                  25                  30

Asn Lys Asn Cys Trp Leu Val Ile Asn Asp Arg Val Leu Asn Val Thr
        35                  40                  45

Lys Phe Leu Glu Glu His Pro Gly Gly Glu Val Ile Leu Glu Val
    50                  55                  60

Ala Gly Lys Asp Ala Thr Lys Glu Phe Asp Asp Ile Gly His Ser Lys
65              70                  75                  80

Ala Ala Gln Asn Leu Val Leu Lys Tyr Gln Val Gly Val Leu Glu Gly
                85                  90                  95

Ala Lys Val Glu Lys Ile Asp Asn Met Asp Phe Val Glu Asp Lys Glu
            100                 105                 110

Ser Lys Ser Lys Glu Met Ser Ala Phe Val Val Lys Glu Asp Thr Ser
            115                 120                 125

Ser Lys Thr Ala Thr Phe Leu Glu Leu Phe Val Pro Phe Leu Phe Ala
        130                 135                 140

Phe Ile Tyr Phe Gly Tyr Ser Val Ile Thr Arg Ala Asp Thr Val Gly
145                 150                 155                 160

Tyr

<210> SEQ ID NO 34
<211> LENGTH: 557
<212> TYPE: DNA
<213> ORGANISM: Trifolium repens

<400> SEQUENCE: 34
catagaagaa gctctatagc aacatttctt tgttgagtag aggtatataa ctcaaaaggg      60
ttgctatggc cacggcgcaa tttcgaatta tactattgtt ggtagcatgt ttgcttccat     120
tttctgttga tgctacggtt cgacactaca agttcaatgt tgtgttgaaa atgccacaa     180 gattgtgttc aaccaaacca attgtaacca taaatggaaa atccccaggt cccaccatct     240
atgctagaga agatgacaat gttctaatta aggttgtcaa ccatgtcaaa tacaatgtta     300
gcatacactg gcatggtgtc aaacaactaa gaacgggttg ggccgacggg ccagcataca     360
taacccaatg tccaattcaa ccgggtcagg cctatgttta caacttcact cttacaggcc     420
agagaggcac actttggtgg catgctcata ttctttggct tagagccact gtccatggtg     480
ccttggtcat tttaccaaag cttggagttc cttacccttt tcccaaacct catatggaac     540
aagttattgt attaggt                                                    557

<210> SEQ ID NO 35
<211> LENGTH: 164
<212> TYPE: PRT
<213> ORGANISM: Trifolium repens

<400> SEQUENCE: 35

Met Ala Thr Ala Gln Phe Arg Ile Ile Leu Leu Val Ala Cys Leu
1               5                   10                  15

Leu Pro Phe Ser Val Asp Ala Thr Val Arg His Tyr Lys Phe Asn Val
            20                  25                  30

Val Leu Lys Asn Ala Thr Arg Leu Cys Ser Thr Lys Pro Ile Val Thr
        35                  40                  45

Ile Asn Gly Lys Ser Pro Gly Pro Thr Ile Tyr Ala Arg Glu Asp Asp
    50                  55                  60

Asn Val Leu Ile Lys Val Val Asn His Val Lys Tyr Asn Val Ser Ile
65                  70                  75                  80

His Trp His Gly Val Lys Gln Leu Arg Thr Gly Trp Ala Asp Gly Pro
            85                  90                  95

Ala Tyr Ile Thr Gln Cys Pro Ile Gln Pro Gly Gln Ala Tyr Val Tyr
            100                 105                 110

Asn Phe Thr Leu Thr Gly Gln Arg Gly Thr Leu Trp Trp His Ala His
        115                 120                 125

Ile Leu Trp Leu Arg Ala Thr Val His Gly Ala Leu Val Ile Leu Pro
    130                 135                 140

Lys Leu Gly Val Pro Tyr Pro Phe Pro Lys Pro His Met Glu Gln Val
145                 150                 155                 160

Ile Val Leu Gly

<210> SEQ ID NO 36
<211> LENGTH: 2085
<212> TYPE: DNA
<213> ORGANISM: Trifolium repens

<400> SEQUENCE: 36

```
taagcagtgg taacaacgca gagtacgcgg ggattgcatt gcattttcaa gagagtgatc     60
actagccagc atagaagaag ctctatagca acatttcttt gttgagtaga ggtatataac    120
tcaaagggt tgctatggcc acggcgcaat ttcgaattat actattgttg gtagcatgtt    180
tgcttccatt ttctgttgat gctacggttc gacactacaa gttcaatgtt gtgttgaaaa    240
atgccacaag attgtgttca accaaaccaa ttgtaaccat aaatggaaaa tccccaggtc    300
ccaccatcta tgctagagaa gatgacaatg ttctaattaa ggttgtcaac catgtcaaat    360
acaatgttag catacactgg catggtgtca acaactaag aacggggtgg gccgacgggc    420
cagcatacat aacccaatgt ccaattcaac cgggtcaggc ctatgtttac aacttcactc    480
ttacaggcca gagaggcaca cttggtggc atgctcatat tctttggctt agagccactg    540
tccatggtgc cttggtcatt ttaccaaagc ttggagttcc ttacccttt cccaaacctc    600
atatggaaca agttattgta ttaggtgaat ggtggaaatc agataccgag ctataataa    660
atgaagcttt aaaatctgga ttagctccaa atatttctga tgctcacaca atcaatggtc    720
ttccagggtc tggccaaggt tgtgcttcac aagatggatt ctcattggaa gttcaacaaa    780
aaaaaaccta cttactaaga atcatcaatg ctgcactcaa tgaagaactc ttttcaaaa    840
ttgcaaacca tcaattaact gttgttgaag ttgatgcaac ttatgtaaaa ccattcaaaa    900
ctgacacaat tgttatagca cctggccaaa ccacaaacgt gcttttagaa accaaacaag    960
cactaggaaa ctacttaatt gcagcttctc ctttcatgga tgcaccaatt gttgttgaca   1020
acaaaactgc cattgccaca ttacactatt caaacacact tggttccaca gtcacttcct   1080
taacttcttt acctccaaaa aatgctactc caattgctaa tactttcaca gattctctta   1140
gaggcttaaa ctcgaaaaaa tatccggcta atgttccttt aaagattgat aataaattat   1200
tattcactgt ttctcttggt attaatcctt gtcctacatg tgtcaataat agtcgcgtcg   1260
tagctgattt caacaatgtt acattcgtga tgccgaaaac cgcgcttatt caagcacatt   1320
tttttaagat taaggagtt tttagtgatg attttcctgg aaatcctcct gtggtgtata   1380
attttactgg gacacagtgg acaaattttg ggactactaa agggacaagg ctttatagac   1440
ttgcttataa ttctactgtt gaattggttt tgcaagatac tggaatgata acacctgaga   1500
atcatcctat tcatcttcat ggattcaatt tctttgtagt tggtagtggt aaagggaact   1560
```

-continued

```
ttgattctaa aaaagatgca aaaaagttta atcttgttga tcctgttgag aggaatactg    1620
ttggtgttcc ggccggaggt tggactgcta tcagattcag ggctgataat ccaggggtgt    1680
ggtttatgca ttgtcatttg gagattcata caacatgggg actaaagatg cttttgttg     1740 tggacaatgg taaaggccca atgaatctc tattaccacc tccaagtgac cttcctaagt     1800
gttgaggaaa gtaccaatta acattcaatg ttatttgaag agaacaacat attttaatgg    1860
aaggattaaa caaggcaaat gacaagattt tcttggaata tggaaagaat aagatgtcca    1920
attttcttat aaaaaaaaaa tgtccaattg acatttattg gtatatttta attccttta    1980 gttgtattat tttcattgtt tgtacccatc tttcttcttc ttgaaagata ttttagggtt    2040
aatcaaaatt ttaagaattt ttaagaaatc ttttcttttg ttgcc                    2085
```

<210> SEQ ID NO 37
<211> LENGTH: 556
<212> TYPE: PRT
<213> ORGANISM: Trifolium repens

<400> SEQUENCE: 37

```
Met Ala Thr Ala Gln Phe Arg Ile Ile Leu Leu Leu Val Ala Cys Leu
1               5                   10                  15

Leu Pro Phe Ser Val Asp Ala Thr Val Arg His Tyr Lys Phe Asn Val
                20                  25                  30

Val Leu Lys Asn Ala Thr Arg Leu Cys Ser Thr Lys Pro Ile Val Thr
            35                  40                  45

Ile Asn Gly Lys Ser Pro Gly Pro Thr Ile Tyr Ala Arg Glu Asp Asp
        50                  55                  60

Asn Val Leu Ile Lys Val Val Asn His Val Lys Tyr Asn Val Ser Ile
65                  70                  75                  80

His Trp His Gly Val Lys Gln Leu Arg Thr Gly Trp Ala Asp Gly Pro
                85                  90                  95

Ala Tyr Ile Thr Gln Cys Pro Ile Gln Pro Gly Gln Ala Tyr Val Tyr
            100                 105                 110

Asn Phe Thr Leu Thr Gly Gln Arg Gly Thr Leu Trp Trp His Ala His
        115                 120                 125

Ile Leu Trp Leu Arg Ala Thr Val His Gly Ala Leu Val Ile Leu Pro
    130                 135                 140

Lys Leu Gly Val Pro Tyr Pro Phe Pro Lys Pro His Met Glu Gln Val
145                 150                 155                 160

Ile Val Leu Gly Glu Trp Trp Lys Ser Asp Thr Glu Ala Ile Ile Asn
                165                 170                 175

Glu Ala Leu Lys Ser Gly Leu Ala Pro Asn Ile Ser Asp Ala His Thr
            180                 185                 190

Ile Asn Gly Leu Pro Gly Ser Gly Gln Gly Cys Ala Ser Gln Asp Gly
        195                 200                 205

Phe Ser Leu Glu Val Gln Gln Lys Lys Thr Tyr Leu Leu Arg Ile Ile
    210                 215                 220

Asn Ala Ala Leu Asn Glu Glu Leu Phe Phe Lys Ile Ala Asn His Gln
225                 230                 235                 240

Leu Thr Val Val Glu Val Asp Ala Thr Tyr Val Lys Pro Phe Lys Thr
                245                 250                 255

Asp Thr Ile Val Ile Ala Pro Gly Gln Thr Thr Asn Val Leu Leu Glu
            260                 265                 270

Thr Lys Gln Ala Leu Gly Asn Tyr Leu Ile Ala Ala Ser Pro Phe Met
        275                 280                 285
```

```
Asp Ala Pro Ile Val Val Asp Asn Lys Thr Ala Ile Ala Thr Leu His
    290                 295                 300
Tyr Ser Asn Thr Leu Gly Ser Thr Val Thr Ser Leu Thr Ser Leu Pro
305                 310                 315                 320
Pro Lys Asn Ala Thr Pro Ile Ala Asn Thr Phe Thr Ser Leu Arg
                325                 330                 335
Gly Leu Asn Ser Lys Lys Tyr Pro Ala Asn Val Pro Leu Lys Ile Asp
            340                 345                 350
Asn Lys Leu Leu Phe Thr Val Ser Leu Gly Ile Asn Pro Cys Pro Thr
        355                 360                 365
Cys Val Asn Asn Ser Arg Val Val Ala Asp Phe Asn Asn Val Thr Phe
370                 375                 380
Val Met Pro Lys Thr Ala Leu Ile Gln Ala His Phe Phe Lys Ile Lys
385                 390                 395                 400
Gly Val Phe Ser Asp Asp Phe Pro Gly Asn Pro Val Val Tyr Asn
                405                 410                 415
Phe Thr Gly Thr Gln Leu Thr Asn Phe Gly Thr Thr Lys Gly Thr Arg
            420                 425                 430
Leu Tyr Arg Leu Ala Tyr Asn Ser Thr Val Glu Leu Val Leu Gln Asp
        435                 440                 445
Thr Gly Met Ile Thr Pro Glu Asn His Pro Ile His Leu His Gly Phe
    450                 455                 460
Asn Phe Phe Val Val Gly Ser Gly Lys Gly Asn Phe Asp Ser Lys Lys
465                 470                 475                 480
Asp Ala Lys Lys Phe Asn Leu Val Asp Pro Val Glu Arg Asn Thr Val
                485                 490                 495
Gly Val Pro Ala Gly Gly Trp Thr Ala Ile Arg Phe Arg Ala Asp Asn
            500                 505                 510
Pro Gly Val Trp Phe Met His Cys His Leu Glu Ile His Thr Thr Trp
        515                 520                 525
Gly Leu Lys Met Ala Phe Val Val Asp Asn Gly Lys Gly Pro Asn Glu
    530                 535                 540
Ser Leu Leu Pro Pro Ser Asp Leu Pro Lys Cys
545                 550                 555

<210> SEQ ID NO 38
<211> LENGTH: 885
<212> TYPE: DNA
<213> ORGANISM: Trifolium repens

<400> SEQUENCE: 38
agagaaatgg gaagaggaag agttgaattg aagagaattg agaacaaaat caacagacaa        60
gttacctttg caaaacgaag aaatggtctt ttgaagaaag cttatgaact ttctgttctt       120
tgtgatgctg aggttgctct catcgtcttc tccaatagag gaaaactcta tgagttttgc       180
agcacttcta gcatgctcaa aactcttgag aggtatcaga atgcaactta ggagcacct        240
gaagctaatg tgcatcaaa ggaagctttg gtattggaat taagcagtca acaagaatac        300
ttgaagctta aggcacgtta tgaatctctt caacgctcgc aaaggaatct tatgggagaa       360
gatcttggcc ctctaagtag caaagatctt gaaccacttg aaaggcagct agattcgtcc       420
ttgaagcaaa tcagatccac aaggacccaa ttcatgctgg atcagcttgg tgatcttcaa       480
cgtaaggaac acttgctatg tgaagcaaac agagctctca gacaaggat ggaagggtat        540
caaataaatt ctctccaact gaatctgagt gctgaagata tgggatatgg tcgtcatcat       600
```

-continued

```
ccagttcaca cccagggtga tgaactattt caaccaattg agtgcgaacc aaccttacaa    660
attggatatc aagctgatcc aggatcagtg gtgacagcag gcccaagcat gaataatttc    720
atgggtggat ggttaccatg atgatgttaa agttatatat tgagaacgag tgtgaagcat    780
gcataaagat caaatgaaaa tttgtaatac tagcatgtta tataatggac tacactaaac    840
tatgtattag tgtctactta ctatgtaggc aaaataatat agtaa                    885
```

<210> SEQ ID NO 39
<211> LENGTH: 244
<212> TYPE: PRT
<213> ORGANISM: Trifolium repens

<400> SEQUENCE: 39

```
Met Gly Arg Gly Arg Val Glu Leu Lys Arg Ile Glu Asn Lys Ile Asn
1               5                   10                  15

Arg Gln Val Thr Phe Ala Lys Arg Arg Asn Gly Leu Leu Lys Lys Ala
            20                  25                  30

Tyr Glu Leu Ser Val Leu Cys Asp Ala Glu Val Ala Leu Ile Val Phe
        35                  40                  45

Ser Asn Arg Gly Lys Leu Tyr Glu Phe Cys Ser Thr Ser Ser Met Leu
    50                  55                  60

Lys Thr Leu Glu Arg Tyr Gln Lys Cys Asn Tyr Gly Ala Pro Glu Ala
65                  70                  75                  80

Asn Val Thr Ser Lys Glu Ala Leu Val Leu Glu Leu Ser Ser Gln Gln
                85                  90                  95

Glu Tyr Leu Lys Leu Lys Ala Arg Tyr Glu Ser Leu Gln Arg Ser Gln
            100                 105                 110

Arg Asn Leu Met Gly Glu Asp Leu Gly Pro Leu Ser Ser Lys Asp Leu
        115                 120                 125

Glu Pro Leu Glu Arg Gln Leu Asp Ser Ser Leu Lys Gln Ile Arg Ser
    130                 135                 140

Thr Arg Thr Gln Phe Met Leu Asp Gln Leu Gly Asp Leu Gln Arg Lys
145                 150                 155                 160

Glu His Leu Leu Cys Glu Ala Asn Arg Ala Leu Arg Gln Arg Met Glu
                165                 170                 175

Gly Tyr Gln Ile Asn Ser Leu Gln Leu Asn Leu Ser Ala Glu Asp Met
            180                 185                 190

Gly Tyr Gly Arg His His Pro Val His Thr Gln Gly Asp Glu Leu Phe
        195                 200                 205

Gln Pro Ile Glu Cys Glu Pro Thr Leu Gln Ile Gly Tyr Gln Ala Asp
    210                 215                 220

Pro Gly Ser Val Val Thr Ala Gly Pro Ser Met Asn Asn Phe Met Gly
225                 230                 235                 240

Gly Trp Leu Pro
```

<210> SEQ ID NO 40
<211> LENGTH: 576
<212> TYPE: DNA
<213> ORGANISM: Trifolium repens

<400> SEQUENCE: 40

```
agagaaatgg gaagaggaag agttgaattg aagagaattg agaacaaaat caacagacaa     60
gttacctttg caaaacgaag aaatggtctt ttgaagaaag cttatgaact ttctgttctt    120
tgtgatgctg aggttgctct catcgtcttc tccaatagag aaaaactcta tgagttttgc    180
agcacttcta gcatgctcaa aactcttgag aggtatcaga aatgcaacta tggagcacct    240
```

```
gaagctaatg tgacatcaaa ggaagctttg gtattggaat taagcagtca acaagaatac      300
ttgaagctta aggcacgtta tgaatctctt caacgcacgc aaaggaatct tatgggagaa      360
gatcttggcc ctctaagtag caaagatctt gaaccacttg aaaggcagct agattcgtcc      420
ttgaagcaaa tcagatccac aaggacccaa ttcatgctgg atcagcttgg tgatcttcaa      480
cgtaaggaac acttgctatg tgaagcaaac agagctctca gacaaaggat ggaagggtat      540
caaataaatt ctctccaact gaatctgagt gctgaa                                576

<210> SEQ ID NO 41
<211> LENGTH: 583
<212> TYPE: DNA
<213> ORGANISM: Trifolium repens

<400> SEQUENCE: 41
agagaaatgg gaagaggaag agttgaattg aagagaattg agaacaaaat caacagacaa       60
gttacctttg caaaacgaag aaatggtctt ttgaagaaag cttatgaact ttctgttctt      120
tgtgatgctg aggttgctct catcgtcttc tccaatagag gaaaactcta tgagttttgc      180
agcacttcta gcatgctcaa aactcttgag aggtatcaga atgcaactag tggagcacct      240
gaagctaatg tgacatcaaa ggaagctttg gtattggaat taagcagtca acaagaatac      300
ttgaagctta aggcacgtta tgaatctctt caacgctcgc aaaggaatct tatgggagaa      360
gatcttggcc ctctaagtag caaagatctt gaaccacttg aaaggcagct agattcgtcc      420
ttgaagcaaa tcagatccac aaggacccaa ttcatgctgg atcagcttgg tgatcttcaa      480
cgtaaggaac acttgctatg tgaagcaaac agagctctca gacaaaggat ggaagggtat      540
caaataaatt ctctccaact gaatctgagt gctgaagata tgg                        583

<210> SEQ ID NO 42
<211> LENGTH: 571
<212> TYPE: DNA
<213> ORGANISM: Trifolium repens

<400> SEQUENCE: 42
gaatacttga agcttaaggc acgttatgaa tctcttcaac gctcgcaaag gaatcttatg       60
ggagaagatc ttggccctct aagtagcaaa gatcttgaac cacttgaaag gcagctagat      120
tcgtccttga agcaaatcag atccacaagg acccaattca tgctggatca gcttggtgat      180
cttcaacgta aggaacactt gctatgtgaa gcaaacagag ctctcagaca aaggatggaa      240
gggtatcaaa taaattctct ccaactgaat ctgagtgctg aagatatggg atatggtcgt      300
catcatccag ttcacaccca gggtgatgaa ctatttcaac caattgagtg cgaaccaacc      360
ttacaaattg gatatcaagc tgatccagga tcagtggtga cagcaggccc aagcatgaat      420
aatttcatgg gtggatggtt accatgatga tgttaaagtt atatattgag aacgagtgtg      480
aagcatgcat aaagatcaaa tgaaaatttg taatactagc atgttatata atggactaca      540
ctaaactatg tattagtgtc tacttactat g                                     571

<210> SEQ ID NO 43
<211> LENGTH: 569
<212> TYPE: DNA
<213> ORGANISM: Trifolium repens

<400> SEQUENCE: 43
gttatgaatc tcttcaacgc tcgcaaagga atcttatggg agaagatctt ggccctctaa       60
gtagcaaaga tcttgaacca cttgaaaggc agctagattc gtccttgaag caaatcagat      120
```

```
ccacaaggac ccaattcatg ctggatcagc ttggtgatct tcaacgtaag gaacacttgc     180
tatgtgaagc aaacagagct ctcagacaaa ggatggaagg gtatcaaata aattctctcc     240
aactgaatct gagtgctgaa gatatgggat atggtcgtca tcatccagtt cacacccagg     300
gtgatgaact atttcaacca attgagtgcg aaccaacctt acaaattgga tatcaagctg     360
atccaggatc agtggtgaca gcaggcccaa gcatgaataa tttcatgggt ggatggttac     420
catgatgatg ttaaagttat atattgagaa cgagtgtgaa gcatgcataa agatcaaatg     480
aaaatttgta atactagcat gttatataat ggactacact aaactatgta ttagtgtcta     540
cttactatgt aggcaaaata atatagtaa                                       569

<210> SEQ ID NO 44
<211> LENGTH: 368
<212> TYPE: DNA
<213> ORGANISM: Trifolium repens

<400> SEQUENCE: 44
atcttcaaaa gatgcttctc atattgatgt taaacccggt aatgcctcta atattcatgt      60
taaaaaggca gagttatttc taaaaactat aaggaaggat acatcaaagc agaaggtag      120 caaagaaatc atgaagcaca atatgtatt tcaaacaagg agtcagatcg atatactaga     180
cgatgggttc cgatggagaa agtacgggga aaagttggtg aaaaacaaca aatatcctag     240
aagttattac aaatgcactt atccaggctg caatgcaaag aaacaaatcc aaaggaattc     300
caaacaggat catattgtat aaacaactta cgagggaatg catattcacc ctgtccagaa     360
ctcaactg                                                              368

<210> SEQ ID NO 45
<211> LENGTH: 106
<212> TYPE: PRT
<213> ORGANISM: Trifolium repens

<400> SEQUENCE: 45

Ser Ser Lys Asp Ala Ser His Ile Asp Val Lys Pro Gly Asn Ala Ser
1               5                   10                  15

Asn Ile His Val Lys Lys Ala Glu Leu Phe Leu Lys Thr Ile Arg Lys
            20                  25                  30

Asp Thr Ser Lys Gln Lys Gly Ser Lys Glu Ile Met Lys His Lys Tyr
        35                  40                  45

Val Phe Gln Thr Arg Ser Gln Ile Asp Ile Leu Asp Asp Gly Phe Arg
    50                  55                  60

Trp Arg Lys Tyr Gly Glu Lys Leu Val Lys Asn Asn Lys Tyr Pro Arg
65                  70                  75                  80

Ser Tyr Tyr Lys Cys Thr Tyr Pro Gly Cys Asn Ala Lys Lys Gln Ile
                85                  90                  95

Gln Arg Asn Ser Lys Gln Asp His Ile Val
            100                 105

<210> SEQ ID NO 46
<211> LENGTH: 632
<212> TYPE: DNA
<213> ORGANISM: Trifolium repens

<400> SEQUENCE: 46
cctctctctc tctctctccc ccactccatt atcaccacca cacggtctct tcttcctaac      60
tttctcttct tctctttctt ttccctaatt tacctccaaa attaaccaaa ataaataat      120
```

-continued

```
aaaaattcca tttcatgaat ctttggagcg acgagaactc atcagtgatg gaggctttta    180
tgacctcatc cgatttatca accttatggc catcacaacc acagccgccg tcgtcacaac    240
caccacaaac caccaccgga ttcaaccaag acacactcca acaacgtctt caagctttaa    300
tcgaaggcgc ttccgaaatc tggacttacg ctatcttctg gcaaccttct tacgactatt    360
ccggctcttc tcttctcggt tggggtgacg gttattacaa aggcgaagaa gacaaatcaa    420
aatcaaaatc caaagctact tcaccagctg aacaagaacc cgtagaaaaa gttctccgag    480
aacttaattc tttaatctcc ggtaatccag caccggaaga atcttccgtc gatgaagaag    540
ttacagatac ggaatggttt ttttttagtt tctatgactc aatcttttgt taacggaagt    600
ggacttcctg gacaagctta ttttaattca ac                                  632
```

<210> SEQ ID NO 47
<211> LENGTH: 152
<212> TYPE: PRT
<213> ORGANISM: Trifolium repens

<400> SEQUENCE: 47

```
Met Asn Leu Trp Ser Asp Glu Asn Ser Ser Val Met Glu Ala Phe Met
1               5                   10                  15

Thr Ser Ser Asp Leu Ser Thr Leu Trp Pro Ser Gln Pro Gln Pro Pro
            20                  25                  30

Ser Ser Gln Pro Pro Gln Thr Thr Thr Gly Phe Asn Gln Asp Thr Leu
        35                  40                  45

Gln Gln Arg Leu Gln Ala Leu Ile Glu Gly Ala Ser Glu Ile Trp Thr
    50                  55                  60

Tyr Ala Ile Phe Trp Gln Pro Ser Tyr Asp Tyr Ser Gly Ser Ser Leu
65                  70                  75                  80

Leu Gly Trp Gly Asp Gly Tyr Tyr Lys Gly Glu Glu Asp Lys Ser Lys
                85                  90                  95

Ser Lys Ser Lys Ala Thr Ser Pro Ala Glu Gln Glu His Arg Arg Lys
            100                 105                 110

Val Leu Arg Glu Leu Asn Ser Leu Ile Ser Gly Asn Pro Ala Pro Glu
        115                 120                 125

Glu Ser Ser Val Asp Glu Glu Val Thr Asp Thr Glu Trp Phe Phe Phe
    130                 135                 140

Ser Phe Tyr Asp Ser Ile Phe Cys
145                 150
```

<210> SEQ ID NO 48
<211> LENGTH: 645
<212> TYPE: DNA
<213> ORGANISM: Trifolium repens

<400> SEQUENCE: 48

```
cctctctctc tctctctccc ccactccatt atcaccacca cacggtctct tcttcctaac     60
tttctcttct tctctttctt ttccctaatt tacctccaaa attaaccaaa aataaataat    120
tttctcttct tctctttctt ttccctaatt tacctccaaa attaaccaaa aataaataat    180
aaaaattcca tttcatgaat ctttggagcg acgagaactc atcagtgatg gaggctttta    240
tgacctcttc cgatttatca accttatggc catcacaacc acagccgccg tcgtcacaac    300
caccacaaac caccaccgga ttcaaccaag acacactcca acaacgtctt caagctttaa    360
tcgaaggcgc ttccgaaatc tggacttacg ctatcttctg gcaaccttct tacgactatt    420
ccggctcttc tcttctcggt tggggtgacg gttattacaa aggcgaagaa gacaaatcga    480
```

| | |
|---|---|
| aatcaaaatc caaagctact tcaccagctg aacaagaaca ccgtagaaaa gttctccgag | 540 |
| aacttaattc tttaatctcc ggtaatccgg caccggaaga atcttccgtc gatgaagaag | 600 |
| ttacagatac ggaatggttt tttttagttt ctatgactca atctt | 645 |

<210> SEQ ID NO 49
<211> LENGTH: 467
<212> TYPE: DNA
<213> ORGANISM: Trifolium repens

<400> SEQUENCE: 49

| | |
|---|---|
| tgatggaggc ttttatgacc tcatccgatt tatcaacctt atggccatca caaccacagc | 60 |
| cgccgtcgtc acaaccacca caaaccacca ccggattcaa ccaagacaca ctccaacaac | 120 |
| gtcttcaagc tttaatcgaa ggcgcttccg aaatctggac ttacgctatc ttctggcaac | 180 |
| cttcttacga ctattccggc tcttctcttc tcggttgggg tgacggttat tacaaaggcg | 240 |
| aagaagacaa atcaaaatca aaatccaaag ctacttcacc agctgaacaa gaacaccgta | 300 |
| gaaaagttct ccgagaactt aattctttaa tctccggtaa tccagtaccg aagaatcttc | 360 |
| ccgtcgatga agaagttaca gatacggagt ggttttttttt tagtttctat gactcaatct | 420 |
| tttgttaacg gaagtggact tcctggacaa gcttatttta attcaac | 467 |

<210> SEQ ID NO 50
<211> LENGTH: 2579
<212> TYPE: DNA
<213> ORGANISM: Trifolium repens

<400> SEQUENCE: 50

| | |
|---|---|
| taagcagtgg taacaacgca gagtacgcgg ggattcgtct ctttcttcct ctctctctct | 60 |
| ctctccccca atccattatc accaccacac ggtctcttct tcctaacttt ctcttcttct | 120 |
| ctttctttc cctaatttac ctccaaaatt aaccaaaaat aataataaa aattccattt | 180 |
| catgaatctt tggagcgacg agaactcatc agtgatggag gcttttatga cctcttccga | 240 |
| tttatcaacc ttatggccat cacaaccaca gccgccgtcg tcacaaccac cacaaaccac | 300 |
| caccggattc aaccaagaca cactccaaca acgtcttcaa gctttaatcg aaggcgcttc | 360 |
| cgaaatctgg acttacgcta tcttctggca accttcttac gactattccg gctcttctct | 420 |
| tctcggttgg ggtgacggtt attacaaagg cgaagaagac aaatcgaaat caaaatccaa | 480 |
| agctacttca ccagctgaac aagaacaccg tagaaaagtt ctccgagaac ttaattcttt | 540 |
| aatctccggt aatccggcac cggaagaatc ttccgtcgat gaagaagtta cagatacgga | 600 |
| atggtttttt ttagtttcta tgactcaatc ttttgttaac ggaagtggac ttcctggaca | 660 |
| agcttatttt aattcaactc cggtgtggtt agtcggaggt gagaatctcg ccctctcggt | 720 |
| ttgcgagagg gcgagacaag gtcatgaaca tggtttacag acgctgacgt gtataccgtc | 780 |
| ggcgaacggt gttttagagc ttggatctac tgaattgatt tatcagaata acgatctgat | 840 |
| gaataaagtt aagatgttgt ttaattttaa taataattct gattttggat cttcttggca | 900 |
| attaggtagt aattctactg taattactca tcaaggtgaa aatgatcttt cttcaatttg | 960 |
| gcttaatgat cctgaaacta gagattctgt tgataataat tctcttgctg cagcaacaac | 1020 |
| aacaacaacg acaacaaaca cttcaatttc aattccaagt catcatcagc aacagcaaca | 1080 |
| gcaccagaac aatagtaata atcagagttt gagtgtgacg aaaacgattc aatttgaaac | 1140 |
| gcgtggttca agtactttaa cagaagctcc tagtgttgtt catgtttcaa gtaagcaaaa | 1200 |
| tcaacaagga ttgttttcta aagaaatgaa tcttttggag tacggtgggg gtaatagtca | 1260 |

```
gcagcgttcg ttgaagccgg aatctggtga gattttgagt tttggtggtg agagtaaaaa    1320
gagttcttat gttgctaata atggaaattc gaattcgaat ttttctctg gtcaatcaca     1380
gttagtttca gttgctgagg agaatgggaa tggaaatgga atgggaaga ggaggtctcc     1440
gaattcgaga ggaagcaata atgatgatgg aatgctatct tttacttctg gtgtaattgt    1500
tccaccggtg aatttgaaat ctctctggtgg tactggtggt ggtgattccg accattcgga   1560
tcttgaagct tcggtggtga aggaagtgga tagtagtcgt gtggtggagc cggagaagaa    1620
gccgaggaag agagggagga aaccggcgaa tggaagagag gaaccgttga atcatgttga    1680
agccgagaga caacgaagag agaagctgaa tcagagattc tatgctcttc gtgcagttgt    1740
tcctaatgtt tcaaagatgg ataaagcttc acttttgggt gatgctatat catacattac    1800
tgagctgaaa acaaagcttg tgaaaactga atccgataaa gatgaattag aaaaacaact    1860
tgatgcagtg aagaatgagc ttcagaaagt caatgaaaac tcgtctcatc caccgcctca    1920
acctcaacaa ctacaacaac aacaacaagt acccgataaa ccctcttcca atcaagcttt    1980
aatcgattta gatattgatg tgaagattat aggttgggat gcaatgataa gggtccaatg    2040
cagtaagaaa aaccaccctg cagcgaagtt gatggcggcg ttgatggagc ttgacctaga    2100
agtgcaccac gcaagtgttt ccgtggtgaa tgatttgatg atacaacaag caaccgtgaa    2160
gatgggggt cgtttttaca cccaggagca gcttcgggca gcattgtcct ctaaagttgg     2220
ggatgttcaa taaagtctgt aaattgctgc aatgtgaaat taattgggaa tgttatgtat    2280
gtaaatttct cattcctcca taattttggg gctctgggat attttactga ttcccggtaa    2340
ctatgtaaac tagaagtgtc tttgtttttg gtagcttagt atgaattttg aggtaatttt    2400
atttgggaat ttgtatggag atgaagtact agaactagag gtagcgtcga tgaagtaagt    2460
aaaaactaag tgtaatttct ccgcaatgcg tgcccgtgtg tgtatataga tgttgttgta    2520
taattctcat aaatgggtaa catggtgaaa attctgaata ttattattct cagcttacc    2579
```

<210> SEQ ID NO 51
<211> LENGTH: 683
<212> TYPE: PRT
<213> ORGANISM: Trifolium repens

<400> SEQUENCE: 51

Met Asn Leu Trp Ser Asp Glu Asn Ser Ser Val Met Glu Ala Phe Met
1               5                   10                  15

Thr Ser Ser Asp Leu Ser Thr Leu Trp Pro Ser Gln Pro Gln Pro Pro
            20                  25                  30

Ser Ser Gln Pro Pro Gln Thr Thr Gly Phe Asn Gln Asp Thr Leu
        35                  40                  45

Gln Gln Arg Leu Gln Ala Leu Ile Glu Gly Ala Ser Glu Ile Trp Thr
    50                  55                  60

Tyr Ala Ile Phe Trp Gln Pro Ser Tyr Asp Tyr Ser Gly Ser Ser Leu
65                  70                  75                  80

Leu Gly Trp Gly Asp Gly Tyr Tyr Lys Gly Glu Asp Lys Ser Lys
                85                  90                  95

Ser Lys Ser Lys Ala Thr Ser Pro Ala Glu Gln Glu His Arg Arg Lys
            100                 105                 110

Val Leu Arg Glu Leu Asn Ser Leu Ile Ser Gly Asn Pro Ala Pro Glu
        115                 120                 125

Glu Ser Ser Val Asp Glu Glu Val Thr Asp Thr Glu Trp Phe Phe Leu
    130                 135                 140

Val Ser Met Thr Gln Ser Phe Val Asn Gly Ser Gly Leu Pro Gly Gln

-continued

```
            145                 150                 155                 160
        Ala Tyr Phe Asn Ser Thr Pro Val Trp Leu Val Gly Gly Glu Asn Leu
                        165                 170                 175

Ala Leu Ser Val Cys Glu Arg Ala Arg Gln Gly His Glu His Gly Leu
                    180                 185                 190

Gln Thr Leu Thr Cys Ile Pro Ser Ala Asn Gly Val Leu Glu Leu Gly
                195                 200                 205

Ser Thr Glu Leu Ile Tyr Gln Asn Asn Asp Leu Met Asn Lys Val Lys
                210                 215                 220

Met Leu Phe Asn Phe Asn Asn Asn Ser Asp Phe Gly Ser Ser Trp Gln
        225                 230                 235                 240

Leu Gly Ser Asn Ser Thr Val Ile Thr His Gln Gly Glu Asn Asp Leu
                        245                 250                 255

Ser Ser Ile Trp Leu Asn Asp Pro Glu Thr Arg Asp Ser Val Asp Asn
                    260                 265                 270

Asn Ser Leu Ala Ala Thr Thr Thr Thr Thr Thr Asn Thr Ser
                275                 280                 285

Ile Ser Ile Pro Ser His His Gln Gln Gln Gln His Gln Asn Asn
            290                 295                 300

Ser Asn Asn Gln Ser Leu Ser Val Thr Lys Thr Ile Gln Phe Glu Thr
        305                 310                 315                 320

Arg Gly Ser Ser Thr Leu Thr Glu Ala Pro Ser Val Val His Val Ser
                        325                 330                 335

Ser Lys Gln Asn Gln Gln Gly Leu Phe Ser Lys Glu Met Asn Leu Leu
                    340                 345                 350

Glu Tyr Gly Gly Gly Asn Ser Gln Gln Arg Ser Leu Lys Pro Glu Ser
                355                 360                 365

Gly Glu Ile Leu Ser Phe Gly Gly Glu Ser Lys Lys Ser Ser Tyr Val
            370                 375                 380

Ala Asn Asn Gly Asn Ser Asn Ser Asn Phe Phe Ser Gly Gln Ser Gln
        385                 390                 395                 400

Leu Val Ser Val Ala Glu Glu Asn Gly Asn Gly Asn Gly Asn Gly Lys
                        405                 410                 415

Arg Arg Ser Pro Asn Ser Arg Gly Ser Asn Asn Asp Asp Gly Met Leu
                    420                 425                 430

Ser Phe Thr Ser Gly Val Ile Val Pro Pro Val Asn Leu Lys Phe Ser
                435                 440                 445

Gly Gly Thr Gly Gly Gly Asp Ser Asp His Ser Asp Leu Glu Ala Ser
            450                 455                 460

Val Val Lys Glu Val Asp Ser Ser Arg Val Val Glu Pro Glu Lys Lys
        465                 470                 475                 480

Pro Arg Lys Arg Gly Arg Lys Pro Ala Asn Gly Arg Glu Glu Pro Leu
                        485                 490                 495

Asn His Val Glu Ala Glu Arg Gln Arg Arg Glu Lys Leu Asn Gln Arg
                    500                 505                 510

Phe Tyr Ala Leu Arg Ala Val Val Pro Asn Val Ser Lys Met Asp Lys
                515                 520                 525

Ala Ser Leu Leu Gly Asp Ala Ile Ser Tyr Ile Thr Glu Leu Lys Thr
            530                 535                 540

Lys Leu Val Lys Thr Glu Ser Asp Lys Asp Glu Leu Glu Lys Gln Leu
        545                 550                 555                 560

Asp Ala Val Lys Asn Glu Leu Gln Lys Val Asn Glu Asn Ser Ser His
                        565                 570                 575
```

```
Pro Pro Pro Gln Pro Gln Gln Leu Gln Gln Gln Gln Val Pro Asp
            580                 585                 590

Lys Pro Ser Ser Asn Gln Ala Leu Ile Asp Leu Asp Ile Asp Val Lys
        595                 600                 605

Ile Ile Gly Trp Asp Ala Met Ile Arg Val Gln Cys Ser Lys Lys Asn
    610                 615                 620

His Pro Ala Ala Lys Leu Met Ala Ala Leu Met Glu Leu Asp Leu Glu
625                 630                 635                 640

Val His His Ala Ser Val Ser Val Val Asn Asp Leu Met Ile Gln Gln
                    645                 650                 655

Ala Thr Val Lys Met Gly Gly Arg Phe Tyr Thr Gln Glu Gln Leu Arg
            660                 665                 670

Ala Ala Leu Ser Ser Lys Val Gly Asp Val Gln
        675                 680

<210> SEQ ID NO 52
<211> LENGTH: 601
<212> TYPE: DNA
<213> ORGANISM: Trifolium repens

<400> SEQUENCE: 52
ataaaccctt tctagggaga gactaattga atatattgca caaatctagg gactctatct      60
cactctaaaa ctaagatggg ggggagagat aagtgcaatg taaaagacaa gaatttatat    120
cttcaaaccc caactttcat tgaatggctc aaaccttctt catcactttc atcttctcct    180
tcatcatctt taactcatca acaagaaata tctcaagaaa cttttcagtt tttacccatc    240
tatagtggaa ttaagtcctt tgaggaaaac catgggatgc aaaaggaaga tttagaagta    300
aaagaagaga agtgtgaaaa agtaactgtg gcttttgcaca ttggattgcc taacatagga    360
ggaggtgaat cttatgatca tgaagagaag aataaggttt ttgatgagaa caataaagtt    420
aatgaaaaag aattaaagaa aaacttgcat ggttttttgtt ttaaggaaga agaaggtttt    480
tggataccaa ctcctgctca gatccttgtt ggacctatgc aatttgcttg ctccatatgc    540
aacaagactt tcaatagata caacaatatg cagatgcata tgtggggaca tggatcagaa    600
t                                                                    601

<210> SEQ ID NO 53
<211> LENGTH: 175
<212> TYPE: PRT
<213> ORGANISM: Trifolium repens

<400> SEQUENCE: 53

Met Gly Gly Arg Asp Lys Cys Asn Val Lys Asp Lys Asn Leu Tyr Leu
1               5                   10                  15

Gln Thr Pro Thr Phe Ile Glu Trp Leu Lys Pro Ser Ser Ser Leu Ser
            20                  25                  30

Ser Ser Pro Ser Ser Ser Leu Thr His Gln Gln Glu Ile Ser Gln Glu
        35                  40                  45

Thr Phe Gln Phe Leu Pro Ile Tyr Ser Gly Ile Lys Ser Phe Glu Glu
    50                  55                  60

Asn His Gly Met Gln Lys Glu Asp Leu Glu Val Lys Glu Glu Lys Val
65                  70                  75                  80

Glu Lys Val Thr Val Ala Leu His Ile Gly Leu Pro Asn Ile Gly Gly
                85                  90                  95

Gly Glu Ser Tyr Asp His Glu Glu Lys Asn Lys Val Phe Asp Glu Asn
            100                 105                 110
```

```
Asn Lys Val Asn Glu Lys Glu Leu Lys Lys Asn Leu His Gly Phe Cys
        115                 120                 125

Phe Lys Glu Glu Arg Arg Phe Trp Ile Pro Thr Pro Ala Gln Ile Leu
    130                 135                 140

Val Gly Pro Met Gln Phe Ala Cys Ser Ile Cys Asn Lys Thr Phe Asn
145                 150                 155                 160

Arg Tyr Asn Asn Met Gln Met His Met Trp Gly His Gly Ser Glu
                165                 170                 175

<210> SEQ ID NO 54
<211> LENGTH: 601
<212> TYPE: DNA
<213> ORGANISM: Trifolium repens

<400> SEQUENCE: 54 ataaacccctt tctagggaga gactaattga atatattgca caaatctagg gactctatct    60
cactctaaaa ctaagatggg tttgagagat aagtgcaatg taaaagacaa gaatttatat   120
cttcaaaccc caactttcat tgaatggctc aaaccttctt catcactttc atcttctcct   180
tcatcatctt taactcatca acaagaaata tctcaagaaa cttttcagtt tttacccatc   240
tatagtggaa ttaagtcctt tgaggaaaac catgggatgc aaaaggaaga tttagaagta   300
aaagaagaga agtgaaaaa agtaactgtg ctttgcaca ttggattgcc taacatagga   360
ggaggtgaat cttatgatca tgaagagaag aataaggttt ttgatgagaa caataaagtt   420
aatgaaaaag aattaaagaa aaacttgcat ggttttgtt ttaaggaaga aagaaggttt   480
tggataccaa ctcctgctca gatccttgtt ggacctatgc aatttgcttg ctccatatgc   540
aacaagactt tcaatagata caacaatatg cagatgcata tgtggggaca tggatcagaa   600
t                                                                   601

<210> SEQ ID NO 55
<211> LENGTH: 591
<212> TYPE: DNA
<213> ORGANISM: Trifolium repens
<220> FEATURE:
<221> NAME/KEY: misc_feature
<222> LOCATION: (74)..(74)
<223> OTHER INFORMATION: n is a, c, g, or t

<400> SEQUENCE: 55 taaaccccttt ctaggagag actaattgaa tatattgcac aaatctaggg actctatctc    60
actctaaaac taanatgggg gggagagata agtgcaatgt agaagacaag aatttatatc   120
ttcaaacccc aactttcatt gaatggctca accttcttc atcactttca tcttctcctt   180
catcatcttt aactcatcaa caagaaatat ctcaagaaac ttttcagttt ttacccatct   240
atagtggaat taagtccttt gaggaaaacc atgggatgca aaaggaagat ttagaagtaa   300
aagaagagaa agtggaaaaa gtaactgtgg ctttgcacat tggattgcct aacataggag   360
gaggtgaatc ttatgatcat gaagagaaga ataaggtttt tgatgagaac aataaagtta   420
atgaaaaaga attaaagaaa aacttgcatg gttttgttt taaggaagaa agaaggtttt   480
ggataccaac tcctgctcag atccttgttg gacctatgca atttgcttgc tccatatgca   540
acaagacttt caatagatac aacaatatgc agatgcatat gtggggacat g           591

<210> SEQ ID NO 56
<211> LENGTH: 768
<212> TYPE: DNA
<213> ORGANISM: Trifolium repens
```

<400> SEQUENCE: 56

```
tacacacaca acaaacaata tggacatgga ttcaacaggt ggttcttctt gttggctcta    60
tgattatggc tatgatattt ctgttcctgc acctgattc atgccttctg atcatcactc   120
tcctgcttct gttttcacct ggaatatgcc tcagactcat atcatcaagc ctccttcctc   180
caatatcagc ttggaaatgg aatactcact ggactcaact gtactggaaa gtggtccttc   240
atcaaagcgc ttggaaatgg aatactcact ggattcaact gtactggaaa atggcccttc   300
aaagcggtta agacagaat catgtgcatc tggctccaag gcatgtcgcg agaaacagcg   360
cagggataaa ctgaatgaca gtttatgga attgagttct gtcttagagc ctgatacact   420
gcccaaaaca gacaaagtta ccttattaaa tgacgcggtt cgtgtggtta cacaattaag   480
aaatgaagca gaaggctga aggaaaggaa tgacgaattg cgcgaaaaag ttaaagaact   540
taagactgag aaaaatgagc ttcgcgatga gaaaaataag ctgaagttag acaaagaaaa   600
gttggaacag caagtgaaat taacaagtgt acagtccagc atcctctcga atgccatggc   660
ggctaaagga caatctgctg ctaaccacaa gctgatgcct ttcattggtt atcctggaat   720
ttcggtgtgg cagtttatgt cacctgctac agttgataca tcacagga              768
```

<210> SEQ ID NO 57
<211> LENGTH: 255
<212> TYPE: PRT
<213> ORGANISM: Trifolium repens

<400> SEQUENCE: 57

```
Thr His Thr Thr Asn Asn Met Asp Met Asp Ser Thr Gly Gly Ser Ser
1               5                   10                  15

Cys Trp Leu Tyr Asp Tyr Gly Tyr Asp Ile Ser Val Pro Ala Pro Asp
            20                  25                  30

Phe Met Pro Ser Asp His His Ser Pro Ala Ser Val Phe Thr Trp Asn
        35                  40                  45

Met Pro Gln Thr His Ile Ile Lys Pro Pro Ser Ser Asn Ile Ser Leu
    50                  55                  60

Glu Met Glu Tyr Ser Leu Asp Ser Thr Val Leu Glu Ser Gly Pro Ser
65                  70                  75                  80

Ser Lys Arg Leu Glu Met Glu Tyr Ser Leu Asp Ser Thr Val Leu Glu
                85                  90                  95

Asn Gly Pro Ser Lys Arg Leu Lys Thr Glu Ser Cys Ala Ser Gly Ser
            100                 105                 110

Lys Ala Cys Arg Glu Lys Gln Arg Arg Asp Lys Leu Asn Asp Lys Phe
        115                 120                 125

Met Glu Leu Ser Ser Val Leu Glu Pro Asp Thr Leu Pro Lys Thr Asp
    130                 135                 140

Lys Val Thr Leu Leu Asn Asp Ala Val Arg Val Thr Gln Leu Arg
145                 150                 155                 160

Asn Glu Ala Glu Arg Leu Lys Glu Arg Asn Asp Glu Leu Arg Glu Lys
                165                 170                 175

Val Lys Glu Leu Lys Thr Glu Lys Asn Glu Leu Arg Asp Glu Lys Asn
            180                 185                 190

Lys Leu Lys Leu Asp Lys Glu Lys Leu Glu Gln Gln Val Lys Leu Thr
        195                 200                 205

Ser Val Gln Ser Ser Ile Leu Ser Asn Ala Met Ala Ala Lys Gly Gln
    210                 215                 220

Ser Ala Ala Asn His Lys Leu Met Pro Phe Ile Gly Tyr Pro Gly Ile
225                 230                 235                 240
```

```
Ser Val Trp Gln Phe Met Ser Pro Ala Thr Val Asp Thr Ser Gln
            245                 250                 255

<210> SEQ ID NO 58
<211> LENGTH: 658
<212> TYPE: DNA
<213> ORGANISM: Trifolium repens

<400> SEQUENCE: 58
tacacacaca acaaacaata tggacatgga ttcaactggt ggttcttctt gttggctcta      60
tgattatggc tatgatattt ctgttcctgc acctgatttc atgccttctg atcactctcc     120
tgcttctgtt ttcacctgga atatgcctca gactcatatc atcaagcctc cttcctccaa     180
tatcagcttg gaaatggaat actcactgga ctcaactgta ctggaaagtg gtccttcatc     240
aaagcgcttg gaaatggaat actcactgga ttcaactgta ctggaaaatg gcccttcaaa     300
gcggttaaag acagaatcat gtgcatctgg ctccaaggca tgtcgcgaga aattgcgcag     360
ggataaactg aatgacaagt ttatggaatt gagttctgtc ttagagcctg atacactgcc     420
caaaacagac aaagttactt tattaaatga cgcggttcgt gtggttacgc aattaagaaa     480
tgaagcagaa aggctgaagg aaaggaatga cgaattgcgc gaaaaagtta agaacttaa      540 ggctgagaag aatgagcttc gcgatgagaa aaataagctg aagttagaca agaaaagtt      600 ggaacagcaa gtgaaattaa caagtgtaca gtccagcttc ctctcggatg ccatggcg      658

<210> SEQ ID NO 59
<211> LENGTH: 760
<212> TYPE: DNA
<213> ORGANISM: Trifolium repens

<400> SEQUENCE: 59
acacaacaaa caatatggac atggattcca caggtggttc ttcttgttgg ctctatgatt      60
gtggctatga tatttctgtt cctgcacctg atttcatggc ttctgatcat cactctcctg     120
cttctgtttt cacctggaat atgcctcaga ctcatatcat caagcctcct tcctccaata     180
tcagcttgga aatggaatac tcactggact caactgtatt ggaaagtggt ccttcaaagc     240
gcttggaaat ggaatactca ctggattcaa ctgtactgga aaatggtcct tcaaagcggt     300
taaagacaga atcatgtgca tctggctcga aggcatgtcg cgagaaacag cgcagggata     360
aactgaatga caagtttctg gaattgagtt ctgtcttaga gcctgataca ctgccgaaaa     420
cagacaaagt taccttatta aatgacgcgg ttcgtgtggt tacacaatta agaaatgaag     480
cagaaaggct gaaggaaagg aatgatgaat gcgcgaaaaa agttagagaa cttaagactg     540
agaaaactga gcttcgcgat gagaaaaata gctgaagtt agacaaagaa agttggaac      600 agcaagtgaa attaacaagt gtacagtcca gcatcctctc gaatgccatg gcggctaaag     660
gacaatctgc tgctaaccac aagctgatgc ctttcattgg ttatcctgga atttcggtgt     720
ggcagtttat gtcacctgct acagttgata catcacagga                           760

<210> SEQ ID NO 60
<211> LENGTH: 594
<212> TYPE: DNA
<213> ORGANISM: Trifolium repens

<400> SEQUENCE: 60
tgagagagag agagagagag agagaggcta tgggaagcag ctccttgttg tgacaaagac      60
aaagttaaga gaggaccatg gtctcctgat gaagatgcaa aactcaagaa ttatttagca     120
```

-continued

```
attcatggca ctgttggaaa ttggattgca ttgcctaaaa aagctggcct taagcggtgt        180
ggaaagagtt gtcgtctaag gtggctgaat tatcttaggc ctgacatcaa acatggaagc        240
tttactgagg aagaagatac catcatttgt accctctatg ctcaaatggg tagcagatgg        300
tctgccatag catcaaaact acctgggaga acagacaatg atgtaaaaaa ctattggaac        360
acaaaactga gaagaaaat tatggcagga aaagttggcc tcaaatcatt gactgaaaat         420
gacaatactg tcccttcaac cccatcagtg actcaaaatt gcaacattat gttagacaat        480
aattttgatg ctagttatgg attcaagaat aatgaaaaaa acattggttt tgatcaaatt        540
catgatgttg gtgtctcaga aattggtgca agtaacaaca atattgatat taat              594
```

```
<210> SEQ ID NO 61
<211> LENGTH: 197
<212> TYPE: PRT
<213> ORGANISM: Trifolium repens

<400> SEQUENCE: 61

Glu Arg Glu Arg Glu Arg Glu Arg Leu Trp Glu Ala Ala Pro Cys Cys
1               5                   10                  15

Asp Lys Asp Lys Val Lys Arg Gly Pro Trp Ser Pro Asp Glu Asp Ala
                20                  25                  30

Lys Leu Lys Asn Tyr Leu Ala Ile His Gly Thr Val Gly Asn Trp Ile
            35                  40                  45

Ala Leu Pro Lys Lys Ala Gly Leu Lys Arg Cys Gly Lys Ser Cys Arg
        50                  55                  60

Leu Arg Trp Leu Asn Tyr Leu Arg Pro Asp Ile Lys His Gly Ser Phe
65                  70                  75                  80

Thr Glu Glu Asp Thr Ile Ile Cys Thr Leu Tyr Ala Gln Met Gly
                85                  90                  95

Ser Arg Trp Ser Ala Ile Ala Ser Lys Leu Pro Gly Arg Thr Asp Asn
                100                 105                 110

Asp Val Lys Asn Tyr Trp Asn Thr Lys Leu Lys Lys Ile Met Ala
            115                 120                 125

Gly Lys Val Gly Leu Lys Ser Leu Thr Glu Asn Asp Asn Thr Val Pro
    130                 135                 140

Ser Thr Pro Ser Val Thr Gln Asn Cys Asn Ile Met Leu Asp Asn Asn
145                 150                 155                 160

Phe Asp Ala Ser Tyr Gly Phe Lys Asn Asn Glu Lys Asn Ile Gly Phe
                165                 170                 175

Asp Gln Ile His Asp Val Gly Val Ser Glu Ile Gly Ala Ser Asn Asn
            180                 185                 190

Asn Ile Asp Ile Asn
        195
```

```
<210> SEQ ID NO 62
<211> LENGTH: 568
<212> TYPE: DNA
<213> ORGANISM: Trifolium repens

<400> SEQUENCE: 62
tgagagagag agagagagag agagaggcta tgggaagagc tccttgttgt gacaaagaca        60
aagttaagag aggaccatgg tctcctgatg aagatgcaaa actcaagaat tatttagcaa        120
ttcatggcac tgttggaaat tggattgcat tgcctaaaaa agctggcctt aagcggtgtg        180
gaaagagttg tcgtctaagg tggctgaatt atcttaggcc tgacatcaaa catggaagct        240
ttactgagga agaagatacc atcatttgta ccctctatgc tcaaatgggt agcagatggt        300
```

```
ctgccatagc atcaaaacta cctgggagaa cagacaatga tgtaaaaaac tattggaaca    360
caaaactgaa gaagaaaatt atggcaggaa aagttggcct caaatcattg actgaaaatg    420
acaatactgt ccccttcaacc ccatcagtga ctcaaaattg caacattatg ttagacaata    480
attttgatgc tagttatgga ttcaagaata atgaaaaaaa cattggtttt gatcaaattc    540
atgatgttgg tgtctcagaa attggtgc                                        568
```

<210> SEQ ID NO 63
<211> LENGTH: 581
<212> TYPE: DNA
<213> ORGANISM: Trifolium repens

<400> SEQUENCE: 63

```
gagagagaga gaggctatgg gaagcagctc cttgttgtga caaagacaaa gttaagagag     60
gaccatggtc tcctgatgaa gatgcaaaac tcaagaatta tttagcaatt catggcactg    120
ttggaaattg gattgcattg cctaaaaaag ctggccttaa gcggtgtgga aagagttgtc    180
gtctaaggtg gctgaattat cttaggcctg acatcaaaca tggaagcttt actgaggaag    240
aagataccat catttgtacc ctctatgctc aaatgggtag cagatggtct gccatagcat    300
caaaactacc tgggagaaca gacaatgatg taaaaaacta ttggaacaca aaactgaaga    360
agaaaattat ggcaggaaaa gttggcctca atcattgac tgaaaatgac aatactgtcc     420
cttcaacccc atcagtgact caaaattgca acattatgtt agacaataat tttgatgcta    480
gttatggatt caagaataat gaaaaaaaca ttggttttga tcaaattcat gatgttggtg    540
tctcagaaat tggtgcaagt aacaacaata ttgatattaa t                         581
```

<210> SEQ ID NO 64
<211> LENGTH: 1045
<212> TYPE: DNA
<213> ORGANISM: Trifolium repens

<400> SEQUENCE: 64

```
taagcagtgg taacaacgca gagtacgcgg gggagtgaga gagagagaga gagagagaga     60
ggctatggga agagctcctt gttgtgacaa agacaaagtt aagagaggac catggtctcc    120
tgatgaagat gcaaaactca agaattattt agcaattcat ggcactgttg gaaattggat    180
tgcattgcct aaaaaagctg gccttaagcg gtgtggaaag agttgtcgtc taaggtggct    240
gaattatctt aggcctgaca tcaaacatgg aagctttact gaggaagaag ataccatcat    300
ttgtaccctc tatgctcaaa tgggtagcag atggtctgcc atagcatcaa aactacctgg    360
gagaacagac aatgatgtaa aaaactattg aacacaaaa ctgaagaaga aaattatggc     420
aggaaaagtt ggcctcaaat cattgactga aaatgacaat actgtccctt caaccccatc    480
agtgactcaa aattgcaaca ttatgttaga caataatttt gatgctagtt atggattcaa    540
gaataatgaa aaaacattg gttttgatca aattcatgat gttggtgtct cagaaattgg     600
tgcaagtaac aacaatattg atattaatcc tatggtgtca atatctcaag acaattcaag    660
cattggagtg aacaacaatt gtgtatcact tcaagatcaa gctggtgatg aatctttgga    720
accactaatg gattttggct ttggagttgg tagtgatttt gcttcaagtt gttgctttcc    780
tgagtgggtt gattttagtt atgctgacat taagacaaat tgactggttc aaaatcttgc    840
attgtctagt tctagtaatt aaatatggga ttaattaatt atgtaatagc aaaattacat    900
tacataggta aaatattttt agttttgcta agtattaaat ttaattttc ttccaacaat     960 aaattggtct gagtgataaa catttaagt ccccttaagca gttagtcggg gattgcaagt    1020
```
tcttcaacaa aatttattca tcatt                                    1045

<210> SEQ ID NO 65
<211> LENGTH: 252
<212> TYPE: PRT
<213> ORGANISM: Trifolium repens

<400> SEQUENCE: 65

Met Gly Arg Ala Pro Cys Cys Asp Lys Asp Lys Val Lys Arg Gly Pro
1               5                   10                  15

Trp Ser Pro Asp Glu Asp Ala Lys Leu Lys Asn Tyr Leu Ala Ile His
            20                  25                  30

Gly Thr Val Gly Asn Trp Ile Ala Leu Pro Lys Lys Ala Gly Leu Lys
        35                  40                  45

Arg Cys Gly Lys Ser Cys Arg Leu Arg Trp Leu Asn Tyr Leu Arg Pro
    50                  55                  60

Asp Ile Lys His Gly Ser Phe Thr Glu Glu Asp Thr Ile Ile Cys
65                  70                  75                  80

Thr Leu Tyr Ala Gln Met Gly Ser Arg Trp Ser Ala Ile Ala Ser Lys
                85                  90                  95

Leu Pro Gly Arg Thr Asp Asn Asp Val Lys Asn Tyr Trp Asn Thr Lys
            100                 105                 110

Leu Lys Lys Lys Ile Met Ala Gly Lys Val Gly Leu Lys Ser Leu Thr
        115                 120                 125

Glu Asn Asp Asn Thr Val Pro Ser Thr Pro Ser Val Thr Gln Asn Cys
130                 135                 140

Asn Ile Met Leu Asp Asn Asn Phe Asp Ala Ser Tyr Gly Phe Lys Asn
145                 150                 155                 160

Asn Glu Lys Asn Ile Gly Phe Asp Gln Ile His Asp Val Gly Val Ser
                165                 170                 175

Glu Ile Gly Ala Ser Asn Asn Asn Ile Asp Ile Asn Pro Met Val Ser
            180                 185                 190

Ile Ser Gln Asp Asn Ser Ser Ile Gly Val Asn Asn Cys Val Ser
        195                 200                 205

Leu Gln Asp Gln Ala Gly Asp Glu Ser Leu Glu Pro Leu Met Asp Phe
    210                 215                 220

Gly Phe Gly Val Gly Ser Asp Phe Ala Ser Ser Cys Cys Phe Pro Glu
225                 230                 235                 240

Trp Val Asp Phe Ser Tyr Ala Asp Ile Lys Thr Asn
                245                 250

<210> SEQ ID NO 66
<211> LENGTH: 589
<212> TYPE: DNA
<213> ORGANISM: Trifolium repens

<400> SEQUENCE: 66
agctgcatgg aaaattgccg ataagtctcc tcctcagaat tggccgagtc atggcactat    60
agagttaaat aatttacagg ttaggtacag gccaaacact cctctagttc ttaagggaat   120
ctctctaacc attgaaggtg gagaaaaagt tggtgtcgtt ggtcgtacag gaagtggaaa   180
atcaacactt attcaagtgt tatttagatt aattgagcct tcagctggta aaattattat   240
tgatggtatc aatatttcca atattggcct tcatgattta aggtcacgtt ttggaattat   300
accacaagag cctgtcctct ttcaaggaac agtaagaacc aatattgacc ctcttggagt   360
atattcagaa gaagaaattt ggaagagtct cgagcgctgc caattgaaag aagtggtggc   420

```
tgcaaagcct gagaaactcg aggcttcagt ggttgatggt ggagacaatt ggagtgtggg    480
acaaagacag cttctatgct taggaaggat catgctaaaa cgaagccaaa tactattcat    540
ggacgaagca acagcatctg tcgattcaca aactgatgct gtaatacaa               589
```

```
<210> SEQ ID NO 67
<211> LENGTH: 196
<212> TYPE: PRT
<213> ORGANISM: Trifolium repens

<400> SEQUENCE: 67

Ala Ala Trp Lys Ile Ala Asp Lys Ser Pro Pro Gln Asn Trp Pro Ser
 1               5                  10                  15

His Gly Thr Ile Glu Leu Asn Asn Leu Gln Val Arg Tyr Arg Pro Asn
            20                  25                  30

Thr Pro Leu Val Leu Lys Gly Ile Ser Leu Thr Ile Glu Gly Gly Glu
        35                  40                  45

Lys Val Gly Val Val Gly Arg Thr Gly Ser Gly Lys Ser Thr Leu Ile
    50                  55                  60

Gln Val Leu Phe Arg Leu Ile Glu Pro Ser Ala Gly Lys Ile Ile Ile
65                  70                  75                  80

Asp Gly Ile Asn Ile Ser Asn Ile Gly Leu His Asp Leu Arg Ser Arg
                85                  90                  95

Phe Gly Ile Ile Pro Gln Glu Pro Val Leu Phe Gln Gly Thr Val Arg
            100                 105                 110

Thr Asn Ile Asp Pro Leu Gly Val Tyr Ser Glu Glu Ile Trp Lys
        115                 120                 125

Ser Leu Glu Arg Cys Gln Leu Lys Glu Val Val Ala Ala Lys Pro Glu
    130                 135                 140

Lys Leu Glu Ala Ser Val Val Asp Gly Gly Asp Asn Trp Ser Val Gly
145                 150                 155                 160

Gln Arg Gln Leu Leu Cys Leu Gly Arg Ile Met Leu Lys Arg Ser Gln
                165                 170                 175

Ile Leu Phe Met Asp Glu Ala Thr Ala Ser Val Asp Ser Gln Thr Asp
            180                 185                 190

Ala Val Ile Gln
        195
```

```
<210> SEQ ID NO 68
<211> LENGTH: 105
<212> TYPE: PRT
<213> ORGANISM: Trifolium repens

<400> SEQUENCE: 68

Val Lys Arg Gly Pro Trp Ser Pro Asp Glu Asp Ala Lys Leu Lys Asn
 1               5                  10                  15

Tyr Leu Ala Ile His Gly Thr Val Gly Asn Trp Ile Ala Leu Pro Lys
            20                  25                  30

Lys Ala Gly Leu Lys Arg Cys Gly Lys Ser Cys Arg Leu Arg Trp Leu
        35                  40                  45

Asn Tyr Leu Arg Pro Asp Ile Lys His Gly Ser Phe Thr Glu Glu Glu
    50                  55                  60

Asp Thr Ile Ile Cys Thr Leu Tyr Ala Gln Met Gly Ser Arg Trp Ser
65                  70                  75                  80

Ala Ile Ala Ser Lys Leu Pro Gly Arg Thr Asp Asn Asp Val Lys Asn
                85                  90                  95
```

```
Tyr Trp Asn Thr Lys Leu Lys Lys Lys
            100                 105

<210> SEQ ID NO 69
<211> LENGTH: 104
<212> TYPE: PRT
<213> ORGANISM: Petunia x hybrida

<400> SEQUENCE: 69

Leu Lys Lys Gly Pro Trp Thr Pro Glu Glu Asp Gln Lys Leu Leu Ala
1               5                   10                  15

Tyr Ile Glu Glu His Gly His Gly Ser Trp Arg Ala Leu Pro Ala Lys
                20                  25                  30

Ala Gly Leu Gln Arg Cys Gly Lys Ser Cys Arg Leu Arg Trp Thr Asn
            35                  40                  45

Tyr Leu Arg Pro Asp Ile Lys Arg Gly Lys Phe Thr Leu Gln Glu Glu
        50                  55                  60

Gln Thr Ile Ile Gln Leu His Ala Leu Leu Gly Asn Arg Trp Ser Ala
65                  70                  75                  80

Ile Ala Thr His Leu Pro Lys Arg Thr Asp Asn Glu Ile Lys Asn Tyr
                85                  90                  95

Trp Asn Thr His Leu Lys Lys Arg
            100

<210> SEQ ID NO 70
<211> LENGTH: 104
<212> TYPE: PRT
<213> ORGANISM: Antirrhinum majus

<400> SEQUENCE: 70

Val Lys Lys Gly Pro Trp Thr Val Asp Glu Asp Gln Lys Leu Leu Ala
1               5                   10                  15

Tyr Ile Glu Glu His Gly His Gly Ser Trp Arg Ser Leu Pro Leu Lys
                20                  25                  30

Ala Gly Leu Gln Arg Cys Gly Lys Ser Cys Arg Leu Arg Trp Ala Asn
            35                  40                  45

Tyr Leu Arg Pro Asp Ile Lys Arg Gly Pro Phe Ser Leu Gln Glu Glu
        50                  55                  60

Gln Thr Ile Ile Gln Leu His Ala Leu Leu Gly Asn Arg Trp Ser Ala
65                  70                  75                  80

Ile Ala Ser His Leu Pro Lys Arg Thr Asp Asn Glu Ile Lys Asn Tyr
                85                  90                  95

Trp Asn Thr His Leu Lys Lys Arg
            100

<210> SEQ ID NO 71
<211> LENGTH: 104
<212> TYPE: PRT
<213> ORGANISM: Arabidopsis thaliana

<400> SEQUENCE: 71

Tyr Lys Lys Gly Leu Trp Thr Val Glu Glu Asp Asn Ile Leu Met Asp
1               5                   10                  15

Tyr Val Leu Asn His Gly Thr Gly Gln Trp Asn Arg Ile Val Arg Lys
                20                  25                  30

Thr Gly Leu Lys Arg Cys Gly Lys Ser Cys Arg Leu Arg Trp Met Asn
            35                  40                  45

Tyr Leu Ser Pro Asn Val Asn Lys Gly Asn Phe Thr Glu Gln Glu Glu
        50                  55                  60
```

```
Asp Leu Ile Ile Arg Leu His Lys Leu Leu Gly Asn Arg Trp Ser Leu
65                  70                  75                  80

Ile Ala Lys Arg Val Pro Gly Arg Thr Asp Asn Gln Val Lys Asn Tyr
                85                  90                  95

Trp Asn Thr His Leu Ser Lys Lys
            100

<210> SEQ ID NO 72
<211> LENGTH: 104
<212> TYPE: PRT
<213> ORGANISM: Arabidopsis thaliana

<400> SEQUENCE: 72

Tyr Lys Lys Gly Leu Trp Thr Val Glu Glu Asp Lys Ile Leu Met Asp
1               5                   10                  15

Tyr Val Lys Ala His Gly Lys Gly His Trp Asn Arg Ile Ala Lys Lys
                20                  25                  30

Thr Gly Leu Lys Arg Cys Gly Lys Ser Cys Arg Leu Arg Trp Met Asn
            35                  40                  45

Tyr Leu Ser Pro Asn Val Lys Arg Gly Asn Phe Thr Glu Gln Glu Glu
        50                  55                  60

Asp Leu Ile Ile Arg Leu His Lys Leu Leu Gly Asn Arg Trp Ser Leu
65                  70                  75                  80

Ile Ala Lys Arg Val Pro Gly Arg Thr Asp Asn Gln Val Lys Asn Tyr
                85                  90                  95

Trp Asn Thr His Leu Ser Lys Lys
            100

<210> SEQ ID NO 73
<211> LENGTH: 104
<212> TYPE: PRT
<213> ORGANISM: Arabidopsis thaliana

<400> SEQUENCE: 73

Leu Asn Arg Gly Ala Trp Thr Asp His Glu Asp Lys Ile Leu Arg Asp
1               5                   10                  15

Tyr Ile Thr Thr His Gly Glu Gly Lys Trp Ser Thr Leu Pro Asn Gln
                20                  25                  30

Ala Gly Leu Lys Arg Cys Gly Lys Ser Cys Arg Leu Arg Trp Lys Asn
            35                  40                  45

Tyr Leu Arg Pro Gly Ile Lys Arg Gly Asn Ile Ser Ser Asp Glu Glu
        50                  55                  60

Glu Leu Ile Ile Arg Leu His Asn Leu Leu Gly Asn Arg Trp Ser Leu
65                  70                  75                  80

Ile Ala Gly Arg Leu Pro Gly Arg Thr Asp Asn Glu Ile Lys Asn His
                85                  90                  95

Trp Asn Ser Asn Leu Arg Lys Arg
            100

<210> SEQ ID NO 74
<211> LENGTH: 104
<212> TYPE: PRT
<213> ORGANISM: Vitis vinifera

<400> SEQUENCE: 74

Leu His Arg Gly Ser Trp Thr Ala Arg Glu Asp Thr Leu Leu Thr Lys
1               5                   10                  15

Tyr Ile Gln Ala His Gly Glu Gly His Trp Arg Ser Leu Pro Lys Lys
```

```
                         20                  25                  30

Ala Gly Leu Leu Arg Cys Gly Lys Ser Cys Arg Leu Arg Trp Met Asn
            35                  40                  45

Tyr Leu Arg Pro Asp Ile Lys Arg Gly Asn Ile Thr Pro Asp Glu Asp
 50                  55                  60

Asp Leu Ile Ile Arg Leu His Ser Leu Leu Gly Asn Arg Trp Ser Leu
 65                  70                  75                  80

Ile Ala Gly Arg Leu Pro Gly Arg Thr Asp Asn Glu Ile Lys Asn Tyr
                85                  90                  95

Trp Asn Thr His Leu Ser Lys Lys
                100

<210> SEQ ID NO 75
<211> LENGTH: 104
<212> TYPE: PRT
<213> ORGANISM: Arabidopsis thaliana

<400> SEQUENCE: 75

Leu Lys Arg Gly Arg Trp Thr Ala Glu Glu Asp Glu Ile Leu Thr Lys
 1               5                  10                  15

Tyr Ile Gln Thr Asn Gly Glu Gly Ser Trp Arg Ser Leu Pro Lys Lys
                20                  25                  30

Ala Gly Leu Leu Arg Cys Gly Lys Ser Cys Arg Leu Arg Trp Ile Asn
            35                  40                  45

Tyr Leu Arg Arg Asp Leu Lys Arg Gly Asn Ile Thr Ser Asp Glu Glu
 50                  55                  60

Glu Ile Ile Val Lys Leu His Ser Leu Leu Gly Asn Arg Trp Ser Leu
 65                  70                  75                  80

Ile Ala Thr His Leu Pro Gly Arg Thr Asp Asn Glu Ile Lys Asn Tyr
                85                  90                  95

Trp Asn Ser His Leu Ser Arg Lys
                100

<210> SEQ ID NO 76
<211> LENGTH: 104
<212> TYPE: PRT
<213> ORGANISM: Zea mays

<400> SEQUENCE: 76

Leu Lys Arg Gly Arg Trp Thr Ala Glu Glu Asp Gln Leu Leu Ala Asn
 1               5                  10                  15

Tyr Ile Ala Glu His Gly Glu Gly Ser Trp Arg Ser Leu Pro Lys Asn
                20                  25                  30

Ala Gly Leu Leu Arg Cys Gly Lys Ser Cys Arg Leu Arg Trp Ile Asn
            35                  40                  45

Tyr Leu Arg Ala Asp Val Lys Arg Gly Asn Ile Ser Lys Glu Glu Glu
 50                  55                  60

Asp Ile Ile Ile Lys Leu His Ala Thr Leu Gly Asn Arg Trp Ser Leu
 65                  70                  75                  80

Ile Ala Ser His Leu Pro Gly Arg Thr Asp Asn Glu Ile Lys Asn Tyr
                85                  90                  95

Trp Asn Ser His Leu Ser Arg Gln
                100

<210> SEQ ID NO 77
<211> LENGTH: 104
<212> TYPE: PRT
<213> ORGANISM: Zea mays
```

-continued

<400> SEQUENCE: 77

Val Lys Arg Gly Ala Trp Thr Ser Lys Glu Asp Ala Leu Ala Ala
1               5                   10                  15

Tyr Val Lys Ala His Gly Glu Gly Lys Trp Arg Glu Val Pro Gln Lys
            20                  25                  30

Ala Gly Leu Arg Arg Cys Gly Lys Ser Cys Arg Leu Arg Trp Leu Asn
        35                  40                  45

Tyr Leu Arg Pro Asn Ile Arg Arg Gly Asn Ile Ser Tyr Asp Glu Glu
    50                  55                  60

Asp Leu Ile Ile Arg Leu His Arg Leu Leu Gly Asn Arg Trp Ser Leu
65                  70                  75                  80

Ile Ala Gly Arg Leu Pro Gly Arg Thr Asp Asn Glu Ile Lys Asn Tyr
                85                  90                  95

Trp Asn Ser Thr Leu Gly Arg Arg
            100

<210> SEQ ID NO 78
<211> LENGTH: 104
<212> TYPE: PRT
<213> ORGANISM: Vitis vinifera

<400> SEQUENCE: 78

Leu Lys Arg Gly Pro Trp Thr Pro Glu Glu Asp Glu Leu Leu Ala Asn
1               5                   10                  15

Tyr Val Lys Arg Glu Gly Glu Gly Arg Trp Arg Thr Leu Pro Lys Arg
            20                  25                  30

Ala Gly Leu Leu Arg Cys Gly Lys Ser Cys Arg Leu Arg Trp Met Asn
        35                  40                  45

Tyr Leu Arg Pro Ser Val Lys Arg Gly Gln Ile Ala Pro Asp Glu Glu
    50                  55                  60

Asp Leu Ile Leu Arg Leu His Arg Leu Leu Gly Asn Arg Trp Ser Leu
65                  70                  75                  80

Ile Ala Gly Arg Ile Pro Gly Arg Thr Asp Asn Glu Ile Lys Asn Tyr
                85                  90                  95

Trp Asn Thr His Leu Ser Lys Lys
            100

<210> SEQ ID NO 79
<211> LENGTH: 104
<212> TYPE: PRT
<213> ORGANISM: Vitis vinifera

<400> SEQUENCE: 79

Leu Lys Arg Gly Pro Trp Thr Pro Glu Glu Asp Glu Val Leu Ala Asn
1               5                   10                  15

Tyr Ile Lys Lys Glu Gly Glu Gly Arg Trp Arg Thr Leu Pro Lys Arg
            20                  25                  30

Ala Gly Leu Leu Arg Cys Gly Lys Ser Cys Arg Leu Arg Trp Met Asn
        35                  40                  45

Tyr Leu Arg Pro Ser Val Lys Arg Gly Gln Ile Ala Pro Asp Glu Glu
    50                  55                  60

Asp Leu Ile Leu Arg Leu His Arg Leu Leu Gly Asn Arg Trp Ala Leu
65                  70                  75                  80

Ile Ala Gly Arg Ile Pro Gly Arg Thr Asp Asn Glu Ile Lys Asn Tyr
                85                  90                  95

Trp Asn Thr His Leu Ser Lys Lys

<210> SEQ ID NO 80
<211> LENGTH: 104
<212> TYPE: PRT
<213> ORGANISM: Petunia x hybrida

<400> SEQUENCE: 80

Leu Lys Arg Gly Pro Trp Thr Pro Glu Glu Asp Glu Ile Leu Thr Asn
1               5                   10                  15

Tyr Ile Asn Lys Glu Gly Glu Gly Arg Trp Arg Thr Leu Pro Lys Lys
            20                  25                  30

Ala Gly Leu Leu Arg Cys Gly Lys Ser Cys Arg Leu Arg Trp Met Asn
        35                  40                  45

Tyr Leu Arg Pro Ser Val Lys Arg Gly His Ile Ala Pro Asp Glu Glu
    50                  55                  60

Asp Leu Ile Leu Arg Leu His Arg Leu Leu Gly Asn Arg Trp Ser Leu
65                  70                  75                  80

Ile Ala Gly Arg Ile Pro Gly Arg Thr Asp Asn Glu Ile Lys Asn Tyr
                85                  90                  95

Trp Asn Thr His Leu Ser Lys Lys
            100

<210> SEQ ID NO 81
<211> LENGTH: 104
<212> TYPE: PRT
<213> ORGANISM: Arabidopsis thaliana

<400> SEQUENCE: 81

Met Lys Arg Gly Pro Trp Thr Val Glu Glu Asp Glu Ile Leu Val Ser
1               5                   10                  15

Phe Ile Lys Lys Glu Gly Glu Gly Arg Trp Arg Ser Leu Pro Lys Arg
            20                  25                  30

Ala Gly Leu Leu Arg Cys Gly Lys Ser Cys Arg Leu Arg Trp Met Asn
        35                  40                  45

Tyr Leu Arg Pro Ser Val Lys Arg Gly Gly Ile Thr Ser Asp Glu Glu
    50                  55                  60

Asp Leu Ile Leu Arg Leu His Arg Leu Leu Gly Asn Arg Trp Ser Leu
65                  70                  75                  80

Ile Ala Gly Arg Ile Pro Gly Arg Thr Asp Asn Glu Ile Lys Asn Tyr
                85                  90                  95

Trp Asn Thr His Leu Arg Lys Lys
            100

<210> SEQ ID NO 82
<211> LENGTH: 104
<212> TYPE: PRT
<213> ORGANISM: Oryza sativa

<400> SEQUENCE: 82

Leu Lys Arg Gly Pro Trp Thr Pro Glu Glu Asp Glu Val Leu Ala Arg
1               5                   10                  15

Phe Val Ala Arg Glu Gly Cys Asp Arg Trp Arg Thr Leu Pro Arg Arg
            20                  25                  30

Ala Gly Leu Leu Arg Cys Gly Lys Ser Cys Arg Leu Arg Trp Met Asn
        35                  40                  45

Tyr Leu Arg Pro Asp Ile Lys Arg Cys Pro Ile Ala Asp Asp Glu Glu
    50                  55                  60

```
Asp Leu Ile Leu Arg Leu His Arg Leu Leu Gly Asn Arg Trp Ser Leu
 65                  70                  75                  80

Ile Ala Gly Arg Leu Pro Gly Arg Thr Asp Asn Glu Ile Lys Asn Tyr
                 85                  90                  95

Trp Asn Ser His Leu Ser Lys Lys
            100

<210> SEQ ID NO 83
<211> LENGTH: 104
<212> TYPE: PRT
<213> ORGANISM: Vitis vinifera

<400> SEQUENCE: 83

Val Arg Lys Gly Ala Trp Ile Gln Glu Glu Asp Val Leu Leu Arg Lys
 1               5                  10                  15

Cys Ile Glu Lys Tyr Gly Glu Gly Lys Trp His Leu Val Pro Leu Arg
                20                  25                  30

Ala Gly Leu Asn Arg Cys Arg Lys Ser Cys Arg Leu Arg Trp Leu Asn
             35                  40                  45

Tyr Leu Lys Pro Asp Ile Lys Arg Gly Glu Phe Ala Leu Asp Glu Val
         50                  55                  60

Asp Leu Met Ile Arg Leu His Asn Leu Leu Gly Asn Arg Trp Ser Leu
 65                  70                  75                  80

Ile Ala Gly Arg Leu Pro Gly Arg Thr Ala Asn Asp Val Lys Asn Tyr
                 85                  90                  95

Trp His Ser His His Phe Lys Lys
            100

<210> SEQ ID NO 84
<211> LENGTH: 104
<212> TYPE: PRT
<213> ORGANISM: Vitis vinifera

<400> SEQUENCE: 84

Val Arg Lys Gly Ala Trp Thr Gln Glu Glu Asp Val Leu Leu Arg Lys
 1               5                  10                  15

Cys Ile Glu Lys Tyr Gly Glu Gly Lys Trp His Leu Val Pro Leu Arg
                20                  25                  30

Ala Gly Leu Asn Arg Cys Leu Lys Ser Cys Arg Leu Arg Trp Leu Asn
             35                  40                  45

Tyr Leu Lys Pro Asp Ile Lys Arg Gly Glu Phe Ala Leu Asp Glu Val
         50                  55                  60

Asp Leu Met Ile Arg Leu His Asn Leu Leu Gly Asn Arg Trp Ser Leu
 65                  70                  75                  80

Ile Ala Gly Arg Leu Pro Gly Arg Thr Ala Asn Asp Val Lys Asn Tyr
                 85                  90                  95

Trp His Gly His His Leu Lys Lys
            100

<210> SEQ ID NO 85
<211> LENGTH: 104
<212> TYPE: PRT
<213> ORGANISM: Petunia x hybrida

<400> SEQUENCE: 85

Val Arg Lys Gly Ala Trp Thr Glu Glu Asp Leu Leu Leu Arg Glu
 1               5                  10                  15

Cys Ile Asp Lys Tyr Gly Glu Gly Lys Trp His Leu Val Pro Val Arg
                20                  25                  30
```

```
Ala Gly Leu Asn Arg Cys Arg Lys Ser Cys Arg Leu Arg Trp Leu Asn
            35                  40                  45

Tyr Leu Arg Pro His Ile Lys Arg Gly Asp Phe Ser Leu Asp Glu Val
        50                  55                  60

Asp Leu Ile Leu Arg Leu His Lys Leu Leu Gly Asn Arg Trp Ser Leu
 65                  70                  75                  80

Ile Ala Gly Arg Leu Pro Gly Arg Thr Ala Asn Asp Val Lys Asn Tyr
                85                  90                  95

Trp Asn Thr His Leu Arg Lys Lys
                100
```

<210> SEQ ID NO 86
<211> LENGTH: 104
<212> TYPE: PRT
<213> ORGANISM: Lycopersicon esculentum

<400> SEQUENCE: 86

```
Val Arg Lys Gly Ser Trp Thr Asp Glu Glu Asp Phe Leu Leu Arg Lys
 1               5                  10                  15

Cys Ile Asp Lys Tyr Gly Glu Gly Lys Trp His Leu Val Pro Ile Arg
                20                  25                  30

Ala Gly Leu Asn Arg Cys Arg Lys Ser Cys Arg Leu Arg Trp Leu Asn
            35                  40                  45

Tyr Leu Arg Pro His Ile Lys Arg Gly Asp Phe Glu Gln Asp Glu Val
        50                  55                  60

Asp Leu Ile Leu Arg Leu His Lys Leu Leu Gly Asn Arg Trp Ser Leu
 65                  70                  75                  80

Ile Ala Gly Arg Leu Pro Gly Arg Thr Ala Asn Asp Val Lys Asn Tyr
                85                  90                  95

Trp Asn Thr Asn Leu Leu Arg Lys
                100
```

<210> SEQ ID NO 87
<211> LENGTH: 104
<212> TYPE: PRT
<213> ORGANISM: Arabidopsis thaliana

<400> SEQUENCE: 87

```
Leu Arg Lys Gly Ala Trp Thr Thr Glu Glu Asp Ser Leu Leu Arg Gln
 1               5                  10                  15

Cys Ile Asn Lys Tyr Gly Glu Gly Lys Trp His Gln Val Pro Val Arg
                20                  25                  30

Ala Gly Leu Asn Arg Cys Arg Lys Ser Cys Arg Leu Arg Trp Leu Asn
            35                  40                  45

Tyr Leu Lys Pro Ser Ile Lys Arg Gly Lys Leu Ser Ser Asp Glu Val
        50                  55                  60

Asp Leu Leu Leu Arg Leu His Arg Leu Leu Gly Asn Arg Trp Ser Leu
 65                  70                  75                  80

Ile Ala Gly Arg Leu Pro Gly Arg Thr Ala Asn Asp Val Lys Asn Tyr
                85                  90                  95

Trp Asn Thr His Leu Ser Lys Lys
                100
```

<210> SEQ ID NO 88
<211> LENGTH: 104
<212> TYPE: PRT
<213> ORGANISM: Arabidopsis thaliana -continued

```
<400> SEQUENCE: 88

Leu Arg Lys Gly Ala Trp Thr Ala Glu Glu Asp Ser Leu Leu Arg Leu
1               5                   10                  15

Cys Ile Asp Lys Tyr Gly Glu Gly Lys Trp His Gln Val Pro Leu Arg
            20                  25                  30

Ala Gly Leu Asn Arg Cys Arg Lys Ser Cys Arg Leu Arg Trp Leu Asn
        35                  40                  45

Tyr Leu Lys Pro Ser Ile Lys Arg Gly Arg Leu Ser Asn Asp Glu Val
    50                  55                  60

Asp Leu Leu Arg Leu His Lys Leu Leu Gly Asn Arg Trp Ser Leu
65                  70                  75                  80

Ile Ala Gly Arg Leu Pro Gly Arg Thr Ala Asn Asp Val Lys Asn Tyr
                85                  90                  95

Trp Asn Thr His Leu Ser Lys Lys
            100

<210> SEQ ID NO 89
<211> LENGTH: 104
<212> TYPE: PRT
<213> ORGANISM: Picea mariana

<400> SEQUENCE: 89

Leu Asn Lys Gly Ala Trp Ser Ala Glu Glu Asp Ser Leu Leu Gly Lys
1               5                   10                  15

Tyr Ile Gln Thr His Gly Glu Gly Asn Trp Arg Ser Leu Pro Lys Lys
            20                  25                  30

Ala Gly Leu Arg Arg Cys Gly Lys Ser Cys Arg Leu Arg Trp Leu Asn
        35                  40                  45

Tyr Leu Arg Pro Cys Ile Lys Arg Gly Asn Ile Thr Ala Asp Glu Glu
    50                  55                  60

Glu Leu Ile Ile Arg Met His Ala Leu Leu Gly Asn Arg Trp Ser Ile
65                  70                  75                  80

Ile Ala Gly Arg Val Pro Gly Arg Thr Asp Asn Glu Ile Lys Asn Tyr
                85                  90                  95

Trp Asn Thr Asn Leu Ser Lys Lys
            100

<210> SEQ ID NO 90
<211> LENGTH: 19
<212> TYPE: DNA
<213> ORGANISM: Artificial Sequence
<220> FEATURE:
<223> OTHER INFORMATION: Synthetic

<400> SEQUENCE: 90
cagcatacat aacccaatg                                              19

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
gaatggtgga aatcagatac                                             20

<210> SEQ ID NO 92
<211> LENGTH: 18
<212> TYPE: DNA
```

```
<213> ORGANISM: Artificial Sequence
<220> FEATURE:
<223> OTHER INFORMATION: Synthetic

<400> SEQUENCE: 92
acgactattc cggctctt                                                  18

<210> SEQ ID NO 93
<211> LENGTH: 20
<212> TYPE: DNA
<213> ORGANISM: Artificial Sequence
<220> FEATURE:
<223> OTHER INFORMATION: Synthetic

<400> SEQUENCE: 93
ctgaacaaga acaccgtaga                                                20

<210> SEQ ID NO 94
<211> LENGTH: 22
<212> TYPE: DNA
<213> ORGANISM: Artificial Sequence
<220> FEATURE:
<223> OTHER INFORMATION: Synthetic

<400> SEQUENCE: 94
gcaattaggt agtaattcta ct                                             22

<210> SEQ ID NO 95
<211> LENGTH: 21
<212> TYPE: DNA
<213> ORGANISM: Artificial Sequence
<220> FEATURE:
<223> OTHER INFORMATION: Synthetic

<400> SEQUENCE: 95
ctactgtaat tactcatcaa g                                              21

<210> SEQ ID NO 96
<211> LENGTH: 19
<212> TYPE: DNA
<213> ORGANISM: Artificial Sequence
<220> FEATURE:
<223> OTHER INFORMATION: Synthetic

<400> SEQUENCE: 96
gctcctagtg ttgttcatg                                                 19

<210> SEQ ID NO 97
<211> LENGTH: 19
<212> TYPE: DNA
<213> ORGANISM: Artificial Sequence
<220> FEATURE:
<223> OTHER INFORMATION: Synthetic

<400> SEQUENCE: 97
ctccgaattc gagaggaag                                                 19

<210> SEQ ID NO 98
<211> LENGTH: 19
<212> TYPE: DNA
<213> ORGANISM: Artificial Sequence
<220> FEATURE:
<223> OTHER INFORMATION: Synthetic

<400> SEQUENCE: 98
atcatacatt actgagctg                                                 19
```

<210> SEQ ID NO 99
<211> LENGTH: 18
<212> TYPE: DNA
<213> ORGANISM: Artificial Sequence
<220> FEATURE:
<223> OTHER INFORMATION: Synthetic

<400> SEQUENCE: 99
gcttgaagac gttgttgg                                                 18

<210> SEQ ID NO 100
<211> LENGTH: 20
<212> TYPE: DNA
<213> ORGANISM: Artificial Sequence
<220> FEATURE:
<223> OTHER INFORMATION: Synthetic

<400> SEQUENCE: 100
caggtagttt tgatgctatg                                               20

<210> SEQ ID NO 101
<211> LENGTH: 51
<212> TYPE: DNA
<213> ORGANISM: Artificial Sequence
<220> FEATURE:
<223> OTHER INFORMATION: Synthetic

<400> SEQUENCE: 101
ggggacaagt ttgtacaaaa aagcaggctt catggccacg gcgcaatttc g            51

<210> SEQ ID NO 102
<211> LENGTH: 54
<212> TYPE: DNA
<213> ORGANISM: Artificial Sequence
<220> FEATURE:
<223> OTHER INFORMATION: Synthetic

<400> SEQUENCE: 102
ggggaccact ttgtacaaga aagctgggtc tcaacactta ggaaggtcac ttgg          54

<210> SEQ ID NO 103
<211> LENGTH: 57
<212> TYPE: DNA
<213> ORGANISM: Artificial Sequence
<220> FEATURE:
<223> OTHER INFORMATION: Synthetic

<400> SEQUENCE: 103
ggggacaagt ttgtacaaaa aagcaggctt catgaatctt tggagcgacg agaactc      57

<210> SEQ ID NO 104
<211> LENGTH: 58
<212> TYPE: DNA
<213> ORGANISM: Artificial Sequence
<220> FEATURE:
<223> OTHER INFORMATION: Synthetic

<400> SEQUENCE: 104
ggggaccact ttgtacaaga aagctgggtc ttattgaaca tccccaactt tagaggac     58

<210> SEQ ID NO 105
<211> LENGTH: 55
<212> TYPE: DNA
<213> ORGANISM: Artificial Sequence
<220> FEATURE:
<223> OTHER INFORMATION: Synthetic

<400> SEQUENCE: 105
ggggacaagt tgtacaaaa aagcaggctt catgggaaga gctccttgtt gtgac    55

<210> SEQ ID NO 106
<211> LENGTH: 56
<212> TYPE: DNA
<213> ORGANISM: Artificial Sequence
<220> FEATURE:
<223> OTHER INFORMATION: Synthetic

<400> SEQUENCE: 106
ggggaccact tgtacaaga aagctgggtc tcaatttgtc ttaatgtcag cataac    56

<210> SEQ ID NO 107
<211> LENGTH: 23
<212> TYPE: DNA
<213> ORGANISM: Artificial Sequence
<220> FEATURE:
<223> OTHER INFORMATION: Synthetic

<400> SEQUENCE: 107
tcaagtatgg gcatcattcg cac    23

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
tgctcaaacc gggcagaacg    20

<210> SEQ ID NO 109
<211> LENGTH: 21
<212> TYPE: DNA
<213> ORGANISM: Artificial Sequence
<220> FEATURE:
<223> OTHER INFORMATION: Synthetic

<400> SEQUENCE: 109
tcgagaagga agctgctgaa a    21

<210> SEQ ID NO 110
<211> LENGTH: 22
<212> TYPE: DNA
<213> ORGANISM: Artificial Sequence
<220> FEATURE:
<223> OTHER INFORMATION: Synthetic

<400> SEQUENCE: 110
cccaggcata cttgaatgac ct    22

<210> SEQ ID NO 111
<211> LENGTH: 24
<212> TYPE: DNA
<213> ORGANISM: Artificial Sequence
<220> FEATURE:
<223> OTHER INFORMATION: Synthetic

<400> SEQUENCE: 111
tgaatctttg gaaccactaa tgga    24

<210> SEQ ID NO 112
<211> LENGTH: 24
<212> TYPE: DNA

```
<213> ORGANISM: Artificial Sequence
<220> FEATURE:
<223> OTHER INFORMATION: Synthetic

<400> SEQUENCE: 112
aagcaacaac ttgaagcaaa atca                                              24
```

The invention claimed is:

1. A construct comprising a substantially purified or isolated nucleic acid encoding a MYB protein, or a nucleic acid which is complementary or antisense to a sequence encoding a MYB protein, said nucleic acid or nucleic acid fragment being selected from the group consisting of:
    (a) a nucleic acid or nucleic acid fragment comprising a nucleotide sequence selected from the group consisting of SEQ ID Nos: 60, 62, 63 and 64;
    (b) a variant of a sequence in (a) encoding a protein with MYB activity and having at least 95% nucleic acid identity to the sequence in (a), wherein the variant sequence differs from the sequence in (a) of which it is a variant such that any changes in the amino acid sequence of the encoded protein are conservative amino acid substitutions;
    (c) the complement of a sequence recited in (a) or (b), wherein the complement has the same length as the sequence in (a) or (b) of which it is the complement; and
    (d) a sequence antisense to a sequence recited in (a) or (c), said antisense sequence having a length of at least 30 nucleotides, wherein the entire length of the antisense sequence is antisense to a contiguous region in the sequence recited in (a) or (c), said contiguous region being of equal length to the antisense sequence.

2. The construct of claim 1, wherein said polypeptide is from a clover species.

3. The construct of claim 1, wherein the nucleic acid or nucleic acid fragment is a nucleic acid comprising a nucleotide sequence selected from the group consisting of SEQ ID Nos: 60, 62, 63 and 64.

4. The construct of claim 1, wherein the nucleic acid is a nucleic acid comprising a variant of SEQ ID Nos: 60, 62, 63 or 64 encoding a protein with MYB activity and having at least 95% nucleic identity to the sequence of which it is a variant, wherein the variant sequence differs from the sequence in (a) of which it is a variant such that any changes in the amino acid sequence of the encoded protein are conservative amino acid substitutions.

5. The construct of claim 1, wherein the nucleic acid is a nucleic acid comprising the complement of SEQ ID Nos: 60, 62, 63 or 64, or the complement of a variant of SEQ ID Nos: 60, 62, 63 or 64 encoding a protein with MYB activity and having at least 95% nucleic identity to the sequence of which it is a variant, wherein the variant sequence differs from the sequence in (a) of which it is a variant such that any changes in the amino acid sequence of the encoded protein are conservative amino acid substitutions.

6. The construct of claim 1, wherein the nucleic acid has a length of at least 30 bases and has a sequence that is antisense to SEQ ID Nos: 60, 62, 63 or 64.

7. The construct of claim 1, wherein the nucleic acid is a nucleic acid comprising a variant of SEQ ID Nos: 60, 62, 63 or 64 encoding a protein with MYB activity and having at least 95% nucleic identity to the sequence of which it is a variant, wherein the variant sequence differs from the sequence in (a) of which it is a variant such that any changes in the nucleic acid sequence are conservative nucleic acid changes such that the amino acid sequence encoded by the variant is the same as the amino acid sequence encoded by the sequence in (a) on which the variant is based.

8. A vector including a construct according to claim 1.

9. The vector according to claim 8, further including a promoter and a terminator, said promoter, nucleic acid or nucleic acid fragment and terminator being operatively linked.

10. A plant cell, plant, plant seed or other plant part, including a vector according to claim 8.

11. A plant, plant seed or other plant part derived from a plant cell or plant according to claim 10 and including the vector.

12. A method of modifying
    (a) flavonoid biosynthesis in a plant;
    (b) protein binding, metal chelation, anti-oxidation, and/or UV-light absorption in a plant;
    (c) pigment production in a plant;
    (d) plant defense to a biotic stress; or
    (e) forage quality of a plant by disrupting protein foam and/or conferring protection from rumen pasture bloat;
    said method including introducing into said plant an effective amount of a construct according to claim 1.

13. The method according to claim 12 wherein said method is modifying plant defense to a biotic stress and said biotic stress is selected from the group consisting of viruses, microorganisms, insects and fungal pathogens.

* * * * *